United States Patent
Tobinaga et al.

(10) Patent No.: US 11,578,084 B2
(45) Date of Patent: *Feb. 14, 2023

(54) CONDENSED RING COMPOUNDS HAVING DOPAMINE D3 RECEPTOR ANTAGONISTIC EFFECT

(71) Applicant: Shionogi & Co., Ltd., Osaka (JP)

(72) Inventors: Hiroyuki Tobinaga, Osaka (JP); Koji Masuda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 112 days.

This patent is subject to a terminal disclaimer.

(21) Appl. No.: 16/964,305

(22) PCT Filed: Jan. 25, 2019

(86) PCT No.: PCT/JP2019/002396
§ 371 (c)(1),
(2) Date: Jul. 23, 2020

(87) PCT Pub. No.: WO2019/146739
PCT Pub. Date: Aug. 1, 2019

(65) Prior Publication Data
US 2021/0040117 A1  Feb. 11, 2021

(30) Foreign Application Priority Data

Jan. 26, 2018 (JP) .................. JP2018-011086
Nov. 22, 2018 (JP) .................. JP2018-219158

(51) Int. Cl.
C07D 513/04 (2006.01)
C07D 471/04 (2006.01)
C07D 519/00 (2006.01)
A61P 25/00 (2006.01)

(52) U.S. Cl.
CPC ............ *C07D 513/04* (2013.01); *A61P 25/00* (2018.01); *C07D 471/04* (2013.01); *C07D 519/00* (2013.01)

(58) Field of Classification Search
CPC ... C07D 513/04; C07D 471/04; C07D 519/00
See application file for complete search history.

(56) References Cited

U.S. PATENT DOCUMENTS

| | | | |
|---|---|---|---|
| 4,988,699 A | 1/1991 | Caprathe et al. | |
| 5,294,621 A | 3/1994 | Russell | |
| 5,703,091 A | 12/1997 | Steiner et al. | |
| 6,143,762 A | 11/2000 | Nash et al. | |
| 6,605,607 B1 * | 8/2003 | Hadley | C07D 409/12 514/217.01 |
| 10,870,660 B2 * | 12/2020 | Tobinaga | A61K 31/5377 |
| 11,345,716 B2 * | 5/2022 | Tobinaga | A61P 43/00 |
| 2003/0195216 A1 | 10/2003 | Goldstein et al. | |
| 2006/0079504 A1 | 4/2006 | Rudolf et al. | |
| 2006/0241137 A1 | 10/2006 | Starck et al. | |
| 2007/0299091 A1 | 12/2007 | Gmeiner et al. | |
| 2009/0143398 A1 | 6/2009 | Szalai et al. | |
| 2011/0021490 A1 | 1/2011 | De Nanteuil et al. | |
| 2011/0319423 A1 | 12/2011 | Li et al. | |
| 2016/0096811 A1 | 4/2016 | Li et al. | |
| 2018/0297975 A1 | 10/2018 | Huang et al. | |
| 2019/0161501 A1 * | 5/2019 | Tobinaga | C07D 513/08 |

FOREIGN PATENT DOCUMENTS

| | | |
|---|---|---|
| CA | 2 342 432 | 9/2002 |
| CN | 1948315 | 4/2007 |
| CN | 107793408 | 3/2018 |
| EP | 0 431 580 | 6/1991 |
| EP | 0 465 254 | 7/1991 |
| EP | 1 275 647 | 1/2003 |
| EP | 1 870 405 | 12/2007 |
| EP | 2 955 617 | 3/2016 |
| WO | 95/15327 | 6/1995 |

(Continued)

OTHER PUBLICATIONS

Sheridan et al. J. Chem. Inf. Comput. Sci., 2002, 42, 103-108 (Year: 2002).*
Patani et al. Chem. Rev. 1996, 96, 3147-3176 (Year: 1996).*
Extended European Search Report dated Oct. 11, 2021 in corresponding European Patent Application No. 19744162.9.
International Search Report dated Mar. 19, 2019 in International (PCT) Application No. PCT/JP2019/002396 with English language translation.
Translation of Written Opinion of the International Searching Authority dated Oct. 3, 2017 in International (PCT) Application No. PCT/JP2017/027141.

(Continued)

*Primary Examiner* — Matthew P Coughlin
(74) *Attorney, Agent, or Firm* — Wenderoth, Lind & Ponack, L.L.P.

(57) ABSTRACT

Novel compounds having a D3 receptor antagonistic effect are provided.

The compound represented by Formula (IA)':

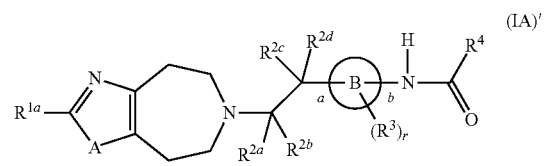

wherein A is S or O; $R^{1a}$ is substituted or unsubstituted alkyloxy or the like, $R^{2a}$ to $R^{2d}$ are each independently hydrogen atoms or the like, ring B is a 4- to 8-membered non-aromatic carbocycle or the like, $R^3$ is each independently halogen or the like, r is an integer of 0 to 4, $R^4$ is substituted or unsubstituted aromatic heterocyclyl or the like, or a pharmaceutically acceptable salt thereof.

4 Claims, 1 Drawing Sheet

(56) References Cited

FOREIGN PATENT DOCUMENTS

| | | |
|---|---|---|
| WO | 96/02249 | 2/1996 |
| WO | 97/38998 | 10/1997 |
| WO | 97/43262 | 11/1997 |
| WO | 98/06699 | 2/1998 |
| WO | 98/49145 | 11/1998 |
| WO | 98/50363 | 11/1998 |
| WO | 98/50364 | 11/1998 |
| WO | 98/51671 | 11/1998 |
| WO | 99/59974 | 11/1999 |
| WO | 99/64412 | 12/1999 |
| WO | 00/21950 | 4/2000 |
| WO | 00/21951 | 4/2000 |
| WO | 00/24717 | 5/2000 |
| WO | 02/40471 | 5/2002 |
| WO | 02/066446 | 8/2002 |
| WO | 02/066468 | 8/2002 |
| WO | 02/066469 | 8/2002 |
| WO | 02/079151 | 10/2002 |
| WO | 03/029233 | 4/2003 |
| WO | 2004/037810 | 5/2004 |
| WO | 2004/069830 | 8/2004 |
| WO | 2004/091490 | 10/2004 |
| WO | 2005/012266 | 2/2005 |
| WO | 2005/094834 | 10/2005 |
| WO | 2006/050239 | 5/2006 |
| WO | 2006/050976 | 5/2006 |
| WO | 2006/082456 | 8/2006 |
| WO | 2006/102610 | 9/2006 |
| WO | 2007/056155 | 5/2007 |
| WO | 2007/148208 | 12/2007 |
| WO | 2008/125891 | 10/2008 |
| WO | 2009/011904 | 1/2009 |
| WO | 2009/013212 | 1/2009 |
| WO | 2009/015067 | 1/2009 |
| WO | 2009/056805 | 5/2009 |
| WO | 2009/095438 | 8/2009 |
| WO | 2009/112568 | 9/2009 |
| WO | 2010/025235 | 3/2010 |
| WO | 2010/031735 | 3/2010 |
| WO | 2010/034646 | 4/2010 |
| WO | 2010/034648 | 4/2010 |
| WO | 2010/034656 | 4/2010 |
| WO | 2010/060854 | 6/2010 |
| WO | 2011/109441 | 9/2011 |
| WO | 2011/161009 | 12/2011 |
| WO | 2012/004206 | 1/2012 |
| WO | 2012/080149 | 6/2012 |
| WO | 2012/110470 | 8/2012 |
| WO | 2012/117001 | 9/2012 |
| WO | 2012/121919 | 9/2012 |
| WO | 2012/150231 | 11/2012 |
| WO | 2014/059265 | 4/2014 |
| WO | 2014/064038 | 5/2014 |
| WO | 2014/086098 | 6/2014 |
| WO | 2014/140246 | 9/2014 |
| WO | 2014/0180165 | 11/2014 |
| WO | 2017/021920 | 2/2017 |
| WO | 2017/122116 | 7/2017 |
| WO | 2018/021447 | 2/2018 |
| WO | WO-2018021447 A1 * | 2/2018 ........... A61K 31/437 |
| WO | 2019/146740 | 8/2019 |

OTHER PUBLICATIONS

Joyce et al., "Dopamine D3 receptor antagonists as therapeutic agents," Drug Discovery Today, 2005, vol. 10, No. 13, pp. 917-925.

Joyce, J., "Dopamine D3 receptor as a therapeutic target for antipsychotic and antiparkinsonian drugs," Pharmacology & Therapeutics, 2001, vol. 90, pp. 231-259.

Barth et al., "In Vivo Occupancy of Dopamine D3 Receptors by Antagonists Produces Nemochemical and Behavioral Effects of Potential Relevance to Attention-Deficit-Hyperactivity Disorder," Journal of Pharmacology and Experimental Therapeutics, 2013, vol. 344, pp. 501-510.

Mach et al., "Development of Novel 1, 2, 3, 4-Tetrahydroisoquinoline Derivatives and Closely Related Compounds as Potent and Selective Dopamine D3 Receptor Ligands," ChemBioChem, 2004, vol. 5, pp. 508-518.

Shonberg et al., "Structure-Activity Study of N-((trans)-4-(2-(7-Cyano-3,4-dihydroisoquinolin-2(1H)-yl)ethyl)cyclohexyl)-1H-indole-2-carboxamide (SB69652), a Bitopic Ligand That Acts as a Negative Allosteric Modulator of the Dopamine D2 Receptor," Journal of Medicinal Chemistry, 2015, vol. 58, pp. 5287-5307.

Fang et al., "CCLab-a multi-objective genetic algorithm based combinatorial library design software and an application for histone deacetylase inhibitor design," Bioorganic & Medicinal Chemistry Letters, 2012, vol. 22, No. 14, pp. 4540-4545.

Austin et al., "Novel 2, 3, 4, 5-Tetrahydro-1H-3-benzazepines with High Affinity and Selectivity for the Dopamine D3 Receptor," Bioorganic & Medicinal Chemistry Letters, 2000, vol. 10, pp. 2553-2555.

Macdonald et al., "Design and Synthesis of trans-3-(2-(4-((3-(3-(5-Methyl-1,2,4-oxadiazolyl))-phenyl)carboxamido)cyclohexyl)ethyl)-7-methylsulfonyl-2,3,4,5-tetrahydro-1H-3-benzazepine (SB-414769): A Potent and Selective Dopamine D3 Receptor Antagonist," Journal of Medicinal Chemistry, 2003, vol. 46, pp. 4952-4964.

Zajdel et al., "Arene- and quinoline-sulfonamides as novel 5-HT7 receptor ligands," Bioorganic & Medicinal Chemistry, 2011, vol. 19, No. 22, pp. 6750-6759.

Chen et al., "Synthesis and pharmacological characterization of novel N-(trans-4-(2-(4-(benzo[d]isothiazol-3-yl)piperazin-1-yl)ethyl)cyclohexyl) amides as potential multireceptor atypical antipsychotics," European Journal of Medicinal Chemistry, 2016, vol. 123, pp. 332-353.

Belliotti et al., "Novel Cyclohexyl Amides as Potent and Selective D3 Dopamine Receptor Ligands," Bioorganic & Medicinal Chemistry Letters, 1997, vol. 7, No. 18, pp. 2403-2408.

Chen et al., "Tranylcypromine Subtitled cis-Hydroxycyclobutylnaphthemides as Potent and Selective Dopamine D3 Receptor Antagonists," Journal of Medicinal Chemistry, 2014, vol. 57, pp. 4962-4968.

Chen et al., "High-affinity and selective dopamine D3 receptor full agonists," Bioorganic & Medicinal Chemistry Letters, 2012, vol. 22, No. 17, pp. 5612-5617.

Ortore et al., "Different Binding Modes of Structurally Diverse Ligands for Human D3DAR," Journal of Chemical Informahon and Modeling, 2010, vol. 50, No. 12, pp. 2162-2175.

Micheli et al., "Exploration of the Amine Terminus in a Novel Series of 1,2,4-Triazolo-3-yl-azabicyclo[3.1.0]hexanes as Selective Dopamine D3 Receptor Antagonists," Journal of Medicinal Chemistry, 2010, vol. 53, No. 19, pp. 7129-7139.

Micheli et al., "1,2,4-Triazol-3-yl-thiopropyl-tetrahydrobenzazepines: A Series of Potent Selective Dopamine D3 Receptor Antagonists," Journal of Medicinal Chemistry, 2007, vol. 50, No. 21, pp. 5076-5089.

Lacroix et al., "Selective dopamine D3 receptor antagonists enhance cortical acetylcholine levels measured with high-performance liquid chromatography/tandem mass spectrometry without anticholinesterases," Journal of Neuroscience Methods, 2006, vol. 157, No. 1, pp. 25-31.

Kim et al., "Classification of dopamine antagonists using functional feature hypothesis and topological descriptors," Bioorganic & Medicinal Chemistry, 2006, vol. 14, No. 5, pp. 1454-1461.

Heidbreder et al., "The role of central dopamine D3 receptors in drug addiction: a review of pharmacological evidence," Brain Research Reviews, 2005, vol. 49, No. 1, pp. 77-105.

Agai-Csongor et al., "Novel sulfonamides having dual dopamine D2 and D3 receptor affinity show in vivo antipsychotic efficacy with beneficial cognitive and EPS profile," Bioorganic & Medicinal Chemistry Letters, 2007, vol. 17, No. 19, pp. 5340-5344.

Wustrow et al., "Aminopyrimidines with High Affinity for Both Serotonin and Dopamine Receptors," Journal of Medicinal Chemistry, 1998, vol. 41, No. 5, pp. 760-771.

(56) References Cited

OTHER PUBLICATIONS

Mistry et al., "Discovery of a Novel Class of Negative Allosteric Modulator of the Dopamine D2 Receptor Through Fragmentation of Bitopic Ligand," Journal of Medicinal Chemistry, 2015, vol. 58, pp. 6819-6843.

Stemp et al., "Design and Synthesis of trans-N-[4-[2-(6-Cyano-1,2,3,4-tetrahydroisoquinolin-2-yl)ethyl]cyclohexyl]-4-quinolinecarboxamide (SB-277011): A Potent and Selective Dopamine D3 Receptor Antagonist with High Oral Bioavailability and CNS Penetration in the Rat," Journal of Medicinal Chemistry, 2000, vol. 43, No. 9, pp. 1878-1885.

Kumar et al., "Synthesis and Pharmacological Characterization of Novel trans-Cyclopropylmethyl-Linked Bivalent Ligands That Exhibit Selectivity and Allosteric Pharmacology at the Dopamine D3 Receptor (D3R)," Journal of Medicinal Chemistry, 2017, vol. 60, pp. 1478-1494.

Gadhiya et al., "New Dopamine D3-Selective Receptor Ligands Containing a 6-Methoxy-1,2,3,4-tetrahydroisoquinolin-7-ol Motif," ACS Medicinal Chemistry Letters, 2018, vol. 9, pp. 990-995.

Chen et al., "Design of novel hexahydropyrazinoquinolines as potent and selective dopamine D3 receptor ligands with improved solubility," Bioorganic & Medicinal Chemistry Letters, 2006, vol. 16, pp. 443-446.

Micheli et al., "New fused benzazepine as selective D3 receptor antagonists. Synthesis and biological evaluation. Part 2: [g]-Fused and hetero-fused systems," Bioorganic & Medicinal Chemistry Letters, 2008, vol. 18, pp. 908-912.

Chen et al., "Pramipexole Derivatives as Potent and Selective Dopamine D3 Receptor Agonists with Improved Human Microsomal Stability," ChemMedChem 2014, vol. 9, pp. 2653-2660.

Vass et al., "Multiple Fragment Docking and Linking in Primary and Secondary Pockets of Dopamine Receptors," ACS Medicinal Chemistry Letters, 2014, vol. 5, pp. 1010-1014.

Chen et al., "CJ-1639: A Potent and Highly Selective Dopamine D3 Receptor Full Agonist," ACS Medicinal Chemistry Letters, 2011, vol. 2, pp. 620-625.

Brindisi et al., "Targeting Dopamine D3 and Serotonin 5-HT1A and 5-HT2A Receptors for Developing Effective Antipsychotics: Synthesis, Biological Characterization, and Behavioral Studies," Journal of Medicinal Chemistry, 2014, vol. 57, pp. 9578-9597.

Keck et al., "Identifying Medication Targets for Psychostimulant Addiction: Unraveling the Dopamine D3 Receptor Hypothesis," Journal of Medicinal Chemistry, 2015, vol. 58, pp. 5361-5380.

Tschammer et al., "Highly Potent 5-Aminotetrahydropyrazolopyridines: Enantioselective Dopamine D3 Receptor Binding, Functional Selectivity, and Analysis of Receptor-Ligand Interactions," Journal of Medicinal Chemistry, 2011, vol. 54, pp. 2477-2491.

Arakawa et al., "Positron Emission Tomography Measurement of Dopamine D2 Receptor Occupancy in the Pituitary and Cerebral Cortex: Relation to Antipsychotic-Induced Hyperprolactinemia," Journal of Clinical Psychiatry, 2010, vol. 71, 9, pp. 1131-1137.

Watson et al., "Selective Blockade of Dopamine D3 Receptors Enhances while D2 Receptor Antagonism Impairs Social Novelty Discrimination and Novel Object Recognition in Rats: A Key Role for the Prefrontal Cortex," Neuropsychopharmacology, 2012, vol. 37, pp. 770-786.

Mehta et al., "Dopamine D2 receptor occupancy levels of acute sulpiride challenges that produce working memory and learning impairments in healthy volunteers," Psychopharmacology, 2008, vol. 196, No. 1, pp. 157-165.

Uchida et al., "D2 Receptor Blockade by Risperidone Correlates With Attention Deficits in Late-Life Schizophrenia," Journal of Clinical Psychopharmacology, 2009, vol. 29, No. 6, pp. 571-575.

Deak et al., "Physico-chemical characterization of a novel group of dopamine D3/D2 receptor ligands, potential atypical antipsychotic agents," Journal of Pharmaceutical and Biomedical Analysis, 2008, vol. 48, No. 3, pp. 678-684.

RN2180090-16-6(Entered STN: Feb. 26, 2018).

RN2180085-11-2(Entered STN: Feb. 26, 2018).

Jordan et al., "The highly selective dopamine D3R antagonist, R-VK4-40 attenuates oxycodone reward and augments analgesia in rodents," Neuropharmacology, (2019), vol. 158, pp. 1-11.

Extended European Search Report dated Feb. 6, 2020 in European Patent Application No. 17834449.5.

Translation of the International Preliminary Report on Patentability dated Aug. 6, 2020 in International (PCT) Application No. PCT/JP2019/002396.

* cited by examiner

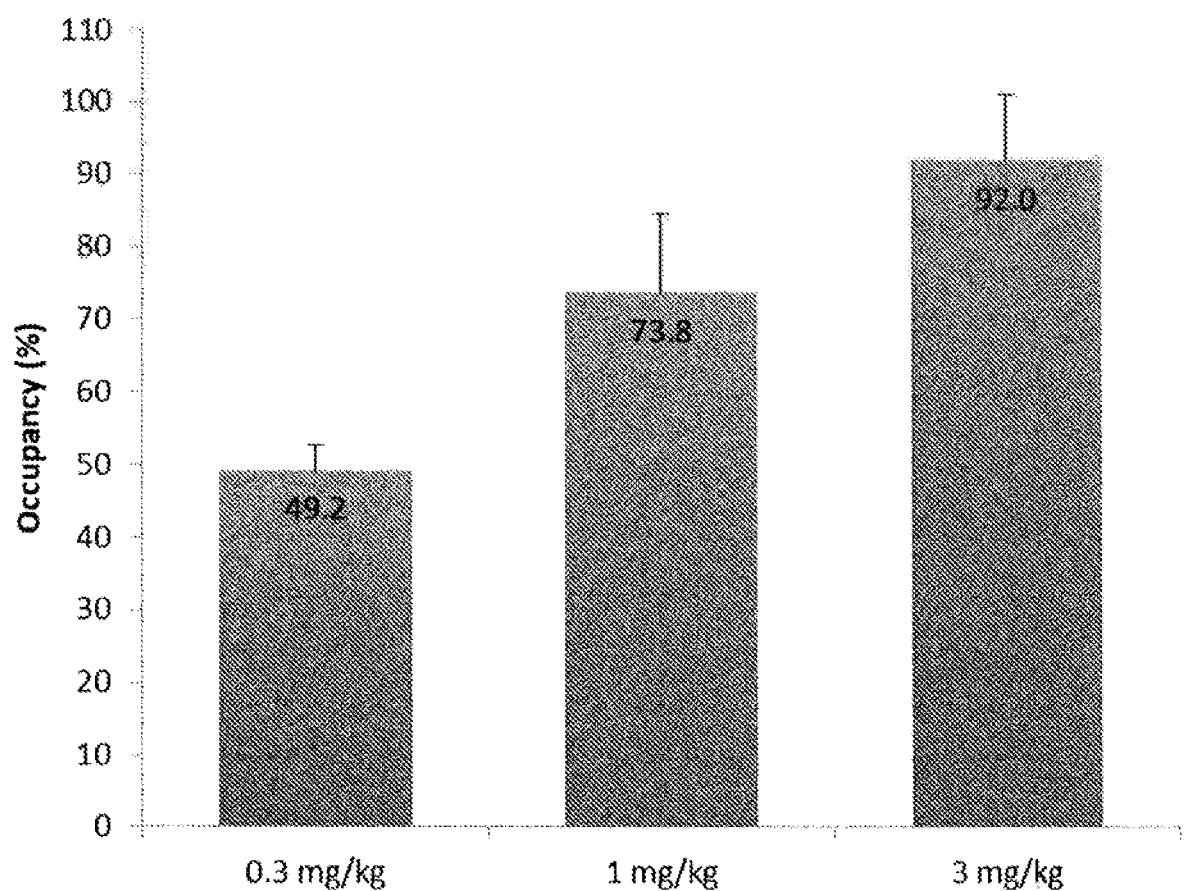

CONDENSED RING COMPOUNDS HAVING DOPAMINE D3 RECEPTOR ANTAGONISTIC EFFECT

TECHNICAL FIELD

The present invention relates to a compound which has an antagonistic activity for dopamine D3 receptor (hereinafter referred to as D3 receptor) and is useful as an agent for treating and/or preventing diseases induced by D3 receptor, or a pharmaceutically acceptable salt thereof, and a pharmaceutical composition containing the same.

BACKGROUND ART

Dopamine is an important neuromediator in central nervous system. The biological activities of dopamine are mediated through G protein-coupled receptors (GPCRs) and involved in the regulation of a variety of functions which include emotion, cognition, and motor functions. In human, five different dopamine receptors D1 to D5 have been identified. These receptors can be divided into two subtypes: D2-like receptors consisting of D2, D3 and D4 receptors, and D1-like receptors consisting of D1 and D5 receptors.

D3 receptor is selectively distributed in marginal brain area, such as nucleus accumbens, Calleja island, and olfactory tubercle. Some research reports suggest that D3 receptor antagonists are useful for treating and/or preventing a number of neurosises, such as schizophrenia, Parkinson's disease, drug dependence, any forms of stress, anxiety, and somnipathy. Furthermore, it is considered that D3/D2 selective D3 receptor antagonists would have less D2 receptor-mediated side-effects (extrapyramidal symptom, elevated prolactin, reduced cognitive function, and the like) compared to existing antipsychotics which are D2 receptor antagonists (Non-patent Documents 1 to 6).

It is also suggested that D3 receptor antagonists are useful for treating and/or preventing attention-deficit/hyperactivity disorder (AD/HD) (Non-patent Document 7).

Thus, it is highly likely that compounds having antagonistic activity for D3 receptor, especially preferably compounds having high D3/D2 selectivity, are useful as an agent for treating and/or preventing diseases associated with D3 receptor.

The compounds having affinity for D3 receptor are described in Patent Documents 1 to 15 and 19, and Non-patent Documents 8, 11, 12 and 13. However, substantially disclosed compounds have different structure from the compounds of the present invention. The compounds substantially disclosed in Patent Documents 16 to 18, and Non-patent Documents 9 and 10 have different structure from the compounds of the present invention, and there is neither disclosure nor suggestion about an antagonistic activity for D3 receptor.

PRIOR ART DOCUMENTS

Patent Documents

[Patent Document 1] WO 9602249
[Patent Document 2] WO 9738998
[Patent Document 3] WO 9806699
[Patent Document 4] WO 9849145
[Patent Document 5] WO 9850363
[Patent Document 6] WO 9850364
[Patent Document 7] WO 9851671
[Patent Document 8] WO 9959974
[Patent Document 9] WO 9964412
[Patent Document 10] WO 2000/021950
[Patent Document 11] WO 2000/021951
[Patent Document 12] WO 2000/024717
[Patent Document 13] WO 2002/040471
[Patent Document 14] WO 2004/069830
[Patent Document 15] WO 2006/050976
[Patent Document 16] U.S. Pat. No. 5,294,621
[Patent Document 17] WO 2011/109441
[Patent Document 18] WO 2009/011904
[Patent Document 19] WO 2017/021920
[Patent Document 20] WO 2018/021447

Non-Patent Documents

[Non-patent Document 1] Drug Discovery Today, 2005, 10(13), 917-925
[Non-patent Document 2] Pharmacology & Therapeutics, 2001, 90, 231-259
[Non-patent Document 3] Journal of Clinical Psychiatry, 2010, 71(9), 1131-1137
[Non-patent Document 4] Neuropsychopharmacology, 2012, 37, 770-786
[Non-patent Document 5] Psychopharmacology, 2008, 196 (1), 157-165
[Non-patent Document 6] Journal of Clinical Psychopharmacology, 2009, 29(6), 571-575
[Non-patent Document 7] Journal of Pharmacology and Experimental Therapeutics, 2013, 344, 501-510
[Non-patent Document 8] ChemBioChem, 2004, 5, 508-518
[Non-patent Document 9] Journal of Medicinal Chemistry, 2015, 58, 5287-5307
[Non-patent Document 10] Bioorganic & Medicinal Chemistry Letters, 2012, 22(14), 4540-4545
[Non-patent Document 11] Bioorganic & Medicinal Chemistry Letters, 2000, 10, 2553-2555
[Non-patent Document 12] Journal of Medicinal Chemistry, 2003, 46, 4952-4964
[Non-patent Document 13] Bioorganic & Medicinal Chemistry Letters, 1997, 7(18), 2403-2408

SUMMARY OF THE INVENTION

Problems to be Solved by the Invention

The objective of the present invention is to provide a compound which has an antagonistic activity for D3 receptor, and preferably high D3/D2 selectivity, and is useful as an agent for treating and/or preventing diseases associated with D3 receptor, or a pharmaceutically acceptable salt thereof, and a pharmaceutical composition containing the same.

Means for Solving the Problems

The present invention relates to, for example, the following inventions.
(1)" A compound represented by Formula (IA)' or (IB):

[Chemical Formula 1]

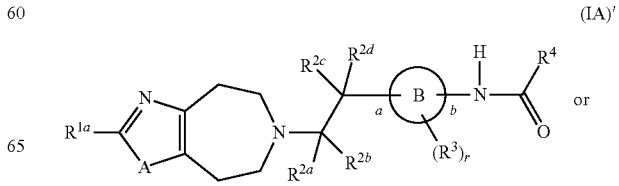

-continued (IB)

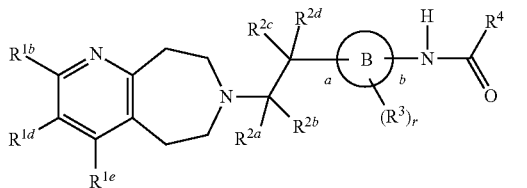

wherein

A is S or O;

$R^{1a}$ is substituted or unsubstituted alkyloxy, or substituted or unsubstituted non-aromatic carbocyclyloxy;

$R^{1b}$ is substituted or unsubstituted alkyloxy, substituted or unsubstituted non-aromatic carbocyclyloxy, or substituted or unsubstituted alkyl;

$R^{1d}$ and $R^{1e}$ are each independently a hydrogen atom, halogen, hydroxy, cyano, substituted or unsubstituted C1-C6 alkyl, or substituted or unsubstituted C1-C6 alkyloxy;

$R^{2a}$ to $R^{2d}$ are each independently a hydrogen atom, halogen, hydroxy, cyano, substituted or unsubstituted C1-C6 alkyl, or substituted or unsubstituted C1-C6 alkyloxy;

$R^3$ is each independently halogen, hydroxy, cyano, substituted or unsubstituted C1-C6 alkyl, or substituted or unsubstituted C1-C6 alkyloxy;

two $R^3$ s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom;

a bonding hand "a" is bonded to —$CR^{2c}R^{2d}$;

a bonding hand "b" is bonded to —NH—;

Ring B is a non-aromatic carbocycle or a non-aromatic heterocycle;

r is an integer of 0 to 4;

$R^4$ is substituted or unsubstituted aromatic carbocyclyl, substituted or unsubstituted non-aromatic heterocyclyl, substituted or unsubstituted aromatic heterocyclyl, —$CR^{5a}R^{5b}$—$R^6$, or —$CR^{7a}$=$CR^{7b}$—$R^8$;

$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;

$R^6$ is substituted or unsubstituted non-aromatic heterocyclyl, substituted or unsubstituted aromatic heterocyclyl, substituted or unsubstituted aromatic heterocyclyloxy, or substituted or unsubstituted non-aromatic heterocyclyloxy;

$R^8$ is substituted or unsubstituted non-aromatic heterocyclyl, or substituted or unsubstituted aromatic heterocyclyl, provided that the following compounds (i) to (viii) are excluded:

(i) a compound represented by Formula (IA)' or (IB), wherein A is S; $R^{1a}$ or $R^{1b}$ is a group represented by:

[Chemical Formula 2]

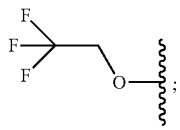

$R^{1d}$ and $R^{1e}$ are hydrogen atoms; $R^{2a}$ to $R^{2c}$ are hydrogen atoms; $R^{2d}$ is a hydrogen atom, hydroxy, or halogen;

a group represented by:

[Chemical Formula 3]

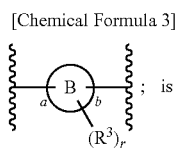; is

[Chemical Formula 4]

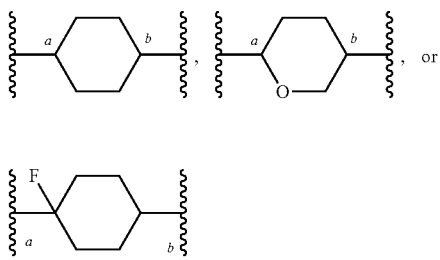

$R^4$ is non-aromatic heterocyclyl unsubstituted or substituted with one or more group(s) selected from oxo, methyl, and ethyl; aromatic heterocyclyl unsubstituted or substituted with only one methyl; —$CH_2$—$R^6$ (wherein $R^6$ is 5-membered aromatic heterocyclyl (provided that triazolyl is excluded) substituted with only one methyl; 5-membered aromatic heterocyclyl (provided that triazolyl is excluded) substituted with only one alkyloxy; pyridyl substituted with only one methyl; pyridyloxy unsubstituted or substituted with only one methyl; or pyrimidyloxy substituted with only one methyl); or —CH=CH—$R^8$ (wherein $R^8$ is unsubstituted aromatic carbocyclyl; or 5-membered aromatic heterocyclyl substituted with only one methyl), (ii) a compound represented by Formula (IA)' or (IB), wherein A is S; $R^{1e}$ is a hydrogen atom; $R^{2a}$ to $R^{2d}$ are hydrogen atoms; ring B is a cyclohexane ring; r is 0; and $R^4$ is a group represented by

[Chemical Formula 5]

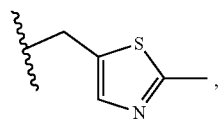, (iii) a compound represented by Formula:

[Chemical Formula 6]

[Chemical Formula 6]

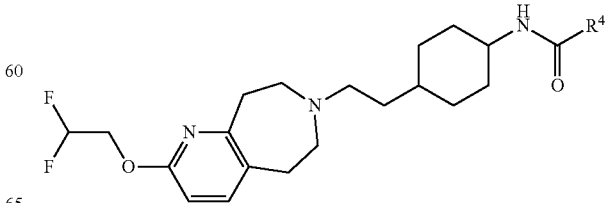

wherein R⁴ is a group represented by:
[Chemical Formula 7]
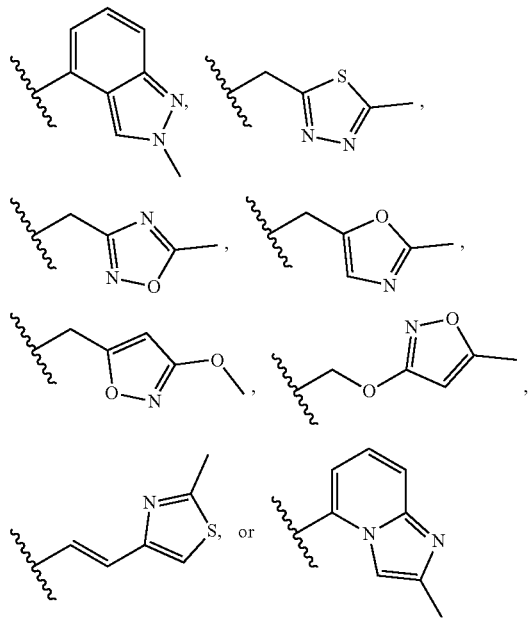
(iv) a compound represented by Formula:
[Chemical Formula 8]
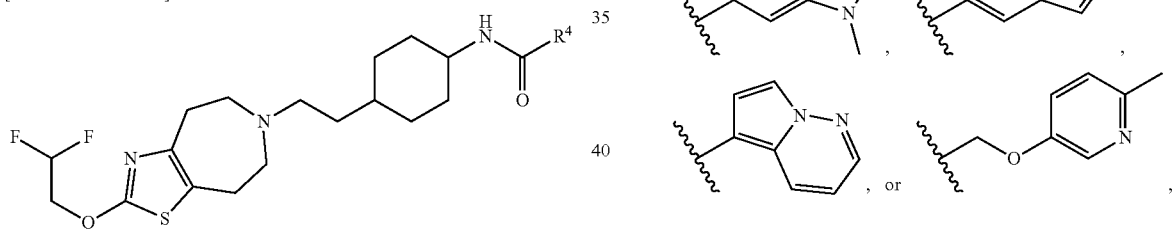
wherein R⁴ is a group represented by:
[Chemical Formula 9]
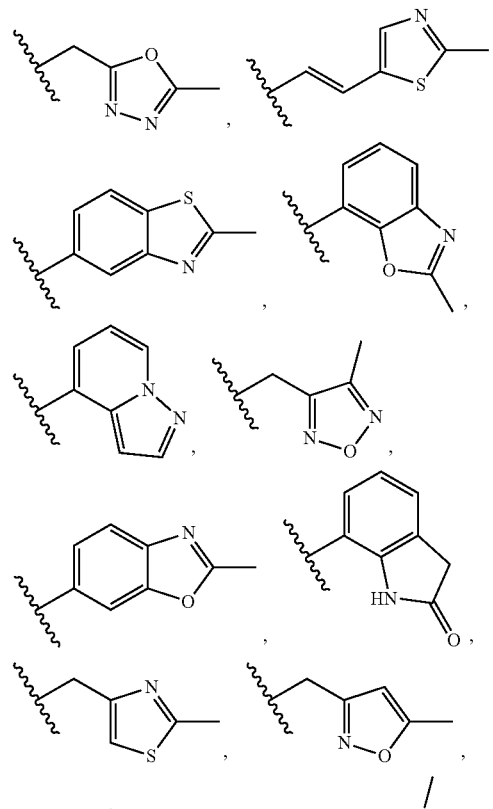
(v) a compound represented by Formula:
[Chemical Formula 10]
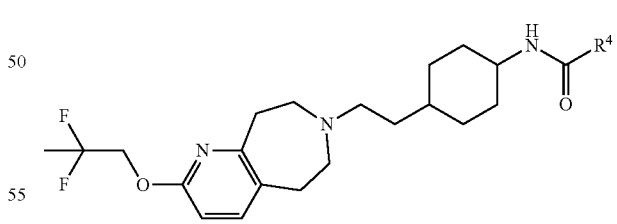
wherein R⁴ is a group represented by
[Chemical Formula 11]

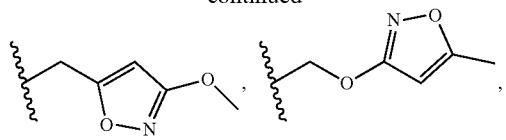
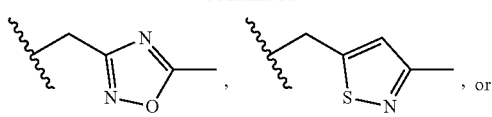
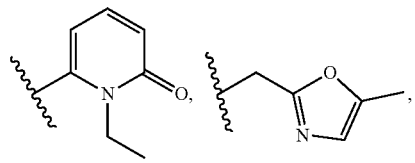
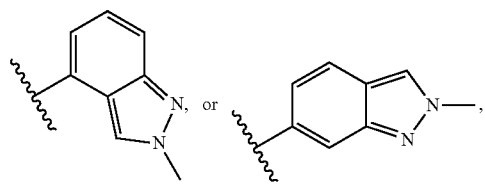
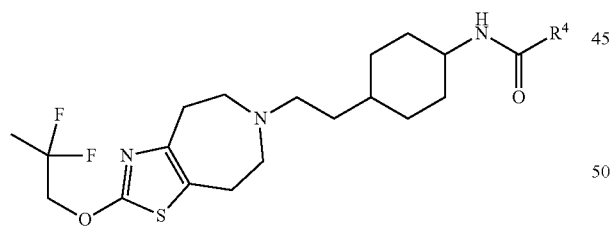
(vi) a compound represented by Formula
[Chemical Formula 12]
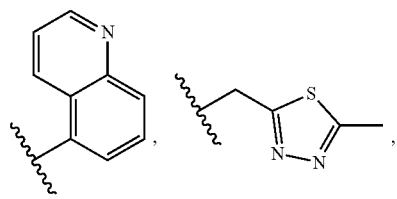
wherein R⁴ is a group represented by:
[Chemical Formula 13]
(vii) a compound represented by Formula:
[Chemical Formula 14]
wherein R$^{1a}$ is a group represented by:
[Chemical Formula 15]

and
(viii) the following compounds:
[Chemical Formula 16]
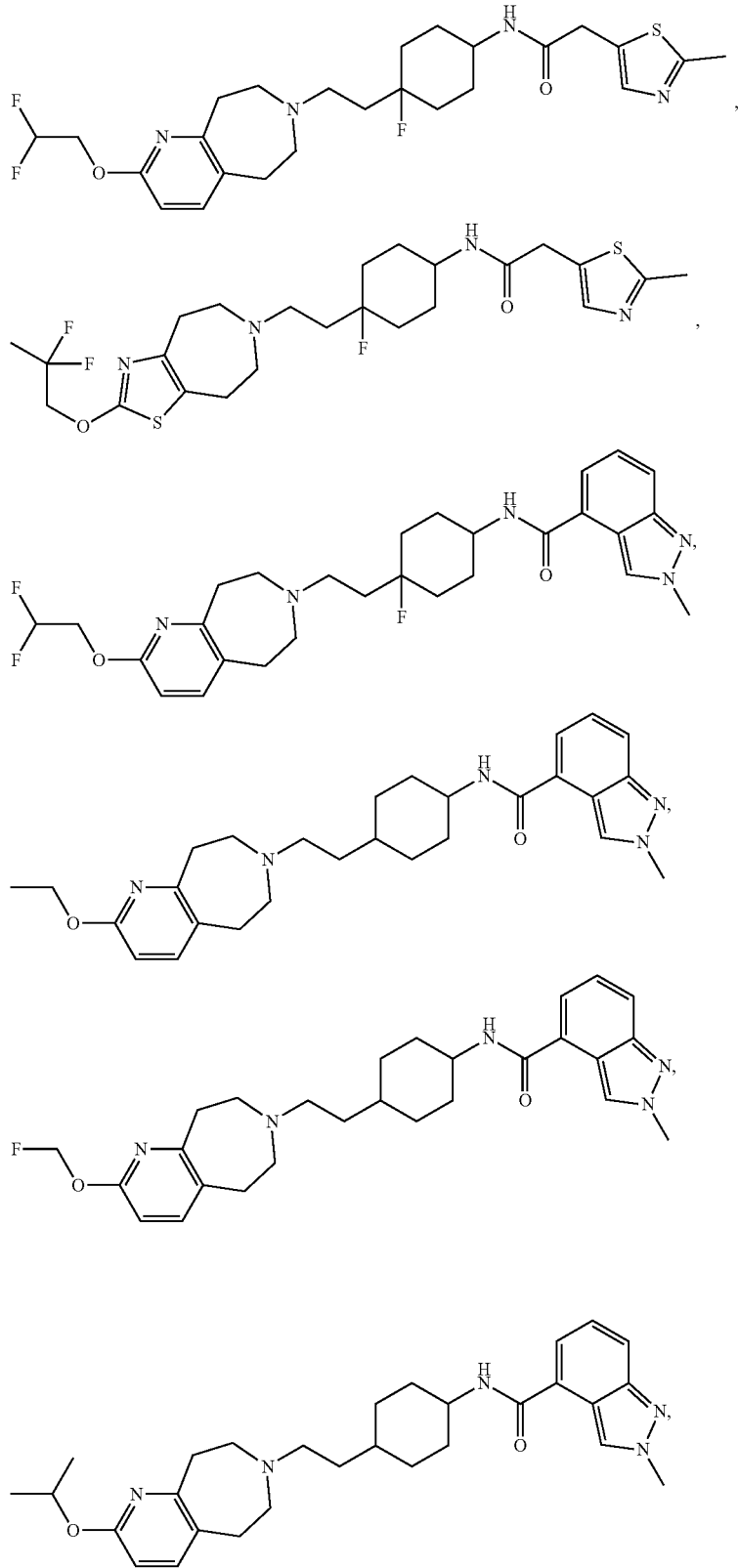

-continued
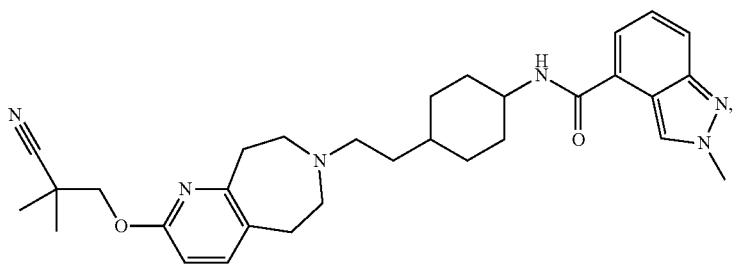
[Chemical Formula 17]
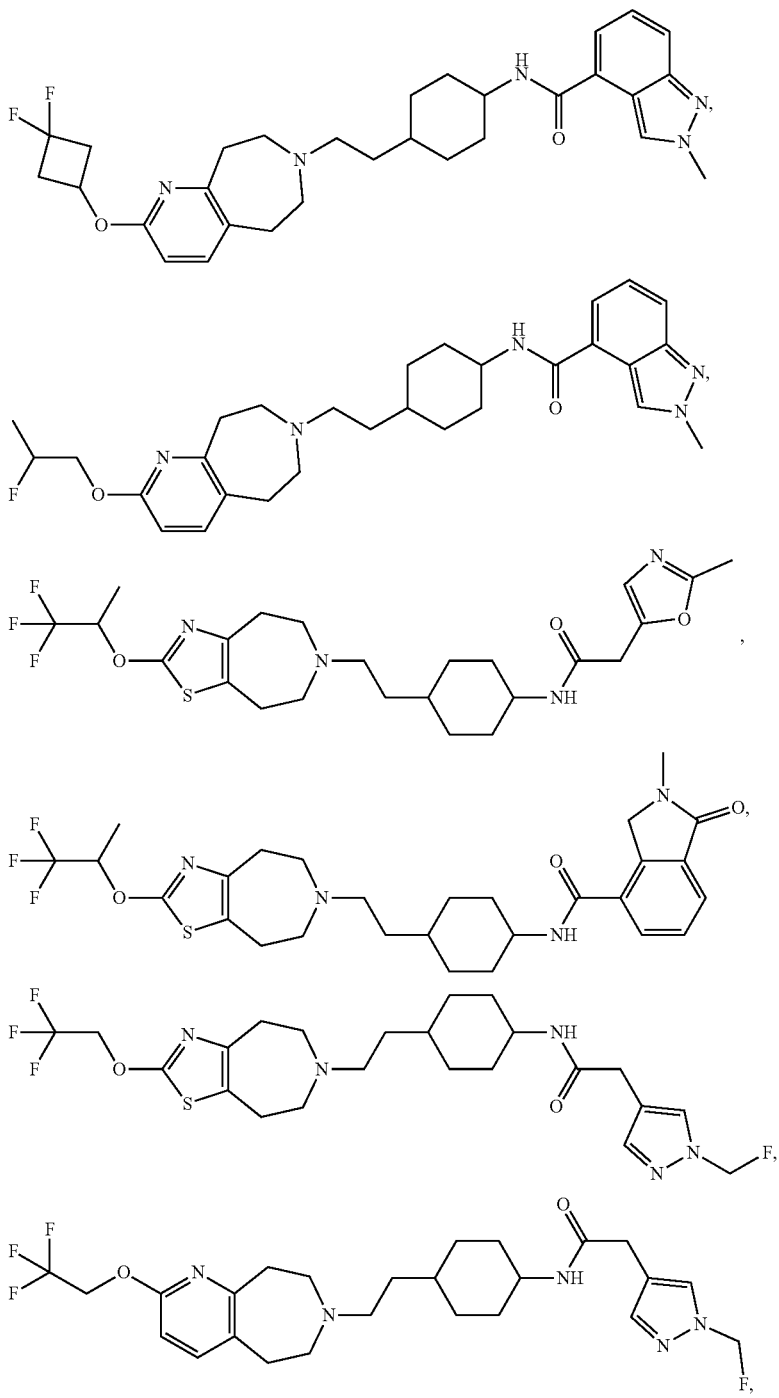

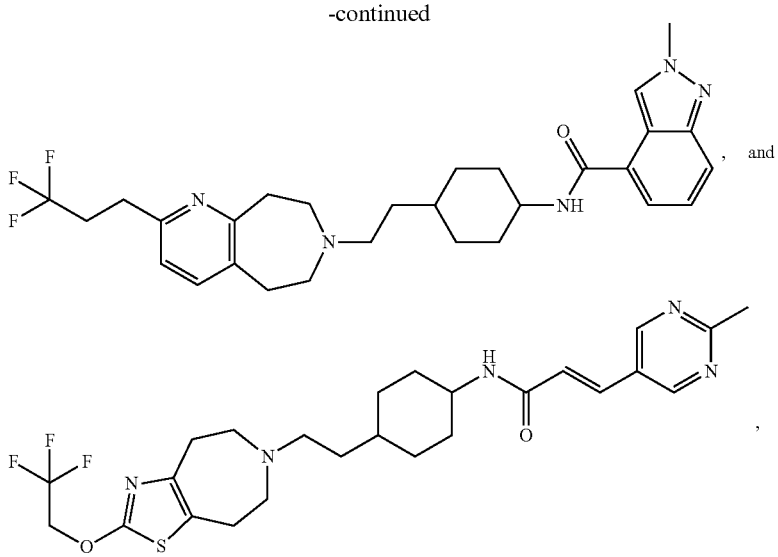
, and or a pharmaceutically acceptable salt thereof.

(1) A compound represented by Formula (IA) or (IB):

[Chemical Formula 18]

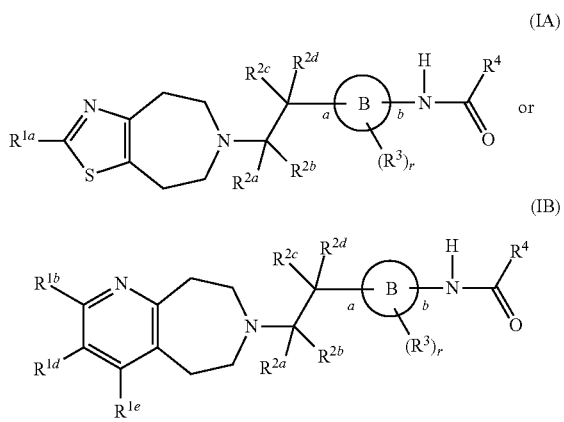

wherein $R^{1a}$ is each independently substituted or unsubstituted alkyloxy, or substituted or unsubstituted non-aromatic carbocyclyloxy;

$R^{1b}$ is substituted or unsubstituted alkyloxy, substituted or unsubstituted non-aromatic carbocyclyloxy, or substituted or unsubstituted alkyl;

$R^{1d}$ and $R^{1e}$ are each independently a hydrogen atom, halogen, hydroxy, cyano, substituted or unsubstituted C1-C6 alkyl, or substituted or unsubstituted C1-C6 alkyloxy;

$R^{2a}$ to $R^{2d}$ are each independently a hydrogen atom, halogen, hydroxy, cyano, substituted or unsubstituted C1-C6 alkyl, or substituted or unsubstituted C1-C6 alkyloxy;

$R^3$ is each independently halogen, hydroxy, cyano, substituted or unsubstituted C1-C6 alkyl, or substituted or unsubstituted C1-C6 alkyloxy;

two $R^3$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom;

a bonding hand "a" is bonded to —$CR^{2c}R^{2d}$—;
a bonding hand "b" is bonded to —NH—;
Ring B is a non-aromatic carbocycle or a non-aromatic heterocycle;
r is an integer of 0 to 4;
$R^4$ is substituted or unsubstituted aromatic carbocyclyl, substituted or unsubstituted non-aromatic heterocyclyl, substituted or unsubstituted aromatic heterocyclyl, —$CR^{5a}R^{5b}$—$R^6$, or —$CR^{7a}$=$CR^{7b}$—$R^8$;

$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;

$R^6$ is substituted or unsubstituted non-aromatic heterocyclyl, substituted or unsubstituted aromatic heterocyclyl, substituted or unsubstituted aromatic heterocyclyloxy, or substituted or unsubstituted non-aromatic heterocyclyloxy;

$R^8$ is substituted or unsubstituted non-aromatic heterocyclyl or substituted or unsubstituted aromatic heterocyclyl, provided that the following compounds (i) to (viii) are excluded:

(i) a compound, wherein $R^{1a}$ or $R^{1b}$ is a group represented by:

[Chemical Formula 19]

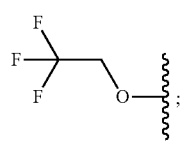

$R^{1d}$ and $R^{1e}$ are hydrogen atoms; $R^{2a}$ to $R^{2c}$ are hydrogen atoms; $R^{2d}$ is a hydrogen atom, hydroxy, or halogen; a group represented by:

[Chemical Formula 20]

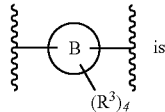

is

-continued

[Chemical Formula 21]

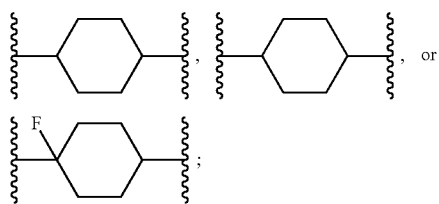, or

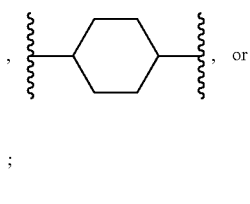;

$R^4$ is non-aromatic heterocyclyl unsubstituted or substituted with one or more group(s) selected from oxo, methyl, and ethyl; aromatic heterocyclyl unsubstituted or substituted with only one methyl; —$CH_2$—$R^6$ (wherein $R^6$ is 5-membered aromatic heterocyclyl substituted with only one methyl; 5-membered aromatic heterocyclyl substituted with only one alkyloxy; pyridyl substituted with only one methyl; or aromatic heterocyclyloxy unsubstituted or substituted with only one methyl); or —CH=CH—$R^8$ (wherein $R^6$ is unsubstituted aromatic carbocyclyl; or aromatic heterocyclyl substituted with only one methyl), (ii) a compound, wherein $R^{1e}$ is a hydrogen atom; $R^{2a}$ to $R^{2d}$ are hydrogen atoms; ring B is a cyclohexane ring; r is 0; and $R^4$ is a group represented by:

[Chemical Formula 22]

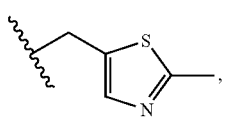

(iii) a compound represented by Formula:

[Chemical Formula 23]

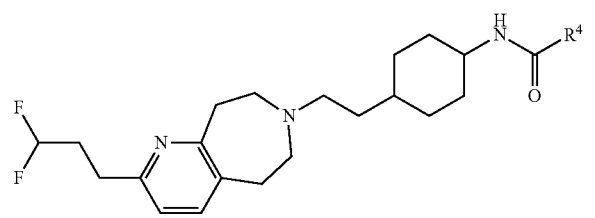

wherein $R^4$ is a group represented by:

[Chemical Formula 24]

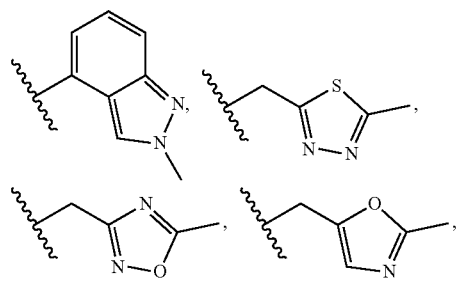

-continued

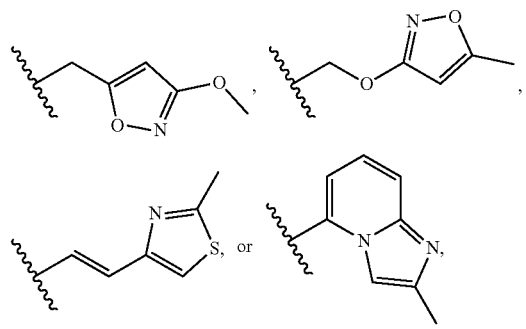

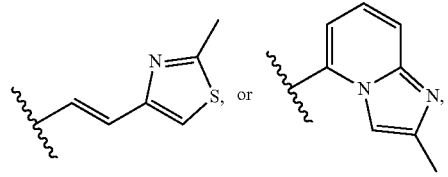

(iv) a compound represented by Formula:

[Chemical Formula 25]

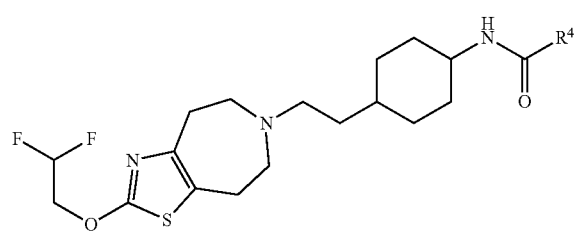

wherein $R^4$ is a group represented by:

[Chemical Formula 26]

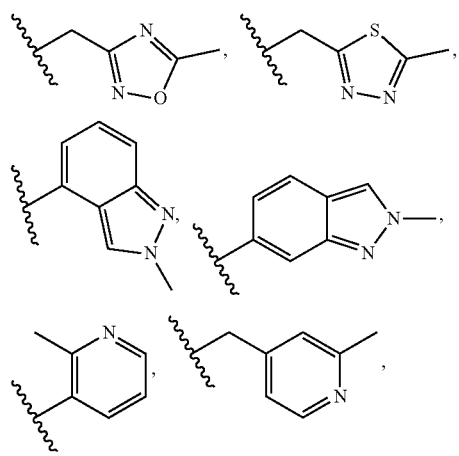

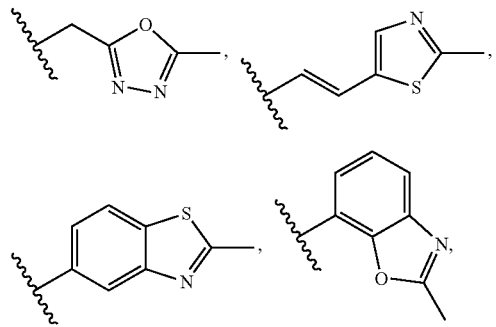

-continued
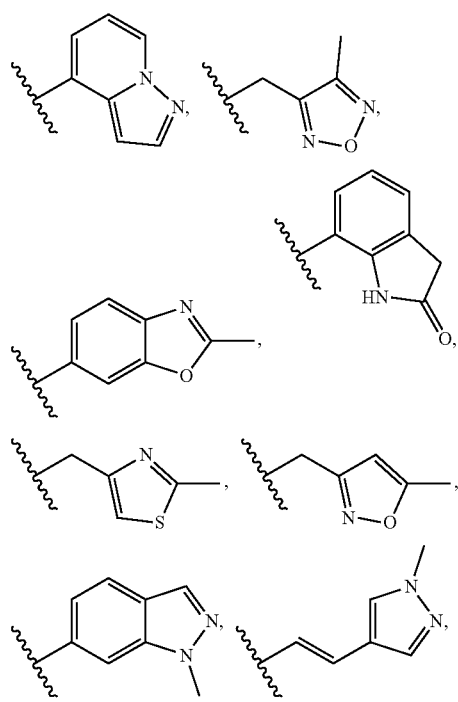
(v) a compound represented by Formula:
[Chemical Formula 27]
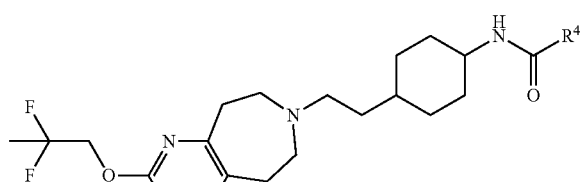
wherein R⁴ is a group represented by:
[Chemical Formula 28]
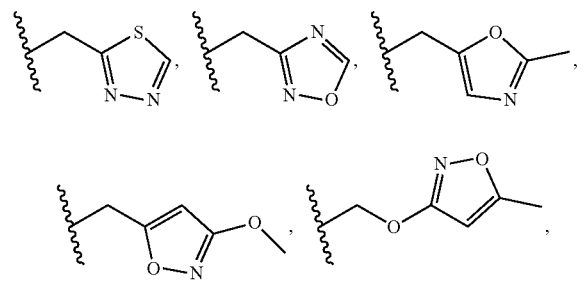
-continued
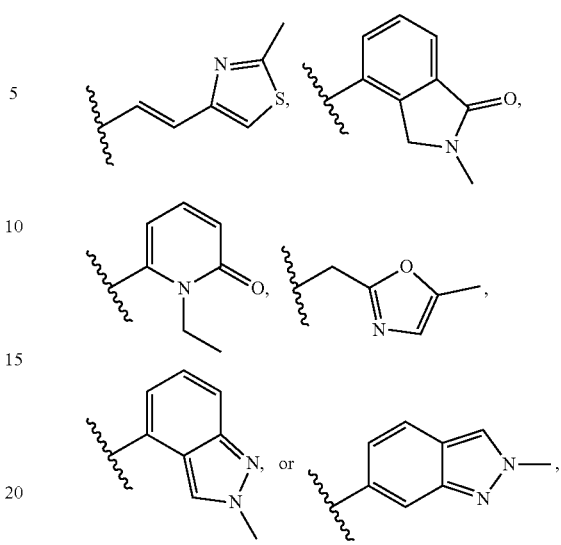
(vi) a compound represented by Formula:
[Chemical Formula 29]
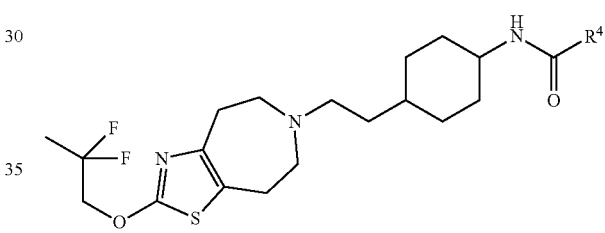
wherein R⁴ is a group represented by:
[Chemical Formula 30]
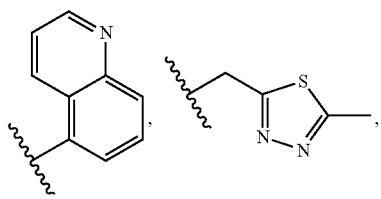

(vii) a compound represented by Formula:
[Chemical Formula 31]
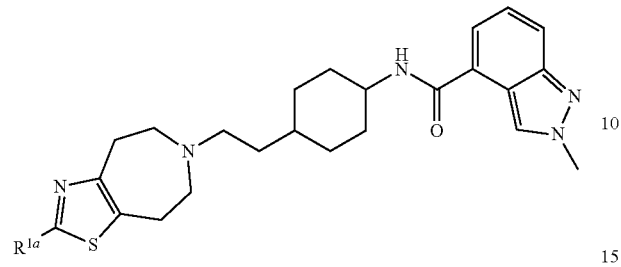
wherein $R^{1a}$ is a group represented by:
[Chemical Formula 32]
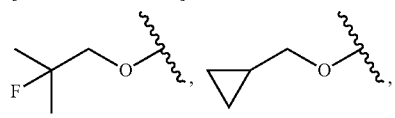
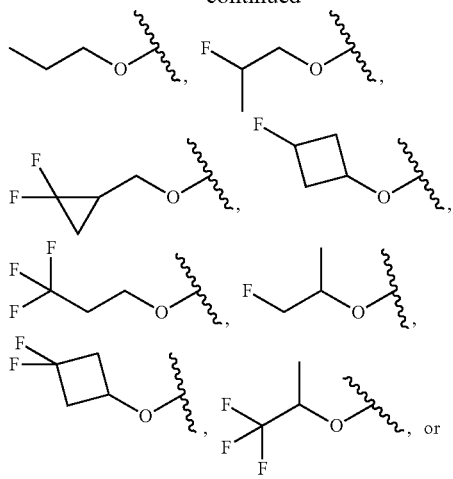
and
(viii) the following compounds:
[Chemical Formula 33]
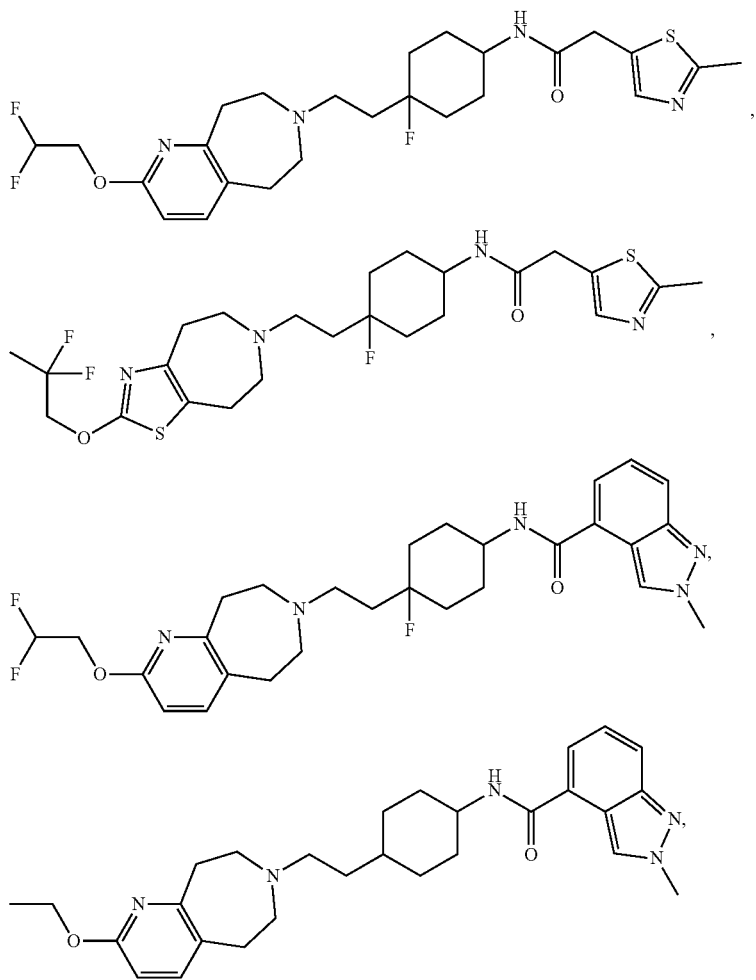

-continued
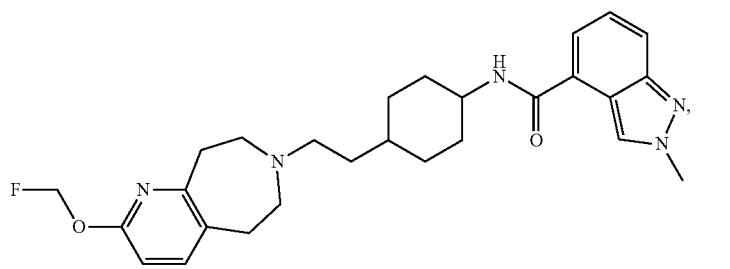
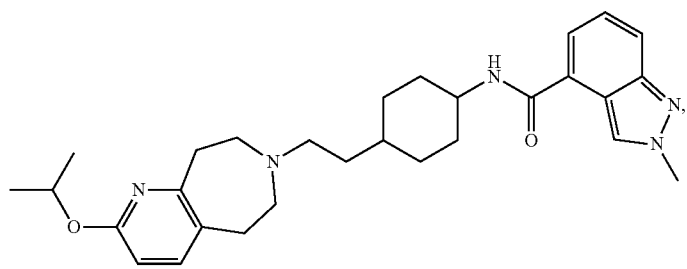
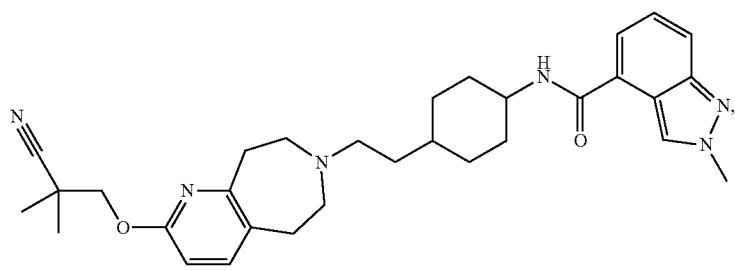
[Chemical Formula 34]

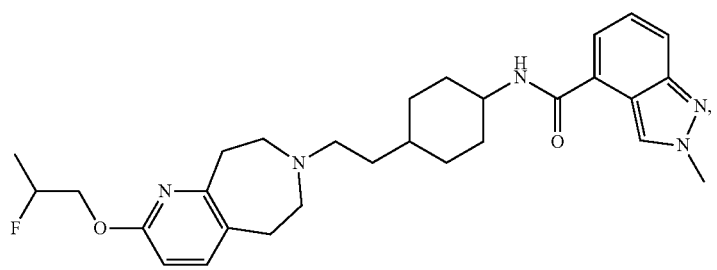
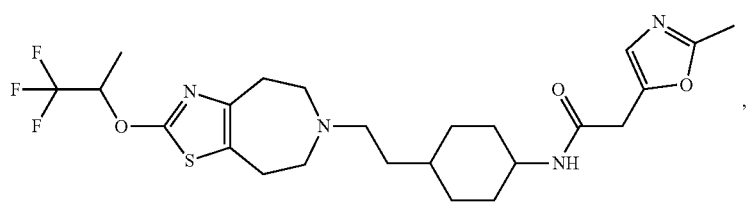

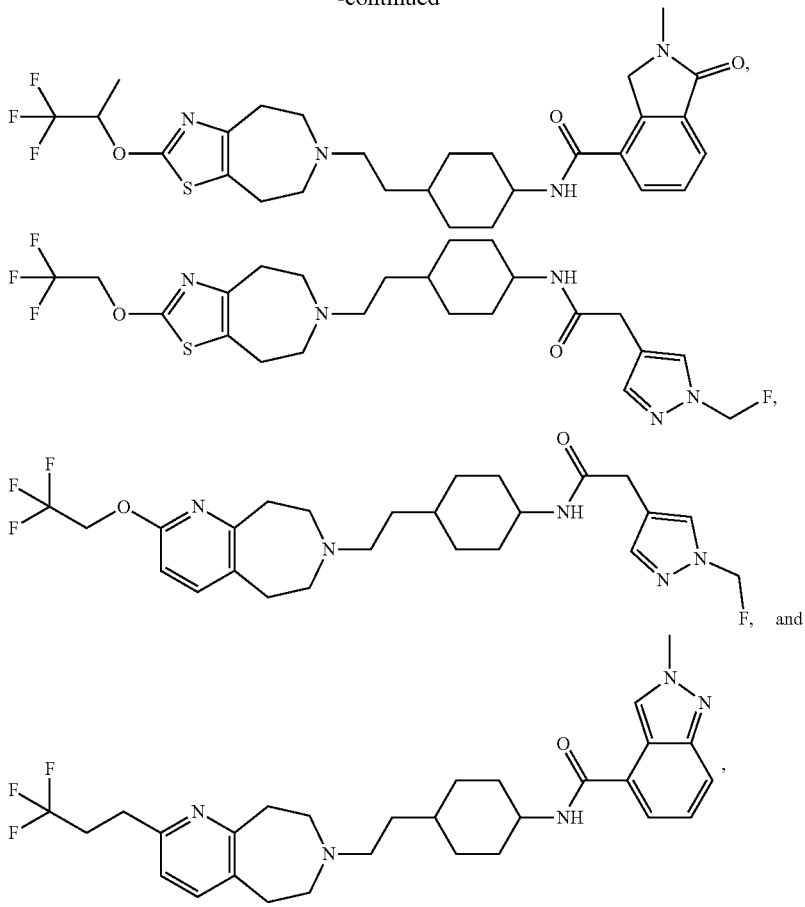

or a pharmaceutically acceptable salt thereof.

(1)' The compound according to above (1)", represented by Formula (IA) or (IB):

[Chemical Formula 35]

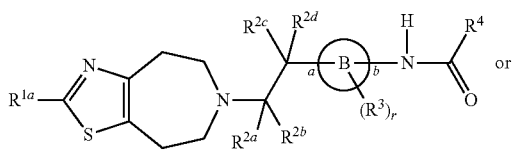
(IA)

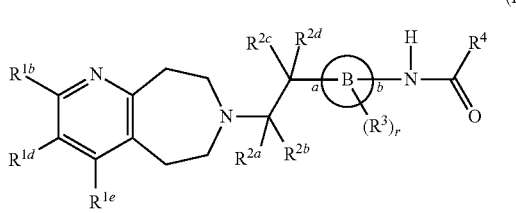
(IB)

wherein each symbol is the same as defined in above (1)", or a pharmaceutically acceptable salt thereof, preferably, in Formula (IA) or (IB), when $R^{1a}$ or $R^{1b}$ is a group represented by:

[Chemical Formula 36]

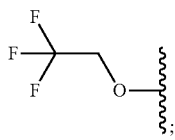

$R^{1d}$ and $R^{1e}$ are hydrogen atoms; $R^{2a}$ to $R^{2c}$ are hydrogen atoms; $R^{2d}$ is a hydrogen atom, hydroxy, or halogen; and a group represented by:

[Chemical Formula 37]

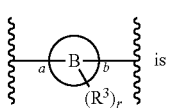 is

[Chemical Formula 38]

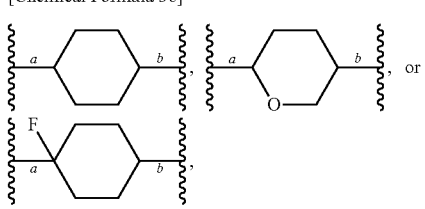

then $R^4$ is aromatic heterocyclyl substituted with haloalkyl (wherein the aromatic heterocyclyl may be further substituted with one or more group(s) selected from halogen and alkyl), non-aromatic heterocyclyl substituted with haloalkyl (wherein the non-aromatic heterocyclyl may be further substituted with one or more group(s) selected from oxo, halogen, and alkyl), or $-CR^{5a}R^{5b}-R^6$, and $R^6$ is substituted or unsubstituted triazolyl, or substituted or unsubstituted pyrazinyloxy.

(2) The compound according to any one of above (1), (1)', and (1)", wherein $R^{1a}$ is C2-C4 alkyloxy unsubstituted or substituted with one or more halogen; or cyclobutyloxy unsubstituted or substituted with one or more halogen;

$R^{1b}$ is C2-C4 alkyloxy unsubstituted or substituted with one or more halogen; C2-C4 alkyl unsubstituted or substituted with one or more halogen; cyclopentyloxy unsubstituted or substituted with one or more halogen; or cyclobutyloxy unsubstituted or substituted with one or more halogen, or a pharmaceutically acceptable salt thereof.

(3) The compound according to any one of above (1), (2), (1)', and (1)", wherein $R^{1a}$ and $R^{1b}$ are each independently a group represented by:

[Chemical Formula 39]

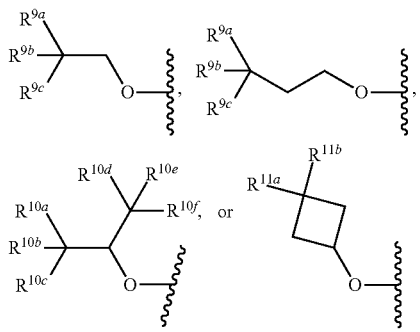

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen, or a pharmaceutically acceptable salt thereof.

(4) The compound according to any one of above (1) to (3), (1)', and (1)", wherein $R^{1a}$ and $R^{1b}$ are each independently a group represented by:

[Chemical Formula 40]

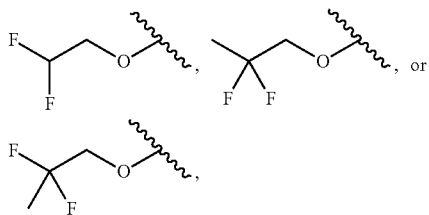

or a pharmaceutically acceptable salt thereof.

(5) The compound according to any one of above (1) to (4), (1)', and (1)", represented by Formula (IB):

[Chemical Formula 41]

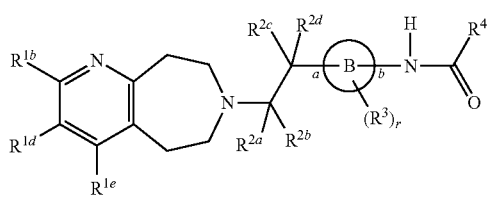

(IB)

wherein, $R^{1b}$ is unsubstituted alkyloxy or unsubstituted non-aromatic carbocyclyloxy, or a pharmaceutically acceptable salt thereof.

(5)" The compound according to any one of above (1) to (4), (1)', and (1)", represented by Formula (IA)

[Chemical Formula 42]

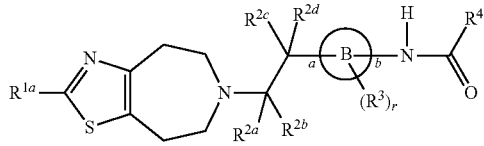

(IA)

wherein each symbol is the same as defined in above (1)", or a pharmaceutically acceptable salt thereof.

(6) The compound according to any one of the above (1) to (5), (1)', and (1)", wherein $R^{1d}$ and $R^{1e}$ are hydrogen atoms, or a pharmaceutically acceptable salt thereof.

(6)" The compound represented by Formula (IC)':

[Chemical Formula 43]

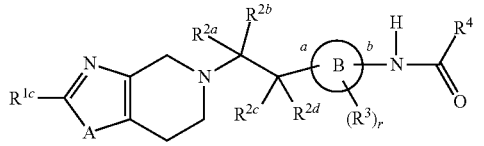

(IC)' wherein
A is S or O;
$R^{1c}$ is substituted or unsubstituted C2-C4 alkyloxy, substituted or unsubstituted cyclobutyl, or substituted or unsubstituted cyclobutyloxy;
$R^{2a}$ to $R^{2d}$ are each independently a hydrogen atom, halogen, hydroxy, substituted or unsubstituted C1-C6 alkyl, or substituted or unsubstituted C1-C6 alkyloxy;
$R^3$ is each independently halogen, hydroxy, cyano, substituted or unsubstituted C1-C6 alkyl, or substituted or unsubstituted C1-C6 alkyloxy;
two $R^3$s attached to different ring-constituting atoms may be taken together to form a substituted or unsubstituted (C1-C3) bridge wherein one of carbon atoms constituting the (C1-C3) bridge may be replaced with an oxygen atom or a nitrogen atom;
a bonding hand "a" is bonded to $-CR^{2c}R^{2d}-$;
a bonding hand "b" is bonded to $-NH-$;
Ring B is a 6- to 8-membered non-aromatic carbocycle or a 6- to 8-membered non-aromatic heterocycle;

r is an integer of 0 to 4;

R[4] is substituted or unsubstituted aromatic carbocyclyl, substituted or unsubstituted non-aromatic heterocyclyl, substituted or unsubstituted aromatic heterocyclyl, —CR[5a]R[5b]—R[6], or —CR[7a]=CR[7b]—R[8];

R[5a], R[5b], R[7a] and R[7b] are each independently a hydrogen atom, halogen, substituted or unsubstituted C1-C6 alkyl, or substituted or unsubstituted C1-C6 alkyloxy;

R[6] is substituted or unsubstituted non-aromatic heterocyclyl, substituted or unsubstituted aromatic heterocyclyl, substituted or unsubstituted aromatic heterocyclyloxy, or substituted or unsubstituted non-aromatic heterocyclyloxy;

R[8] is substituted or unsubstituted non-aromatic heterocyclyl or substituted or unsubstituted aromatic heterocyclyl;
provided that
(a) when A is S, R[c] is substituted or unsubstituted C2-C4 alkyloxy; and R[2a] to R[2d] are hydrogen atoms, then ring B is a cyclohexane ring, a piperidine ring or a spiroheptane ring;
(b) when A is S, R c is substituted or unsubstituted C2-C4 alkyloxy; R[2a] to R[2d] are hydrogen atoms; ring B is a cyclohexane ring; and r is 0,
then R[4] is indazolyl substituted with halogen and alkyl, or —CR[5a]R[5b]—R[6]; R[6] is substituted or unsubstituted triazolyl, or substituted or unsubstituted pyrazinyloxy;
and R[5a] and R[5b] are the same as defined above, provided that following compounds (i) to (iii) are excluded:
(i) a compound represented by Formula:

[Chemical Formula 44]

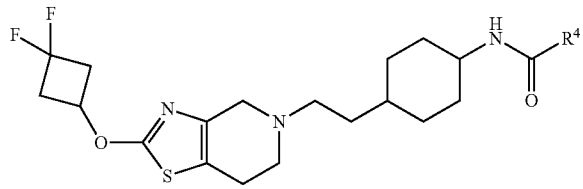

wherein R[4] is a group represented by:

[Chemical Formula 45]

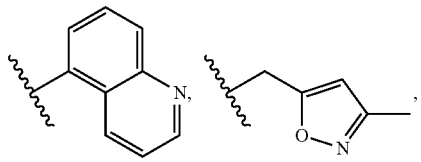

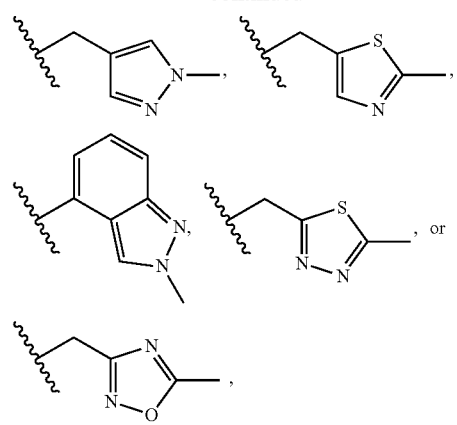

(ii) a compound represented by Formula

[Chemical Formula 46]

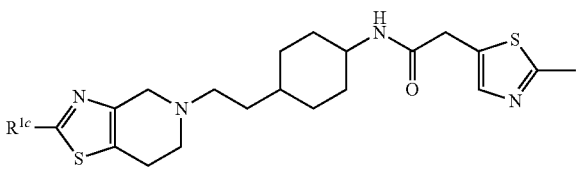

wherein R[1c] is a group represented by

[Chemical Formula 47]

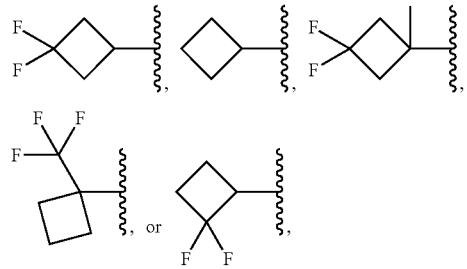

and
(iii) the following compounds:

[Chemical Formula 48]

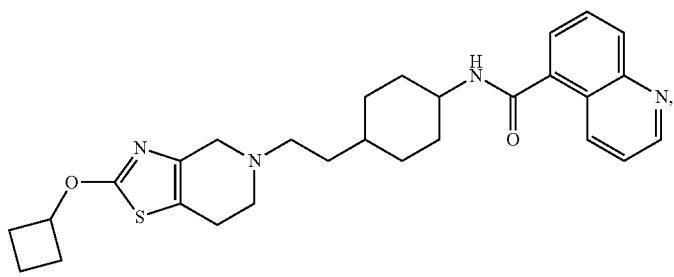

-continued
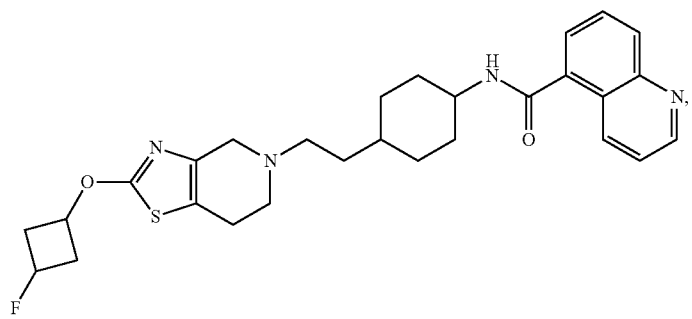
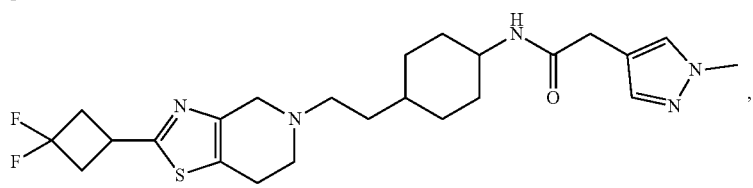
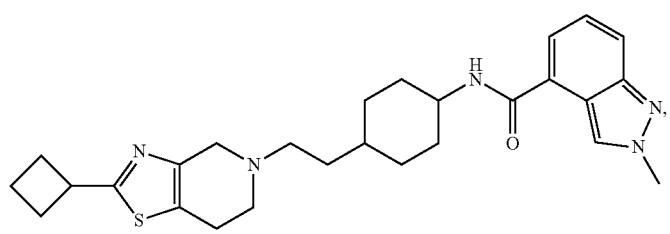
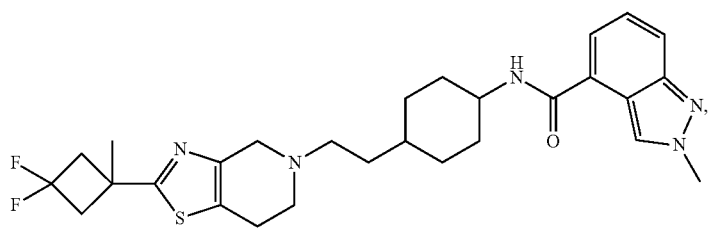
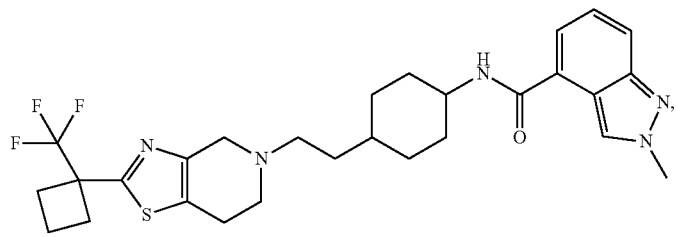
[Chemical Formula 49]
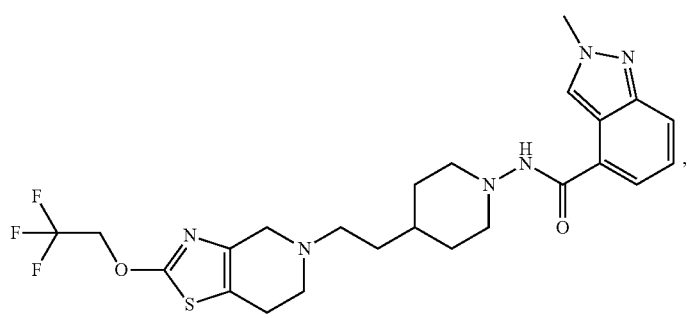

-continued
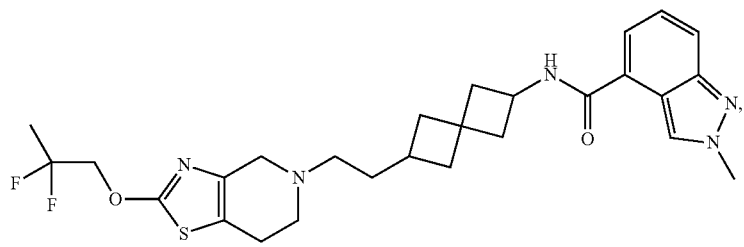
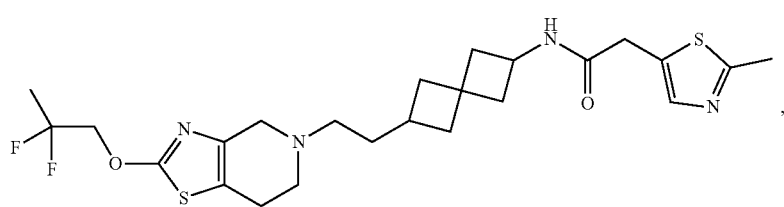
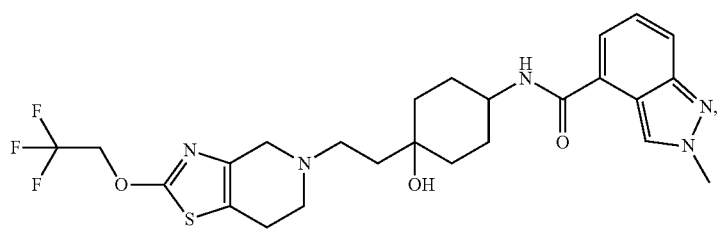
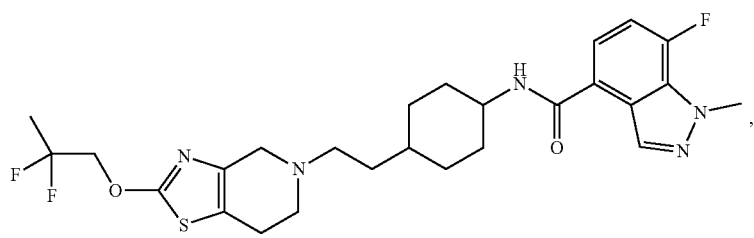
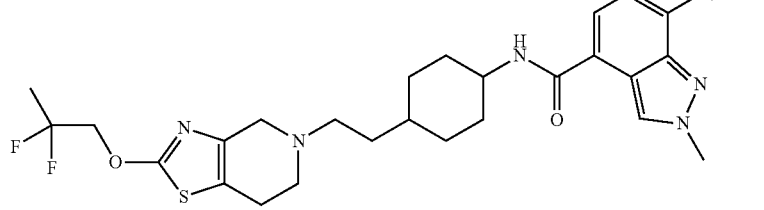

-continued

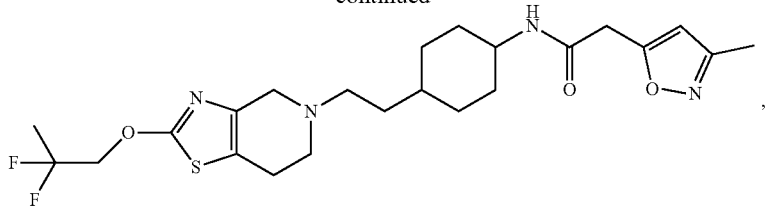

or a pharmaceutically acceptable salt thereof.
(7) The compound according to above (6)", represented by Formula (IC):

[Chemical Formula 50]

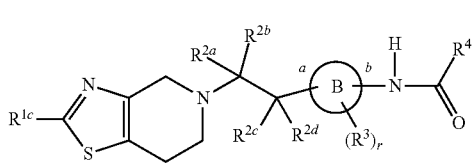

(IC)

wherein each symbol is the same as defined in above (6)", or a pharmaceutically acceptable salt thereof.
(8) The compound according to above (6)" or (7), wherein $R^{1c}$ is:

[Chemical Formula 51]

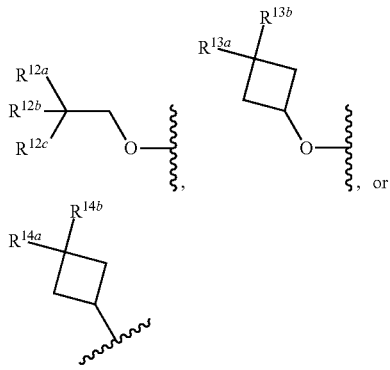

wherein $R^{12a}$ is halogen; $R^{12b}$ and $R^{12c}$ are each independently a hydrogen atom, halogen, or methyl; $R^{13a}$ and $R^{14a}$ are each independently halogen; and $R^{13b}$ and $R^{14b}$ are each independently a hydrogen atom or halogen,
or a pharmaceutically acceptable salt thereof.
(9)" A compound represented by Formula (ID-1)' or (IE-1):

[Chemical Formula 52]

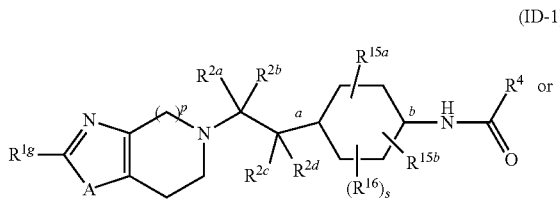

-continued (IE-1)

wherein
A is S or O;
$Y^1$ is $CR^{1d}$ or N; $Y^2$ is $CR^{1e}$ or N; $Y^3$ is N or $CR^{1f}$;
$R^{1d}$ to $R^{1f}$ are each independently a hydrogen atom, halogen, hydroxy, cyano, substituted or unsubstituted C1-C6 alkyl, or substituted or unsubstituted C1-C6 alkyloxy;
$R^{1g}$ to $R^{1h}$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino;
p is 1 or 2;
$R^{2a}$ to $R^{2d}$ are each independently a hydrogen atom, halogen, hydroxy, cyano, substituted or unsubstituted C1-C6 alkyl, or substituted or unsubstituted C1-C6 alkyloxy;
$R^{15a}$ and $R^{15b}$ are attached to different ring-constituting atoms, and $R^{15a}$ and $R^{15b}$ are taken together to form a substituted or unsubstituted (C1-C3) bridge wherein one of the carbon atoms constituting the (C1-C3) bridge may be replaced with an oxygen atom or a nitrogen atom;
$R^{16}$ is each independently halogen, hydroxy, cyano, substituted or unsubstituted C1-C6 alkyl, or substituted or unsubstituted C1-C6 alkyloxy;
a bonding hand "a" is bonded to —$CR^{2c}R^{2d}$—;
a bonding hand "b" is bonded to —NH—;
s is an integer of 0 to 4;
$R^4$ is substituted or unsubstituted aromatic carbocyclyl, substituted or unsubstituted non-aromatic heterocyclyl, substituted or unsubstituted aromatic heterocyclyl, substituted or unsubstituted non-aromatic carbocyclyl, —$(CR^{5a}R^{5b})_m$—$R^6$, or —$CR^{7a}$=$CR^7$—$R^8$;

m is an integer of 1 to 3;

$R^{5a}$ is each independently a hydrogen atom, halogen, substituted or unsubstituted C1-C6 alkyl, or substituted or unsubstituted C1-C6 alkyloxy;

$R^{5b}$ is each independently a hydrogen atom, halogen, substituted or unsubstituted C1-C6 alkyl, or substituted or unsubstituted C1-C6 alkyloxy;

$R^{7a}$ and $R^{7b}$ are each independently a hydrogen atom, halogen, substituted or unsubstituted C1-C6 alkyl, or substituted or unsubstituted C1-C6 alkyloxy;

$R^6$ is substituted or unsubstituted non-aromatic heterocyclyl, substituted or unsubstituted aromatic heterocyclyl, substituted or unsubstituted non-aromatic carbocyclyl, substituted or unsubstituted aromatic carbocyclyl, substituted or unsubstituted aromatic heterocyclyloxy, substituted or unsubstituted non-aromatic heterocyclyloxy, substituted or unsubstituted aromatic carbocyclyloxy, or substituted or unsubstituted non-aromatic carbocyclyloxy;

$R^8$ is substituted or unsubstituted non-aromatic heterocyclyl, substituted or unsubstituted aromatic heterocyclyl, substituted or unsubstituted non-aromatic carbocyclyl, or substituted or unsubstituted aromatic carbocyclyl, or a pharmaceutically acceptable salt thereof.

(9)' The compound according to (9)", represented by Formula (ID-1) or (IE-1):

[Chemical Formula 53]

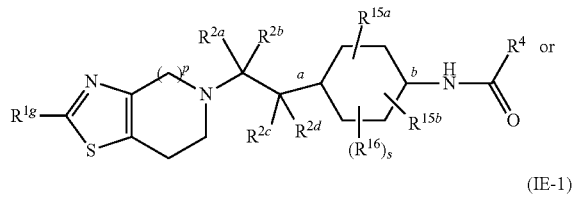

(ID-1)

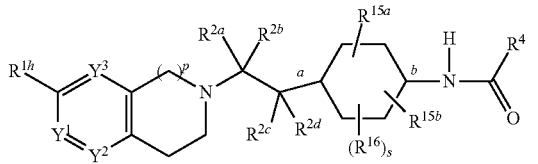

(IE-1)

wherein each symbol is the same as defined in above (9)", or a pharmaceutically acceptable salt thereof.

(10)' The compound according to anyone of above (1) to (8), (1)', (9)', (1)", (5)", (6)" and (9)", wherein a group represented by:

[Chemical Formula 54]

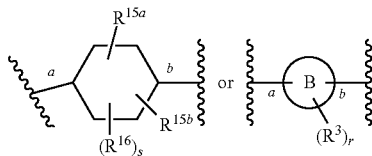

is a group represented by:

[Chemical Formula 55]

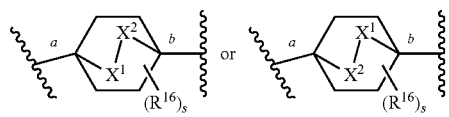

wherein
$X^1$ is $CR^{17a}R^{17b}$, O, or $NR^{18}$;
$X^2$ is $CR^{19a}R^{19b}$;
$R^{17a}$, $R^{17b}$, $R^{19a}$, and $R^{19b}$ are each independently a hydrogen atom, halogen, or C1-C6 alkyl;
$R^{18}$ is a hydrogen atom or C1-C6 alkyl; and
the other symbols are the same as defined in above (9)", or a pharmaceutically acceptable salt thereof.

(11)' The compound according to any one of above (1) to (8), (1)', (9)', (10)', (1)", (5)", (6), and (9)", represented by Formula (ID-2) or (IE-2):

[Chemical Formula 56]

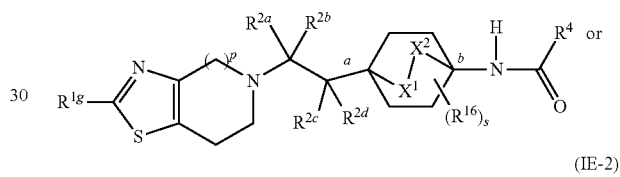

(ID-2)

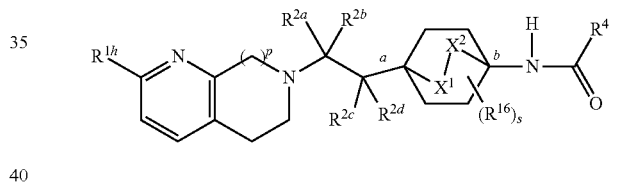

(IE-2)

wherein
$R^{1g}$ and $R^{1h}$ are C1-C6 alkyloxy unsubstituted or substituted with one or more halogen; p is 2; $R^{2a}$ to $R^{2d}$ are hydrogen atoms;
$X^1$ is $CH_2$ or O; $X^2$ is $CH_2$;
$R^{16}$ is each independently halogen; s is an integer of 0 to 2; and the other symbols are the same as defined in above (9)',
or a pharmaceutically acceptable salt thereof.

(12)' The compound according to any one of above (1) to (8), (1)', (9)' to (1)', (1)", (5)", (6)", and (9)", represented by Formula (IA):

[Chemical Formula 57]

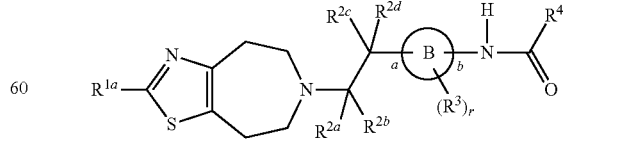

(IA)

wherein $R^{1a}$ is C2-C4 alkyloxy unsubstituted or substituted with one or more halogen, or cyclobutyloxy unsubstituted or substituted with one or more halogen; $R^{2a}$ to $R^{2c}$ are hydrogen atoms; $R^{2d}$ is a hydrogen atom or substituted or unsubstituted C1-C6 alkyloxy; ring B is a 6- to 8-membered non-aromatic carbocycle or a 6- to 8-membered non-aromatic heterocycle;

R³ is each independently halogen or two R³s attached to different ring-constituting atoms may be taken together to form a substituted or unsubstituted C2 bridge; r is an integer of 0 to 4, preferably an integer of 1 to 4; and R⁴ is the same as defined in above (1), or a pharmaceutically acceptable salt thereof.

(13)' The compound according to any one of above (1) to (8), (1)', (9)' to (12)', (1)", (5)", (6)", and (9)", wherein R⁴ is phenyl optionally substituted with the substituent group β1, 6-membered or bicyclic non-aromatic heterocyclyl optionally substituted with the substituent group β2, 6-membered or bicyclic aromatic heterocyclyl optionally substituted with the substituent group β1, —CH₂—R⁶, or —CH=CH—R⁸;

R⁶ is 5- or 6-membered non-aromatic heterocyclyl optionally substituted with the substituent group β2, 5- or 6-membered aromatic heterocyclyl optionally substituted with the substituent group β1, 5- or 6-membered aromatic heterocyclyloxy optionally substituted with the substituent group β1, or 5- or 6-membered non-aromatic heterocyclyloxy optionally substituted with the substituent group β2;

R⁸ is 5- or 6-membered non-aromatic heterocyclyl optionally substituted with the substituent group 82, or 5- or 6-membered aromatic heterocyclyl optionally substituted with the substituent group 61, or a pharmaceutically acceptable salt thereof.

(14)' The compound according to any one of above (1) to (8), (1)', (9)' to (13)', (1)", (5)", (6)", and (9)", wherein R⁴ is a group represented by:

[Chemical Formula 58]

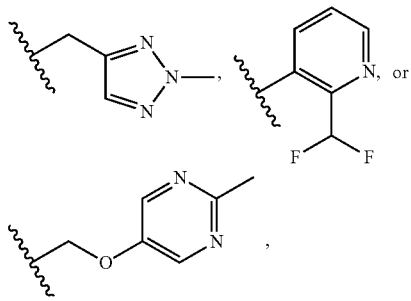

or a pharmaceutically acceptable salt thereof.

(14)" The compound according to any one of above (1) to (8), (1)', (9)' to (13)', (1)", (5)", (6)", and (9)", wherein R⁴ is a group represented by:

[Chemical Formula 59]

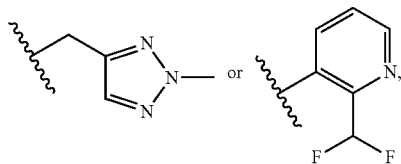

or a pharmaceutically acceptable salt thereof.

(15)' The compound according to any one of above (1) to (8), (1)', (9)' to (14)', (1)", (5)", (6)", (9)", and (14)", provided that the compounds described as examples in WO 2018/021447 are excluded, or a pharmaceutically acceptable salt thereof.

(9) The compound according to any one of above (1) to (8), (1)', (9)' to (15)', (1)", (5)", (6)", (9)", and (14)", wherein R⁴ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, —CR⁵ᵃR⁵ᵇ—R⁶, or —CR⁷ᵃ=CR⁷ᵇ—R⁸;

R⁶ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy;

R⁸ is substituted or unsubstituted pyrimidinyl, or substituted or unsubstituted pyrazolyl, or a pharmaceutically acceptable salt thereof.

(10) The compound according to any one of above (1) to (9), (1)', (9)' to (15)', (1)", (5)", (6)", (9)", and (14)", wherein R⁴ is aromatic heterocyclyl substituted with haloalkyl (wherein the non-aromatic heterocyclyl may be further substituted with one or more group(s) selected from halogen and alkyl), non-aromatic heterocyclyl substituted with haloalkyl (wherein the non-aromatic heterocyclyl may be further substituted with one or more group(s) selected from oxo, halogen, and alkyl), or —CR⁵ᵃR⁵ᵇ—R⁶; and R⁶ is substituted or unsubstituted triazolyl, or substituted or unsubstituted pyrazinyloxy, or a pharmaceutically acceptable salt thereof.

(11) The compound according to any one of above (1) to (10), (1)', (9)' to (15)', (1)", (5)", (6)", (9)", and (14)", wherein Ring B is a piperidine ring or a spiroheptane ring, or a pharmaceutically acceptable salt thereof.

(12) The compound according to any one of above (1) to (11), (1)', (9)' to (1)', (1)", (5)", (6)", (9)", and (14)", wherein r is an integer of 1 to 4, or a pharmaceutically acceptable salt thereof.

(13) The compound according to any one of above (1) to (12), (1)', (9)' to (15)', (1)", (5)", (6)", (9)", and (14)", wherein R³ is each independently halogen, or two R³s attached to different ring-constituting atoms may be taken together to form a substituted or unsubstituted C2 bridge, or a pharmaceutically acceptable salt thereof.

(14) The compound according to any one of above (1) to (13), (1)', (9)' to (1)', (1)", (5)", (6)", (9)", and (14)", wherein R²ᵃ to R²ᶜ are hydrogen atoms, and R²ᵈ is a hydrogen atom or substituted or unsubstituted C1-C6 alkyloxy, or a pharmaceutically acceptable salt thereof.

(15) The compound according to any one of above (1) to (14), (1)', (9)' to (15)', (1)", (5)", (6)", (9)", and (14)", wherein R² d is substituted or unsubstituted C1-C6 alkyloxy, or a pharmaceutically acceptable salt thereof.

(15)" The compound according to any one of above (1) to (14), (1)', (9)' to (15)', (1)", (5)", (6)", (9)", and (14)", wherein A is S, or a pharmaceutically acceptable salt thereof.

(16)' The compound according to any one of above (1) to (15), (1)', (9)' to (15)', (1)", (5)", (6)", (9)", (14)", and (15)", wherein the compound is selected from the group consisting of Examples I-010, I-015, I-019, I-023, I-024, I-026, I-027, I-031, I-043, I-044, I-048, I'-36, I'-37, I'-38, I'-40, I'-41, I'-42, I'-43, I'-44, II-6, II-7, II-8, II-9, II-11, and II-12, or a pharmaceutically acceptable salt thereof.

(16)" The compound according to any one of above (1) to (15), (1)', (9)' to (1)', (1)", (5)", (6)", (9)", (14)", and (15)", wherein the compound is selected from the group consisting of Examples I-010, I-015, I-019, I-023, I-024, I-026, I-027, I-031, I-043, I-044, I-048, I'-36, I'-37, I'-38, I'-40, I'-41, I'-42, I'-43, and I'-44, or a pharmaceutically acceptable salt thereof.

(17)' The compound according to any one of above (1) to (15), (1)', (9)' to (15)', (1)", (5)", (6)", (9)", (14)", (15)" and (16)", wherein the compound is selected from the group consisting of Examples I-010, I-015, I-019, I-023, I-024, I-026, I-027, I-031, I-043, I-044, and I-048, or a pharmaceutically acceptable salt thereof.

(18)' The compound according to any one of above (1) to (15), (1)', (9)' to (15)', (1)", (5)", (6)", (9)", (14)", (15)" and (16)", wherein the compound is selected from the group consisting of Examples I'-36, I'37, I'-38, I'-40, I'-41, I'-42, I'-43, and I'-44, or a pharmaceutically acceptable salt thereof.

(19)' The compound according to any one of above (1) to (15), (1)', (9)' to (1)', (1)", (5)", (6)", (9)", (14)", (15)" and (16)", wherein the compound is selected from the group consisting of Examples II-6, II-7, II-8, II-9, II-11, and II-12, or a pharmaceutically acceptable salt thereof.

(16) A pharmaceutical composition comprising the compound according to any one of
above (1) to (15), (1)', (9)' to (19)', (1)", (5)", (6)", (9)", (14)", (15)" and (16)", or a pharmaceutically acceptable salt thereof.

(17) The pharmaceutical composition according to above (16), wherein the composition is a dopamine D3 receptor antagonist.

(18) A dopamine D3 receptor antagonist comprising the compound according to any one of above (1) to (15), (1)', (9)' to (19)', (1)", (5)", (6)", (9)", (14)", (15)" and (16)", or a pharmaceutically acceptable salt thereof.

(19) The pharmaceutical composition according to any one of above (1) to (15), (1)', (9)' to (19)', (1)", (5)", (6)", (9)", (14)", (15)" and (16)", having effect for treating and/or preventing diseases associated with dopamine D3 receptor.

(20) The pharmaceutical composition according to any one of above (16), (17), and (19), having effect for treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(21) The pharmaceutical composition according to any one of above (16), (17) and (19), having effect for treating and/or preventing attention-deficit/hyperactivity disorder.

(22) A method for treating and/or preventing a disease associated with D3 receptor, comprising administering the compound according to any one of above (1) to (15), (1)', (9)' to (19)', (1)", (5)", (6)", (9)", (14)", (15)" and (16)", or a pharmaceutically acceptable salt thereof.

(23) A method for treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder, comprising administering the compound according to any one of above (1) to (15), (1)', (9)' to (19)', (1)", (5)", (6)", (9)", (14)", (15)" and (16)", or a pharmaceutically acceptable salt thereof.

(24) A method for treating and/or preventing attention-deficit/hyperactivity disorder, comprising administering the compound according to any one of above (1) to (15), (1)', (9)' to (19)', (1)", (5)", (6)", (9)", (14)", (15)" and (16)", or a pharmaceutically acceptable salt thereof.

(25) Use of the compound according to any one of above (1) to (15), (1)', (9)' to (19)', (1)", (5)", (6)", (9)", (14)", (15)" and (16)", or a pharmaceutically acceptable salt thereof, for manufacturing an agent for treating and/or preventing diseases associated with D3 receptor.

(26) Use of the compound according to any one of above (1) to (15), (1)', (9)' to (19)', (1)", (5)", (6)", (9)", (14)", (15)" and (16)", or a pharmaceutically acceptable salt thereof, for manufacturing an agent for treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(27) Use of the compound according to any one of above (1) to (15), (1)', (9)' to (19)', (1)", (5)", (6)", (9)", (14)", (15)" and (16)", or a pharmaceutically acceptable salt thereof, for manufacturing an agent for treating and/or preventing attention-deficit/hyperactivity disorder.

(28) The compound according to any one of above (1) to (15), (1)', (9)' to (19)', (1)", (5)", (6)", (9)", (14)", (15)" and (16)", or a pharmaceutically acceptable salt thereof, for use in treating and/or preventing diseases associated with D3 receptor.

(29) The compound according to any one of above (1) to (15), (1)', (9)' to (19)', (1)", (5)", (6)", (9)", (14)", (15)" and (16)", or a pharmaceutically acceptable salt thereof, for use in treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(30) The compound according to any one of above (1) to (15), (1)', (9)' to (19)', (1)", (5)", (6)", (9)", (14)", (15)" and (16)", or a pharmaceutically acceptable salt thereof, for use in treating and/or preventing attention-deficit/hyperactivity disorder.

(101) A pharmaceutical composition comprising the compound according to any one of above (1) to (15), (1)', (9)' to (19)', (1)", (5)", (6)", (9)", (14)", (15)" and (16)", or a pharmaceutically acceptable salt thereof, for oral administration.

(102) The pharmaceutical composition according to (101), which is a tablet, a powder, a granule, a capsule, a pill, a film, a suspension, an emulsion, an elixir, a syrup, a lemonade, a spirit, an aromatic water, an extract, a decoction or a tincture.

(103) The pharmaceutical composition according to (102), which is a sugar-coated tablet, a film-coated tablet, an enteric-coated tablet, a sustained-release tablet, a troche tablet, a sublingual tablet, a buccal tablet, a chewable tablet, an orally disintegrated tablet, a dry syrup, a soft capsule, a micro capsule or a sustained-release capsule.

(104) A pharmaceutical composition comprising the compound according to any one of above (1) to (15), (1)', (9)' to (19)', (1)", (5)", (6)", (9)", (14)", (15)" and (16)", or a pharmaceutically acceptable salt thereof, for parenteral administration.

(105) The pharmaceutical composition according to (104), for dermal, subcutaneous, intravenous, intraarterial, intramuscular, intraperitoneal, transmucosal, inhalation, transnasal, ophthalmic, inner ear or vaginal administration.

(106) The pharmaceutical composition according to (104) or (105), which is an injection, an infusion, an eye drop, a nose drop, an ear drop, an aerosol, an inhalation, a lotion, an impregnation, a liniment, a mouthwash, an enema, an ointment, a plaster, a jelly, a cream, a patch, a cataplasm, an external powder or a suppository.

(107) A pharmaceutical composition comprising the compound according to any one of above (1) to (15), (1)', (9)' to (19)', (1)", (5)", (6)", (9)", (14)", (15)" and (16)", or a pharmaceutically acceptable salt thereof, for a pediatric or geriatric patient.

Effect of the Invention

The compounds of the present invention have an antagonistic activity for D3 receptor, and preferably have high D3/D2 selectivity, and are useful as an agent for treating or preventing diseases associated with D3 receptor.

BRIEF DESCRIPTION OF DRAWINGS

FIG. 1 shows the measurement results of rat dopamine D3 receptor occupancy of Compound I-015 at dosages of 0.3, 1 and 3 mg/kg. The abscissa shows the dose, and the ordinate shows the occupancy (%).

MODE FOR CARRYING OUT THE INVENTION

The meaning of each term used in the present description is explained below. Each term, unless otherwise indicated, is used in the same sense when used alone, or when used in combination with other terms.

The term "consisting of" means having only components.

The term "comprising" means not restricting with components and not excluding undescribed factors.

"Halogen" includes a fluorine atom, a chlorine atom, a bromine atom and an iodine atom. A fluorine atom and a chlorine atom are preferable. A fluorine atom is more preferable.

"Alkyl" includes a C1 to C15, preferably C1 to C10, more preferably C1 to C6, further preferably C1 to C4 linear or branched hydrocarbon group. Examples thereof include methyl, ethyl, n-propyl, isopropyl, n-butyl, isobutyl, see-butyl, tert-butyl, n-pentyl, isopentyl, neopentyl, n-hexyl, isohexyl, n-heptyl, isoheptyl, n-octyl, isooctyl, n-nonyl, and n-decyl and the like.

Examples of preferred embodiments of "alkyl" and "C1 to C6 alkyl" include methyl, ethyl, n-propyl, isopropyl, n-butyl, isobutyl, sec-butyl, tert-butyl, and n-pentyl. Examples of more preferred embodiments include methyl, ethyl, n-propyl, isopropyl, and tert-butyl.

Examples of "C2 to C4 alkyl" include ethyl, n-propyl, isopropyl, n-butyl, isobutyl, sec-butyl, and tert-butyl, more preferably ethyl, n-propyl, and isopropyl.

"Alkenyl" includes a C2 to C15, preferably C2 to C10, more preferably C2 to C6, further preferably C2 to C4 linear or branched hydrocarbon group having one or more double bond(s) at any position(s). Examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl and the like.

Examples of preferred embodiments of "alkenyl" include vinyl, allyl, propenyl, isopropenyl, and butenyl.

"Alkynyl" includes a C2 to C10, preferably C2 to C8, more preferably C2 to C6, further preferably C2 to C4 linear or branched hydrocarbon group having one or more triple bond(s) at any position(s). Furthermore, it may have double bond(s) at any position(s). Examples thereof include ethynyl, propynyl, butynyl, pentynyl, hexynyl, heptynyl, octynyl, nonynyl, and decynyl and the like.

Examples of preferred embodiments of "alkynyl" include ethynyl, propynyl, butynyl, and pentynyl.

"Aromatic carbocycle" means a cyclic aromatic hydrocarbon ring which is monocyclic or polycyclic having two or more rings. Examples thereof include benzene, naphthalene, anthracene, and phenanthrene and the like.

Examples of preferred embodiments of "aromatic carbocycle" include benzene.

"Aromatic carbocyclyl" means a cyclic aromatic hydrocarbon group which is monocyclic or polycyclic having two or more rings. Examples thereof include phenyl, naphthyl, anthryl, and phenanthryl and the like.

Examples of preferred embodiments of "aromatic carbocyclyl" include phenyl.

"Non-aromatic carbocycle" means a cyclic saturated hydrocarbon ring or a cyclic unsaturated non-aromatic hydrocarbon ring, which is monocyclic or polycyclic having two or more rings. The non-aromatic carbocycle which is polycyclic having two or more rings includes a fused ring wherein a non-aromatic carbocycle, which is monocyclic or polycyclic having two or more rings, is fused with a ring of the above "aromatic carbocycle".

In addition, the "non-aromatic carbocycle" also includes a ring having a bridge or a ring forming a spiro ring as follows.

[Chemical Formula 60]

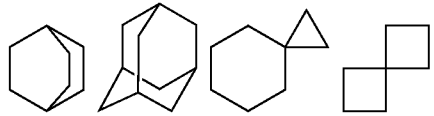

The non-aromatic carbocycle which is monocyclic is preferably C3 to C16, more preferably C3 to C12, and further preferably C3 to C6 carbocycle. Examples thereof include "6-membered non-aromatic carbocycle" such as cyclohexane, cyclohexene, and cyclohexadiene and the like, cyclopropane, cyclobutane, cyclopentane, cycloheptane, cyclooctane, cyclononane, cyclodecane, cyclopropene, cyclobutene, cyclopentene, and cycloheptene and the like.

Examples of the non-aromatic carbocycle which is polycyclic having two or more rings include spiroheptane, bicyclooctane, indane, indene, acenaphthalene, tetrahydronaphthalene, and fluorene and the like.

Another embodiment of the non-aromatic carbocycle is a 6- to 8-membered non-aromatic carbocycle. Examples of the 6- to 8-membered non-aromatic carbocycle include cyclohexane, spiroheptane, and bicyclooctane and the like, for example, cyclohexane.

Examples of preferred embodiments of the "spiroheptane ring" include the ring shown below.

[Chemical Formula 61]

Examples of the "bicyclooctane ring" include a ring shown below.

[Chemical Formula 62]

"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl" which is polycyclic having two or more rings includes a fused ring group wherein a non-aromatic carbocyclyl which is monocyclic or polycyclic having two or more rings is fused with a ring of the above "aromatic carbocyclyl".

In addition, the "non-aromatic carbocyclyl" includes a group having a bridge or a group to form a spiro ring as follows:

[Chemical Formula 63]

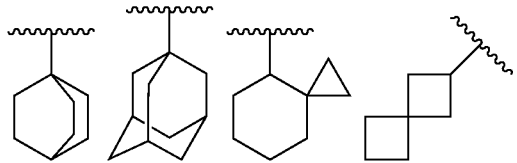

The non-aromatic carbocyclyl which is monocyclic is preferably C3 to C16, more preferably C3 to C12, and further preferably C3 to C6 carbocyclyl. Examples thereof include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl and the like.

Examples of the non-aromatic carbocyclyl which is polycyclic having two or more rings include indanyl, indenyl, acenaphthyl, tetrahydronaphthyl, and fluorenyl.

"Aromatic heterocycle" means an aromatic ring, which is monocyclic or polycyclic having two or more rings, containing one or more identical or different heteroatoms selected independently from O, S and N in the ring.

Aromatic heterocycle which is polycyclic having two or more rings includes a fused ring wherein an aromatic heterocycle which is monocyclic or polycyclic having two or more rings is fused with a ring of the above "aromatic carbocycle".

The aromatic heterocycle which is monocyclic is preferably a 5- to 8-membered, and more preferably 5- or 6-membered ring. Examples thereof include "5-membered aromatic heterocycle" such as pyrrole, imidazole, pyrazole, triazole, tetrazole, furan, thiophene, isoxazole, oxazole, oxadiazole, isothiazole, thiazole, and thiadiazole and the like, and "6-membered aromatic heterocycle" such as pyridine, pyridazine, pyrimidine, pyrazine, and triazine, and the like.

Examples of the aromatic heterocycle which is bicyclic include indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, pyrazolopyridin, imidazopyridine, triazolopyridine, imidazothiazole, pyrazinopyridazine, oxazolopyridine, and thiazolopyridine, and the like.

Examples of the aromatic heterocycle which is polycyclic having three or more rings include carbazole, acridine, xanthene, phenothiazine, phenoxathiine, phenoxazine, and dibenzofuran and the like.

"Aromatic heterocyclyl" means an aromatic cyclyl, which is monocyclic or polycyclic having two or more rings, containing one or more identical or different heteroatoms selected independently from O, S and N in the ring. "Aromatic heterocyclyl" which is polycyclic having two or more rings includes a fused ring group wherein an aromatic heterocyclyl which is monocyclic or polycyclic having two or more rings is fused with a ring of the above "aromatic carbocyclyl".

The aromatic heterocyclyl which is monocyclic is preferably a 5- to 8-membered, and more preferably 5- or 6-membered ring. Examples thereof include "5-membered aromatic heterocyclyl" such as pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl and the like, and "6-membered aromatic heterocyclyl" such as pyridyl, pyridazinyl, pyrimidinyl, pyrazinyl, and triazinyl and the like.

Examples of the aromatic heterocyclyl which is bicyclic include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, pyrazolopyridyl, imidazopyridyl, triazolopyridyl, imidazothiazolyl, pyrazinopyridazinyl, oxazolopyridyl, and thiazolopyridyl and the like.

Examples of the aromatic heterocyclyl which is polycyclic having three or more rings include carbazolyl, acridinyl, xanthenyl, phenothiazinyl, phenoxathiinyl, phenoxazinyl, and dibenzofuryl and the like.

"Non-aromatic heterocycle" means a cyclic non-aromatic ring, which is monocyclic or polycyclic having two or more rings, containing one or more identical or different heteroatoms selected independently from O, S and N in the ring.

The non-aromatic heterocycle which is polycyclic having two or more rings includes a fused ring wherein a non-aromatic heterocycle which is monocyclic or polycyclic having two or more rings is fused with a ring of the above "aromatic carbocycle", "non-aromatic carbocycle" and/or "aromatic heterocycle". The non-aromatic heterocycle which is polycyclic having two or more rings further includes a fused ring wherein an aromatic heterocycle which is monocyclic or polycyclic having two or more rings is fused with a ring of the above "non-aromatic carbocycle".

In addition, the "non-aromatic heterocycle" also includes a ring having a bridge or a ring to form a spiro ring as follows.

[Chemical Formula 64]

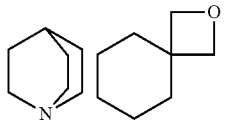

The non-aromatic heterocycle which is monocyclic is preferably a 3- to 8-membered, more preferably 3- to 6-membered, and more preferably 5- or 6-membered ring. Examples thereof include "5-membered non-aromatic heterocycle" such as thiazolidine, pyrrolidine, pyrroline, imidazolidine, imidazoline, pyrazolidine, pyrazoline, tetrahydrofuran, dihydrothiazole, tetrahydrothiazole, tetrahydroisothiazole, dioxolane, and dioxoline and the like, "6-membered non-aromatic heterocycle" such as dioxane, thiane, piperidine, piperazine, morpholine, thiomorpholine, dihydropyridine, tetrahydropyridine, tetrahydropyran, dihydrooxazine, tetrahydropyridazine, hexahydropyrimidine, and thiazine and the like, and thiirane, oxirane, oxetane, oxathiolane, azetidine, hexahydroazepine, tetrahydrodiazepine, dioxazine, aziridine, oxepane, thiolane, and thiine and the like.

Examples of the non-aromatic heterocycle which is bicyclic include oxabicyclooctane, indoline, isoindoline, chromane, isochromane, dihydrobenzofuran, dihydroisobenzofuran, dihydroquinoline, dihydroisoquinoline, tetrahydroquinoline, and tetrahydroisoquinoline and the like.

Another aspect of the non-aromatic carbocycle is a 6- to 8-membered non-aromatic heterocycle. Examples of the 6- to 8-membered non-aromatic heterocycle include piperidine, tetrahydropyran, and oxabicyclooctane and the like, for example, include tetrahydropyran.

Examples of the "oxabicyclooctane ring" include a ring shown below.

[Chemical Formula 65]

"Non-aromatic heterocyclyl" means a cyclic non-aromatic cyclyl, which is monocyclic or polycyclic having two or more rings, containing one or more identical or different heteroatoms selected independently from O, S and N in the ring. The non-aromatic heterocyclyl which is polycyclic having two or more rings includes a fused ring wherein a non-aromatic heterocyclyl which is monocyclic or polycyclic having two or more rings is fused with a ring of the above "aromatic carbocyclyl", "non-aromatic carbocyclyl" and/or "aromatic heterocyclyl".

In addition, the "non-aromatic heterocyclyl" also includes a group having a bridge or a group to form a spiro ring as follows.

[Chemical Formula 66]

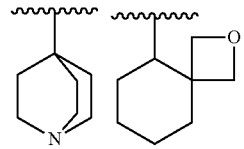

The non-aromatic heterocyclyl which is monocyclic is preferably a 3- to 8-membered, and more preferably 5- or 6-membered ring. Examples thereof include "5-membered non-aromatic heterocyclyl" such as thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydrothiazolyl, tetrahydroisothiazolyl, dioxolanyl, and dioxolinyl and the like, "6-membered non-aromatic heterocyclyl" such as dioxanyl, thianyl, piperidyl, piperazinyl, morpholinyl, morpholino, thiomorpholinyl, thiomorpholino, dihydropyridyl, tetrahydropyridyl, tetrahydropyranyl, dihydrooxazinyl, tetrahydropyridazinyl, hexahydropyrimidinyl, and thiazinyl and the like, and thiiranyl, oxiranyl, oxetanyl, oxathiolanyl, azetidinyl, hexahydroazepinyl, tetrahydrodiazepinyl, dioxazinyl, aziridinyl, oxepanyl, thiolanyl, and thiinyl and the like.

Examples of the non-aromatic heterocyclyl which is bicyclic include indolinyl, isoindolinyl, chromanyl, isochromanyl, dihydrobenzofuryl, dihydroisobenzofuryl, dihydroquinolynyl, dihydroisoquinolynyl, tetrahydroquinolynyl, and tetrahydroisoquinolynyl and the like.

"Hydroxyalkyl" means a group wherein hydrogen atom(s) bonded to carbon atom(s) of the above "alkyl" is replaced with one or more hydroxy group(s). Examples thereof include hydroxymethyl, 1-hydroxyethyl, 2-hydroxyethyl, 1-hydroxypropyl, 2-hydroxypropyl, and 1,2-hydroxyethyl and the like.

Examples of preferred embodiments of "hydroxyalkyl" include hydroxymethyl.

"Alkyloxy" means a group wherein the above "alkyl" is bonded to an oxygen atom. Examples thereof include methoxy, ethoxy, n-propyloxy, isopropyloxy, n-butyloxy, tert-butyloxy, isobutyloxy, sec-butyloxy, pentyloxy, isopentyloxy, and hexyloxy and the like.

Examples of preferred embodiments of "alkyloxy" and "C1 to C6 alkyloxy" include methoxy, ethoxy, n-propyloxy, isopropyloxy and tert-butyloxy.

Examples of "C2-C4 alkyloxy" include ethyloxy, n-propyloxy, isopropyloxy, n-butyloxy, isobutyloxy, sec-butyloxy, and tert-butyloxy, more preferably ethyloxy, n-propyloxy, and isopropyloxy.

"Alkenyloxy" means a group wherein the above "alkenyl" is bonded to an oxygen atom. Examples thereof include vinyloxy, allyloxy, 1-propenyloxy, 2-butenyloxy, 2-pentenyloxy, 2-hexenyloxy, 2-heptenyloxy, and 2-octenyloxy and the like.

"Alkynyloxy" means a group wherein the above "alkynyl" is bonded to an oxygen atom. Examples thereof include ethynyloxy, 1-propynyloxy, 2-propynyloxy, 2-butynyloxy, 2-pentynyloxy, 2-hexynyloxy, 2-heptynyloxy, and 2-octynyloxy and the like.

"Haloalkyl" means a group wherein one or more above "halogen" is bonded to the above "alkyl". Examples thereof include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropan-2-yl and the like.

Examples of preferred embodiments of "haloalkyl" include difluoromethyl, trifluoroethyl, difluoroethyl, trifluoromethyl, and trichloromethyl.

"Haloalkyloxy" means a group wherein the above "haloalkyl" is bonded to an oxygen atom. Examples thereof include monofluoromethoxy, monofluoroethoxy, trifluoromethoxy, trichloromethoxy, trifluoroethoxy, and trichloroethoxy and the like.

Examples of preferred embodiments of "haloalkyloxy" include trifluoroethoxy, difluoroethoxy, trifluoromethoxy, and trichloromethoxy.

"Alkylcarbonyl" means a group wherein the above "alkyl" is bonded to a carbonyl group. Examples thereof include methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, and hexylcarbonyl and the like.

Examples of preferred embodiments of "alkylcarbonyl" include methylcarbonyl, ethylcarbonyl, and n-propylcarbonyl.

"Alkenylcarbonyl" means a group wherein the above "alkenyl" is bonded to a carbonyl group. Examples thereof include ethylenylcarbonyl and propenylcarbonyl and the like.

"Alkynylcarbonyl" means a group wherein the above "alkynyl" is bonded to a carbonyl group. Examples thereof include ethynylcarbonyl and propynylcarbonyl and the like.

"Alkylamino" includes "monoalkylamino" and "dialkylamino".

"Monoalkylamino" means a group wherein one hydrogen atom bonded to a nitrogen atom of an amino group is replaced with the above "alkyl". Examples thereof include methylamino, ethylamino, and isopropylamino and the like.

Examples of preferred embodiments of "monoalkylamino" include methylamino and ethylamino.

"Dialkylamino" means a group wherein two hydrogen atoms bonded to a nitrogen atom of an amino group are replaced with two above "alkyl". These two alkyl groups may be the same or different. Examples thereof include dimethylamino, diethylamino, N,N-diisopropylamino, N-methyl-N-ethylamino, and N-isopropyl-N-ethylamino and the like.

Examples of preferred embodiments of "dialkylamino" include dimethylamino and diethylamino.

"Alkylsulfonyl" means a group wherein the above "alkyl" is bonded to a sulfonyl group. Examples thereof include methylsulfonyl, ethylsulfonyl, propylsulfonyl, isopropylsulfonyl, tert-butylsulfonyl, isobutylsulfonyl, and sec-butylsulfonyl and the like.

Examples of preferred embodiments of "alkylsulfonyl" include methylsulfonyl and ethylsulfonyl.

"Alkenylsulfonyl" means a group wherein the above "alkenyl" is bonded to a sulfonyl group. Examples thereof include ethylenylsulfonyl and propenylsulfonyl and the like.

"Alkynylsulfonyl" means a group wherein the above "alkynyl" is bonded to a sulfonyl group. Examples thereof include ethynylsulfonyl and propynylsulfonyl and the like.

"Alkylcarbonylamino" includes "monoalkylcarbonylamino" and "dialkylcarbonylamino".

"Monoalkylcarbonylamino" means a group wherein one hydrogen atom bonded to a nitrogen atom of an amino group is replaced with the above "alkylcarbonyl". Examples thereof include methylcarbonylamino, ethylcarbonylamino, propylcarbonylamino, isopropylcarbonylamino, tert-butylcarbonylamino, isobutylcarbonylamino, and sec-butylcarbonylamino and the like.

Examples of preferred embodiments of "monoalkylcarbonylamino" include methylcarbonylamino and ethylcarbonylamino.

"Dialkylcarbonylamino" includes a group wherein two hydrogen atoms bonded to a nitrogen atom of an amino group are replaced with two above "alkylcarbonyl". These two alkylcarbonyl groups may be the same or different. Examples thereof include dimethylcarbonylamino, diethylcarbonylamino, N,N-diisopropylcarbonylamino, and ethylcarbonylmethylcarbonylamino and the like.

Examples of preferred embodiments of "dialkylcarbonylamino" include dimethylcarbonylamino and diethylcarbonylamino and the like.

"Alkylimino" means a group wherein a hydrogen atom bonded to a nitrogen atom of an imino group is replaced with the above "alkyl". Examples thereof include methylimino, ethylimino, n-propylimino, and isopropylimino and the like.

"Alkyloxyimino" means a group wherein a hydrogen atom bonded to a nitrogen atom of an imino group is replaced with the above "alkyloxy". Examples thereof include methyloxyimino, ethyloxyimino, n-propyloxyimino, and isopropyloxyimino and the like.

"Alkylsulfonylamino" includes "monoalkylsulfonylamino" and "dialkylsulfonylamino".

"Monoalkylsulfonylamino" means a group wherein one hydrogen atom bonded to a nitrogen atom of an amino group is replaced with the above "alkylsulfonyl". Examples thereof include methylsulfonylamino, ethylsulfonylamino, propylsulfonylamino, isopropylsulfonylamino, tert-butylsulfonylamino, isobutylsulfonylamino and sec-butylsulfonylamino and the like.

Examples of preferred embodiments of "monoalkylsulfonylamino" include methylsulfonylamino and ethylsulfonylamino.

"Dialkylsulfonylamino" means a group wherein two hydrogen atoms attached to a nitrogen atom of an amino group are replaced with two above "alkylsulfonyl". These two alkylsulfonyl groups may be the same or different. Examples thereof include dimethylsulfonylamino, diethylsulfonylamino, and N,N-diisopropylsulfonylamino and the like.

Examples of preferred embodiments of "dialkylsulfonylamino" include dimethylsulfonylamino and diethylsulfonylamino.

"Alkylcarbonyloxy" means a group wherein the above "alkylcarbonyl" is bonded to an oxygen atom. Examples thereof include methylcarbonyloxy, ethylcarbonyloxy, propylcarbonyloxy, isopropylcarbonyloxy, tert-butylcarbonyloxy, isobutylcarbonyloxy, and sec-butylcarbonyloxy and the like.

Examples of preferred embodiments of "alkylcarbonyloxy" include methylcarbonyloxy and ethylcarbonyloxy.

"Alkenylcarbonyloxy" means a group wherein the above "alkenylcarbonyl" is bonded to an oxygen atom. Examples thereof include ethylenylcarbonyloxy and propenylcarbonyloxy and the like.

"Alkynylcarbonyloxy" means a group wherein the above "alkynylcarbonyl" is bonded to an oxygen atom. Examples thereof include ethynylcarbonyloxy and propynylcarbonyloxy and the like.

"Alkyloxycarbonyl" means a group wherein the above "alkyloxy" is bonded to a carbonyl group. Examples thereof include methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, and hexyloxycarbonyl and the like.

Examples of preferred embodiments of "alkyloxycarbonyl" include methyloxycarbonyl, ethyloxycarbonyl, and propyloxycarbonyl.

"Alkenyloxycarbonyl" means a group wherein the above "alkenyloxy" is bonded to a carbonyl group. Examples thereof include ethylenyloxycarbonyl and propenyloxycarbonyl and the like.

"Alkynyloxycarbonyl" means a group wherein the above "alkynyloxy" is bonded to a carbonyl group. Examples thereof include ethynyloxycarbonyl and propynyloxycarbonyl and the like.

"Alkylsulfanyl" means a group wherein a hydrogen atom bonded to a sulfur atom of a sulfanyl group is replaced with the above "alkyl". Examples thereof include methylsulfanyl, ethylsulfanyl, n-propylsulfanyl, and isopropylsulfanyl and the like.

"Alkenylsulfanyl" means a group wherein a hydrogen atom bonded to a sulfur atom of a sulfanyl group is replaced with the above "alkenyl". Examples thereof include ethylenylsulfanyl and propenylsulfanyl and the like.

"Alkynylsulfanyl" means a group wherein a hydrogen atom bonded to a sulfur atom of a sulfanyl group is replaced with the above "alkynyl". Examples thereof include ethynylsulfanyl and propynylsulfanyl and the like.

"Alkylsulfinyl" means a group wherein the above "alkyl" is bonded to a sulfinyl group. Examples thereof include methylsulfinyl, ethylsulfinyl, n-propylsulfinyl and isopropylsulfinyl and the like.

"Alkenylsulfinyl" means a group wherein the above "alkenyl" is bonded to a sulfinyl group. Examples thereof include ethylenylsulfinyl and propenylsulfinyl and the like.

"Alkynylsulfinyl" means a group wherein the above "alkynyl" is bonded to a sulfinyl group. Examples thereof include ethynylsulfinyl and propynylsulfinyl and the like.

"Alkylcarbamoyl" include "monoalkylcarbamoyl" and "dialkylcarbamoyl".

"Monoalkylcarbamoyl" means a group wherein one hydrogen atom bonded to a nitrogen atom of a carbamoyl group is replaced with the above "alkyl". Examples thereof include methylcarbamoyl and ethylcarbamoyl and the like.

"Dialkylcarbamoyl" means a group wherein two hydrogen atoms bonded to a nitrogen atom of a carbamoyl group are replaced with two above "alkyl". These two alkyl groups may be the same or different. Examples thereof include dimethylcarbamoyl, diethylcarbamoyl, and ethylmethylcarbamoyl and the like.

"Alkylsulfamoyl" includes "monoalkylsulfamoyl" and "dialkylsulfamoyl".

"Monoalkylsulfamoyl" means a group wherein one hydrogen atom bonded to a nitrogen atom of a sulfamoyl group is replaced with the above "alkyl". Examples thereof include methylsulfamoyl and ethylsulfamoyl and the like.

"Dialkylsulfamoyl" means a group wherein two hydrogen atoms bonded to a nitrogen atom of a sulfamoyl group are replaced with two above "alkyl". These two alkyl groups may be the same or different. Examples thereof include dimethylsulfamoyl, diethylsulfamoyl, and ethylmethylsulfamoyl and the like.

The alkyl portion of "aromatic carbocyclylalkyl", "non-aromatic carbocyclylalkyl", "aromatic heterocyclylalkyl", and "non-aromatic heterocyclylalkyl" means the same as above "alkyl".

"Aromatic carbocyclylalkyl" means alkyl substituted with one or more above "aromatic carbocyclyl". Examples thereof include benzyl, phenethyl, phenylpropyl, benzhydryl, trityl, naphthylmethyl, and a group shown below

[Chemical Formula 67]

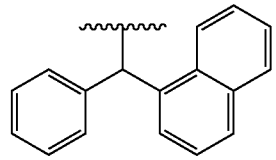

and the like.

Examples of preferred embodiments of "aromatic carbocyclylalkyl" include benzyl, phenethyl, and benzhydryl.

"Non-aromatic carbocyclylalkyl" means alkyl substituted with one or more above "non-aromatic carbocyclyl". Also, "non-aromatic carbocyclylalkyl" includes "non-aromatic carbocyclyl alkyl" wherein the alkyl portion thereof is substituted with one or more above "aromatic carbocyclyl". Examples thereof include cyclopropylmethyl, cyclobutylmethyl, cyclopentylmethyl, cyclohexylmethyl, and a group shown below

[Chemical Formula 68]

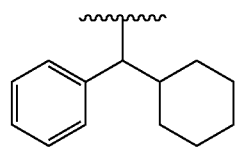

and the like.

"Aromatic heterocyclylalkyl" means alkyl substituted with one or more above "aromatic heterocyclyl". Also, "aromatic heterocyclylalkyl" includes "aromatic heterocyclylalkyl" wherein the alkyl portion thereof is substituted with one or more above "aromatic carbocyclyl" and/or "non-aromatic carbocyclyl". Examples thereof include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, and a group shown below

[Chemical Formula 69]

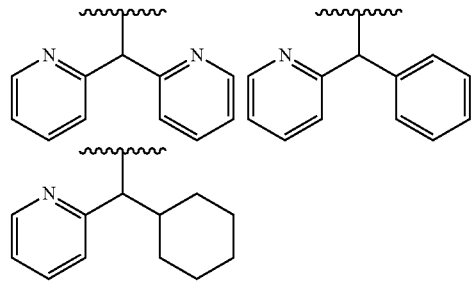

and the like.

"Non-aromatic heterocyclylalkyl" means alkyl substituted with one or more above "non-aromatic heterocyclyl". Also, "non-aromatic heterocyclylalkyl" includes a "non-aromatic heterocyclylalkyl" wherein the alkyl portion thereof is substituted with above "aromatic carbocyclyl", "non-aromatic carbocyclyl" and/or "aromatic heterocyclyl". Examples thereof include tetrahydropyranylmethyl, morpholinylethyl, piperidinylmethyl, piperazinylmethyl, and a group shown below

[Chemical Formula 70]

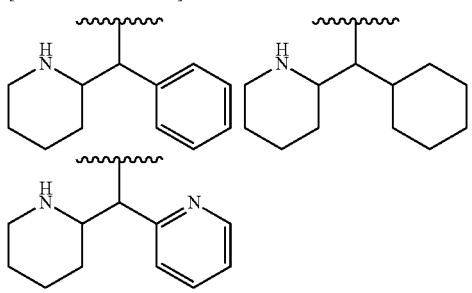

and the like.

The "aromatic carbocycle" portion of "aromatic carbocyclyloxy", "aromatic carbocyclylamino", "aromatic carbocyclylsulfanyl", "aromatic carbocyclylcarbonyl" and "aromatic carbocyclylsulfonyl" means the same as above "aromatic carbocyclyl".

"Aromatic carbocyclyloxy" means a group wherein "aromatic carbocycle" is bonded to an oxygen atom. Examples thereof include phenyloxy and naphthyloxy and the like.

"Aromatic carbocyclylamino" means a group wherein a hydrogen atom attached to a nitrogen atom of an amino group is replaced with "aromatic carbocycle". Examples thereof include phenylamino and naphthylamino and the like. Another hydrogen atom bonded to the nitrogen atom of the amino group may be replaced with the above "alkyl".

"Aromatic carbocyclylsulfanyl" means a group wherein a hydrogen atom bonded to a sulfur atom of a sulfanyl group is replaced with "aromatic carbocycle". Examples thereof include phenylsulfanyl and naphthylsulfanyl and the like.

"Aromatic carbocyclylcarbonyl" means a group wherein "aromatic carbocycle" is bonded to a carbonyl group. Examples thereof include phenylcarbonyl and naphthylcarbonyl and the like.

"Aromatic carbocyclylsulfonyl" means a group wherein "aromatic carbocycle" is bonded to a sulfonyl group. Examples thereof include phenylsulfonyl and naphthylsulfonyl and the like.

The "non-aromatic carbocycle" portion of "non-aromatic carbocyclyloxy", "non-aromatic carbocyclylamino", and "non-aromatic carbocyclylsulfanyl" means the same as above "non-aromatic carbocyclyl".

"Non-aromatic carbocyclyloxy" means a group wherein "non-aromatic carbocycle" is bonded to an oxygen atom. Examples thereof include cyclopropyloxy, cyclohexyloxy, and cyclohexenyloxy and the like.

"Non-aromatic carbocyclylamino" means a group wherein a hydrogen atom attached to a nitrogen atom of an amino group is replaced with "non-aromatic carbocycle". Examples thereof include cyclopropylamino, cyclohexylamino, and cyclohexenylamino and the like. Another hydrogen atom bonded to the nitrogen atom of the amino group may be replaced with the above "alkyl".

"Non-aromatic carbocyclylsulfanyl" means a group wherein a hydrogen atom bonded to a sulfur atom of a sulfanyl group is replaced with "non-aromatic carbocycle". Examples thereof include cyclopropylsulfanyl, cyclohexylsulfanyl, and cyclohexenylsulfanyl and the like.

"Non-aromatic carbocyclylcarbonyl" means a group wherein "non-aromatic carbocycle" is bonded to a carbonyl group. Examples thereof include cyclopropylcarbonyl, cyclohexylcarbonyl, and cyclohexenylcarbonyl and the like.

"Non-aromatic carbocyclylsulfonyl" means a group wherein "non-aromatic carbocycle" is bonded to a sulfonyl group. Examples thereof include cyclopropylsulfonyl, cyclohexylsulfonyl, and cyclohexenylsulfonyl and the like.

The "aromatic heterocycle" portion of "aromatic heterocyclyloxy", "aromatic heterocyclylamino", and "aromatic heterocyclylsulfanyl" means the same as above "aromatic heterocyclyl".

"Aromatic heterocyclyloxy" means a group wherein "aromatic heterocycle" is bonded to an oxygen atom. Examples thereof include pyridyloxy and oxazolyloxy and the like.

"Aromatic heterocyclylamino" means a group wherein a hydrogen atom attached to a nitrogen atom of an amino group is replaced with "aromatic heterocycle". Examples thereof include pyridylamino and oxazolylamino and the like. Another hydrogen atom bonded to the nitrogen atom of the amino group may be replaced with the above "alkyl".

"Aromatic heterocyclylsulfanyl" means a group wherein a hydrogen atom bonded to a sulfur atom of a sulfanyl group is replaced with "aromatic heterocycle". Examples thereof include pyridylsulfanyl and oxazolylsulfanyl and the like.

"Aromatic heterocyclylcarbonyl" means a group wherein "aromatic heterocycle" is bonded to a carbonyl group. Examples thereof include pyridylcarbonyl and oxazolylcarbonyl and the like.

"Aromatic heterocyclylsulfonyl" means a group wherein "aromatic heterocycle" is bonded to a sulfonyl group. Examples thereof include pyridylsulfonyl and oxazolylsulfonyl and the like.

The "non-aromatic heterocycle" portion of "non-aromatic heterocyclyloxy", "non-aromatic heterocyclylamino", "non-aromatic heterocyclylsulfanyl", "non-aromatic heterocyclylcarbonyl" and "non-aromatic heterocyclylsulfonyl" means the same as above "non-aromatic heterocyclyl".

"Non-aromatic heterocyclyloxy" means a group wherein "non-aromatic heterocycle" is bonded to an oxygen atom. Examples thereof include piperidinyloxy and tetrahydrofuryloxy and the like.

"Non-aromatic heterocyclylamino" means a group wherein a hydrogen atom attached to a nitrogen atom of an amino group is replaced with the "non-aromatic heterocycle". Examples thereof include piperidinylamino and tetrahydrofurylamino and the like. Another hydrogen atom bonded to the nitrogen atom of the amino group may be replaced with the above "alkyl".

"Non-aromatic heterocyclylsulfanyl" means a group wherein a hydrogen atom bonded to a sulfur atom of a sulfanyl group is replaced with "non-aromatic heterocycle". Examples thereof include piperidinylsulfanyl and tetrahydrofurylsulfanyl and the like.

"Non-aromatic heterocyclylcarbonyl" means a group wherein "non-aromatic heterocycle" is bonded to a carbonyl group. Examples thereof include piperidinylcarbonyl and tetrahydrofurylcarbonyl and the like.

"Non-aromatic heterocyclylsulfonyl" means a group wherein "non-aromatic heterocycle" is bonded to a sulfonyl group. Examples thereof include piperidinylsulfonyl and tetrahydrofurylsulfonyl and the like.

"Substituted or unsubstituted non-aromatic carbocyclyl" and "substituted or unsubstituted non-aromatic heterocyclyl" may be substituted with "oxo". When substituted with "oxo", it means a group wherein two hydrogen atoms on a carbon atom are replaced as follows:

[Chemical Formula 71]

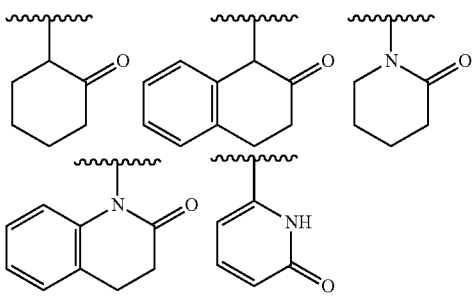

Non-aromatic carbocycle and non-aromatic heterocycle portions of the above "substituted or unsubstituted non-aromatic carbocyclyloxy", "substituted or unsubstituted non-aromatic carbocyclylamino", "substituted or unsubstituted non-aromatic carbocyclylsulfanyl", "substituted or unsubstituted non-aromatic carbocyclylcarbonyl", "substituted or unsubstituted non-aromatic carbocyclylsulfonyl", "substituted or unsubstituted non-aromatic heterocyclyloxy", "substituted or unsubstituted non-aromatic heterocyclylamino", "substituted or unsubstituted non-aromatic heterocyclylsulfanyl", "substituted or unsubstituted non-aromatic heterocyclylcarbonyl", and "substituted or unsubstituted non-aromatic heterocyclylsulfonyl" may be substituted with "oxo" similarly as described above.

The substituents of "substituted or unsubstituted alkyl", "substituted or unsubstituted C1-C6 alkyl" "substituted or unsubstituted alkyloxy", "substituted or unsubstituted C1-C6 alkyloxy" and "substituted or unsubstituted C2-C4 alkyloxy" include the following substituent group C1, and preferably the substituent group C2. They can be substituted with one or more substituents selected from the group.

The substituent group C1: halogen, hydroxy, carboxy, amino, carbamoyl, sulfamoyl, cyano, nitro, ureido, amidino, guanidino, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylimino optionally substituted with one or more group(s) selected from the substituent group A, alkyloxyimino optionally substituted with one or more group(s) selected from the substituent group A, alkylcarbonyl optionally substituted with one or more group(s) selected from the substituent group A, alkylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, aromatic carbocyclyl optionally substituted with one or more group(s) selected from the substituent group B1, non-aromatic carbocyclyl optionally substituted with one or more group(s) selected from the substituent group B1', aromatic heterocyclyl optionally substituted with one or more group(s) selected from the substituent group B1, non-aromatic heterocyclyl optionally substituted with one or more group(s) selected from the substituent group B1', aromatic carbocyclyloxy optionally substituted with one or more group(s) selected from the substituent group B1, non-aromatic carbocyclyloxy optionally substituted with one or more group(s) selected from the substituent group B1', aromatic heterocyclyloxy optionally substituted with one or more group(s) selected from the substituent group B1, non-aromatic heterocyclyloxy optionally substituted with one or more group(s) selected from the substituent group B1', aromatic carbocyclylsulfanyl optionally substituted with one or more group(s) selected from the substituent group B1, non-aromatic carbocyclylsulfanyl optionally substituted with one or more group(s) selected from the substituent group B1', aromatic heterocyclylsulfanyl optionally substituted with one or more group(s) selected from the substituent group B1, non-aromatic heterocyclylsulfanyl optionally substituted with one or more group(s) selected from the substituent group B1', aromatic carbocyclylamino optionally substituted with one or more group(s) selected from the substituent group B1, non-aromatic carbocyclylamino optionally substituted with one or more group(s) selected from the substituent group B1', aromatic heterocyclylamino optionally substituted with one or more group(s) selected from the substituent group B, and non-aromatic heterocyclylamino optionally substituted with one or more group(s) selected from the substituent group B1', aromatic carbocyclylcarbonyl optionally substituted with one or more group(s) selected from the substituent group B1, non-aromatic carbocyclylcarbonyl optionally substituted with one or more group(s) selected from the substituent group B1', aromatic heterocyclylcarbonyl optionally substituted with one or more group(s) selected from the substituent group B1, non-aromatic heterocyclylcarbonyl optionally substituted with one or more group(s) selected from the substituent group B1', aromatic carbocyclylsulfonyl optionally substituted with one or more group(s) selected from the substituent group B1, non-aromatic carbocyclylsulfonyl optionally substituted with one or more group(s) selected from the substituent group B1', aromatic heterocyclylsulfonyl optionally substituted with one or more group(s) selected from the substituent group B1, and non-aromatic heterocyclylsulfonyl optionally substituted with one or more group(s) selected from the substituent group B1'.

The substituent group A: halogen, hydroxy, carboxy, amino, carbamoyl, sulfamoyl, cyano, and nitro.

One embodiment of the substituent group A is halogen and hydroxy.

One embodiment of the substituent group A is halogen.

Substituent group B1: halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkenylcarbonyl optionally substituted with one or more group(s) selected from the substituent group A, alkynylcarbonyl optionally substituted with one or more group(s) selected from the substituent group A, alkylsulfonyl optionally substituted with one or more group(s) selected from the substituent group A, alkenylsulfonyl optionally substituted with one or more group(s) selected from the substituent group A, alkynylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylcarbonyl, non-aromaticcarbocyclylcarbonyl, aromaticheterocyclylcarbonyl, non-aromatic heterocyclylcarbonyl, aromatic carbocyclylsulfonyl, non-aromatic carbocyclylsulfonyl, aromatic heterocyclylsulfonyl, and non-aromatic heterocyclylsulfonyl (each aromatic carbocycle, non-aromatic carbocycle, aromatic heterocycle and non-aromatic heterocycle may be substituted with one or more groups selected from halogen, alkyl, hydroxy and alkyloxy).

Substituent group B1': oxo, halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkenylcarbonyl optionally substituted with one or more group(s) selected from the substituent group A, alkynylcarbonyl optionally substituted with one or more group(s) selected from the substituent group A, alkylsulfonyl optionally substituted with one or more group(s) selected from the substituent group A, alkenylsulfonyl optionally substituted with one or more group(s) selected from the substituent group A, alkynylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylcarbonyl, non-aromaticcarbocyclylcarbonyl, aromaticheterocyclylcarbonyl, non-aromatic heterocyclylcarbonyl, aromatic carbocyclylsulfonyl, non-aromatic carbocyclylsulfonyl, aromatic heterocyclylsulfonyl, and non-aromatic heterocyclylsulfonyl (each aromatic carbocycle, non-aromatic carbocycle, aromatic heterocycle and non-aromatic heterocycle may be substituted with one or more groups selected from halogen, alkyl, hydroxy and alkyloxy).

Substituent group C2 halogen, hydroxy, cyano, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, aromatic carbocyclyl optionally substituted with one or more group(s) selected from the substituent group B2, non-aromatic carbocyclyl optionally substituted with one or more group(s) selected from the substituent group B2', aromatic heterocyclyl optionally substituted with one or more group(s) selected from the substituent group B2, non-aromatic heterocyclyl optionally substituted with one or more group(s) selected from the substituent group B2', aromatic carbocyclyloxy optionally substituted with one or more group(s) selected from the substituent group B2, non-aromatic carbocyclyloxy optionally substituted with one or more group(s) selected from the substituent group B2', aromatic heterocyclyloxy optionally substituted with one or more group(s) selected from the substituent group B2, and non-aromatic heterocyclyloxy optionally substituted with one or more group(s) selected from the substituent group B2'.

Substituent group B2: halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, and alkynyloxy optionally substituted with one or more group(s) selected from the substituent group A.

Substituent group B2': oxo, halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, and alkylsulfonyl optionally substituted with one or more group(s) selected from the substituent group A.

Examples of the substituents on the ring of the "aromatic carbocycle" and "aromatic heterocycle" of "substituted or unsubstituted aromatic carbocyclyl", "substituted or unsubstituted aromatic heterocyclyl", "substituted or unsubstituted aromatic carbocyclyloxy" and "substituted or unsubstituted aromatic heterocyclyloxy" include the substituent group B1, and preferably the substituent group B2. They can be substituted with one or more substituents selected from the group.

Examples of the substituents on the ring of the "non-aromatic carbocycle", "cyclobutyl ring" and "non-aromatic heterocycle" of "substituted or unsubstituted non-aromatic carbocyclyl", "substituted or unsubstituted cyclobutyl", "substituted or unsubstituted non-aromatic heterocyclyl", "substituted or unsubstituted non-aromatic carbocyclyloxy", "substituted or unsubstituted cyclobutyloxy" and "substituted or unsubstituted non-aromatic heterocyclyloxy" include the substituent group B1', and preferably the substituent group B2'. They can be substituted with one or more substituents selected from the group.

Examples of preferred substituents of the "substituted or unsubstituted alkyloxy" in $R^{1a}$ include halogen. They can be substituted with one or more substituents selected from the group.

Examples of preferred substituents of the "substituted or unsubstituted alkyl" and "substituted or unsubstituted alkyloxy" in $R^{1b}$ include halogen. They can be substituted with one or more substituents selected from the group.

Examples of preferred substituents of the "substituted or unsubstituted C2-C4 alkyloxy" in $R^{1a}$ include halogen. They can be substituted with one or more substituents selected from the group.

Examples of preferred substituents of the "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylamino", "substituted or unsubstituted alkenylamino", and "substituted or unsubstituted alkynylamino" in $R^{1g}$ and $R^{1h}$ include halogen. They can be substituted with one or more substituents selected from the group.

Examples of preferred substituents on the ring of the "substituted or unsubstituted non-aromatic carbocyclyloxy" in $R^{1a}$ and $R^{1b}$ include halogen, alkyl, and haloalkyl, particularly preferably halogen. They can be substituted with one or more substituents selected from the group.

Examples of preferred substituents on the ring of the "substituted or unsubstituted cyclobutyl" and "substituted or unsubstituted cyclobutyloxy" in $R^{1c}$ include halogen, alkyl, and haloalkyl, particularly preferably halogen. They can be substituted with one or more substituents selected from the group.

Examples of preferred substituents on the ring of the "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclylamino" in $R^{1g}$ and $R^{1h}$ include halogen, alkyl, and haloalkyl, particularly preferably halogen. They can be substituted with one or more substituents selected from the group.

Examples of preferred substituents of the "substituted or unsubstituted C1-C6 alkyl" and "substituted or unsubstituted C1-C6 alkyloxy" in $R^{1d}$ and $R^{1e}$, $R^{1f}$, $R^{2a}$ to $R^{2d}$, $R^3$, $R^{5a}$, $R^{5b}$, $R^{7a}$, and $R^{7b}$ include halogen and hydroxy, particularly preferably halogen.

Examples of preferred substituents on the ring of the "substituted or unsubstituted aromatic carbocyclyl" in $R^4$ and $R^8$ include the substituent group β1, for example, halogen, alkyl and haloalkyl. They can be substituted with one or more substituents selected from the group.

Substituent group β1: halogen, alkyl, haloalkyl, alkyloxy, and haloalkyloxy.

Examples of preferred substituents on the ring of the "substituted or unsubstituted aromatic heterocyclyl" in $R^4$ and $R^8$ include the substituent group β1, for example, halogen, alkyl and haloalkyl. They can be substituted with one or more substituents selected from the group.

Examples of preferred substituents on the ring of the "substituted or unsubstituted aromatic heterocyclyl", "substituted or unsubstituted aromatic heterocyclyloxy", "substituted or unsubstituted aromatic carbocyclyl", and "substituted or unsubstituted aromatic carbocyclyloxy" in $R^6$ include the substituent group β1, for example, halogen, alkyl and haloalkyl. They can be substituted with one or more substituents selected from the group.

Examples of preferred substituents on the ring of the "substituted or unsubstituted non-aromatic heterocyclyl" and "substituted or unsubstituted non-aromatic carbocyclyl" in $R^4$ and $R^8$ include the substituent group β2, for example, oxo, halogen, and alkyl. They can be substituted with one or more substituents selected from the group.

Substituent group β2: oxo, halogen, alkyl, haloalkyl, alkyloxy, and haloalkyloxy.

Examples of preferred substituents on the ring of the "substituted or unsubstituted non-aromatic heterocyclyl", "substituted or unsubstituted non-aromatic heterocyclyloxy", "substituted or unsubstituted non-aromatic carbocyclyl", and "substituted or unsubstituted non-aromatic carbocyclyloxy" in $R^6$ include the substituent group β2, for example, oxo, halogen, and alkyl. They can be substituted with one or more substituents selected from the group.

Preferable examples of the pyridyl of the "substituted or unsubstituted pyridyl" in $R^4$ include a group represented by:

[Chemical Formula 72]

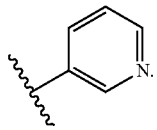

Preferable examples of the triazolyl of the "substituted or unsubstituted triazolyl" in Re include 1,2,3-triazolyl.

Preferable examples of the triazolyl of the "substituted or unsubstituted triazolyl" in $R^6$ include a group represented by:

[Chemical Formula 73]

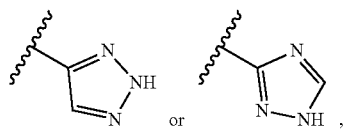

particularly preferably:

[Chemical Formula 74]

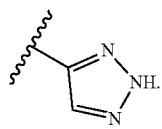

In a group represented by:

[Chemical Formula 75]

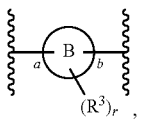

any ring-constituting atom, to which a substituent can attach, may be substituted with substituent $R^3$. For example, when

[Chemical Formula 76]

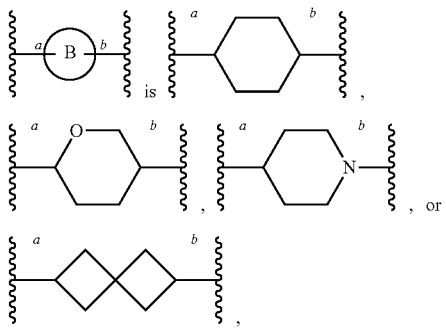

any ring-constituting atom, to which a substituent can attach, may be substituted with substituent $R^3$.

When "two $R^3$ s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom", then a hydrogen atom or alkyl may be attached to the nitrogen atom, and the carbon atoms constituting the (C1-C3) bridge can be substituted with alkyl or halogen. Examples thereof include the following:

[Chemical Formula 77]

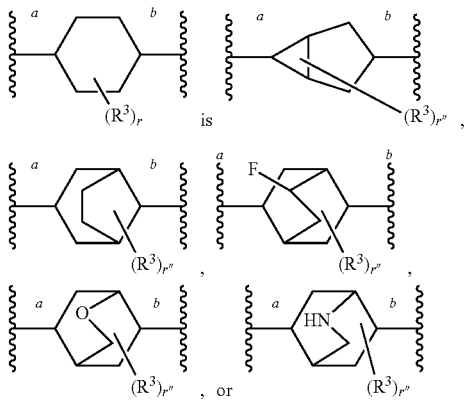

wherein r" is an integer of 0 to 2, $R^3$ is the same as defined above.

In a group represented by

[Chemical Formula 78]

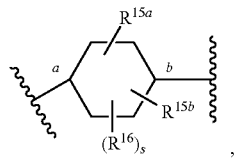

any ring-constituting atom, to which a substituent can attach, may be substituted with substituents $R^{15a}$, $R^{15b}$, and $R^{16}$.

When "$R^{15a}$ and $R^{15b}$ are attached to different ring-constituting atoms, and $R^{15a}$ and $R^{15b}$ are taken together to form a substituted or unsubstituted (C1-C3) bridge wherein one of the carbon atoms constituting the (C1-C3) bridge may be replaced with an oxygen atom or a nitrogen atom", then a hydrogen atom or alkyl may be attached to the nitrogen atom, and the carbon atoms constituting the (C1-C3) bridge may be substituted with one or more groups selected from alkyl, haloalkyl and halogen (preferably alkyl and halogen).

Examples of preferred embodiments of a compound represented by Formula (IA)', Formula (IA), Formula (IB), Formula (IC)', Formula (IC), Formula (ID-1)', Formula (ID-1), Formula (IE-1), Formula (ID-2), or Formula (IE-2) (hereinafter referred to as Formula (IA)'(IE-2)), or a pharmaceutically acceptable salt thereof are shown below.

Examples of the compound represented by Formula (IA)' include embodiments of all possible combinations given below.

Examples of the compound represented by Formula (IA) include embodiments of all possible combinations given below.

Examples of the compound represented by Formula (IB) include embodiments of all possible combinations given below.

Examples of the compound represented by Formula (IC)' include embodiments of all possible combinations given below.

Examples of the compound represented by Formula (IC) include embodiments of all possible combinations given below.

Examples of the compound represented by Formula (ID-1)' include embodiments of all possible combinations given below.

Examples of the compound represented by Formula (ID-1) include embodiments of all possible combinations given below.

Examples of the compound represented by Formula (IE-1) include embodiments of all possible combinations given below.

Examples of the compound represented by Formula (ID-2) include embodiments of all possible combinations given below.

Examples of the compound represented by Formula (IE-2) include embodiments of all possible combinations given below.

A is S or O (hereinafter referred to as "A is A1").
A is S (hereinafter referred to as "A is A2").
A is O (hereinafter referred to as "A is A3").
$R^{1a}$ is substituted or unsubstituted alkyloxy, or substituted or unsubstituted non-aromatic carbocyclyloxy (hereinafter referred to as "$R^{1a}$ is R1A1").

$R^{1a}$ is substituted or unsubstituted C2-C4 alkyloxy, or substituted or unsubstituted cyclobutyloxy (hereinafter referred to as "$R^{1a}$ is R1A2").

$R^{1a}$ is C2-C4 alkyloxy unsubstituted or substituted with one or more halogen; or cyclobutyloxy unsubstituted or substituted with one or more halogen (hereinafter referred to as "$R^{1a}$ is R1A3").

$R^{1a}$ is a group represented by:

[Chemical Formula 79]

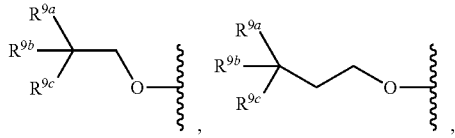

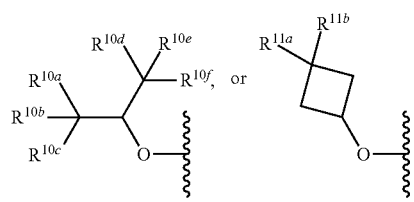

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen (hereinafter referred to as "$R^{1a}$ is R1A4").

$R^{1a}$ is a group represented by:

[Chemical Formula 80]

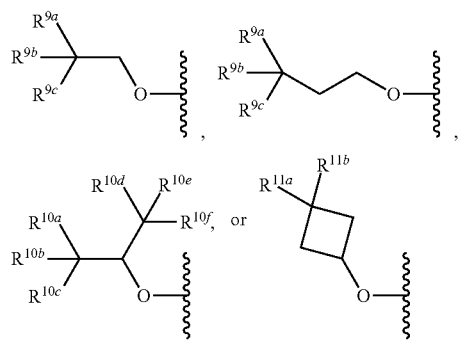

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen, provided that a group represented by:

[Chemical Formula 81]

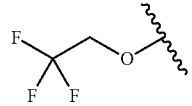

is excluded (hereinafter referred to as "$R^{1a}$ is R1A5").

$R^{1a}$ is a group represented by:

[Chemical Formula 82]

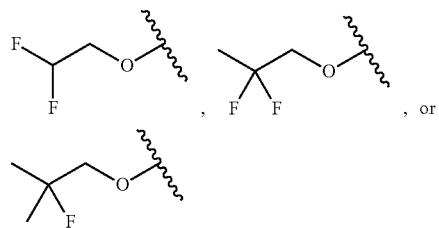

(hereinafter referred to as "$R^{1a}$ is R1A6").

$R^{1a}$ is a group represented by:

[Chemical Formula 83]

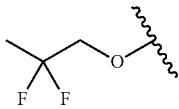

(hereinafter referred to as "$R^{1a}$ is R1A7").

$R^{1a}$ is a group represented by:

[Chemical Formula 84]

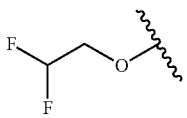

(hereinafter referred to as "$R^{1a}$ is R1A8").

$R^{1a}$ is a group represented by:

[Chemical Formula 85]

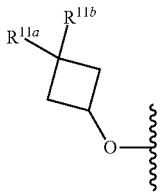

wherein $R^{11a}$ and $R^{11b}$ are each independently halogen (hereinafter referred to as "$R^{1a}$ is R1A9").

$R^{1a}$ is C2-C4 alkyloxy substituted with only two halogen (hereinafter referred to as "$R^{1a}$ is R1A10").

$R^{1a}$ is a group represented by:

[Chemical Formula 86]

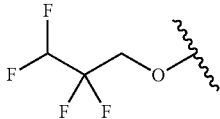

(hereinafter referred to as "$R^{1a}$ is R1A11").

$R^{1a}$ is a group represented by:

[Chemical Formula 87]

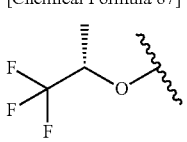

(hereinafter referred to as "$R^{1a}$ is R1A12").

$R^{1a}$ is a group represented by:

[Chemical Formula 88]

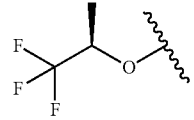

(hereinafter referred to as "$R^{1a}$ is R1A13").

$R^{1b}$ is substituted or unsubstituted alkyloxy, substituted or unsubstituted non-aromatic carbocyclyloxy, or substituted or unsubstituted alkyl (hereinafter referred to as "$R^{1b}$ is R1B1").

$R^{1b}$ is substituted or unsubstituted alkyloxy, or substituted or unsubstituted non-aromatic carbocyclyloxy (hereinafter referred to as "$R^{1b}$ is R1B2").

$R^{1b}$ is substituted or unsubstituted C2-C4 alkyloxy, substituted or unsubstituted C2-C4 alkyl, substituted or unsubstituted cyclopentyloxy, or substituted or unsubstituted cyclobutyloxy (hereinafter referred to as "$R^{1a}$ is R1B3").

$R^{1b}$ is C2-C4 alkyloxy unsubstituted or substituted with one or more halogen; C2-C4 alkyl unsubstituted or substituted with one or more halogen; cyclopentyloxy unsubstituted or substituted with one or more halogen; or cyclobutyloxy unsubstituted or substituted with one or more halogen (hereinafter referred to as "$R^{1b}$ is R1B4").

$R^{1b}$ is a group represented by:

[Chemical Formula 89]

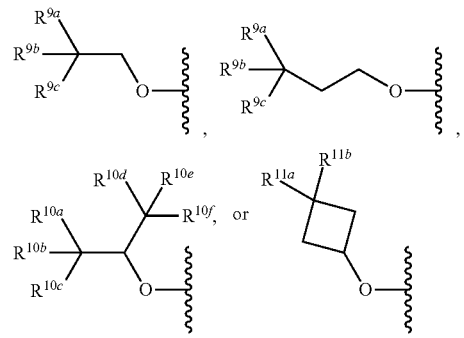

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen (hereinafter referred to as "$R^{1b}$ is R1B5").

$R^{1b}$ is a group represented by:

[Chemical Formula 90]

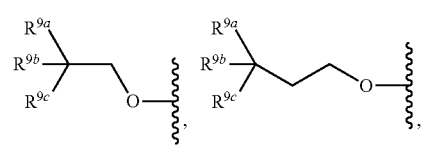

-continued

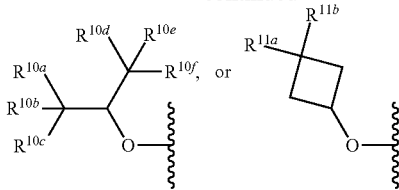

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen, provided that a group represented by:

[Chemical Formula 91]

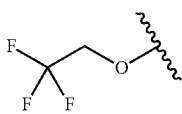

is excluded (hereinafter referred to as "$R^{1b}$ is R1B6").

$R^{1b}$ is a group represented by:

[Chemical Formula 92]

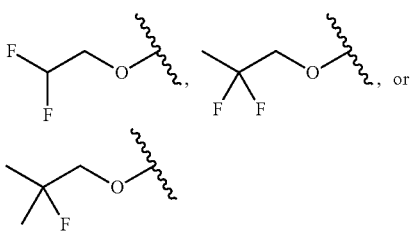

(hereinafter referred to as "$R^{1b}$ is R1B7").

$R^{1b}$ is a group represented by:

[Chemical Formula 93]

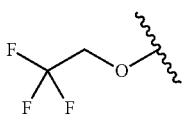

(hereinafter referred to as "$R^{1b}$ is R1B8").

$R^{1b}$ is unsubstituted alkyloxy or unsubstituted non-aromatic carbocyclyloxy (hereinafter referred to as "$R^{1a}$ is R1B9").

$R^{1b}$ is unsubstituted cyclobutyloxy (hereinafter referred to as "$R^{1a}$ is R1B10").

$R^{1b}$ is a group represented by:

[Chemical Formula 94]

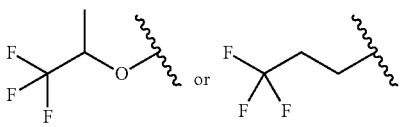

(hereinafter referred to as "$R^{1b}$ is R1B11").

$R^{1b}$ is C2-C4 alkyl unsubstituted or substituted with one or more halogen (hereinafter referred to as "$R^{1b}$ is R1B12").

$R^{1b}$ is C2-C4 alkyloxy substituted with only two halogen (hereinafter referred to as "$R^{1b}$ is R1B13").

$R^{1b}$ is a group represented by:

[Chemical Formula 95]

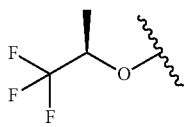

(hereinafter referred to as "$R^{1b}$ is R1B14").

$R^{1d}$ and $R^{1e}$ are each independently a hydrogen atom, halogen, hydroxy, cyano, substituted or unsubstituted C1-C6 alkyl, or substituted or unsubstituted C1-C6 alkyloxy (hereinafter referred to as "$R^{1d}$ and $R^{1e}$ are R1DE1").

$R^{1d}$ and $R^{1e}$ are hydrogen atoms (hereinafter referred to as "$R^{1d}$ and $R^{1e}$ are R1DE2").

$R^{1d}$ and $R^{1e}$ are hydrogen atoms or halogen (hereinafter referred to as "$R^{1d}$ and $R^{1e}$ are R1DE3").

$R^{1c}$ is substituted or unsubstituted C2-C4 alkyloxy, substituted or unsubstituted cyclobutyl, or substituted or unsubstituted cyclobutyloxy (hereinafter referred to as "$R^{1c}$ is R1C1").

$R^{1c}$ is C2-C4 alkyloxy unsubstituted or substituted with halogen; cyclobutyl unsubstituted or substituted with halogen; or cyclobutyloxy unsubstituted or substituted with halogen (hereinafter referred to as "$R^{1c}$ is R1C2").

$R^{1c}$ is cyclobutyl unsubstituted or substituted with halogen; or cyclobutyloxy unsubstituted or substituted with halogen (hereinafter referred to as "$R^{1c}$ is R1C3").

$R^{1c}$ is a group represented by:

[Chemical Formula 96]

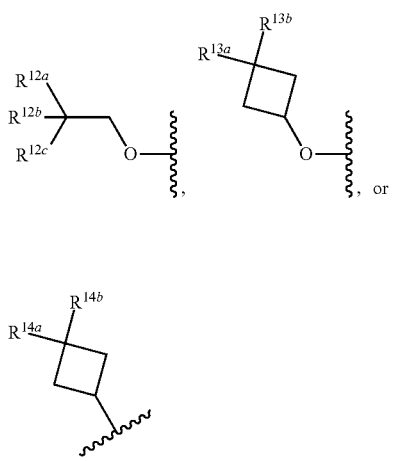

wherein $R^{12a}$ is halogen; $R^{12b}$ and $R^{12c}$ are each independently a hydrogen atom, halogen, or methyl; $R^{13a}$ and $R^{14a}$ are each independently halogen; and $R^{13b}$ and $R^{14b}$ are each independently a hydrogen atom or halogen (hereinafter referred to as "$R^{1c}$ is R1C4").

$R^{1c}$ is a group represented by:

[Chemical Formula 97]

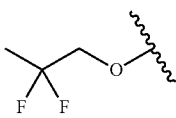

(hereinafter referred to as "$R^{1a}$ is R1C5").
$R^{1c}$ is a group represented by:

[Chemical Formula 98]

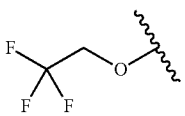

(hereinafter referred to as "$R^{1a}$ is R1C6").
$R^{1c}$ is a group represented by:

[Chemical Formula 99]

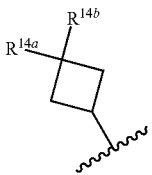

wherein $R^{14a}$ is halogen; and $R^{14b}$ is a hydrogen atom or halogen (hereinafter referred to as "$R^{1a}$ is R1C7").

$Y^1$ is $CR^{1d}$ or N; $Y^2$ is $CR^{1e}$ or N; $Y^3$ is N or $CR^{1f}$ (hereinafter referred to as "$Y^1$ to $Y^3$ are Y1").

$Y^1$ is $CR^{1d}$ or N; $Y^2$ is $CR^{1e}$ or N; $Y^3$ is N or $CR^{1f}$, provided that all of $Y^1$ to $Y^3$ are not simultaneously N (hereinafter referred to as "$Y^1$ to $Y^3$ are Y2").

$Y^1$ is $CR^{1d}$ or N; $Y^2$ is $CR^{1e}$ or N; $Y^3$ is N, provided that all of $Y^1$ to $Y^3$ are not simultaneously N (hereinafter referred to as "$Y^1$ to $Y^3$ are Y3").

$Y^1$ is $CR^{1d}$; $Y^2$ is $CR^{1e}$; $Y^3$ is N (hereinafter referred to as "$Y^1$ to $Y^3$ are Y4").

$R^{1d}$ to $R^{1f}$ are each independently a hydrogen atom, halogen, hydroxy, cyano, substituted or unsubstituted C1-C6 alkyl, or substituted or unsubstituted C1-C6 alkyloxy (hereinafter referred to as "$R^{1d}$ to $R^{1f}$ are R1DEF1").

$R^{1d}$ to $R^{1f}$ are each independently a hydrogen atom or halogen (hereinafter referred to as "$R^{1d}$ to $R^{1f}$ are R1DEF2").

$R^{1d}$ to $R^{1f}$ are hydrogen atoms (hereinafter referred to as "$R^{1d}$ to $R^{1f}$ are R1DEF3").

$R^{1g}$ and $R^{1h}$ are substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino (hereinafter referred to as "$R^{1g}$ and $R^{1h}$ are R1GH1").

$R^{1g}$ and $R^{1h}$ are substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy (hereinafter referred to as "$R^{1g}$ and $R^{1h}$ are R1GH2").

$R^{1g}$ and $R^{1h}$ are C1-C6 alkyl unsubstituted or substituted with one or more halogen; C1-C6 alkyloxy unsubstituted or substituted with one or more halogen; cyclobutyl unsubstituted or substituted with one or more halogen; or cyclobutyloxy unsubstituted or substituted with one or more halogen (hereinafter referred to as "$R^{1g}$ and $R^{1h}$ are R1GH3").

$R^{1g}$ and $R^{1h}$ are substituted or unsubstituted alkyloxy (hereinafter referred to as "$R^{1g}$ and $R^{1h}$ are R1GH4").

$R^{1g}$ and $R^{1h}$ are C1-C6 alkyloxy unsubstituted or substituted with halogen (hereinafter referred to as "$R^{1g}$ and $R^{1h}$ are R1GH5").

$R^{1g}$ and $R^{1h}$ are C1-C6 haloalkyloxy (hereinafter referred to as "$R^{1g}$ and $R^{1h}$ are R1GH6").

p is 1 or 2 (hereinafter referred to as "p is p1").
p is 2 (hereinafter referred to as "p is p2").
p is 1 (hereinafter referred to as "p is p3").

$R^{2a}$ to $R^{2d}$ are each independently a hydrogen atom, halogen, hydroxy, substituted or unsubstituted C1-C6 alkyl, or substituted or unsubstituted C1-C6 alkyloxy (hereinafter referred to as "$R^{2a}$ to $R^{2d}$ are R21").

$R^{2a}$ and $R^{2b}$ are hydrogen atoms, and $R^{2c}$ and $R^{2d}$ are each independently a hydrogen atom or substituted or unsubstituted C1-C6 alkyloxy (hereinafter referred to as "$R^{2a}$ to $R^{2d}$ are R22").

$R^{2a}$ and $R^{2b}$ are hydrogen atoms, $R^{2e}$ is a hydrogen atom, and $R^{2d}$ is substituted or unsubstituted C1-C6 alkyloxy (hereinafter referred to as "$R^{2a}$ to $R^{2d}$ are R23").

$R^{2a}$ and $R^{2b}$ are hydrogen atoms, $R^{2c}$ is a hydrogen atom, and $R^{2d}$ is methoxy (hereinafter referred to as "$R^{2a}$ to $R^{24}$ are R24").

$R^{2a}$ to $R^{2d}$ are each independently a hydrogen atom (hereinafter referred to as "$R^{2a}$ to $R^{2d}$ are R25").

$R^3$ is each independently halogen, hydroxy, cyano, substituted or unsubstituted C1-C6 alkyl, or substituted or unsubstituted C1-C6 alkyloxy;
two $R^3$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom (hereinafter referred to as "$R^3$ is R31").

$R^3$ is each independently halogen, hydroxy, cyano, substituted or unsubstituted C1-C6 alkyl, or substituted or unsubstituted C1-C6 alkyloxy;

two R³s attached to different ring-constituting atoms may be taken together to form a substituted or unsubstituted (C1-C3) bridge wherein one of carbon atoms constituting the (C1-C3) bridge may be replaced with an oxygen atom or a nitrogen atom (hereinafter referred to as "R³ is R32").

R³ is each independently halogen, or two R³s attached to different ring-constituting atoms may be taken together to form a substituted or unsubstituted (C1-C3) bridge (hereinafter referred to as "R³ is R33").

R³ is each independently halogen or two R³s attached to different ring-constituting atoms may be taken together to form a substituted or unsubstituted C2 bridge (hereinafter referred to as "R³ is R34").

R³ is each independently halogen (hereinafter referred to as "R³ is R35").

Two R³s attached to different ring-constituting atoms are taken together to form a C2 bridge (hereinafter referred to as "R³ is R36").

r is an integer of 0 to 4 (hereinafter referred to as "r is r1").
r is an integer of 1 to 4 (hereinafter referred to as "r is r2").
r is 1 or 2 (hereinafter referred to as "r is r3").
r is 1 (hereinafter referred to as "r is r4").
r is 0 (hereinafter referred to as "r is r5").
r is an integer of 2 to 4 (hereinafter referred to as "r is r6").
r is 2 (hereinafter referred to as "r is r7").

$R^{15a}$ and $R^{15b}$ are attached to different ring-constituting atoms, and $R^{15a}$ and $R^{15b}$ are taken together to form a substituted or unsubstituted (C1-C3) bridge wherein one of the carbon atoms constituting the (C1-C3) bridge may be replaced with an oxygen atom or a nitrogen atom (hereinafter referred to as "$R^{15a}$ and $R^{15b}$ are R151").

$R^{15a}$ and $R^{15b}$ are attached to different ring-constituting atoms, and $R^{15a}$ and $R^{15b}$ are taken together to form a substituted or unsubstituted C2 bridge wherein one of the carbon atoms constituting the C2 bridge may be replaced with an oxygen atom (hereinafter referred to as "$R^{15a}$ and $R^{15b}$ are R152").

$R^{16}$ is each independently halogen, hydroxy, cyano, substituted or unsubstituted C1-C6 alkyl, or substituted or unsubstituted C1-C6 alkyloxy (hereinafter referred to as "$R^{16}$ is R161").

$R^{16}$ is each independently halogen (hereinafter referred to as "$R^{16}$ is R162").

s is an integer of 0 to 4 (hereinafter referred to as "s is s1").
s is an integer of 0 to 2 (hereinafter referred to as "s is s2").
s is 0 (hereinafter referred to as "s is s3").

Ring B is a non-aromatic carbocycle or a non-aromatic heterocycle (hereinafter referred to as "Ring B is B1").

Ring B is a 4- to 8-membered non-aromatic carbocycle or a 4- to 8-membered non-aromatic heterocycle (hereinafter referred to as "Ring B is B2").

Ring B is a 6- to 8-membered non-aromatic carbocycle or a 6- to 8-membered non-aromatic heterocycle (hereinafter referred to as "Ring B is B3").

Ring B is a 6-membered non-aromatic carbocycle, a 6-membered non-aromatic heterocycle, or a spiroheptane ring (hereinafter referred to as "Ring B is B4").

Ring B is a piperidine ring or spiroheptane ring (hereinafter referred to as "Ring A is B5").

Ring B is a cyclohexane ring (hereinafter referred to as "Ring B is B6").

Ring B is a tetrahydropyran ring (hereinafter referred to as "Ring B is B7").

Ring B is a piperidine ring (hereinafter referred to as Ring B is B8).

Ring B is a spiroheptane ring (hereinafter referred to as Ring B is B9).

[Chemical Formula 100]

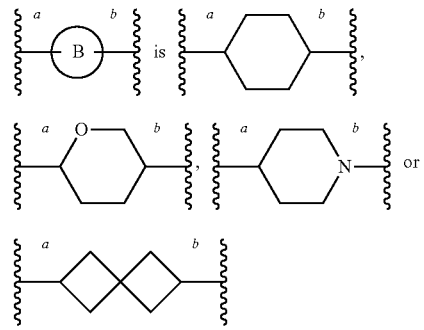

(hereinafter referred to as "Ring B is B10").

[Chemical Formula 101]

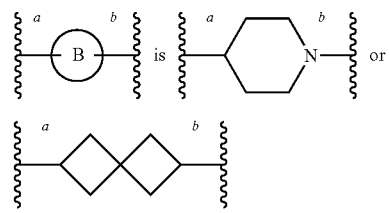

(hereinafter referred to as "Ring B is B11").

Ring B is a bicyclooctane ring or an oxabicyclooctane ring (hereinafter referred to as "Ring B is B12").

[Chemical Formula 102]

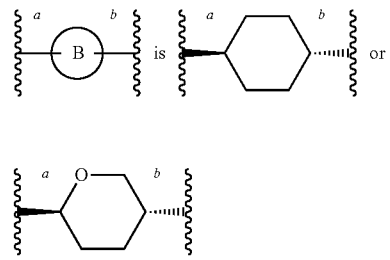

(hereinafter referred to as "Ring B is B13").

$X^1$ is $CR^{17a}R^{17b}$, O, or $NR^{18}$; $X^2$ is $CR^{19a}R^{19b}$; $R^{17a}$, $R^{17b}$, $R^{19a}$, and $R^{19b}$ are each independently a hydrogen atom, halogen, or C1-C6 alkyl; and $R^{18}$ is a hydrogen atom or C1-C6 alkyl (hereinafter referred to as "$X^1$ and $X^2$ are X1").

$X^1$ is $CR^{17a}R^{17b}$ or O; $X^2$ is $CR^{19a}R^{19b}$; and $R^{17a}$, $R^{17b}$, $R^{19a}$ and $R^{19b}$ are each independently a hydrogen atom, halogen, or C1-C6 alkyl (hereinafter referred to as "$X^1$ and $X^2$ are X2").

$X^1$ is $CH_2$ or O; $X^2$ is $CH_2$ (hereinafter referred to as "$X^1$ and $X^2$ are X3").

The group represented by:

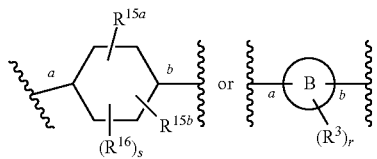

(hereinafter referred to as "cyclyl ab") is a group represented by:

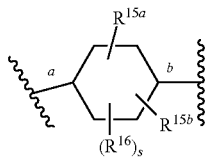

wherein $R^{15a}$ and $R^{15b}$ are R151 (hereinafter referred to as "cyclyl ab is ab1").

The cyclyl ab is a group represented by:

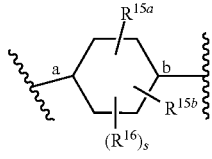

wherein $R^{15a}$ and $R^{15b}$ are R152 (hereinafter referred to as "cyclyl ab is ab2").

The cyclyl ab is a group represented by:

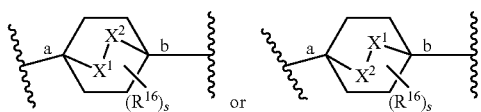

wherein $X^1$ and $X^2$ are X1 (hereinafter referred to as "cyclyl ab is ab3").

The cyclyl ab is a group represented by:

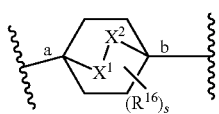

wherein $X^1$ and $X^2$ are X2 (hereinafter referred to as "cyclyl ab is ab4").

The cyclyl ab is a group represented by:

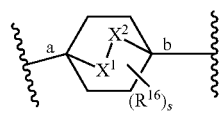

wherein $X^1$ and $X^2$ are X3 (hereinafter referred to as "cyclyl ab is ab5").

The cyclyl ab is a group represented by:

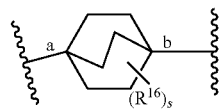

(hereinafter referred to as "cyclyl ab is ab6").

The cyclyl ab is a group represented by:

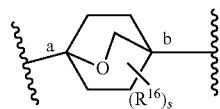

(hereinafter referred to as "cyclyl ab is ab7").

$R^4$ is substituted or unsubstituted aromatic carbocyclyl, substituted or unsubstituted non-aromatic heterocyclyl, substituted or unsubstituted aromatic heterocyclyl, —$CR^{5a}R^{5b}$—$R^6$, or —$CR^{7a}$=$CR^{7b}$—$R^8$;

$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;

$R^6$ is substituted or unsubstituted non-aromatic heterocyclyl, substituted or unsubstituted aromatic heterocyclyl, substituted or unsubstituted aromatic heterocyclyloxy, or substituted or unsubstituted non-aromatic heterocyclyloxy;

$R^8$ is substituted or unsubstituted non-aromatic heterocyclyl or substituted or unsubstituted aromatic heterocyclyl (hereinafter referred to as "$R^4$ is R41").

$R^4$ is substituted or unsubstituted phenyl (examples of the substituents include the substituent group β1), substituted or unsubstituted 6-membered or bicyclic non-aromatic heterocyclyl (examples of the substituents include the substituent group B2), substituted or unsubstituted 6-membered or bicyclic aromatic heterocyclyl (examples of the substituents include the substituent group B1), —$CR^{5a}R^{5b}$—$R^6$, or —$CR^{7a}$=$CR^{7b}$—$R^6$;

$R^{5a}$, $R^{5b}$, $R^{7a}$ and $R^{7b}$ are the same as defined in R41;

$R^6$ is substituted or unsubstituted 5- or 6-membered non-aromatic heterocyclyl (examples of the substituents include the substituent group β2), substituted or unsubstituted 5- or 6-membered aromatic heterocyclyl (examples of the substituents include the substituent group β1), substituted or unsubstituted 5- or 6-membered aromatic heterocyclyloxy (examples of the substituents include the substituent group β1), or substituted or unsubstituted 5- or 6-membered non-aromatic heterocyclyloxy (examples of the substituents include the substituent group β2);

R$^8$ is substituted or unsubstituted 5- or 6-membered non-aromatic heterocyclyl (examples of the substituents include the substituent group 82), or substituted or unsubstituted 5- or 6-membered aromatic heterocyclyl (examples of the substituents include the substituent group β1) (hereinafter referred to as "R$^4$ is R$^{42}$").

R$^4$ is substituted or unsubstituted phenyl, substituted or unsubstituted 6-membered or bicyclic non-aromatic heterocyclyl, substituted or unsubstituted 6-membered or bicyclic aromatic heterocyclyl (provided that indolyl substituted with only one methyl is excluded), —CR$^{5a}$R$^{5b}$—R$^6$, or —CR$^{7a}$=CR$^{7b}$—R$^8$;

R$^{5a}$, R$^{5b}$, R$^{7a}$ and R$^{7b}$ are the same as defined in R41;

R$^6$ is substituted or unsubstituted 5- or 6-membered non-aromatic heterocyclyl, substituted or unsubstituted 5- or 6-membered aromatic heterocyclyl (provided that thiazolyl substituted with only one methyl is excluded), substituted or unsubstituted 5- or 6-membered aromatic heterocyclyloxy, or substituted or unsubstituted 5- or 6-membered non-aromatic heterocyclyloxy;

R$^8$ is substituted or unsubstituted 5- or 6-membered non-aromatic heterocyclyl, or substituted or unsubstituted 5- or 6-membered aromatic heterocyclyl (hereinafter referred to as "R$^4$ is R43").

R$^4$ is substituted or unsubstituted 6-membered or bicyclic non-aromatic heterocyclyl (examples of the substituents include the substituent group β2), or substituted or unsubstituted 6-membered or bicyclic aromatic heterocyclyl (examples of the substituents include the substituent group β1) (hereinafter referred to as "R$^4$ is R44").

R$^4$ is —CR$^{5a}$R$^{5b}$—R$^6$; and R$^{5a}$, R$^{5b}$ and R$^6$ are the same as defined in R41 (hereinafter referred to as "R$^4$ is R$^{45}$").

R$^4$ is —CR$^{7a}$=CR$^{7b}$—R$^8$; and R$^{7a}$, R$^{7b}$ and R$^8$ are the same as defined in R41 (hereinafter referred to as "R$^4$ is R46").

R$^4$ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, —CR$^{5a}$R$^{5b}$—R$^6$, or —CR$^{7a}$=CR$^{7b}$—R$^8$;

R$^{5a}$, R$^{5b}$, R$^{7a}$ and R$^{7b}$ are the same as defined in R41;

R$^6$ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy;

R$^8$ is substituted or unsubstituted pyrimidinyl or substituted or unsubstituted pyrazolyl (hereinafter referred to as "R$^4$ is R47").

R$^4$ is aromatic heterocyclyl substituted with haloalkyl (wherein the non-aromatic heterocyclyl may be further substituted with one or more group(s) selected from halogen and alkyl), non-aromatic heterocyclyl substituted with haloalkyl (wherein the non-aromatic heterocyclyl may be further substituted with one or more group(s) selected from oxo, halogen, and alkyl), or —CR$^{5a}$R$^{5b}$—R$^6$, and R$^6$ is substituted or unsubstituted triazolyl, or substituted or unsubstituted pyrazinyloxy (hereinafter referred to as "R$^4$ is R48").

R$^4$ is pyridyl substituted with haloalkyl, wherein the pyridyl may be further substituted with one or more group(s) selected from halogen and alkyl (hereinafter referred to as "R$^4$ is R49").

R$^4$ is —CH$_2$—R$^6$, and R$^6$ is substituted or unsubstituted triazolyl (hereinafter referred to as "R$^4$ is R410").

R$^4$ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, or substituted or unsubstituted dihydropyridyl (hereinafter referred to as "R$^4$ is R411").

R$^4$ is —CH$_2$—R$^6$, and R$^6$ is the same as defined in R47 (hereinafter referred to as "R$^4$ is R412").

R$^4$ is —CH=CH—R; and R$^8$ is the same as defined in R47 (hereinafter referred to as "R$^4$ is R413").

R$^4$ is substituted or unsubstituted aromatic carbocyclyl, substituted or unsubstituted non-aromatic heterocyclyl, substituted or unsubstituted aromatic heterocyclyl, substituted or unsubstituted non-aromatic carbocyclyl, —(CR$^{5a}$R$^{5b}$)m—R$^6$, or —CR$^{7a}$=CR$^{7b}$—R$^8$;

m is an integer of 1 to 3;

R$^{5a}$ is each independently a hydrogen atom, halogen, substituted or unsubstituted C1-C6 alkyl, or substituted or unsubstituted C1-C6 alkyloxy;

R$^{5b}$ is each independently a hydrogen atom, halogen, substituted or unsubstituted C1-C6 alkyl, or substituted or unsubstituted C1-C6 alkyloxy;

R$^{7a}$ and R$^{7b}$ are each independently a hydrogen atom, halogen, substituted or unsubstituted C1-C6 alkyl, or substituted or unsubstituted C1-C6 alkyloxy;

R$^6$ is substituted or unsubstituted non-aromatic heterocyclyl, substituted or unsubstituted aromatic heterocyclyl, substituted or unsubstituted non-aromatic carbocyclyl, substituted or unsubstituted aromatic carbocyclyl, substituted or unsubstituted aromatic heterocyclyloxy, substituted or unsubstituted non-aromatic heterocyclyloxy, substituted or unsubstituted aromatic carbocyclyloxy, or substituted or unsubstituted non-aromatic carbocyclyloxy;

R$^8$ is substituted or unsubstituted non-aromatic heterocyclyl, substituted or unsubstituted aromatic heterocyclyl, substituted or unsubstituted non-aromatic carbocyclyl, or substituted or unsubstituted aromatic carbocyclyl (hereinafter referred to as "R$^4$ is R414");

R$^4$ is substituted or unsubstituted aromatic carbocyclyl, substituted or unsubstituted non-aromatic heterocyclyl, substituted or unsubstituted aromatic heterocyclyl, substituted or unsubstituted non-aromatic carbocyclyl, —(CR$^{5a}$R$^{6b}$)m—R$^6$, or —CR$^{7a}$=CR$^{7b}$—R; m is 1; and R$^{5a}$, R$^{5b}$, R$^{7a}$, R$^{7b}$, R$^6$ and R$^8$ are the same as defined in R414 (hereinafter referred to as "R$^4$ is R415").

R$^4$ is a group represented by:

[Chemical Formula 111]

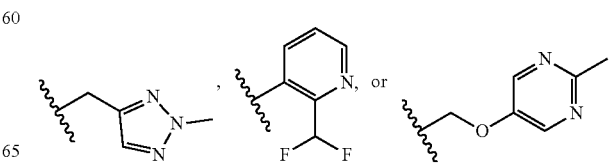

(hereinafter referred to as "R⁴ is R416").

R⁴ is a group represented by:

[Chemical Formula 112]

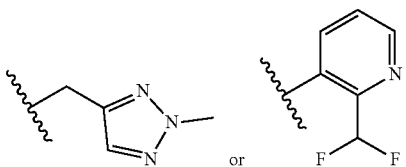

or (hereinafter referred to as "R⁴ is R417").

R⁴ is a group represented by:

[Chemical Formula 113]

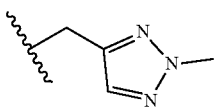

(hereinafter referred to as "R⁴ is R418").

R⁴ is group represented by:

[Chemical Formula 114]

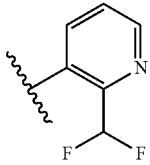

(hereinafter referred to as "R⁴ is R419").

R⁴ is —CH₂—R⁶, and R⁶ is 6-membered aromatic heterocyclyloxy optionally substituted with the substituent group β1 (hereinafter referred to as "R⁴ is R420").

R⁴ is —CH₂—R⁶, and R⁶ is pyrimidinyloxy optionally substituted with alkyl (hereinafter referred to as "R⁴ is R421").

R⁴ is a group represented by:

[Chemical Formula 115]

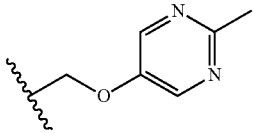

(hereinafter referred to as "R⁴ is R422").

R⁴ is 6-membered aromatic heterocyclyl optionally substituted with the substituent group β1 (hereinafter referred to as "R⁴ is R423").

R⁴ is —CH₂—R⁶, and R⁶ is pyrazinyloxy optionally substituted with the substituent group β1 (hereinafter referred to as "R⁴ is R424").

R⁴ is a group represented by:

[Chemical Formula 116]

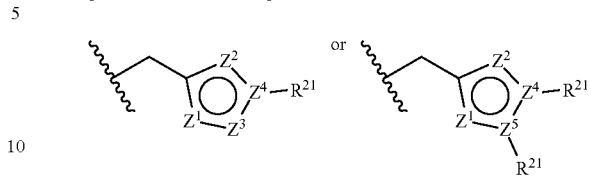

wherein $Z^1$ to $Z^3$ are each independently C, CH, N, O or S; $Z^4$ and $Z^5$ are each independently C or N; a ring composed of $Z^1$ to $Z^4$ and a carbon atom is a 5-membered aromatic heterocycle; a ring composed of $Z^1$, $Z^2$, $Z^4$, $Z^5$ and a carbon atom is a 5-membered aromatic heterocycle; and $R^{21}$ is each independently C1-C3 alkyl (hereinafter referred to as "R⁴ is R425").

R⁴ is a group represented by:

[Chemical Formula 117]

wherein $Z^1$ to $Z^3$ are each independently C, CH, or N; $Z^4$ and $Z^5$ are each independently C or N; a ring composed of $Z^1$ to $Z^4$ and a carbon atom is a triazole ring; a ring composed of $Z^1$, $Z^2$, $Z^4$, $Z^5$ and a carbon atom is a triazole ring; and $R^{21}$ is each independently C1-C3 alkyl (hereinafter referred to as "R⁴ is R426").

R⁴ is a group represented by:

[Chemical Formula 118]

wherein $Z^1$ to $Z^3$ are each independently C, CH, or N; $Z^4$ is C or N; a ring composed of $Z^1$ to $Z^4$ and a carbon atom is a triazole ring; and $R^{21}$ is each independently C1-C3 alkyl (hereinafter referred to as "R⁴ is R427").

R⁴ is a group represented by:

[Chemical Formula 119]

wherein $R^{21}$ is C1-C3 alkyl (hereinafter referred to as "R⁴ is R428").

$R^4$ is a group represented by:

[Chemical Formula 120]

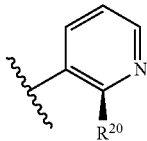

wherein $R^{20}$ is haloalkyl (hereinafter referred to as "$R^4$ is R429").

Examples of the compound represented by Formula (IA)' include all the embodiments which are the combinations of:
A is one embodiment selected from A1 to A3;
$R^{1a}$ is one embodiment selected from R1A1 to R1A13;
$R^{2a}$ to $R^{2d}$ are one embodiment selected from R21 to R25;
$R^3$ is one embodiment selected from R31 to R36;
r is one embodiment selected from r1 to r7;
Ring B is one embodiment selected from B1 to B13; and
$R^4$ is one embodiment selected from R41 to R429.

Examples of other embodiments of the compound represented by Formula (IA)' include all the embodiments which are the combinations of:
A is one embodiment selected from A1 to A3;
$R^{1a}$ is one embodiment selected from R1A1 to R1A13;
$R^{2a}$ to $R^{2d}$ are one embodiment selected from R21 to R25;
cyclyl ab is one embodiment selected from ab1 to ab7;
s is one embodiment selected from s1 to s3;
$R^{16}$ is R161 or R162; and
$R^4$ is one embodiment selected from R41 to R429.

Examples of the compound represented by Formula (IA) include all the embodiments which are the combinations of:
$R^{1a}$ is one embodiment selected from R1A1 to R1A13;
$R^{2a}$ to $R^{2d}$ are one embodiment selected from R21 to R25;
$R^3$ is one embodiment selected from R31 to R36;
r is one embodiment selected from r1 to r7;
Ring B is one embodiment selected from B1 to B13; and
$R^4$ is one embodiment selected from R41 to R428.

Examples of other embodiments of the compound represented by Formula (IA) include all the embodiments which are the combinations of:
$R^{1a}$ is one embodiment selected from R1A1 to R1A13;
$R^{2a}$ to $R^{2d}$ are one embodiment selected from R21 to R25;
cyclyl ab is one embodiment selected from ab1 to ab7;
s is one embodiment selected from s1 to s3;
$R^{16}$ is R161 or R162; and
$R^4$ is one embodiment selected from R41 to R429.

Examples of the compound represented by Formula (IB) include all the embodiments which are the combinations of:
$R^{1b}$ is one embodiment selected from R1B1 to R1B14;
$R^{1d}$ and $R^{1e}$ are R1DE1 or R1DE3;
$R^{2a}$ to $R^{2d}$ are one embodiment selected from R21 to R25;
$R^3$ is one embodiment selected from R31 to R36;
r is one embodiment selected from r1 to r7;
Ring B is one embodiment selected from B1 to B13; and
$R^4$ is one embodiment selected from R41 to R429.

Examples of other embodiments of the compound represented by Formula (IB) include all the embodiments which are the combinations of:
$R^{1b}$ is one embodiment selected from R1B1 to R1B14;
$R^{1d}$ and $R^{1e}$ are R1DE1 or R1DE3;
$R^{2a}$ to $R^{2d}$ are one embodiment selected from R21 to R25;
cyclyl ab is one embodiment selected from ab1 to ab7;
s is one embodiment selected from s1 to s3;
$R^{16}$ is R161 or R162; and
$R^4$ is one embodiment selected from R41 to R429.

Examples of the compound represented by Formula (IC)' include all the embodiments which are the combinations of:
A is one embodiment selected from A1 to A3;
$R^{1a}$ is one embodiment selected from R1C1 to R1C7;
$R^{2a}$ to $R^{2d}$ are one embodiment selected from R21 to R25;
$R^3$ is one embodiment selected from R31 to R36;
r is one embodiment selected from r1 to r7;
Ring B is one embodiment selected from B1 to B13; and
$R^4$ is one embodiment selected from R41 to R429.

Examples of other embodiments of the compound represented by Formula (IC)' include all the embodiments which are the combinations of:
A is one embodiment selected from A1 to A3;
$R^{1a}$ is one embodiment selected from R1C1 to R1C7;
$R^{2a}$ to $R^{2d}$ are one embodiment selected from R21 to R25;
cyclyl ab is one embodiment selected from ab1 to ab7;
s is one embodiment selected from s1 to s3;
$R^{16}$ is R161 or R162; and
$R^4$ is one embodiment selected from R41 to R429.

Examples of the compound represented by Formula (IC) include all the embodiments which are the combinations of:
$R^{1a}$ is one embodiment selected from R1C1 to R1C7;
$R^{2a}$ to $R^{2d}$ are one embodiment selected from R21 to R25;
$R^3$ is one embodiment selected from R31 to R36;
r is one embodiment selected from r1 to r7;
Ring B is one embodiment selected from B1 to B13; and
$R^4$ is one embodiment selected from R41 to R429.

Examples of other embodiments of the compound represented by Formula (IC) include all the embodiments which are the combinations of:
$R^{1a}$ is one embodiment selected from R1C1 to R1C7;
$R^{2a}$ to $R^{2d}$ are one embodiment selected from R21 to R25;
cyclyl ab is one embodiment selected from ab1 to ab7;
s is one embodiment selected from s1 to s3;
$R^{16}$ is R161 or R162; and
$R^4$ is one embodiment selected from R41 to R429.

Examples of the compound represented by Formula (ID-1)' include all the embodiments which are the combinations of:
A is one embodiment selected from A1 to A3;
$R^{1g}$ is one embodiment selected from R1GH1 to R1GH6;
p is one embodiment selected from p1 to p3;
$R^{2a}$ to $R^{2d}$ are one embodiment selected from R21 to R25;
cyclyl ab is one embodiment selected from ab1 to ab7;
$R^{16}$ is R161 or R162;
s is one embodiment selected from s1 to s3;
$R^{16}$ is R161 or R162; and
$R^4$ is one embodiment selected from R41 to R429.

Examples of the compound represented by Formula (ID-1) include all the embodiments which are the combinations of:
$R^{1g}$ is one embodiment selected from R1GH1 to R1GH6;
p is one embodiment selected from p1 to p3;
$R^{2a}$ to $R^{2d}$ are one embodiment selected from R21 to R25;
cyclyl ab is one embodiment selected from ab1 to ab7;
$R^{16}$ is R161 or R162;
s is one embodiment selected from s1 to s3;
$R^{16}$ is R161 or R162; and
$R^4$ is one embodiment selected from R41 to R429.

Examples of the compound represented by Formula (ID-2) include all the embodiments which are the combinations of:

$R^{1g}$ is one embodiment selected from R1GH1 to R1GH6;

p is one embodiment selected from p1 to p3;

$R^{2a}$ to $R^{2d}$ are one embodiment selected from R21 to R25;

$X^1$ and $X^2$ are one embodiment selected from X1 to X3;

s is one embodiment selected from s1 to s3;

$R^{16}$ is R161 or R162; and $R^4$ is one embodiment selected from R41 to R429.

Examples of the compound represented by Formula (IE-1) include all the embodiments which are the combinations of:

$Y^1$ to $Y^3$ are one embodiment selected from Y1 to Y4;

$R^{1h}$ is one embodiment selected from R1GH1 to R1GH6;

$R^{1d}$ to $R^{1f}$ are one embodiment selected from R1DEF1 to R1DEF3;

p is one embodiment selected from p1 to p3;

$R^{2a}$ to $R^{2d}$ are one embodiment selected from R21 to R25;

cyclyl ab is one embodiment selected from R31 to R36;

s is one embodiment selected from s1 to s3;

$R^{16}$ is R161 or R162; and $R^4$ is one embodiment selected from R41 to R429.

Examples of the compound represented by Formula (IE-2) include all the embodiments which are the combinations of:

$R^{1h}$ is one embodiment selected from R1GH1 to R1GH6;

p is one embodiment selected from p1 to p3;

$R^{2a}$ to $R^{2d}$ are one embodiment selected from R21 to R25;

$X^1$ and $X^2$ are one embodiment selected from X1 to X3;

s is one embodiment selected from s1 to s3;

$R^{16}$ is R161 or R162; and $R^4$ is one embodiment selected from R41 to R429.

Examples of other embodiments of a compound represented by Formula (IA)' to (IE-2) or a pharmaceutically acceptable salt thereof are shown below.

In Formula (IA)', A is O;

$R^{1a}$ is substituted or unsubstituted alkyloxy;

$R^{2a}$ to $R^{2d}$ are each independently a hydrogen atom, halogen, hydroxy, cyano, substituted or unsubstituted C1-C6 alkyl, or substituted or unsubstituted C1-C6 alkyloxy;

$R^3$ is each independently halogen;

two $R^3$ s attached to different ring-constituting atoms may be taken together to form a bond or a substituted or unsubstituted C2 bridge wherein one of carbon atoms constituting the C2 bridge may be replaced with an oxygen atom or a nitrogen atom;

Ring B is a 4- to 8-membered non-aromatic carbocycle or a 4- to 8-membered non-aromatic heterocycle;

r is an integer of 0 to 4;

$R^4$ is substituted or unsubstituted aromatic carbocyclyl, substituted or unsubstituted non-aromatic heterocyclyl, substituted or unsubstituted aromatic heterocyclyl, $-CR^{5a}R^{5b}-R^6$, or $-CR^{7a}=CR^{7b}-R^8$;

$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;

$R^6$ is substituted or unsubstituted non-aromatic heterocyclyl, substituted or unsubstituted aromatic heterocyclyl, substituted or unsubstituted aromatic heterocyclyloxy, or substituted or unsubstituted non-aromatic heterocyclyloxy; and $R^8$ is substituted or unsubstituted non-aromatic heterocyclyl or substituted or unsubstituted aromatic heterocyclyl.

In Formula (IA) or (IB), $R^{1a}$ and $R^{1b}$ are each independently a group represented by:

[Chemical Formula 121]

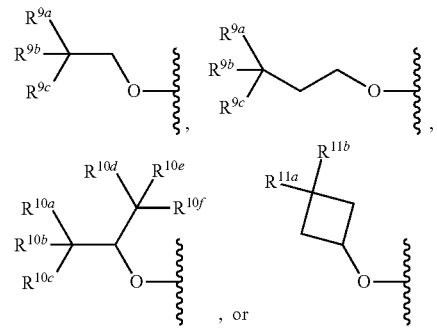

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen; $R^{11d}$ and $R^{11e}$ are hydrogen atoms; $R^{2a}$ and $R^{2b}$ are hydrogen atoms, $R^{2c}$ is a hydrogen atom, $R^{2d}$ is a hydrogen atom or C1-C6 alkyloxy; $R^3$ is halogen, or two $R^3$s attached to different ring-constituting atoms may be taken together to form a substituted or unsubstituted (C1-C3) bridge; r is an integer of 0 to 4; and ring B is a 6-membered non-aromatic carbocycle, a 6-membered non-aromatic heterocycle, or a spiroheptane ring; and $R^4$ is R41, preferably R42, more preferably R47, particularly preferably R416.

More preferably, a case wherein $R^{1a}$ and $R^{1b}$ are groups represented by:

[Chemical Formula 122]

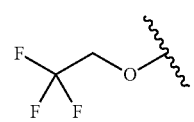

is excluded.

In Formula (IA) or (IB), $R^{1a}$ and $R^{1b}$ are each independently a group represented by:

[Chemical Formula 123]

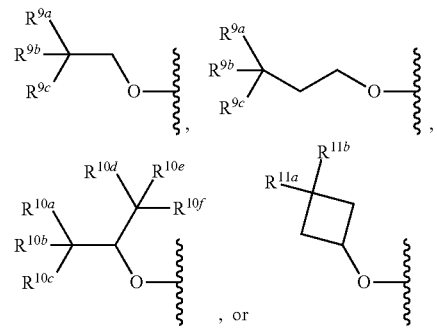

wherein $R^{9a}$ is halogen; $R^{9b}$ and $R^{9c}$ are each independently a hydrogen atom, halogen, or methyl; $R^{10a}$ to $R^{10f}$ are each independently a hydrogen atom, halogen, or methyl; and $R^{11a}$ and $R^{11b}$ are each independently a hydrogen atom or halogen;
$R^{1d}$ and $R^{1e}$ are hydrogen atoms; $R^{2a}$ and $R^{2b}$ are hydrogen atoms, $R^{2c}$ is a hydrogen atom, $R^{2d}$ is a hydrogen atom or C1-C6 alkyloxy; $R^3$ is halogen; r is an integer of 1 to 3; ring B is a 6-membered non-aromatic carbocycle, a 6-membered non-aromatic heterocycle, or a spiroheptane ring; and $R^4$ is R41, preferably R42, more preferably R47, particularly preferably R416.

More preferably, a case wherein $R^{1a}$ and $R^{1b}$ are groups represented by:

[Chemical Formula 124]

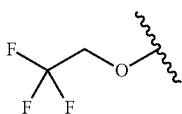

is excluded.

In Formula (IA) or (IB), $R^{1a}$ and $R^{1b}$ are groups represented by:

[Chemical Formula 125]

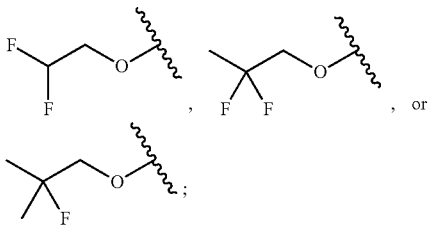

$R^{2a}$ and $R^{2b}$ are hydrogen atoms, $R^{2c}$ is a hydrogen atom, $R^{2d}$ is a hydrogen atom or C1-C6 alkyloxy; $R^3$ is halogen; r is an integer of 0 to 4; ring B is a 6-membered non-aromatic carbocycle, a 6-membered non-aromatic heterocycle, or a spiroheptane ring; and $R^4$ is R42, preferably R43, more preferably R47.

In Formula (IA) or (IB), $R^{1a}$ and $R^{1b}$ are groups represented by:

[Chemical Formula 126]

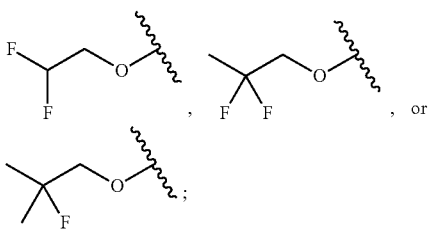

$R^{2a}$ and $R^{2b}$ are hydrogen atoms, $R^{2c}$ is a hydrogen atom, $R^{2d}$ is a hydrogen atom or C1-C6 alkyloxy; $R^3$ is halogen; r is an integer of 1 to 3; ring B is a 6-membered non-aromatic carbocycle, a 6-membered non-aromatic heterocycle, or a spiroheptane ring; and $R^4$ is R42, preferably R43, more preferably R47.

In Formula (IA), $R^{1a}$ is a group represented by:

[Chemical Formula 127]

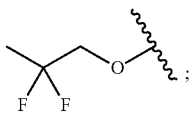

$R^{2a}$ and $R^{2b}$ are hydrogen atoms, $R^{2c}$ is a hydrogen atom, $R^{2d}$ is a hydrogen atom or C1-C6 alkyloxy; $R^3$ is halogen; r is an integer of 0 to 4; ring B is a cyclohexane ring or a tetrahydropyran ring; and $R^4$ is R42, preferably R43, more preferably R47, further more preferably R416, particularly preferably R422.

In Formula (IA), $R^{1a}$ is a group represented by:

[Chemical Formula 128]

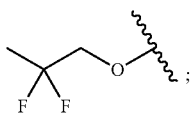

$R^{2a}$ and $R^{2b}$ are hydrogen atoms, $R^{2c}$ and $R^{2d}$ are hydrogen atoms; $R^3$ is halogen; r is an integer of 0 to 2; ring B is a cyclohexane ring or a tetrahydropyran ring; and $R^4$ is —$CH_2$—$R^6$, and Re is triazolyl optionally substituted with the substituent group β1, or 6-membered aromatic heterocyclyloxy optionally substituted with the substituent group β1.

In Formula (IA), $R^{1a}$ is a group represented by:

[Chemical Formula 129]

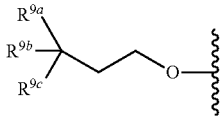

wherein $R^{9a}$ to $R^{9c}$ are each independently halogen;

$R^{2a}$ and $R^{2b}$ are hydrogen atoms, $R^{2c}$ is a hydrogen atom, $R^{2d}$ is a hydrogen atom or C1-C6 alkyloxy; $R^3$ is halogen; r is an integer of 0 to 4; ring B is a cyclohexane ring; and $R^4$ is R42, preferably R43, more preferably R47.

In Formula (IA) or (IB), $R^{1a}$ and $R^{1b}$ are C1-C6 haloalkyloxy; $R^{2a}$ and $R^{2b}$ are hydrogen atoms, $R^{2c}$ is a hydrogen atom, $R^{2d}$ is a hydrogen atom or C1-C6 alkyloxy; $R^3$ is each independently halogen, or two $R^3$ s attached to different ring-constituting atoms may be taken together to form a C2 bridge wherein one of carbon atoms constituting the C2 bridge may be replaced with an oxygen atom; r is an integer of 0 to 4, preferably an integer of 1 to 4; ring B is a cyclohexane ring or a tetrahydropyran ring; and $R^4$ is R47, preferably R48, more preferably R416, further more preferably R417.

In Formula (IA), $R^{1a}$ is a group represented by:

[Chemical Formula 130]

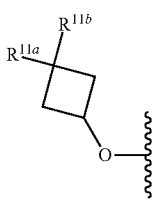

wherein $R^{11a}$ and $R^{11b}$ are each independently halogen; $R^{2a}$ and $R^{2b}$ are hydrogen atoms, $R^{2c}$ is a hydrogen atom, $R^{2d}$ is a hydrogen atom or C1-C6 alkyloxy; r is 0; ring B is a cyclohexane ring;

$R^4$ is substituted or unsubstituted pyridyl, $-CH_2-R^6$, or $-CH=CH-R^8$;

$R^6$ is substituted or unsubstituted oxazolyl, substituted or unsubstituted oxadiazolyl, substituted or unsubstituted pyrazolyl, substituted or unsubstituted triazolyl, substituted or unsubstituted thiadiazolyl, substituted or unsubstituted pyrimidinyloxy, or substituted or unsubstituted isoxazolyloxy; and $R^8$ is substituted or unsubstituted pyrimidinyl.

In Formula (B), $R^{1b}$ is C2-C4 alkyloxy optionally substituted with one or more halogen; $R^{2a}$ and $R^{2b}$ are hydrogen atoms, $R^{2c}$ is a hydrogen atom, $R^{2d}$ is a hydrogen atom or C1-C6 alkyloxy; $R^3$ is each independently halogen; r is an integer of 0 to 4; ring B is a cyclohexane ring or a piperidine ring; and $R^4$ is R42, preferably R43, more preferably R47.

In Formula (IB), $R^{1b}$ is a group represented by:

[Chemical Formula 131]

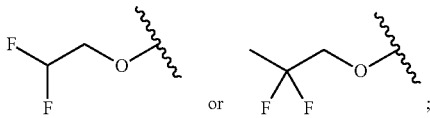

$R^{2a}$ and $R^{2b}$ are hydrogen atoms, $R^{2c}$ is a hydrogen atom, $R^{2d}$ is a hydrogen atom or C1-C6 alkyloxy; $R^3$ is each independently halogen; r is an integer of 1 to 3;

[Chemical Formula 132]

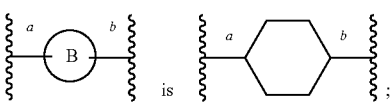

and $R^4$ is R42, preferably R43, more preferably R48.

In Formula (IB), $R^{1b}$ is unsubstituted cyclobutyloxy; $R^{2a}$ and $R^{2b}$ are hydrogen atoms, $R^{2c}$ is a hydrogen atom, $R^{2d}$ is a hydrogen atom or C1-C6 alkyloxy; $R^3$ is each independently halogen; r is an integer of 0 to 4;

[Chemical Formula 133]

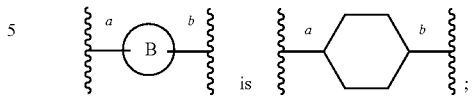

and $R^4$ is R42, preferably R45, more preferably R47.

In Formula (IC), $R^{1c}$ is substituted or unsubstituted C2-C4 alkyloxy; $R^{2a}$ and $R^{2b}$ are hydrogen atoms, $R^{2c}$ is a hydrogen atom, $R^{2d}$ is a hydrogen atom or C1-C6 alkyloxy; $R^3$ is each independently halogen; r is an integer of 0 to 4;

[Chemical Formula 134]

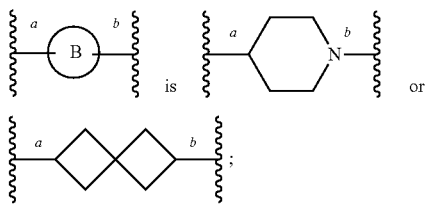

and $R^4$ is R42, preferably R43, more preferably R47.

In Formula (IC), $R^{1c}$ is substituted or unsubstituted C2-C4 alkyloxy; $R^{2a}$ to $R^{2d}$ are hydrogen atoms; r is 0;

[Chemical Formula 135]

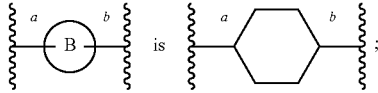

$R^4$ is indazolyl substituted with halogen and alkyl, or $-CH_2-R^6$; and $R^6$ is substituted or unsubstituted triazolyl, or substituted or unsubstituted pyrazinyloxy.

In Formula (IC), $R^{1c}$ is

[Chemical Formula 136]

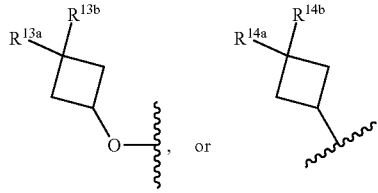

wherein $R^{13a}$ and $R^{14a}$ are each independently halogen; $R^{13b}$ and $R^{14b}$ are each independently a hydrogen atom or halogen;

$R^{2a}$ and $R^{2b}$ are hydrogen atoms, $R^{2c}$ is a hydrogen atom, $R^{2d}$ is a hydrogen atom or C1-C6 alkyloxy; r is 0;

[Chemical Formula 137]

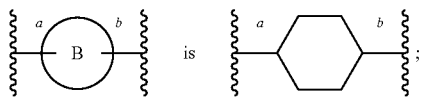 is 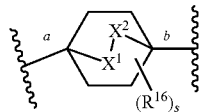 ;

$R^4$ is substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, —$CH_2$—$R^6$, or —CH=CH—$R^8$;

$R^6$ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy; and $R^8$ is substituted or unsubstituted pyrimidinyl or substituted or unsubstituted pyrazolyl.

In Formula (ID-1) or (IE-1), $Y^1$ is $CR^{1d}$ or N; $Y^2$ is $CR^{1e}$ or N; $Y^3$ is N, provided that all of $Y^1$ to $Y^3$ are not simultaneously N;

$R^{1d}$ and $R^{1e}$ are each independently a hydrogen atom or halogen;

$R^{1g}$ and $R^{1h}$ are C1-C6 alkyl unsubstituted or substituted with one or more halogen; C1-C6 alkyloxy unsubstituted or substituted with one or more halogen; cyclobutyl unsubstituted or substituted with one or more halogen; or cyclobutyloxy unsubstituted or substituted with one or more halogen;

p is 1 or 2, preferably 2;

$R^{2a}$ and $R^{2b}$ are hydrogen atoms; $R^{2c}$ and $R^{2d}$ are each independently a hydrogen atom, or C1-C6 alkyloxy unsubstituted or substituted with one or more halogen;

cyclyl ab is a group represented by:

[Chemical Formula 138]

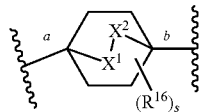

wherein $X^1$ is $CH_2$ or O; $X^2$ is $CH_2$;

$R^{16}$ is each independently halogen; s is an integer of 0 to 2;

$R^4$ is phenyl optionally substituted with the substituent group β1, 6-membered or bicyclic non-aromatic heterocyclyl optionally substituted with the substituent group β2, 6-membered or bicyclic aromatic heterocyclyl optionally substituted with the substituent group β1, —$CH_2$—$R^6$, or —CH=CH—$R^8$;

$R^6$ is 5- or 6-membered non-aromatic heterocyclyl optionally substituted with the substituent group β2, 5- or 6-membered aromatic heterocyclyl optionally substituted with the substituent group β1, 5- or 6-membered aromatic heterocyclyloxy optionally substituted with the substituent group β1, or 5- or 6-membered non-aromatic heterocyclyloxy optionally substituted with the substituent group B2; and $R^8$ is 5- or 6-membered non-aromatic heterocyclyl optionally substituted with the substituent group β2, or 5- or 6-membered aromatic heterocyclyl optionally substituted with the substituent group β1.

Examples of other embodiments of Formula (IA) are illustrated below.

[Chemical Formula 139]

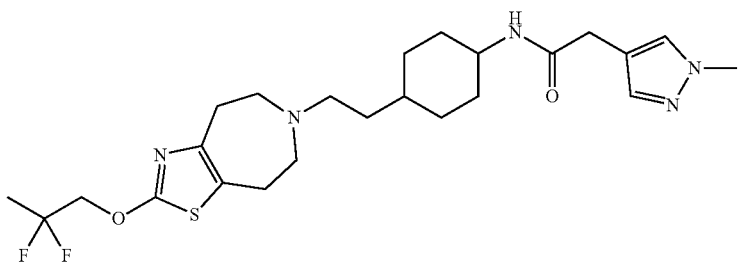

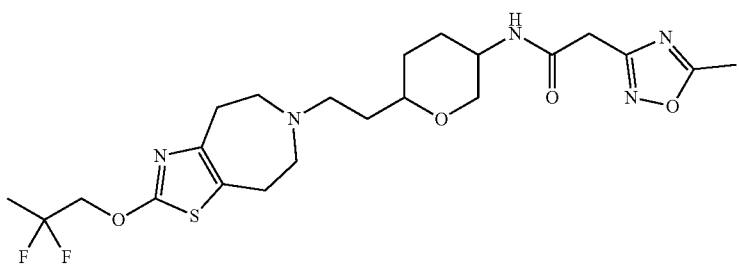

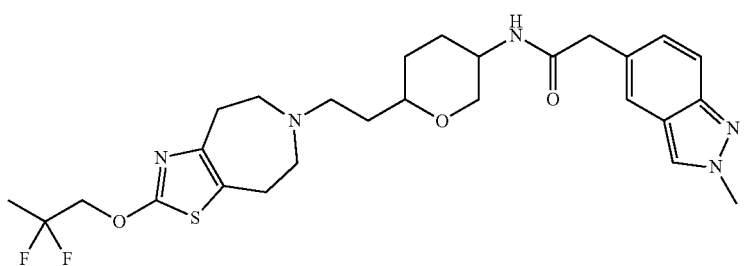
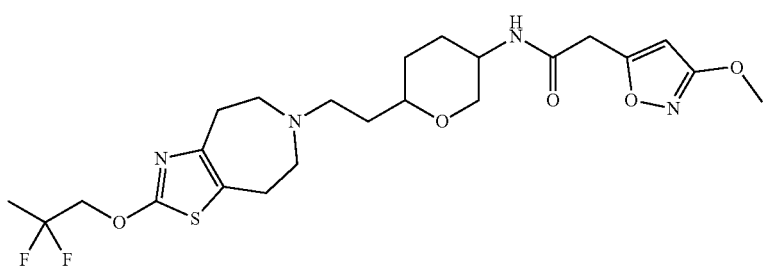
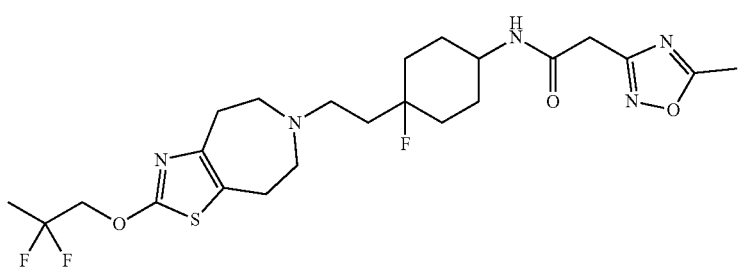
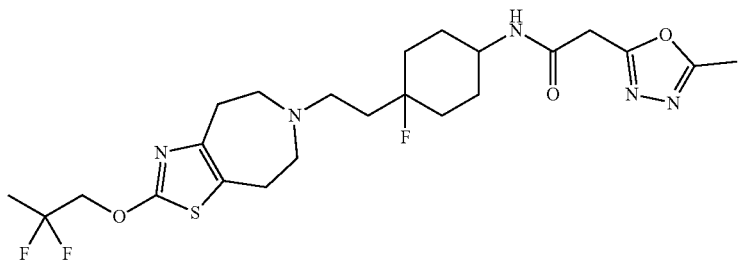
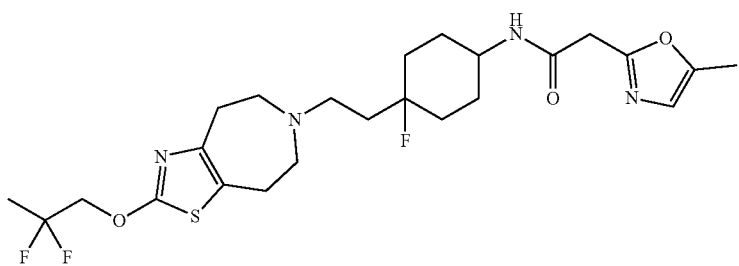
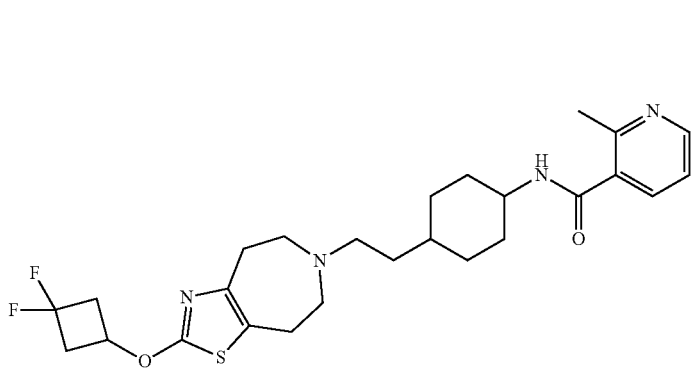

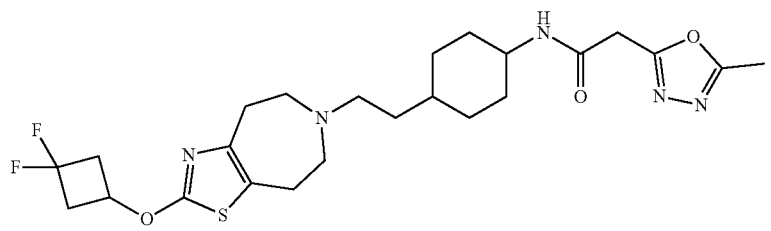
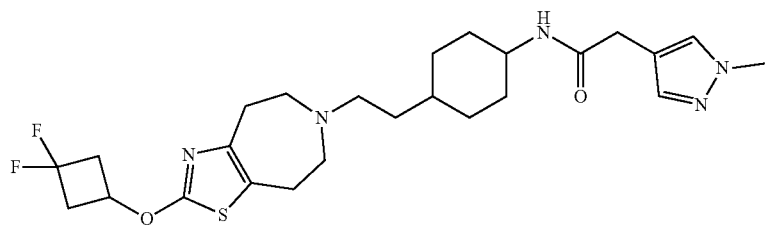
[Chemical Formula 140]
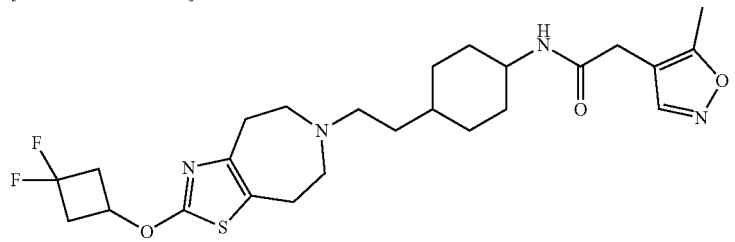
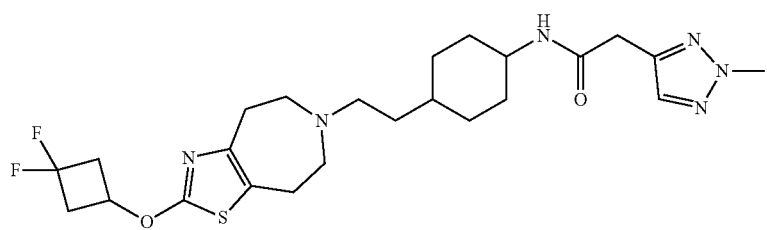
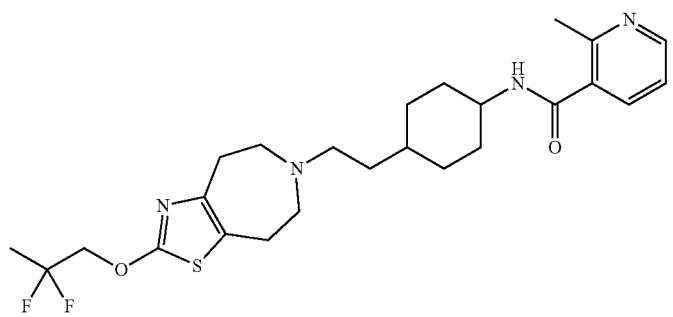
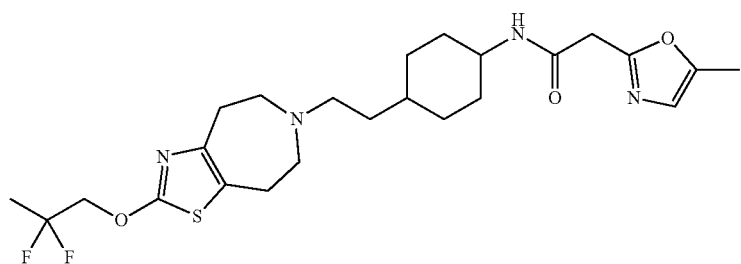

-continued
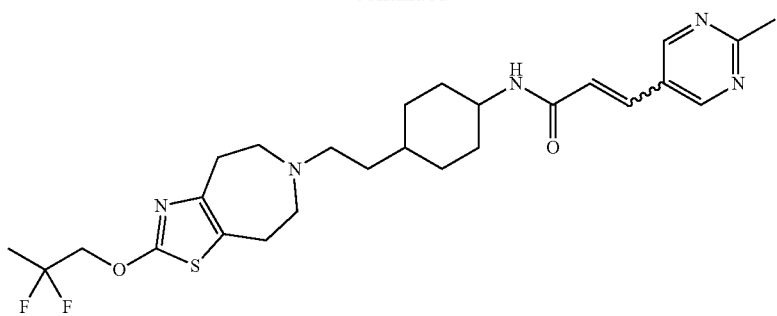
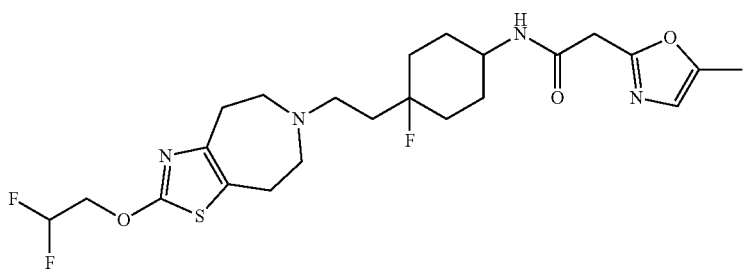
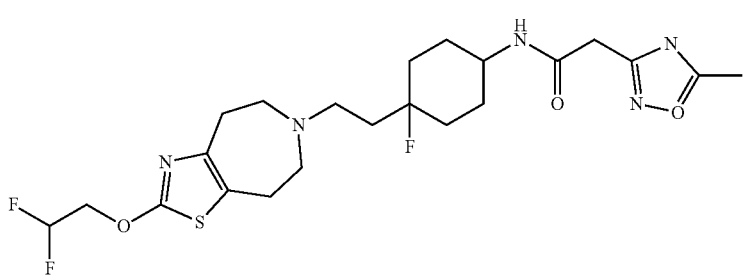
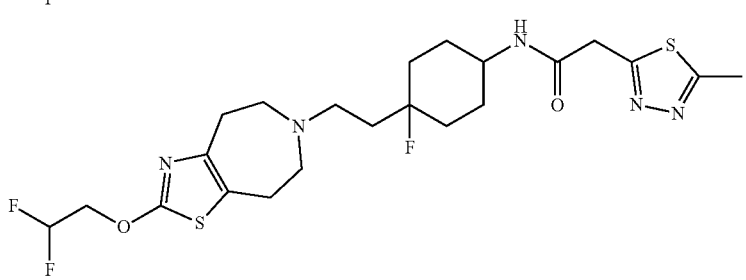
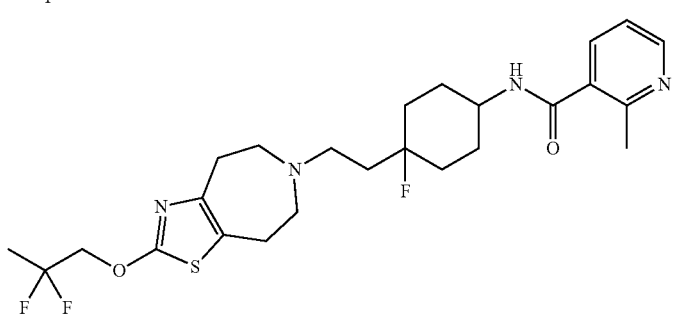
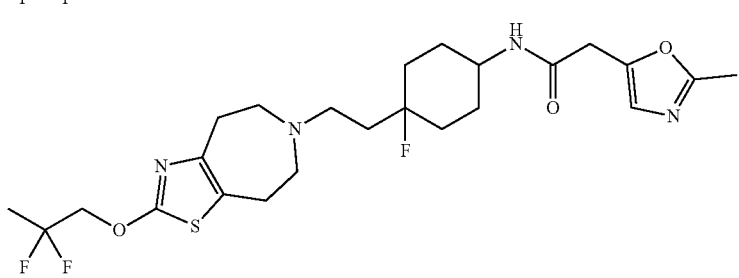

[Chemical Formula 141]
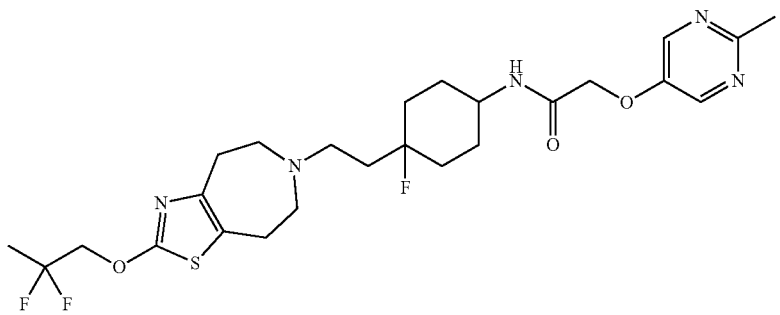
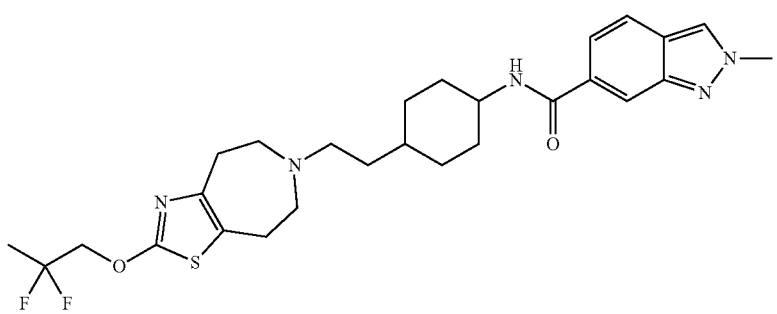
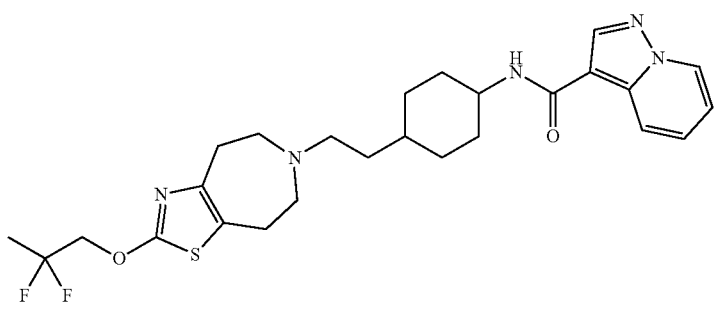
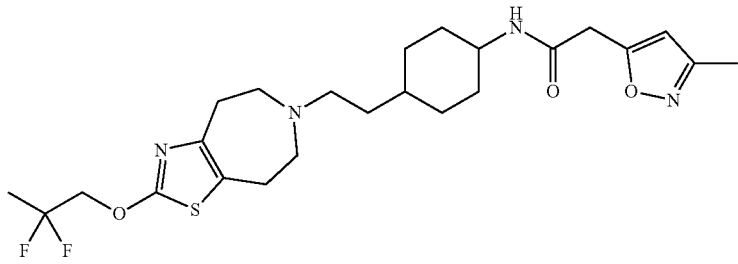
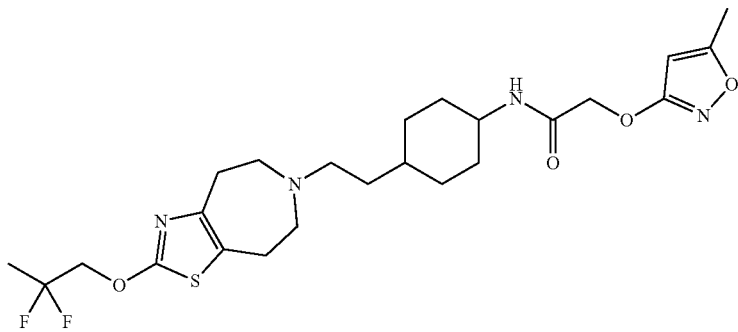

-continued
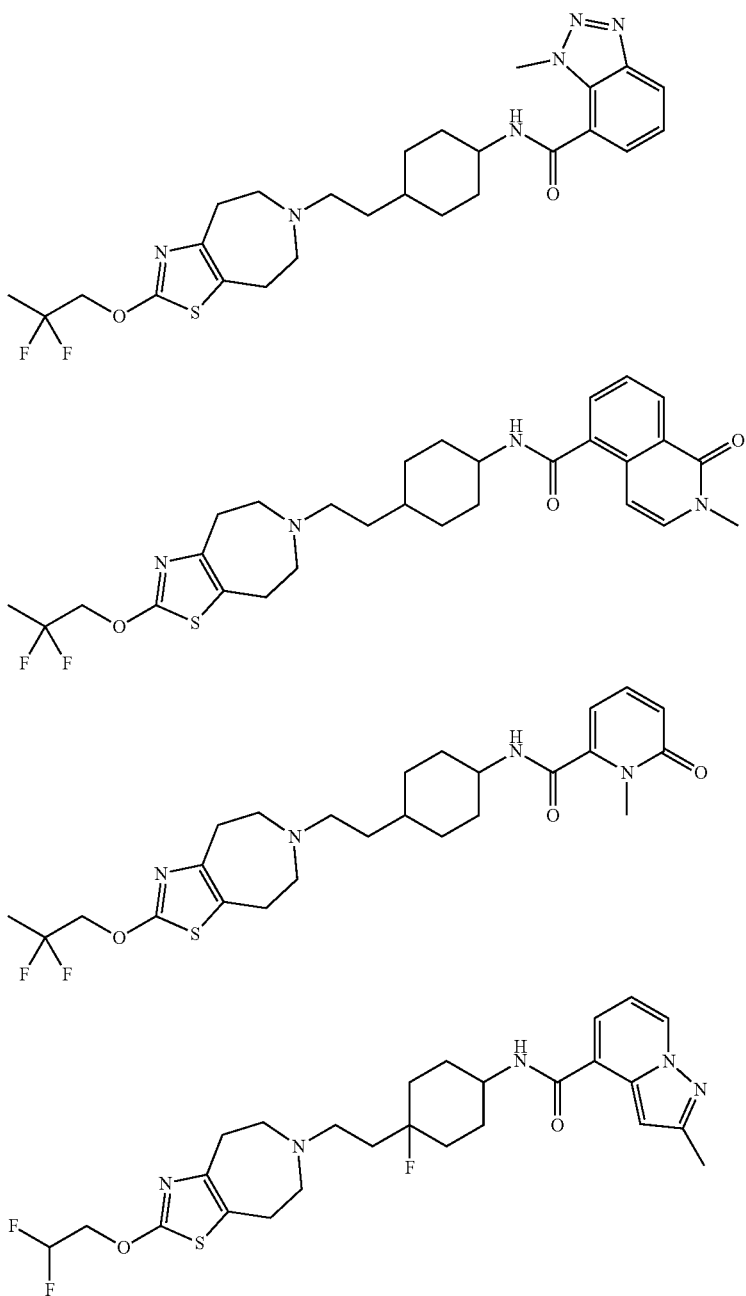
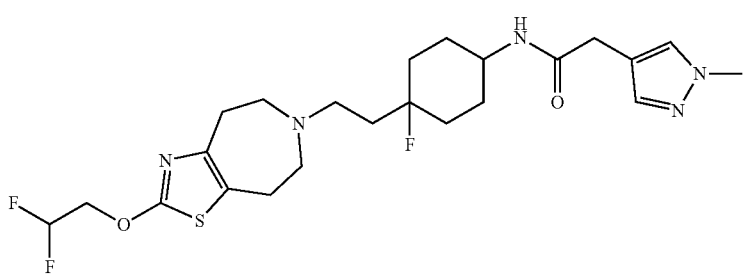

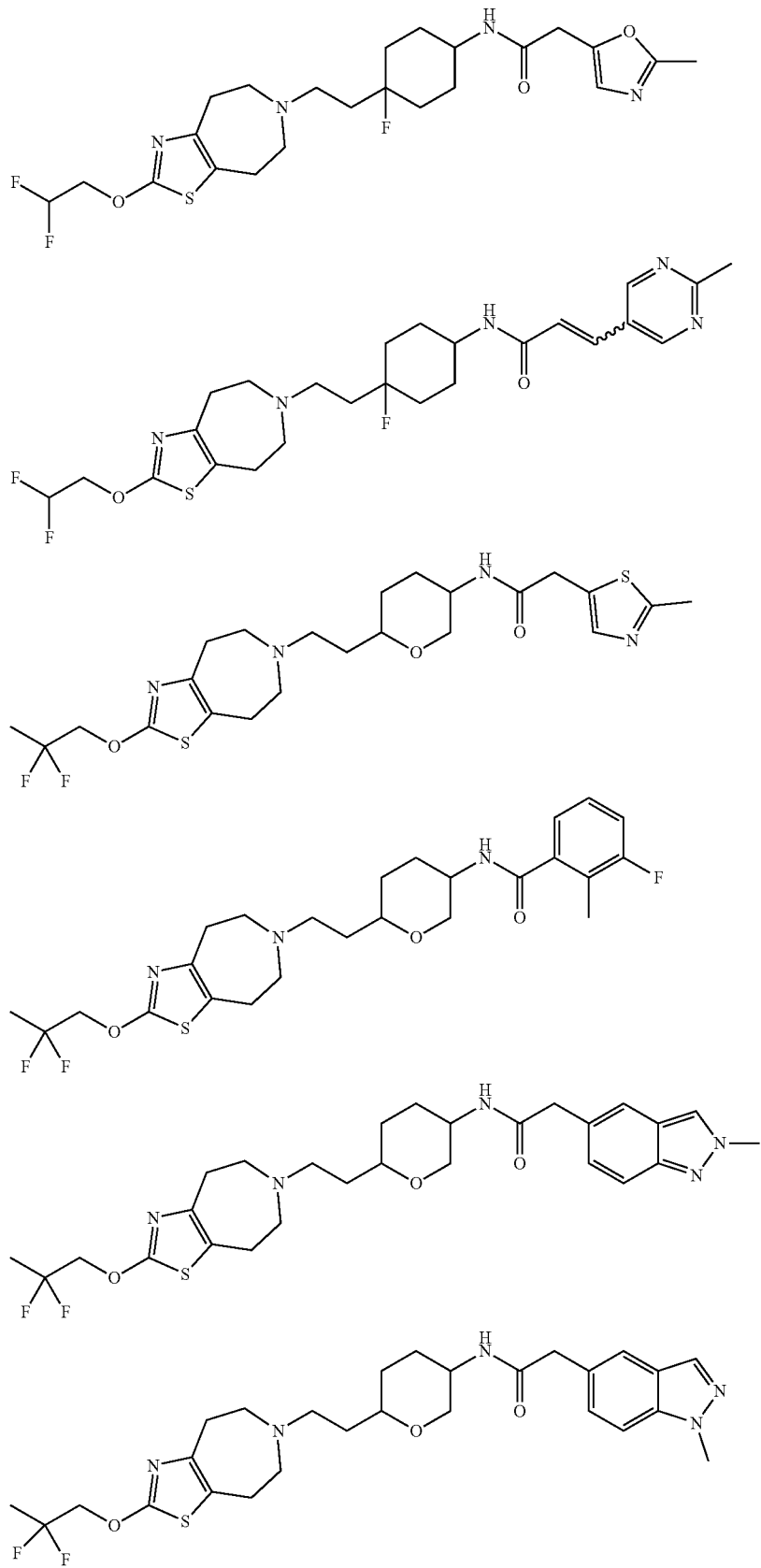

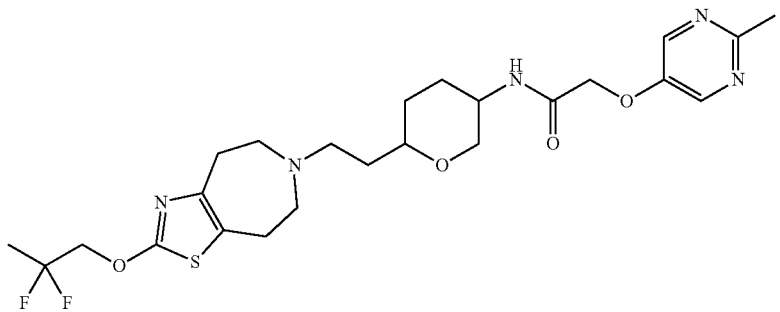
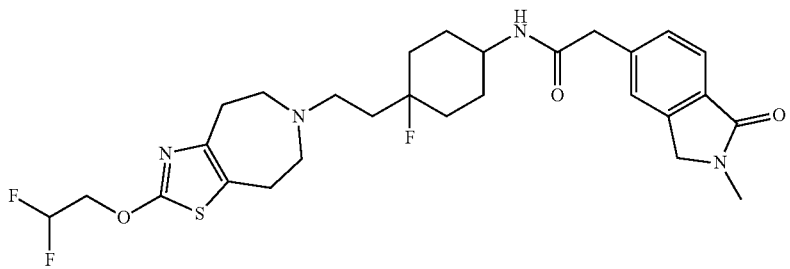
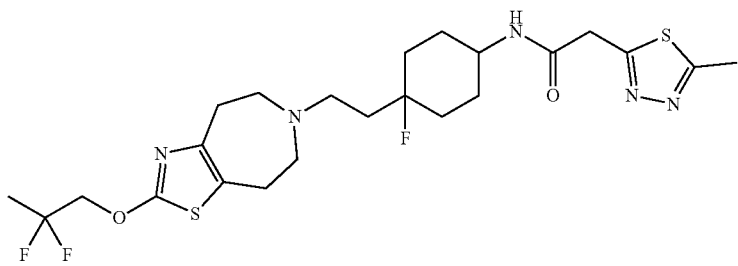
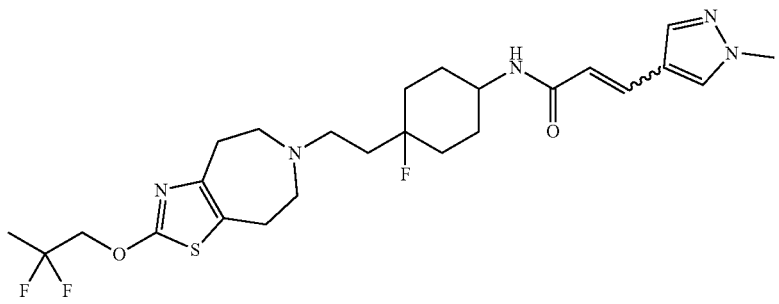
[Chemical Formuka 143]
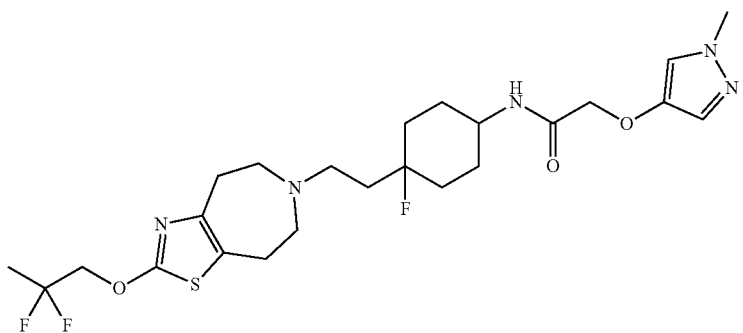

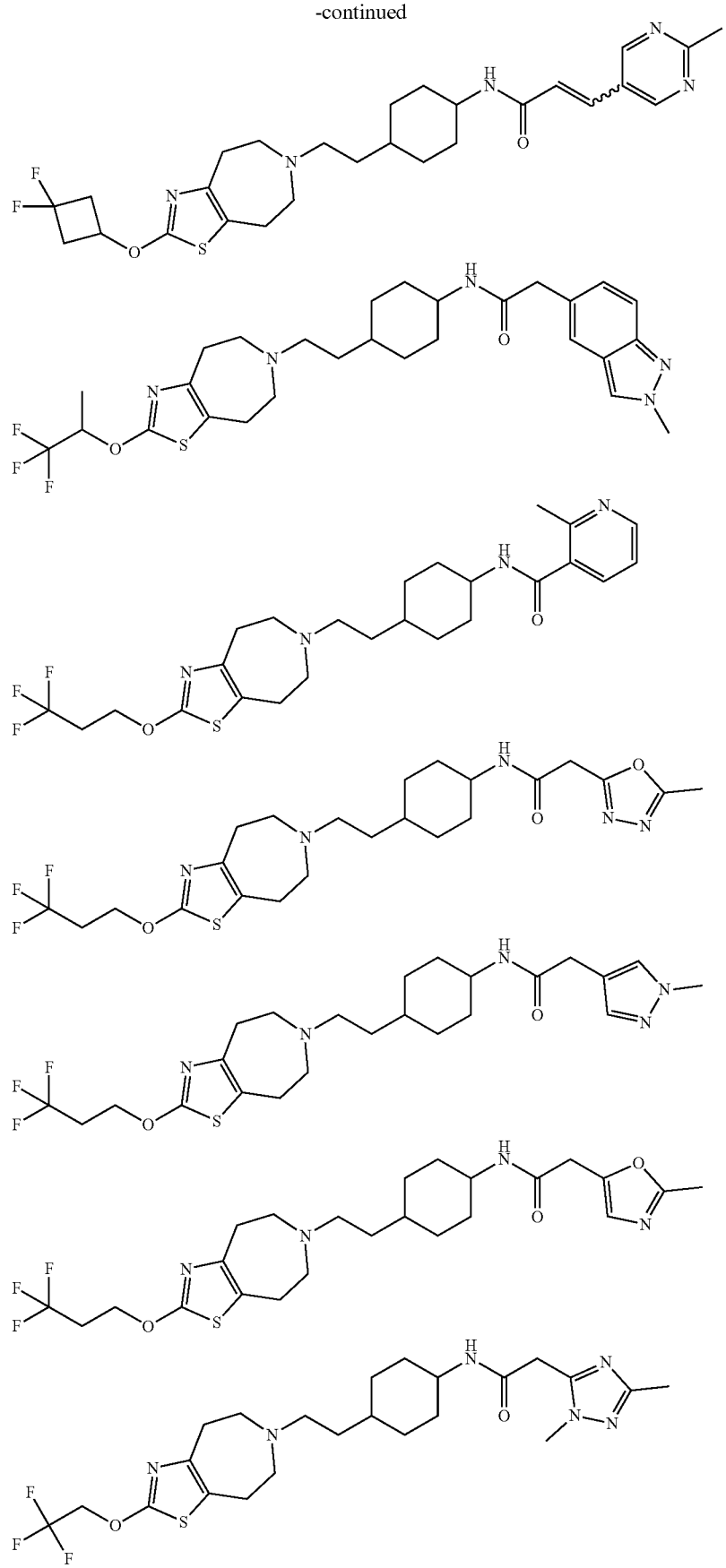

-continued
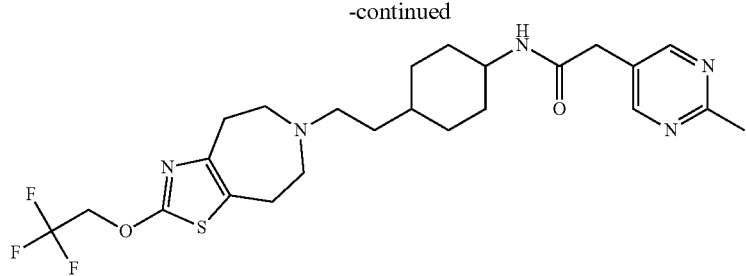
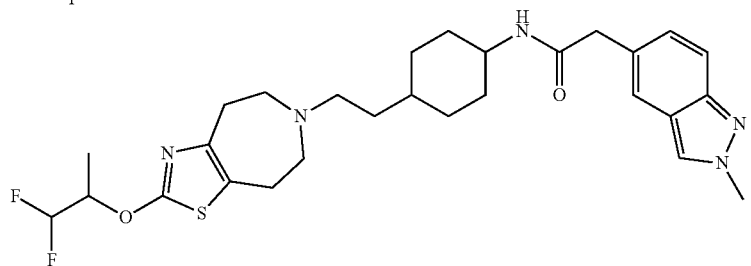
[Chemical Formula 144]
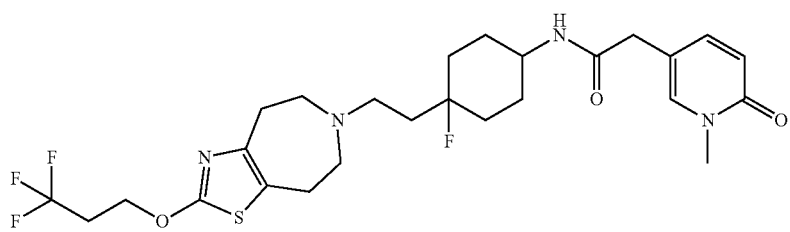
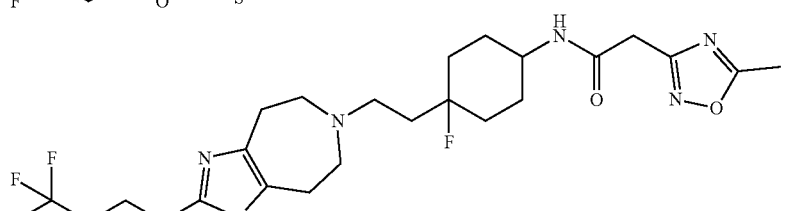
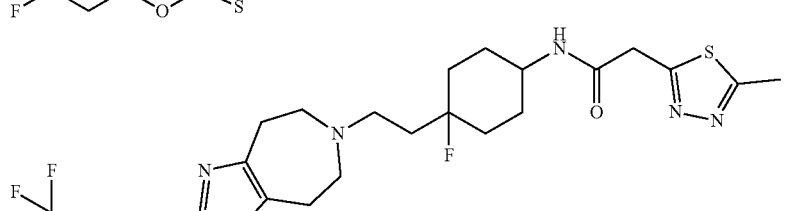
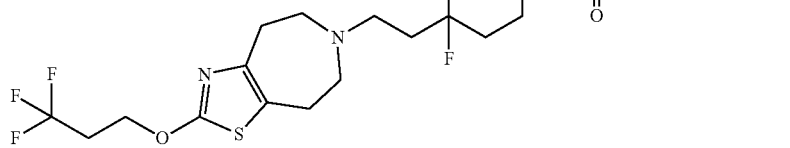
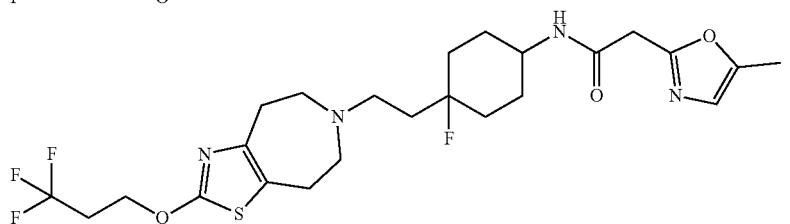

-continued
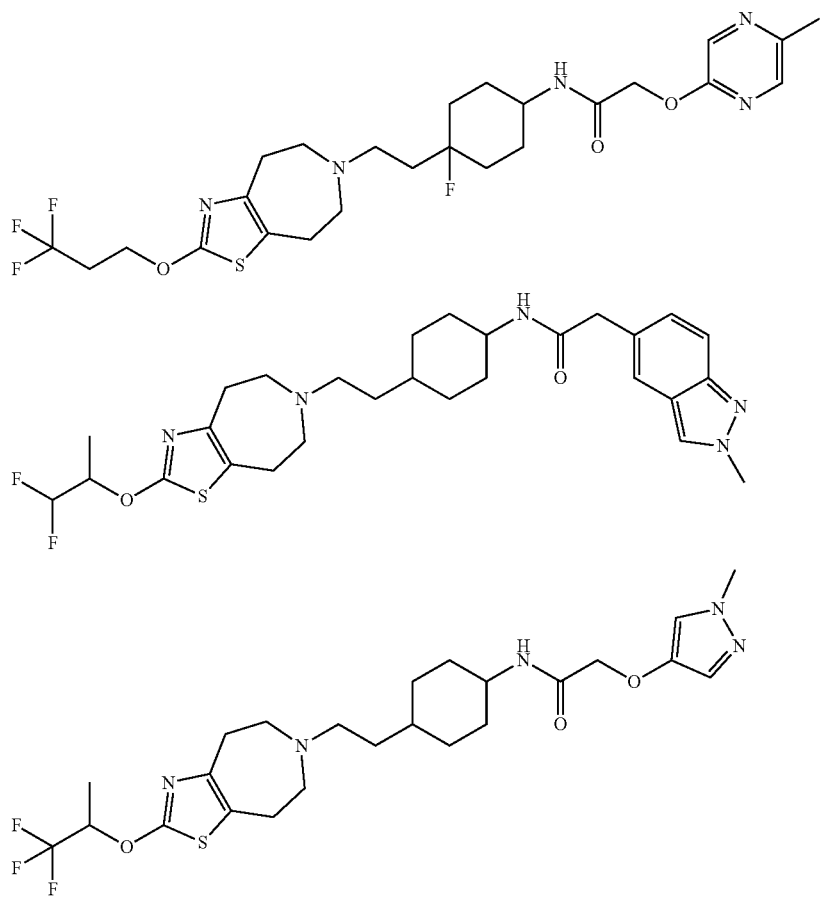
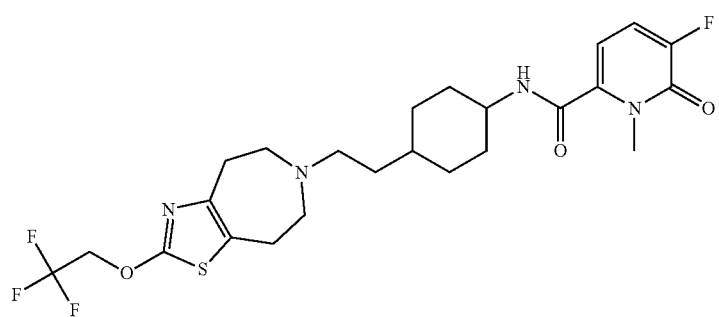
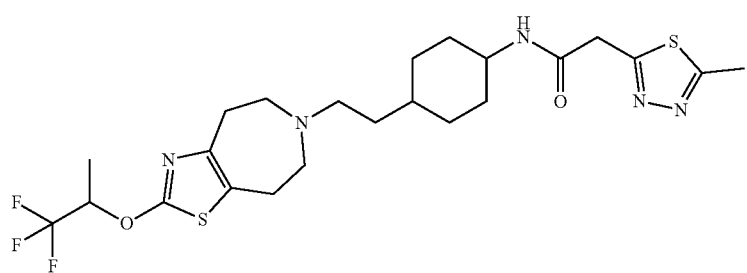

[Chemical Formula 145]
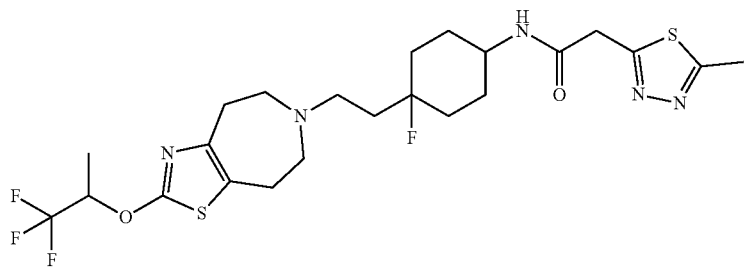
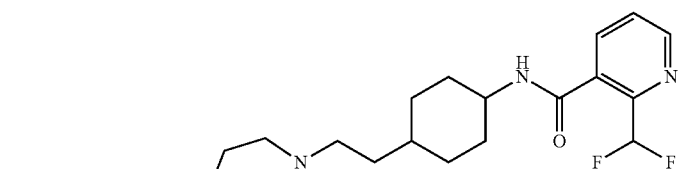
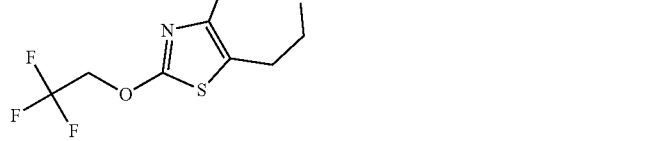
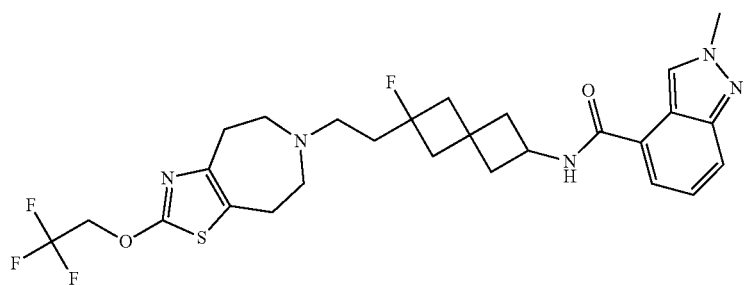
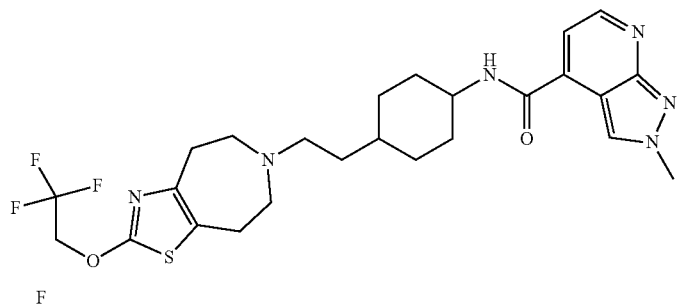
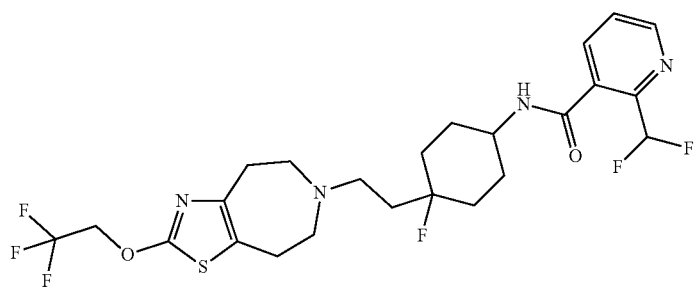

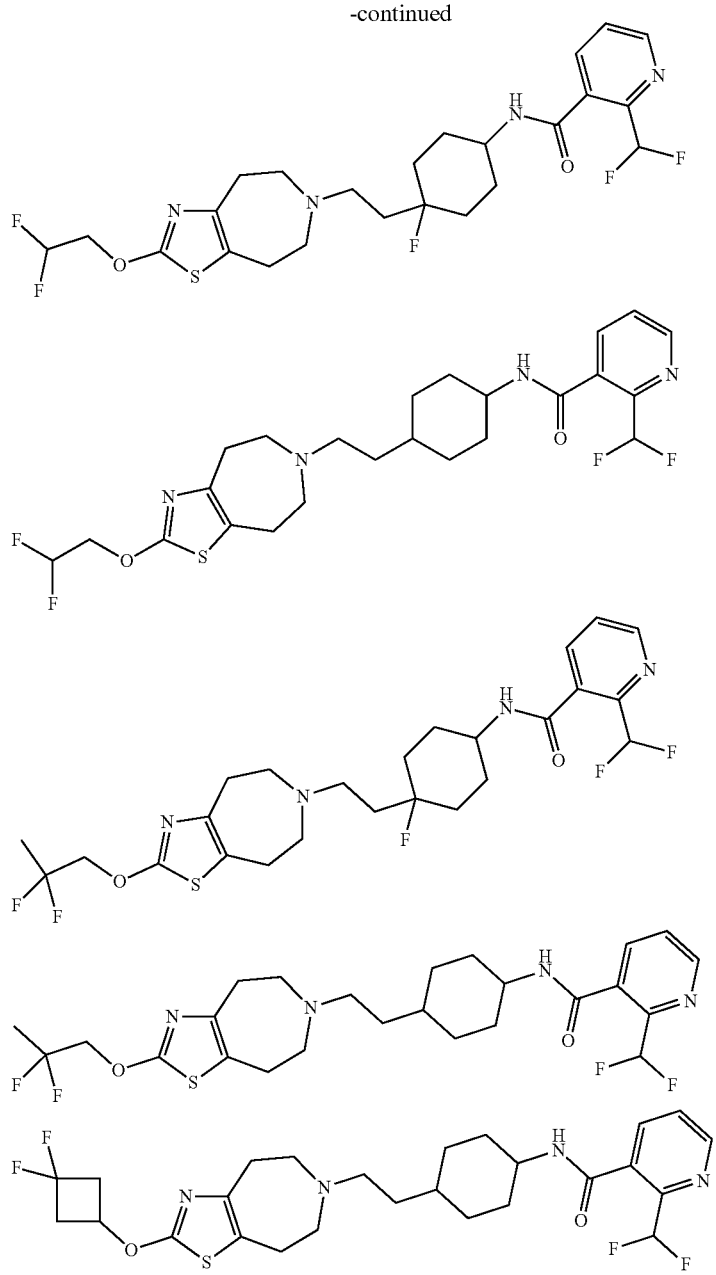
Examples of other embodiments of Formula (IB) are illustrated below.
[Chemical Formula 146]
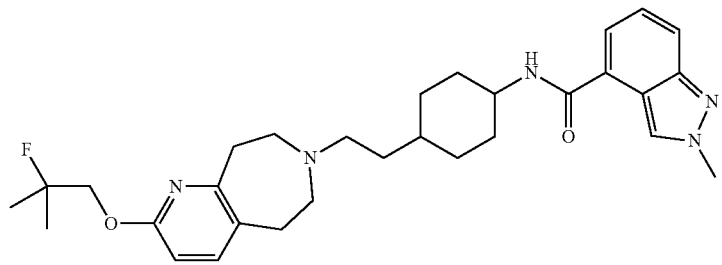

-continued
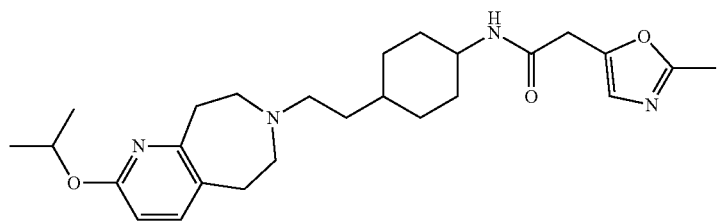
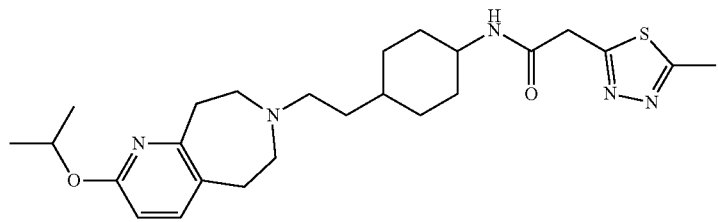
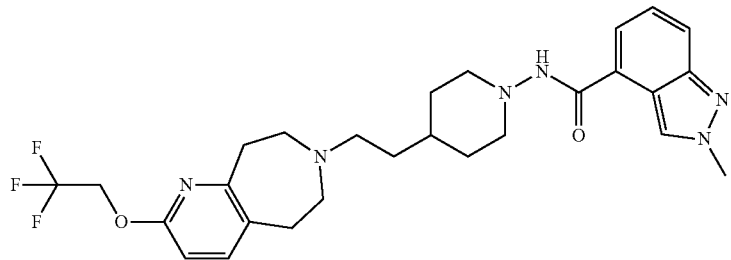
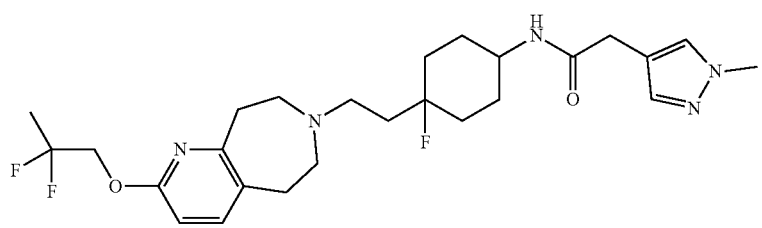
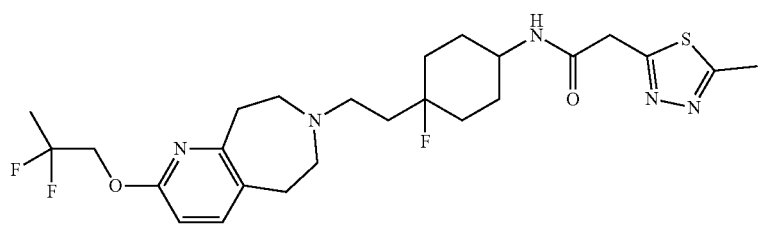
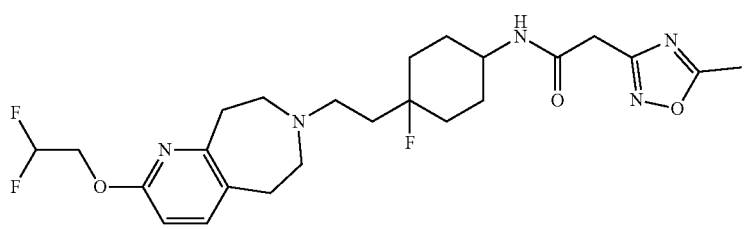
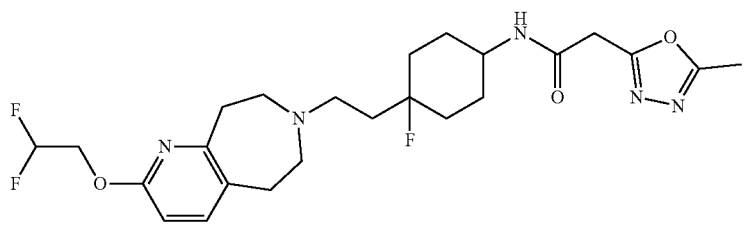

-continued
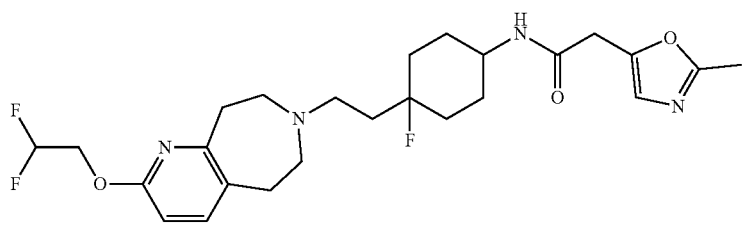
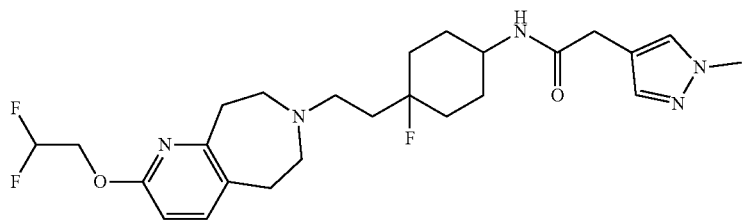
[Chemical Formula 147]
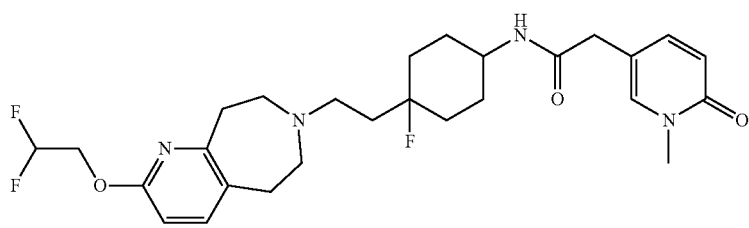
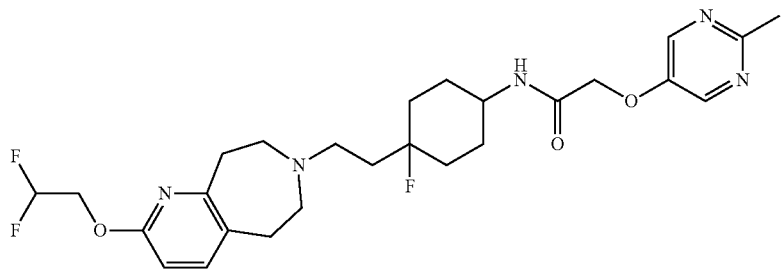
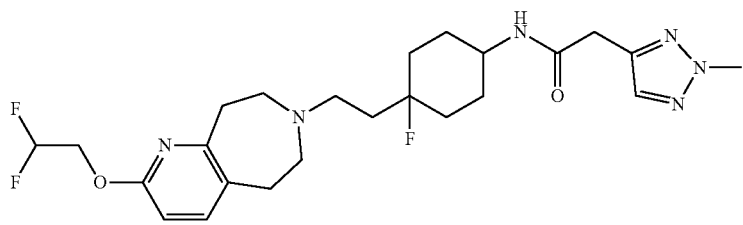
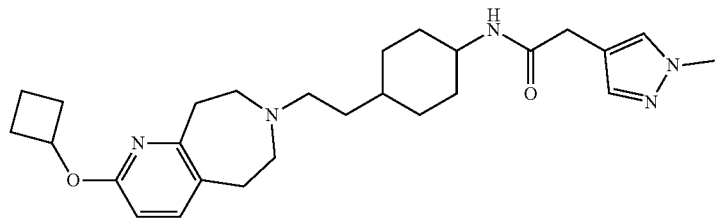
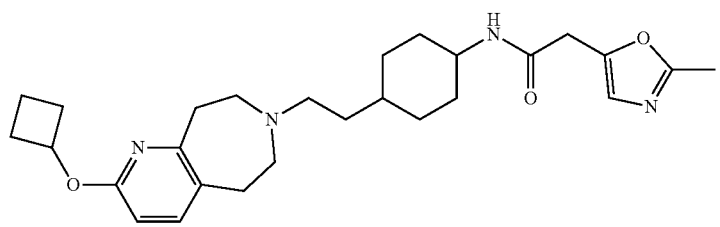

-continued
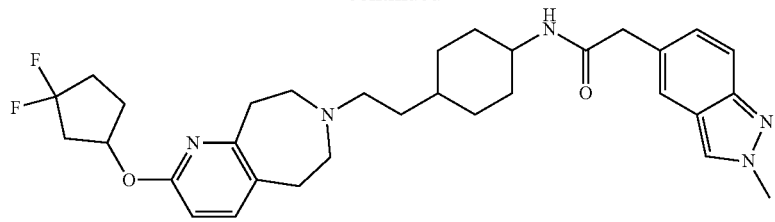
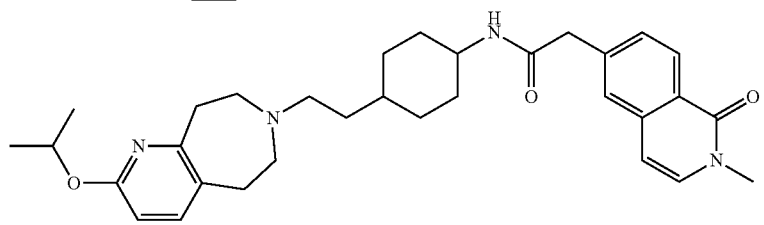
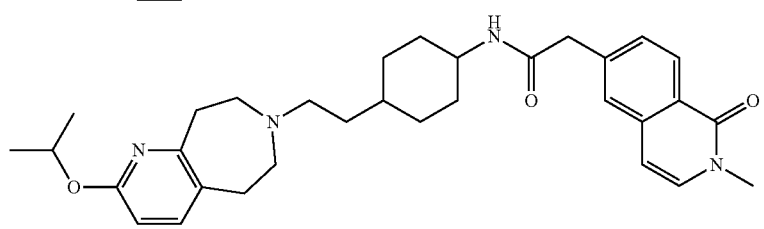
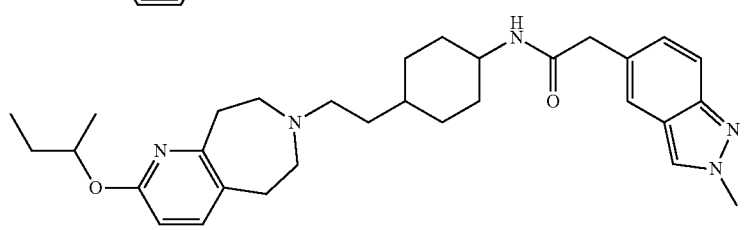
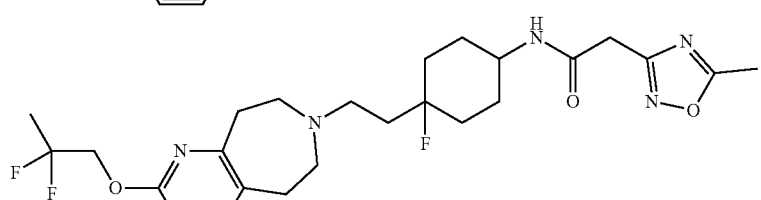
[Chemical Formula 148]
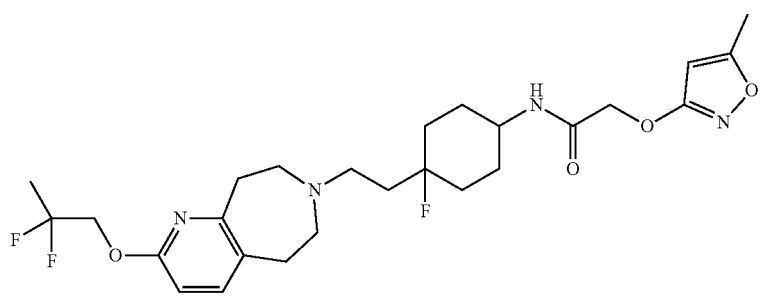
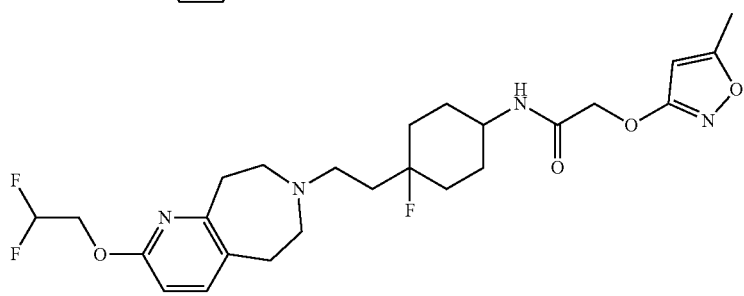

-continued
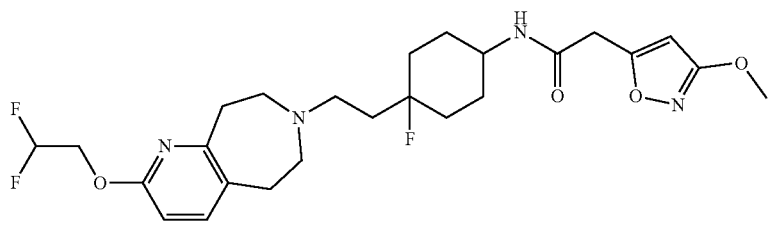
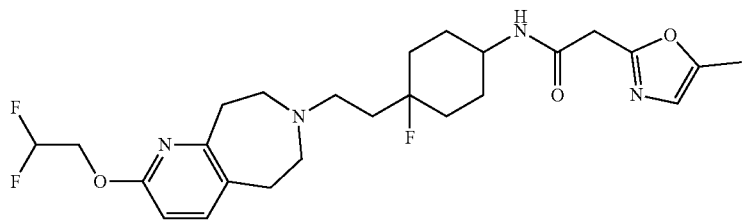
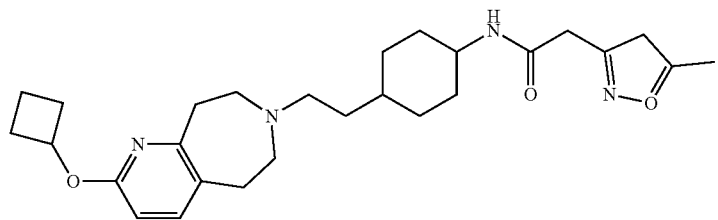
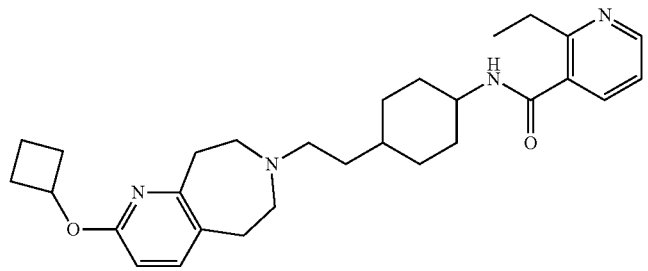
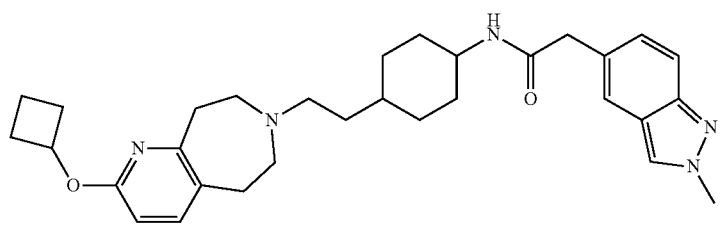
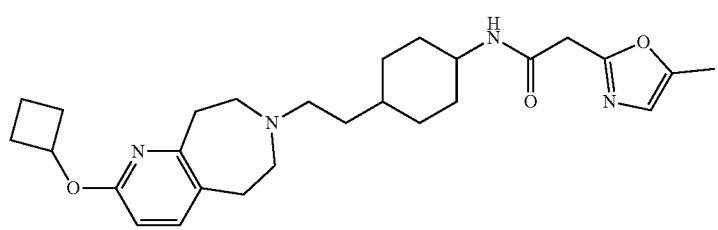
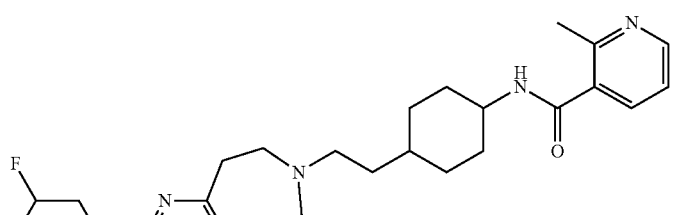

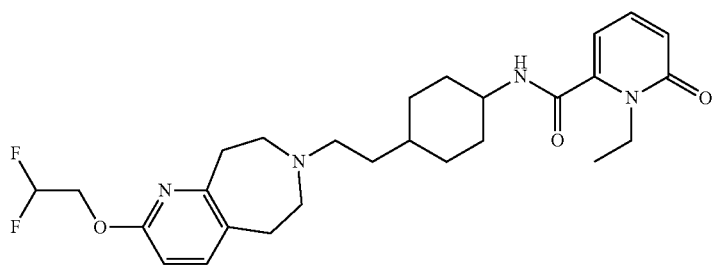
[Chemical Formula 149]
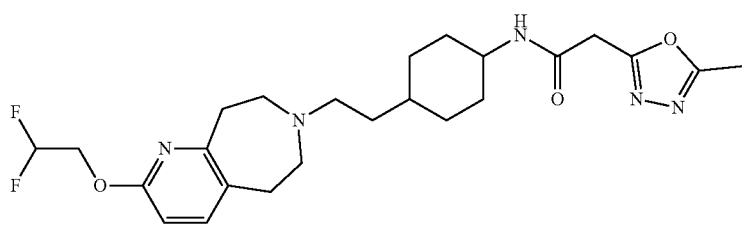
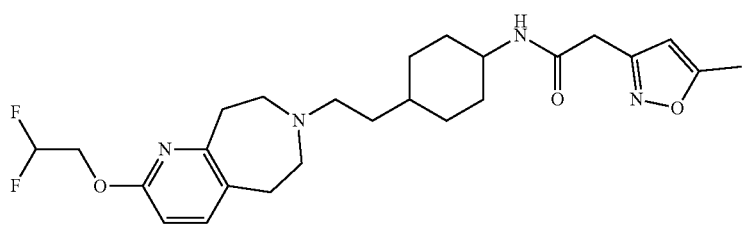
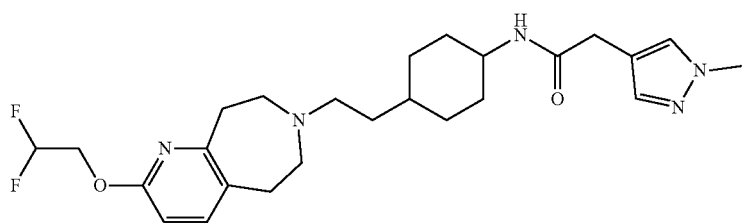
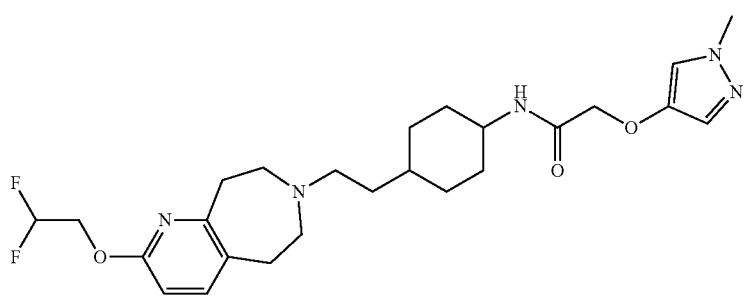
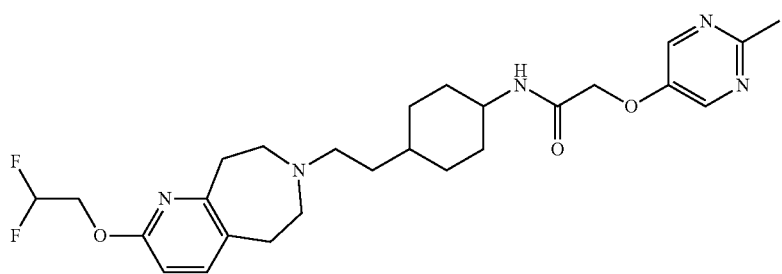

-continued
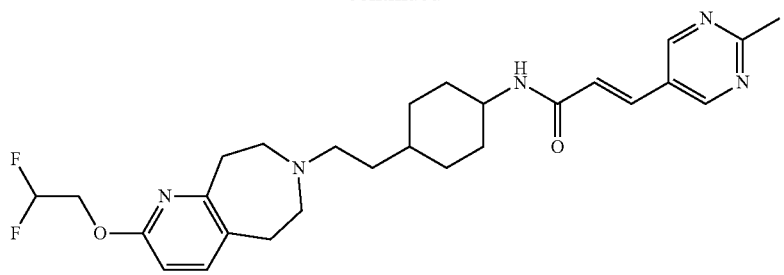
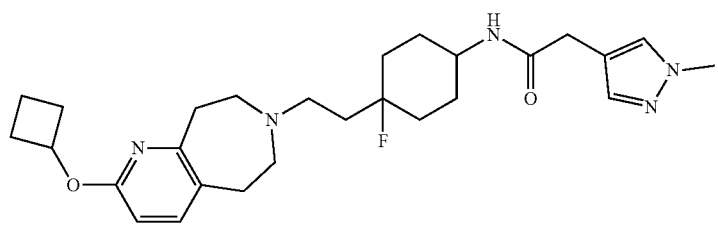
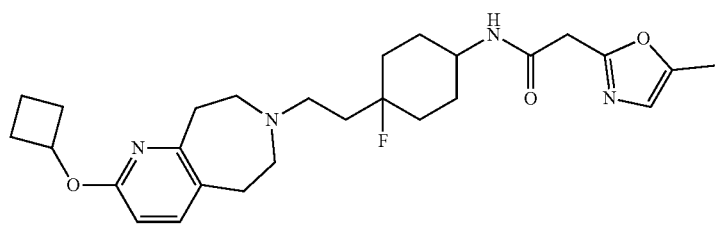
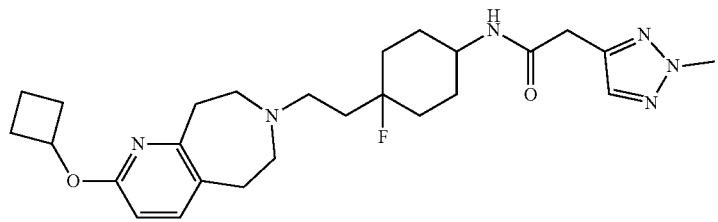
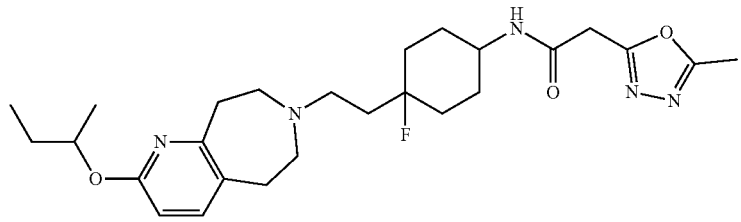
[Chemical Formula 150]
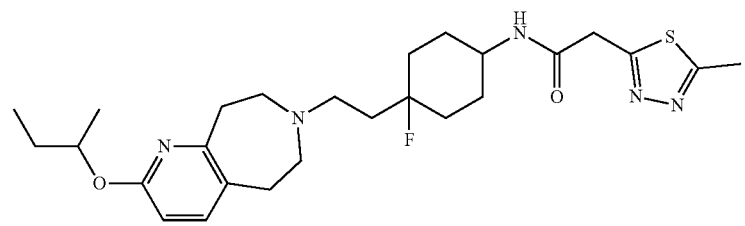
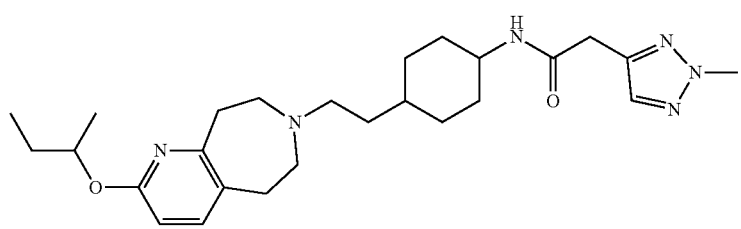

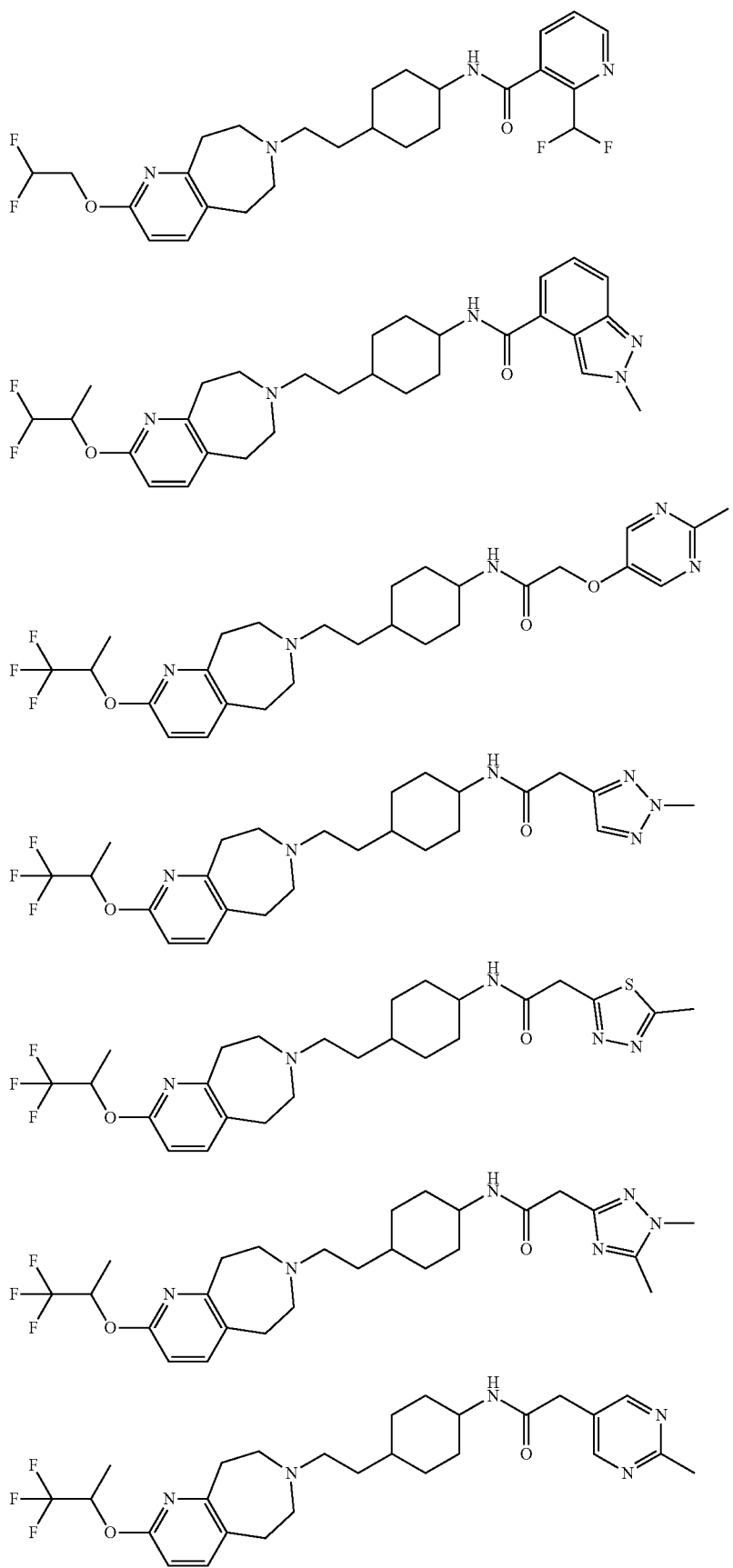

-continued
[Chemical Formula 151]
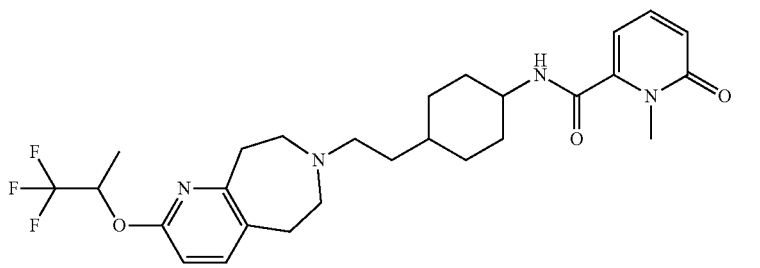
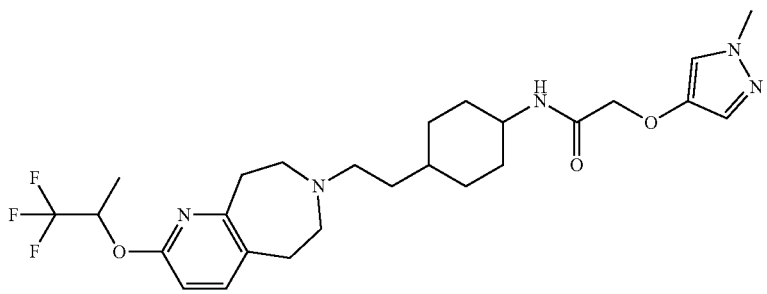
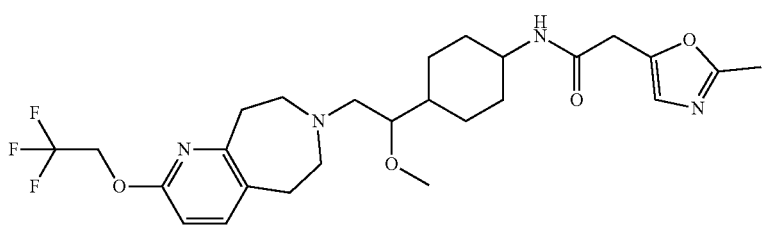
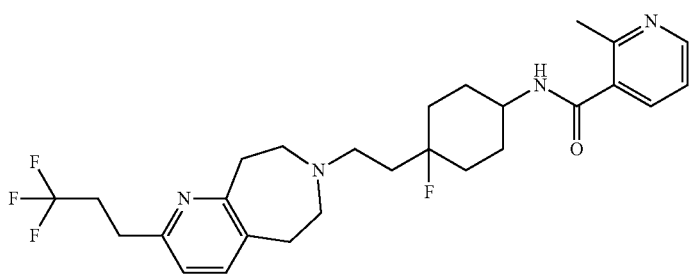
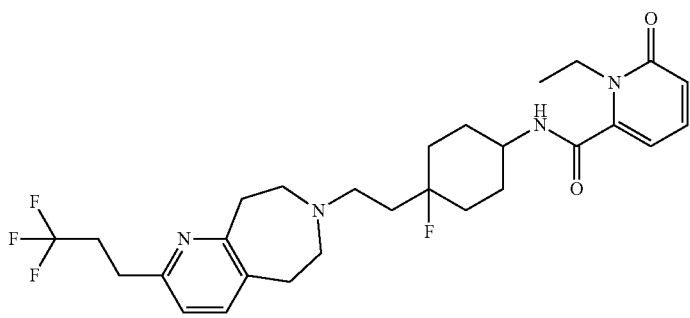
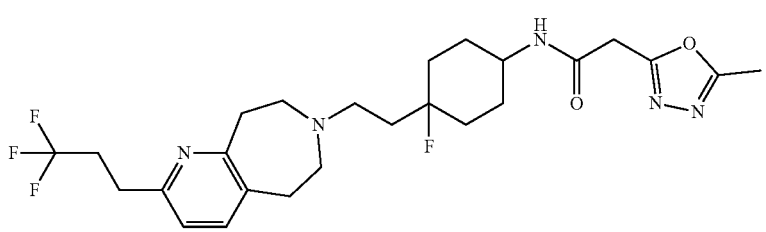

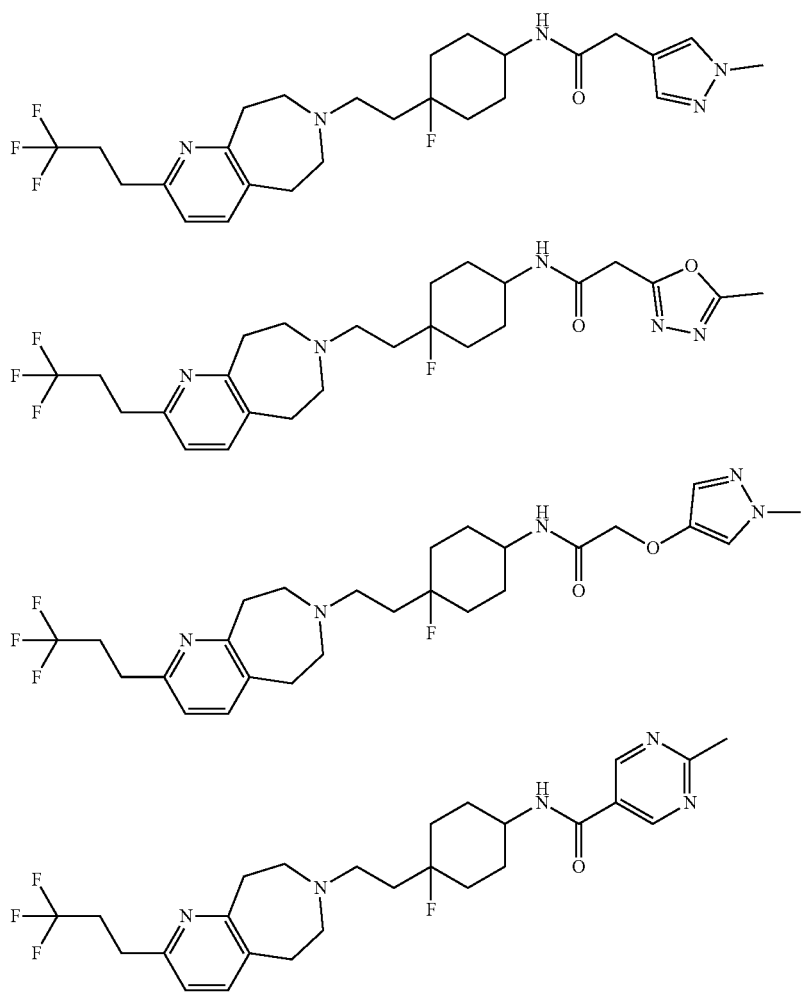
[Chemical Formula 152]
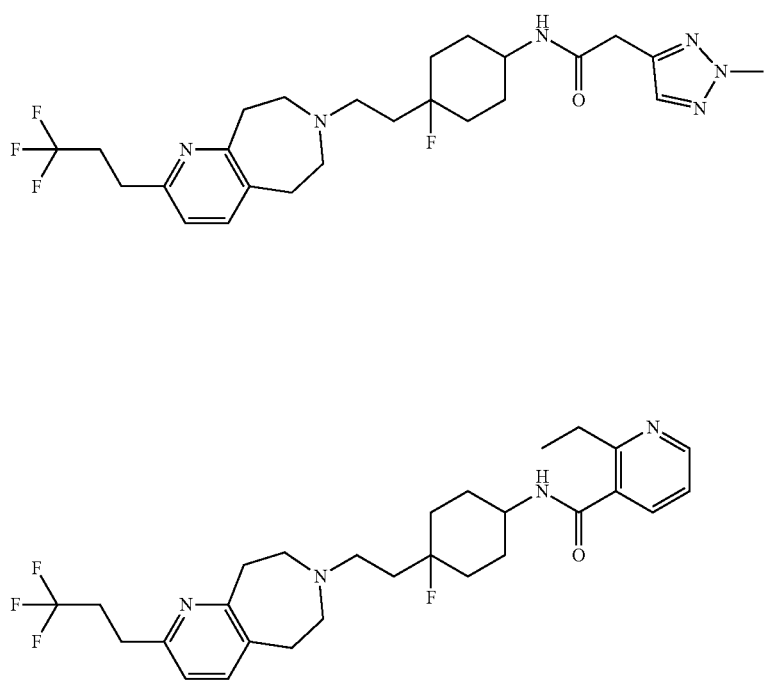

-continued
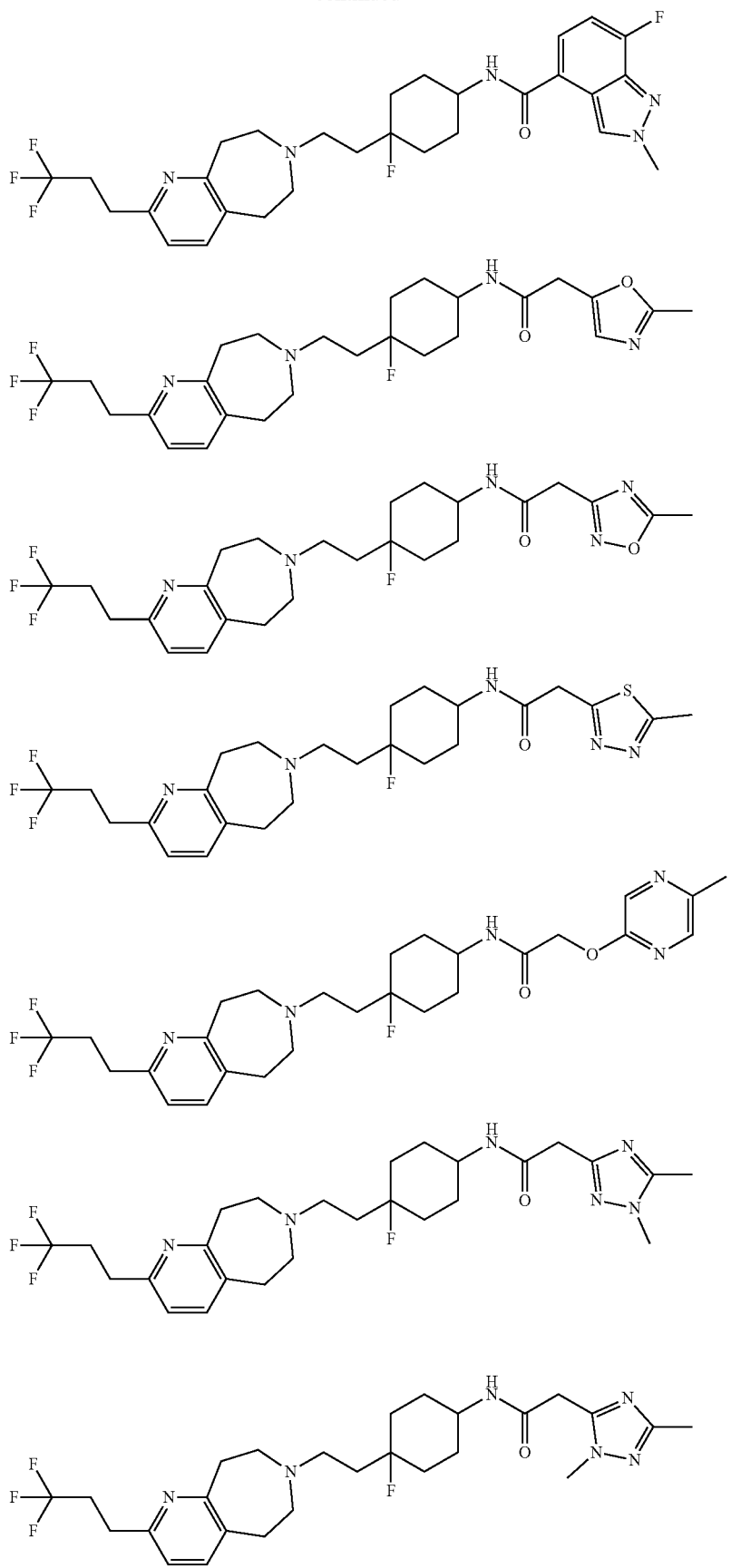

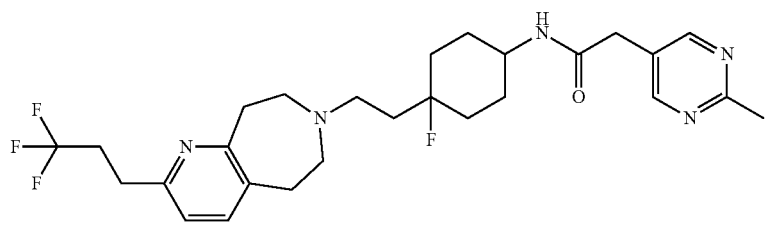
[Chemical Formula 153]
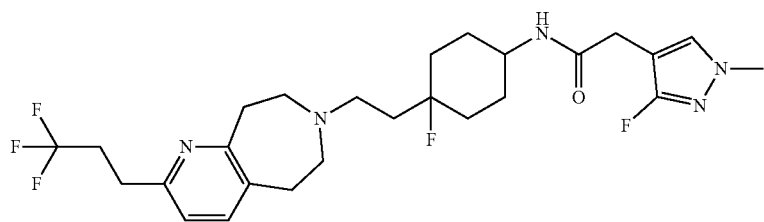
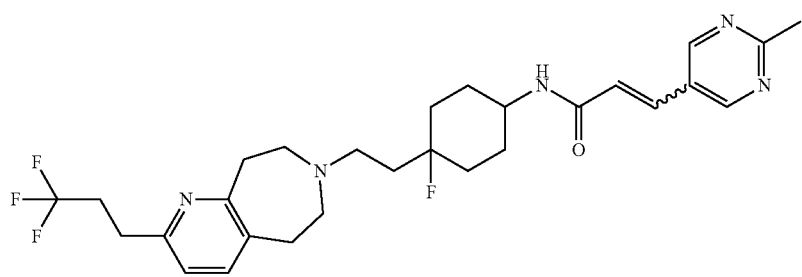
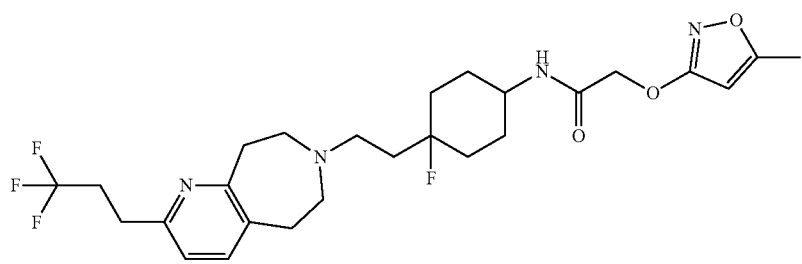
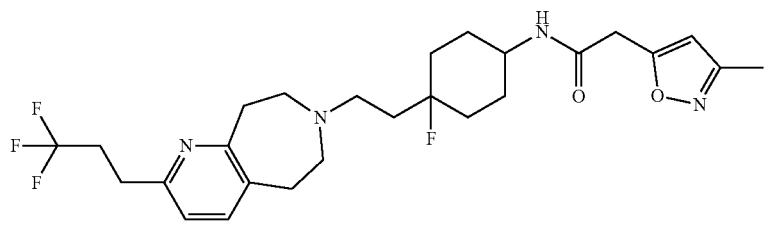
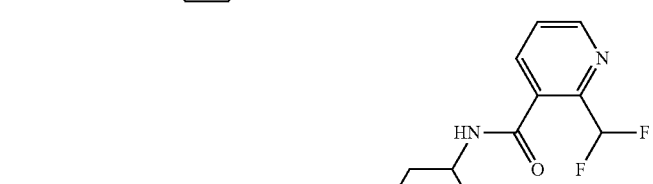
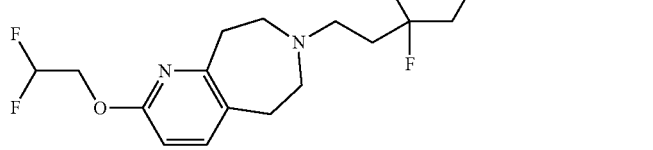

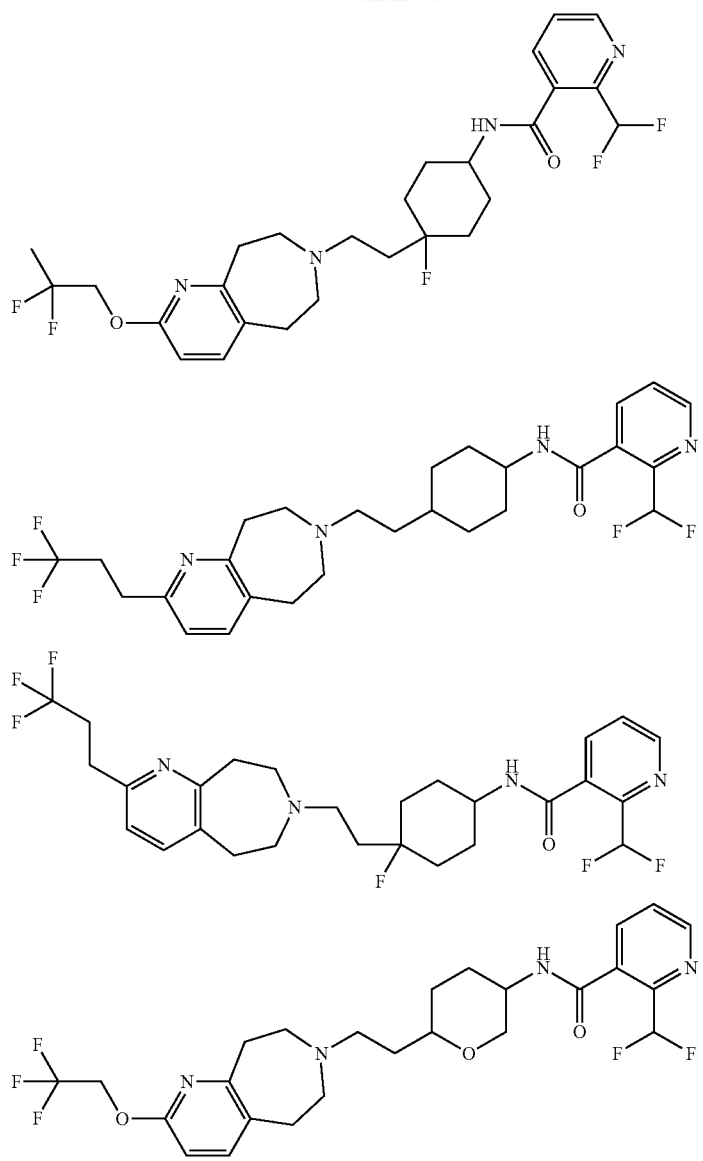
[Chemical Formula 154]
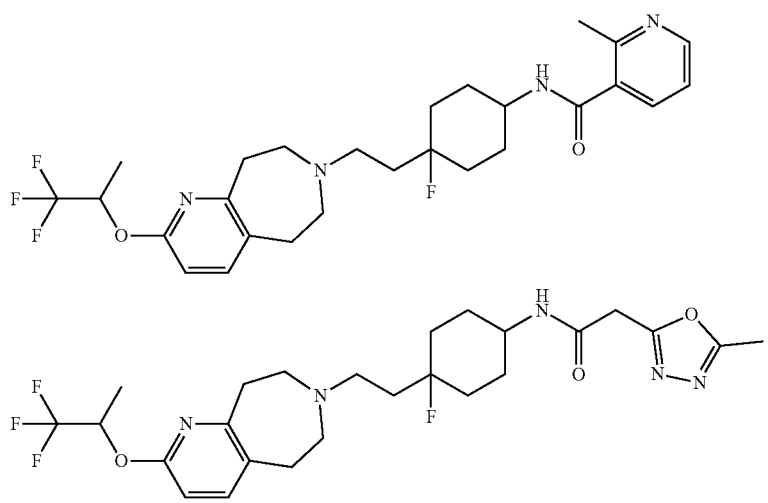

-continued
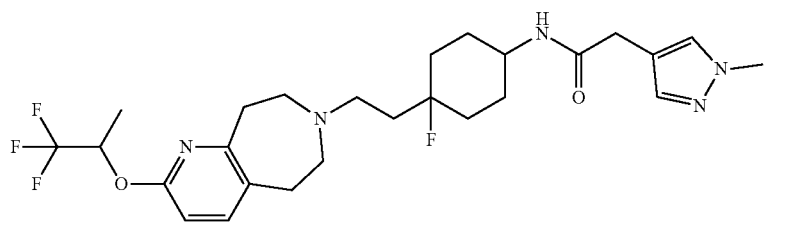
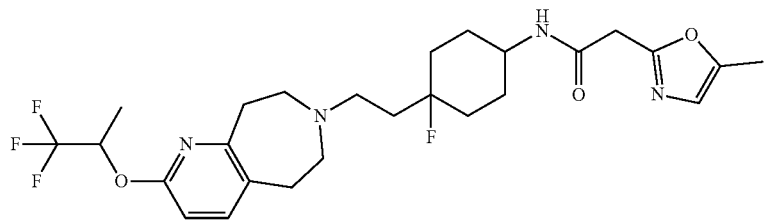
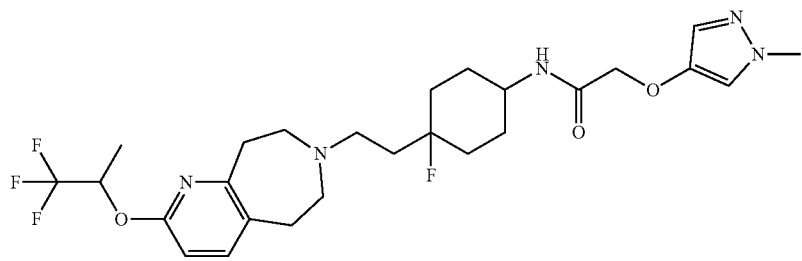
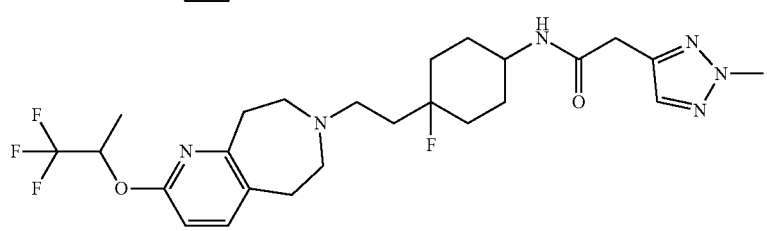
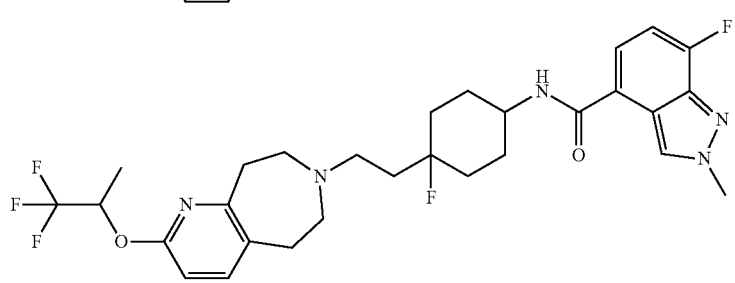
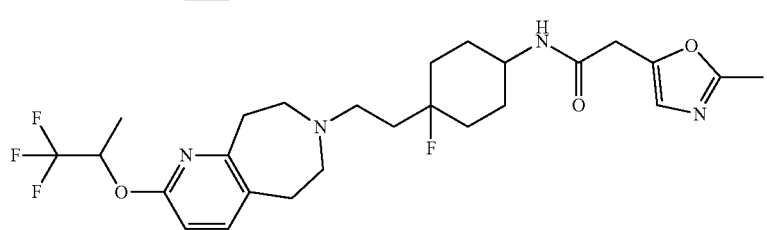
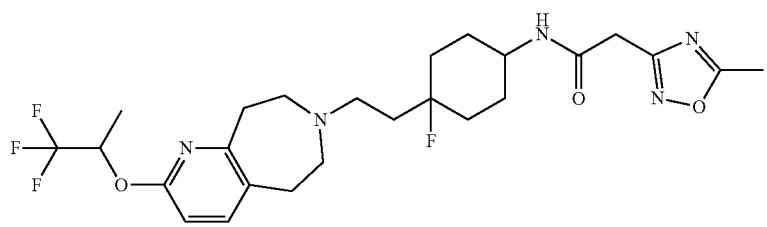

-continued
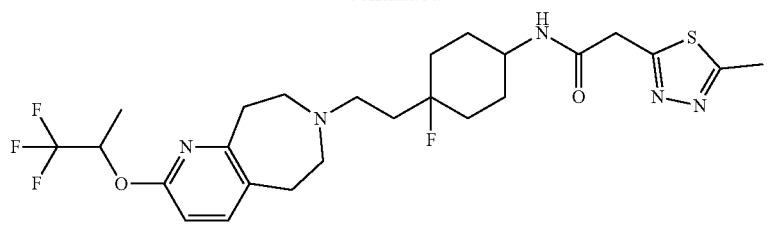
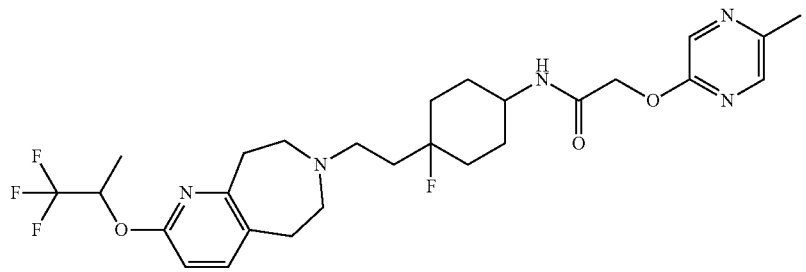
[Chemical Formula 155]
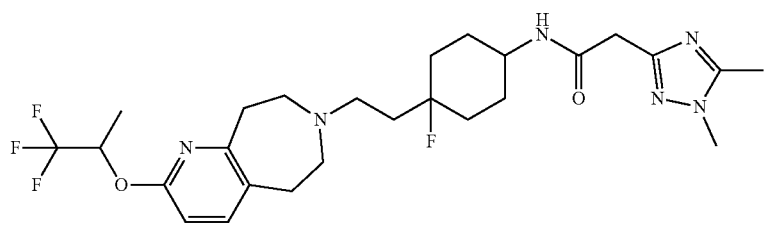
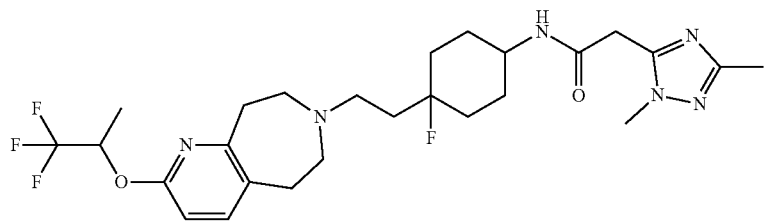
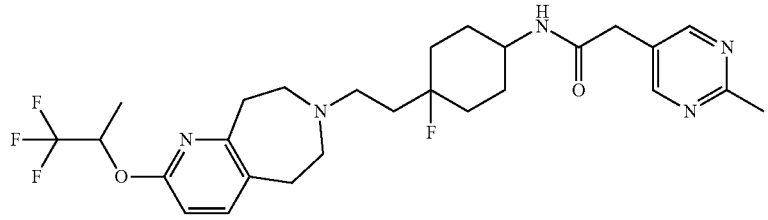
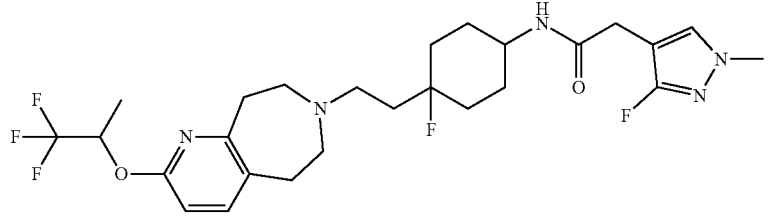
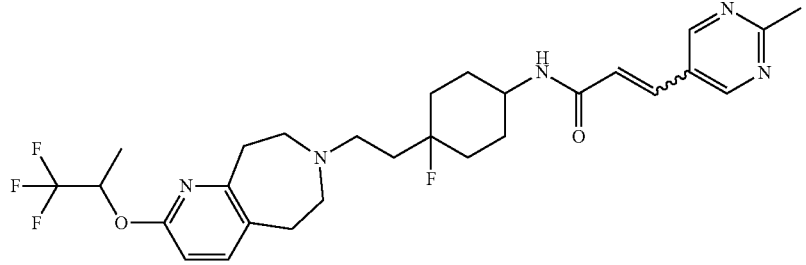

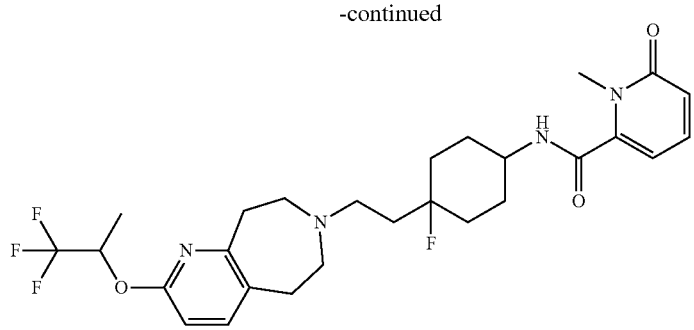
Examples of other embodiments of Formula (IC) are illustrated below.
[Chemical Formula 156]
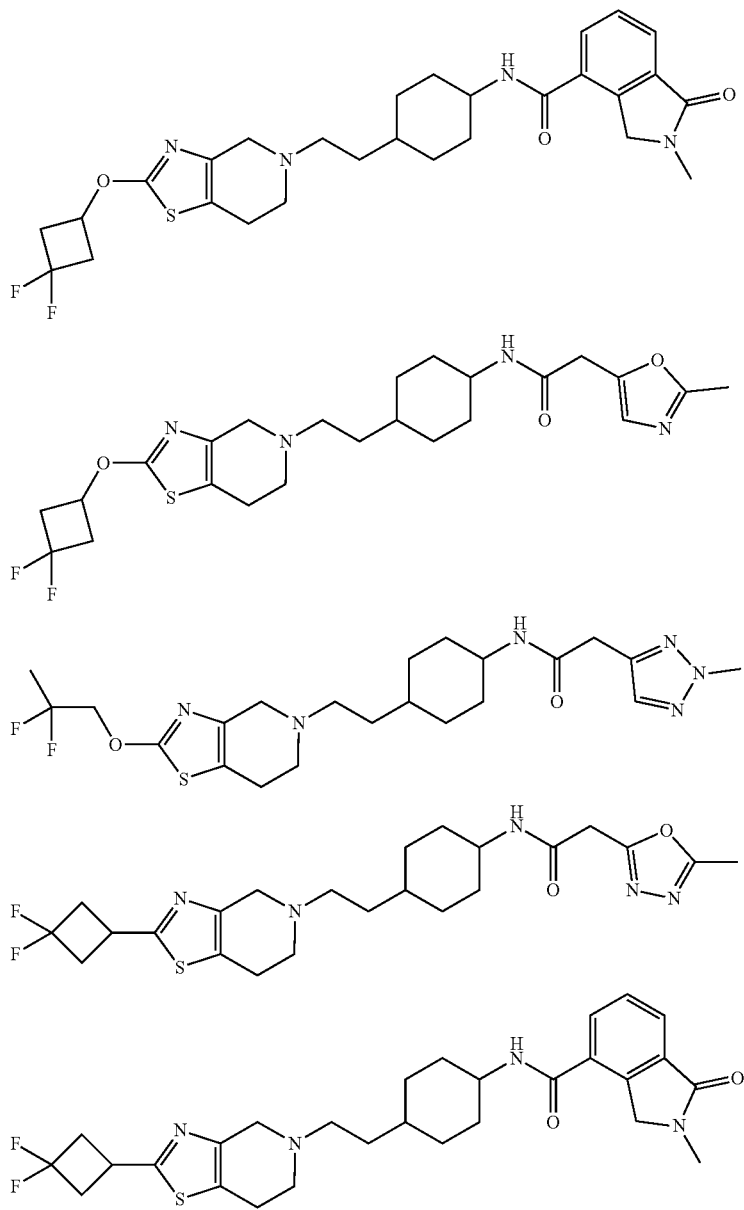

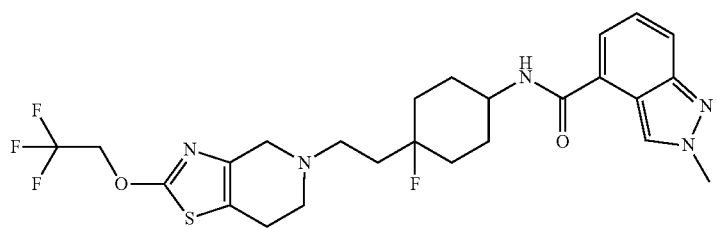
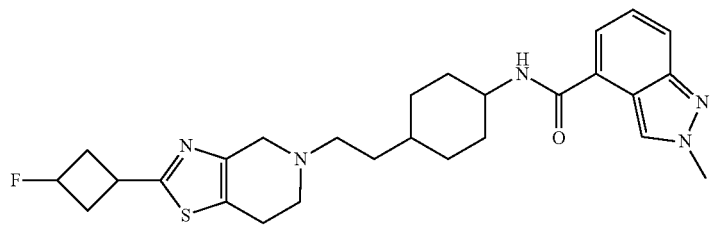
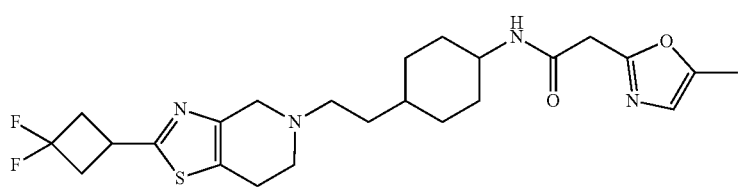
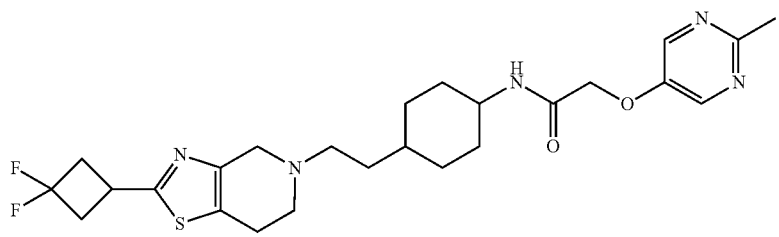
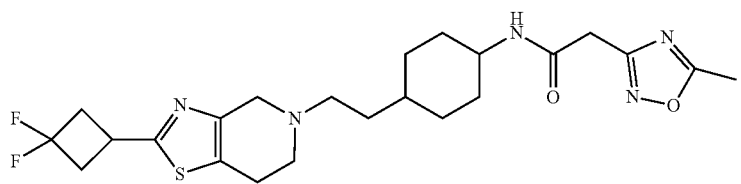
[Chemical Formula 157]
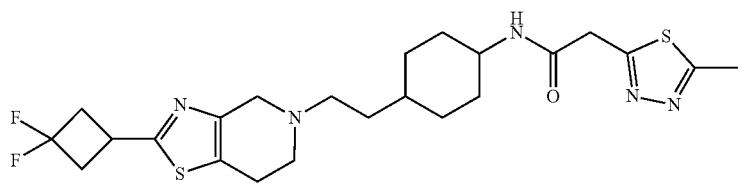
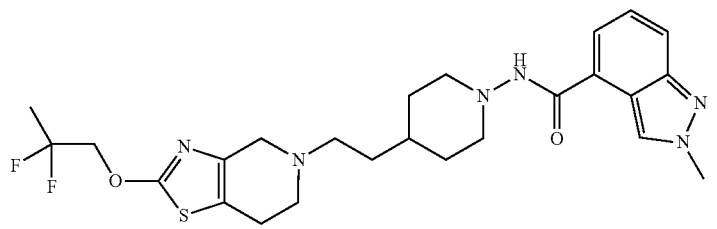

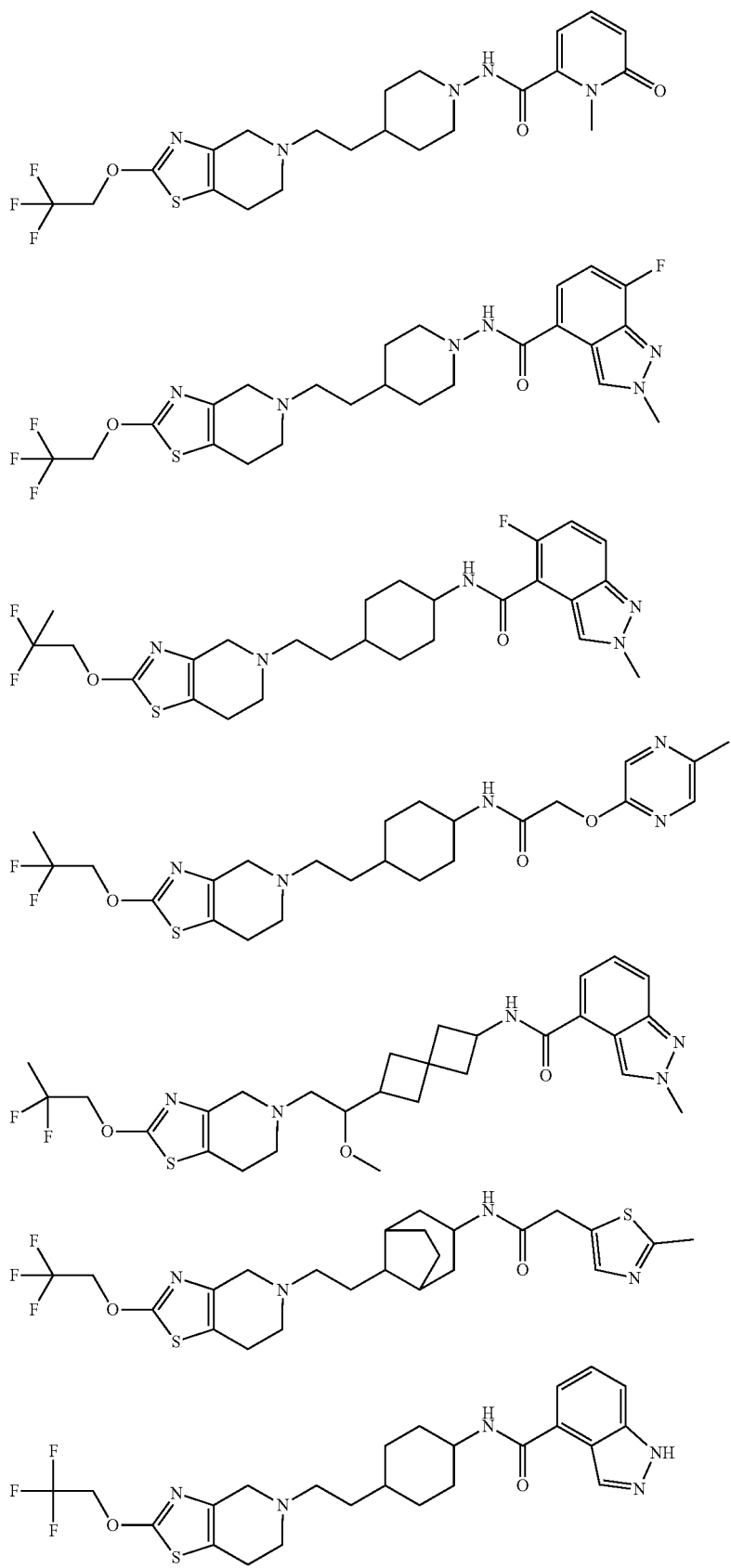

The compounds represented by Formulas (IA)' to (IE-2) are not limited to specific isomers but include all possible isomers (e.g., keto-enol isomers, imine-enamine isomers, diastereoisomers, enantiomers, rotamers, or the like), racemates, or mixtures thereof.

In the present description, a group represented by:

[Chemical Formula 158]

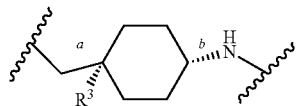

wherein each symbol is the same as defined above, means a group represented by:

[Chemical Formula 159]

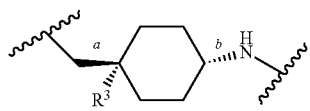

wherein each symbol is the same as defined above.

For example, a group represented by:

[Chemical Formula 160]

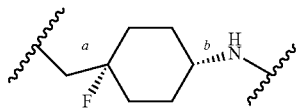

means a group represented by:

[Chemical Formula 161]

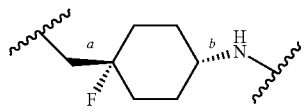

One or more hydrogen, carbon and/or other atoms in the compound represented by Formula (IA)' to (IE-2) may be replaced with isotopes of hydrogen, carbon and/or other atoms, respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively. The compounds represented by Formulas (IA)' to (IE-2) include the compounds replaced with these isotopes. The compounds replaced with the isotopes are useful as medicaments and include all of radiolabeled compounds of the compound represented by Formulas (IA)' to (IE-2). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compound represented by Formula (IA)' to (IE-2) can be prepared by well-known methods in the art. For example, a tritium-labeled compound represented by Formula (IA)' to (IE-2) can be prepared by introducing a tritium to a certain compound represented by Formula (IA)' to (IE-2), through a catalytic dehalogenation reaction using a tritium. This method includes reacting with an appropriately-halogenated precursor of the compound represented by Formula (IA)' to (IE-2) with tritium gas in the presence of an appropriate catalyst, such as Pd/C, and in the presence or absence of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by Formulas (IA)' to (IE-2) include, for example, salts of the compounds represented by Formulas (IA)' to (IE-2) with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by Formulas (IA)' to (IE-2) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by Formulas (IA)' to (IE-2). When the compounds represented by Formulas (IA)' and the like or pharmaceutically acceptable salts thereof are allowed be left stand in the atmosphere, the compounds may absorb water, resulting in attachment of adsorbed water or formation of hydrates. Recrystallization of the compounds represented by Formulas (IA)' to (IE-2) or pharmaceutically acceptable salts thereof may produce crystal polymorphs.

The compounds represented by Formulas (IA)' to (IE-2) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. The prodrug includes, for example, a compound that is converted to the compound represented by Formula (IA)' to (IE-2) through enzymatic oxidation, reduction, hydrolysis, or the like under physiological conditions in vivo, and a compound that is converted to the compound represented by Formula (IA)' to (IE-2) through hydrolysis by gastric juice or the like. Methods for selecting and preparing suitable prodrug derivatives are described in, for example, "Design of Prodrugs, Elsevier, Amsterdam, 1985". Prodrugs themselves may have some activity.

When the compound represented by Formula (IA)' to (IE-2) or a pharmaceutically acceptable salt thereof has a hydroxyl group, examples of the prodrug include prodrugs such as acyloxy derivatives and sulfonyloxy derivatives produced by reacting the compound having a hydroxyl group with an appropriate acyl halide, an appropriate acid anhydride, an appropriate sulfonyl chloride, an appropriate sulfonyl anhydride and a mixed anhydride, or using a condensing agent. Examples thereof include $CH_3COO—$, $C_2H_5COO—$, tert-BuCOO—, $C_{15}H_{31}COO—$, PhCOO—, (m-NaOOCPh)COO—, $NaOOCCH_2CH_2COO—$, $CH_3CH(NH_2)COO—$, $CH_2N(CH_3)_2COO—$, $CH_3SO_3—$, $CH_3CH_2SO_3—$, $CF_3SO_3—$, $CH_2FSO_3—$, $CF_3CH_2SO_3—$, p-$CH_3$O-Ph$SO_3—$, Ph$SO_3—$, and p-$CH_3$Ph$SO_3—$.

(Method for producing the compounds of the present invention) The compounds represented by Formulas (IA)' to (IE-2) of the present invention can be, for example, prepared by the general procedures described below. The starting materials and reagents used for synthesizing these compounds are commercially available or can be manufactured in accordance with well-known methods in the art using commercially available compounds. The methods for extraction, purification and the like may be carried out by usual methods for the experiments of organic chemistry.

The compounds of the present invention can be synthesized by referring to the known methods in the art.

In the following steps, when a substituent which interferes with the reaction, e.g. hydroxy, mercapto, amino, formyl, carbonyl, or carboxyl, is possessed, the substituent may be protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step. All of reaction time, reaction temperature, solvents, reagents, protecting groups, etc. are mere exemplification and not limited as long as they do not cause an adverse effect on a reaction.

The compounds represented by Formulas (IA)' to (IE-2) of the present invention can be, for example, prepared by the synthetic routes described below.
(Method A)

[Chemical Formula 162]

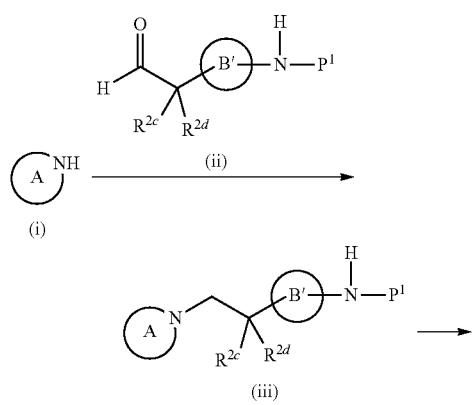

-continued

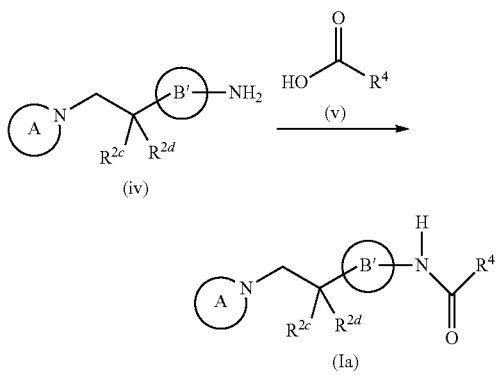

wherein, a group represented by:

[Chemical Formula 163]

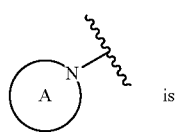 is

[Chemcial Formula 164]

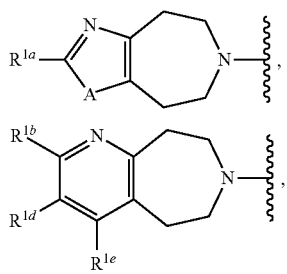

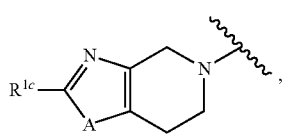

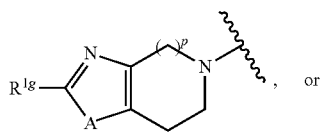, or

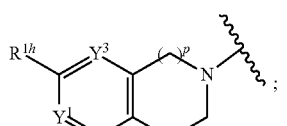;

and a group represented by:
[Chemical Formula 165]

[Chemical Formula 165]

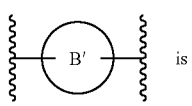 is

149
-continued

[Chemical Formula 166]

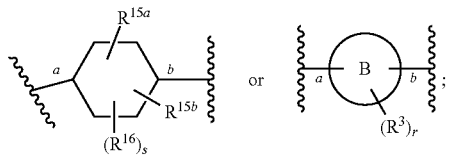

P¹ is a protective group for amino group, and the other symbols are the same as defined above.

(Step 1)

Compound (iii) can be prepared by condensation of Compound (ii) and amine (i) or a salt thereof in the presence or absence of a condensing agent, and reduction of the resulted compound using a reducing agent.

As the condensing agent, 4-toluenesulfonic acid, methanesulfonic acid, acetic acid, magnesium sulfate anhydrous, tetraisopropyl orthotitanate, titanium tetrachloride, molecular sieve and the like are exemplified. The condensing agent can be used in 1 to 10 mole equivalent(s) per an equivalent of Compound (ii).

Amine (i) or the salt thereof can be used in 1 to 10 mole equivalent(s) per an equivalent of Compound (ii).

As the reducing agent, sodium borohydride, sodium cyanoborohydride, sodium triacetoxyborohydride, borane and a complex thereof, lithium borohydride, potassium borohydride, diisobutylaluminium hydride and the like are exemplified. The reducing agent can be used in 1 to 10 mole equivalent(s) per an equivalent of Compound (ii).

The reaction temperature is −78° C. to reflux temperature of the solvent, preferably 0 to 25° C.

The reaction time is 0.5 to 48 hours, preferably 1 hour to 6 hours.

As the reaction solvent, tetrahydrofuran, toluene, dichloromethane, 1,2-dichloroethane, chloroform, methanol, ethanol and the like are exemplified. The reaction solvent can be used alone or in combination.

(Step 2)

Compound (iv) can be synthesized by removing a protective group P¹ of Compound (iii) according to the methods described in Protective Group in Organic Synthesis, Greene (4th edition).

(Step 3)

Compound (Ia) can be prepared by reacting Compound (iv) with Compound (v) in the presence of a condensing agent.

As the condensing agent, dicyclohexylcarbodiimide, carbonyldiimidazole, dicyclohexylcarbodiimide-N-hydroxybenzotriazole, EDC, 4-(4,6-dimethoxy-1,3,5,-triazin-2-yl)-4-methylmorpholinium chloride, HATU and the like are exemplified. The condensing agent can be used in 1 to 5 mole equivalent(s) per an equivalent of Compound (iv).

The reaction temperature is −20° C. to 60C, preferably 0° C. to 30C.

The reaction time is 0.1 hours to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

150
(Method B)

[Chemical Formula 167]

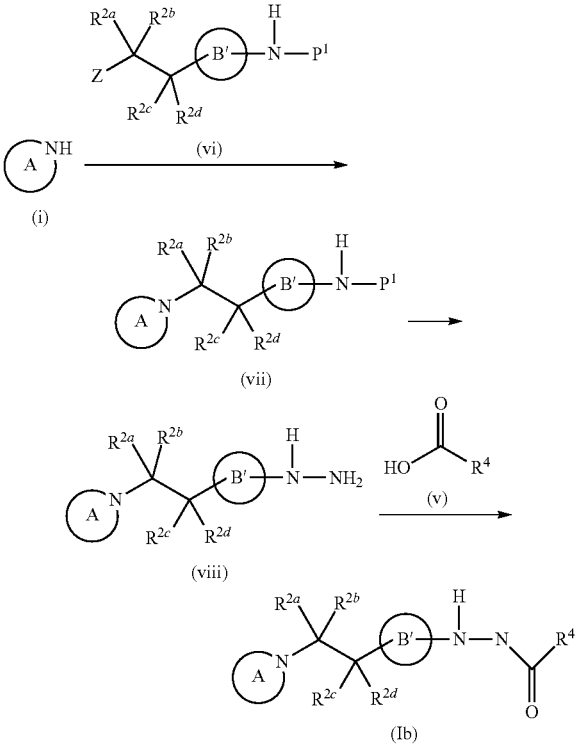

wherein Z is halogen or sulfonate ester, and the other symbols are the same as defined above.

(Step 1)

Compound (vii) can be prepared by reacting Compound (vi) with amine (i) in the presence of a base such as potassium carbonate and the like.

The reaction temperature is 0° C. to reflux temperature of the solvent, preferably room temperature to reflux temperature of the solvent.

The reaction time is 0.1 hours to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

(Step 2)

Compound (viii) can be synthesized according to the similar synthetic procedures described in Step 2 of Method A.

(Step 3)

Compound (Ib) can be synthesized according to the similar synthetic procedures described in Step 3 of Method A.

The compounds of the present invention have an antagonistic activity for D3 receptor and preferably high D3/D2 selectivity, and therefore, are useful as agents for treating and/or preventing diseases associated with D3 receptor. In the present invention, "agents for treating and/or preventing" includes agents for symptom improving.

As diseases associated with D3 receptor, central nervous system diseases are exemplified.

As central nervous system diseases, cognitive disorders (e.g., mild cognitive impairment, Alzheimer's disease and the like), drug addiction, depression, anxiety, drug dependence, gambling addiction, dementias, memory impairment, schizophrenia, schizoaffective disorders, bipolar disorder, mania, acute mania, psychotic disorders including psychotic depression, psychoses including paranoia and delusions, attention-deficit/hyperactivity disorder (AD/HD), attention deficit disorder (ADD), obsessive-compulsive disorder (OCD), dyskinesia disorder, Parkinson's disease, neuroleptic-induced Parkinson's syndrome and tardive dyskinesia, eating disorders (e.g., anorexia or bulimia), sexual dysfunction, intellectual disabilities, learning disabilities, developmental disorders, sleep disorders, emesis, movement disorders, obsessive-compulsive disorder, amnesia, aggression, autism, vertigo, circadian rhythm disorders and gastric motility disorders, drug abuse (e.g., opioid drugs, alcohol, cocaine and nicotine addiction and the like), and psychological dependence due to drug abuse and the like are exemplified.

As central nervous system diseases, more preferably, attention-deficit/hyperactivity disorder (AD/HD) is exemplified.

The compounds of the present invention not only have an antagonistic activity for D3 receptor but also are useful as a medicament and have any or all of the following superior characteristics:
a) The inhibitory activity for CYP enzymes (e.g., CYP1A2, CYP2C9, CYP2C19, CYP2D6, CYP3A4 and the like) is weak.
b) The compound demonstrates good pharmacokinetics, such as a high bioavailability, moderate clearance and the like.
c) The compound has a high metabolic stability.
d) The compound has no irreversible inhibitory action against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound has a high D3 receptor selectivity (e.g., the compound has a high D3 receptor selectivity over D2 receptor, muscarinic receptor, adrenergic α1 receptor, histamine H1 receptor, and/or serotonin 5HT2c receptor).
i) The compound has a high D3 receptor selectivity over D2 receptor, in other words, high D3/D2 selectivity (e.g., the compound has higher affinity for D3 receptor compared to affinity for D2 receptor).
j) The compound has a high safety (e.g., mydriasis or somnolence can be reduced, teratogenicity risk is low, or the like).
k) The compound has high brain distribution ability.
l) The compound has a low propensity to be P-gp substrate.
m) The compound shows high D3 receptor occupancy. For example, the compound shows high D3 receptor occupancy at low doses.

Since the compounds of the present invention have a high antagonistic activity against D3 receptor and/or a high D3 receptor selectivity over other receptor(s), e.g., D2 receptor (e.g., have higher affinity for D3 receptor compared to affinity for other receptor(s), e.g., D2 receptor), it can be a medicament with reduced side effects. Examples of the side effects include extrapyramidal symptoms, elevated prolactin, and reduced cognitive function.

As D3 receptor antagonists, for example, preferably compounds which show Ki value of less than or equal to 10 μM, more preferably less than or equal to 100 nM, further more preferably less than or equal to 5 nM in the test of binding inhibition for dopamine D3 receptor, which is described later, are exemplified.

As D3 receptor antagonists, for example, preferably compounds which has D3/D2 selectivity of more than or equal to 10 folds, more preferably more than or equal to 100 folds, further more preferably more than or equal to 500 folds in the test of binding inhibition for dopamine D3 receptor and the test of binding inhibition for dopamine D2 receptor, which are described later, are exemplified.

Here, D3/D2 selectivity can be calculated, for example, from (Ki value in the test of binding inhibition for dopamine D2 receptor/Ki value in the test of binding inhibition for dopamine D3 receptor).

A pharmaceutical composition of the present invention can be administered orally or parenterally. Examples of methods for parenteral administration include dermal, subcutaneous, intravenous, intraarterial, intramuscular, intraperitoneal, transmucosal, inhalation, transnasal, ophthalmic, inner ear, and vaginal administration.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is in the range of 0.05 to 100 mg/kg/day and preferably 0.1 to 10 mg/kg/day. For parenteral administration, although the dosage highly varies with administration routes, a usual dosage is in the range of 0.005 to 10 mg/kg/day and preferably 0.01 to 1 mg/kg/day. The dose may be administered once daily or may be divided into multiple daily doses.

The compound of the present invention can be used in combination with other drugs such as central nervous system stimulants (Methylphenidate, Lisdexamfetamine and the like), noradrenaline reuptake inhibitor, dopamine-noradrenaline reuptake inhibitor, serotonin-noradrenaline reuptake inhibitor (Atomoxetine and the like), α2A adrenergic receptor agonist (Guanfacine and the like) and the like (hereinafter referred to as a concomitant medicament). The compound of the present invention can be administered in combination with the concomitant medicament for the purpose of enforcement of the activity of the compound of the present invention or the concomitant medicament or reduction of the dosage of the compound of the present invention or the concomitant medicament or the like.

In this case, timing of administration of the compound of the present invention and the concomitant medicament are not limited and these may be administered to the subject simultaneously or at regular intervals. Furthermore, the compound of the present invention and the concomitant medicament may be administered as two different formulations containing each active ingredient or as a single formulation containing both active ingredients.

The dose for concomitant medicaments may be appropriately selected in reference to the clinical dose. The compounding ratio of the compound of the present invention and the concomitant medicament may be appropriately selected depending on the subject of administration, administration route, disease to be treated, symptoms, combination of the drugs and the like. For example, when the subject of administration is human, the concomitant medicament can be used in the range of 0.01 to 100 parts by weight relative to 1 part by weight of the compound of the present invention.

EXAMPLE

The present invention will be described in more detail with reference to, but not limited to, the following Examples and Test Examples.

In this present description, the meaning of each abbreviation is as follows:
Me methyl
Et ethyl
Boc tert-butoxycarbonyl
Bn benzyl
Tf trifluoromethanesulfonyl
TFA trifluoroacetic acid
THF tetrahydrofuran
EDC 1-ethyl-3-(3-dimethylaminopropyl)carbodiimide
TBAF tetrabutylammonium fluoride
DMSO dimethyl sulfoxide
DMF dimethylformamide
DMA dimethylacetamide
DME 1,2-dimethoxyethane
dba dibenzylideneacetone
dppf 1,1'-bis(diphenylphosphino)ferrocene
DIAD diisopropyl azodicarboxylate
DEAD diethyl azodicarboxylate
DIEA N,N-diisopropylethylamine
DIBAL diisobutylaluminium hydride
LHMDS lithium hexamethyldisilazide
NaHMDS sodium hexamethyldisilazide
NBS N-bromosuccinimide
TBS tert-butyldimethylsilyl
HATU 1-[bis(dimethylamino)methylene]-1H-1,2,3-triazolo[4,5-b]pyridinium 3-oxide hexafluorophosphate
HOBt 1-hydroxybenzotriazole
Pd2(dba)3 tris(dibenzylideneacetone)dipalladium(0)
xantphos 4,5-bis(diphenylphosphino)-9,9-dimethylxanthene
CDCl3 deuterochloroform
CD3OD tetradeuteromethanol
MS mass spectrometry
SFC supercritical fluid chromatography NMR analysis of each example was performed by 400 MHz using DMSO-d6, CDCl3, or CD3OD. Sometimes not all the peaks detected are shown in NMR data.

LC/MS data of the compounds of the present invention were measured under the conditions as below. Retention time (min) and m/z are described.
(Method 1)
Column: ACQUITY UPLC(R) BEH C18 (1.7 μm, i.d.2.1×50 mm) (Waters)
Flow rate: 0.8 mL/min
UV detection wavelength: 254 nm
Mobile phases: [A] 10 mM aqueous ammonium carbonate solution, [B] acetonitrile
Gradient: linear gradient of 5% to 100% solvent [B] was performed for 3.5 minutes, and then 100% solvent [B] was maintained for 0.5 minutes.
(Method 2)
Column: ACQUITY UPLC(R) BEH C18 (1.7 μm, i.d.2.1×50 mm) (Waters)
Flow rate: 0.8 mL/min
UV detection wavelength: 254 nm
Mobile phases: [A] 0.1% aqueous formic acid solution, [B] 0.1% formic acid in acetonitrile solvent
Gradient: linear gradient of 5% to 100% solvent [B] was performed for 3.5 minutes, and 100% solvent [B] was maintained for 0.5 minutes.
(Method 3)
Column: Shim-pack XR-ODS (2.2 μm, i.d.3.0×50 mm) (Shimadzu)
Flow rate: 1.6 mL/min
UV detection wavelength: 254 nm
Mobile phases: [A] 0.1% aqueous formic acid solution, [B] 0.1% formic acid in acetonitrile solvent
Gradient: linear gradient of 10% to 100% solvent [B] was performed for 3 minutes, and 100% solvent [B] was maintained for 0.5 minutes.
(Method 4)
Column: ACQUITY UPLC(R) BEH C18 (1.7 μm, i.d.2.1×50 mm)(Waters)
Flow rate: 0.55 mL/min
UV detection wavelength: 254 nm
Mobile phases: [A] 0.1% aqueous formic acid solution, [B] 0.1% formic acid in acetonitrile solvent
Gradient: linear gradient of 5% to 100% solvent [B] was performed for 3 minutes, and 100% solvent [B] was maintained for 0.5 minutes.

Reference Example 1 Synthesis of Compound 6a

[Chemical Formula 168]

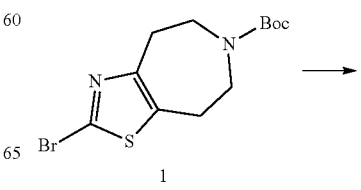

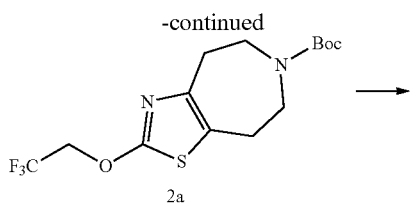

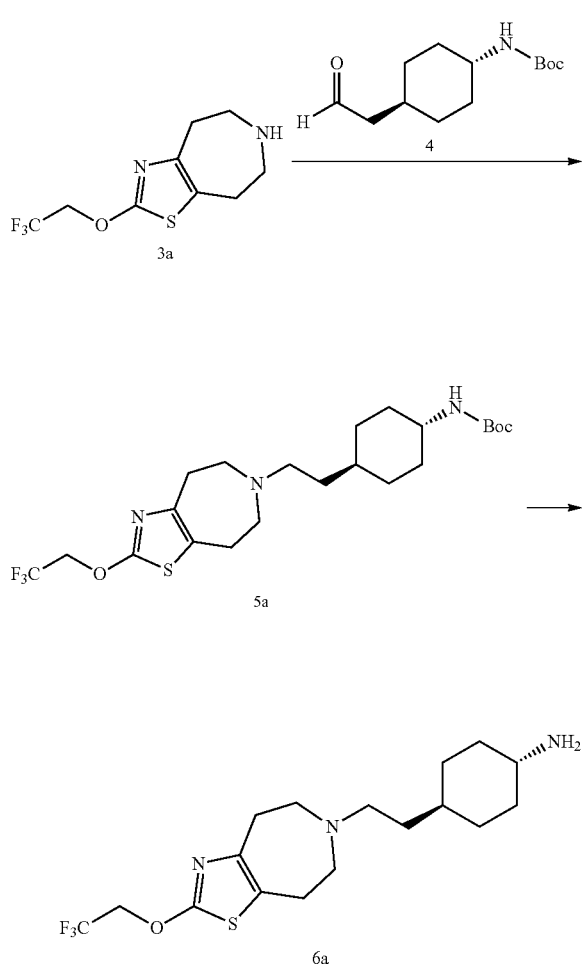

Step 1 Synthesis of Compound 2a

Under nitrogen atmosphere, a solution of 2,2,2-trifluoroethanol (2.70 g, 27.0 mmol) in DMF (60 mL) was cooled with ice. To the solution was added sodium hydride (60 wt %, 1.08 g, 27.0 mmol) portionwise. The mixture was stirred at 0° C. for 1 hour. To the mixture was added Compound 1 (3.0 g, 9.00 mmol) portionwise. Then, the mixture was stirred at 65° C. for 4 hours. To the reaction mixture was added water. The mixture was extracted with ethyl acetate. The organic layer was washed with water and brine, and then dried over anhydrous sodium sulfate. The solvent was evaporated under reduced pressure. The obtained residue was purified by silica-gel column chromatography (hexane-ethyl acetate) to give Compound 2a (2.72 g, yield 86%).

1H-NMR (CDCl3) δ: 1.48 (s, 9H), 2.74-2.82 (brm, 2H), 2.85-2.92 (brm, 2H), 3.54-3.65 (brm, 4H), 4.72 (q, J=8.3 Hz, 2H).

Step 2 Synthesis of Compound 3a

Compound 2a (6.69 g, 18.99 mmol) was dissolved in methanol (33.5 mL). To the solution was added 4 mol/L hydrochloric acid/1,4-dioxane solution (33.5 mL, 134 mmol). The mixture was stirred at room temperature for 1 hour. The solvent was evaporated under reduced pressure. To the residue was added 2 mol/L aqueous sodium carbonate solution. The mixture was extracted with chloroform. The organic layer was dried over anhydrous sodium sulfate. The solvent was then evaporated under reduced pressure to give Compound 3a (4.17 g, yield 87%).

1H-NMR (CDCl3) δ: 2.71-2.74 (m, 2H), 2.83-2.86 (m, 2H), 2.95-2.98 (m, 2H), 3.01-3.04 (m, 2H), 4.72 (q, J=8.4 Hz, 2H).

Step 3 Synthesis of Compound 5a

To Compound 3a (6.0 g, 23.79 mmol) were added dichloromethane (120 mL), triethylamine (6.59 mL, 47.6 mmol) and Compound 4 (6.31 g, 26.2 mmol) at 0° C. The mixture was stirred for 30 minutes. Under ice cooling, sodium triacetoxyborohydride (7.56 g, 35.7 mmol) was added portionwise. The mixture was stirred at room temperature for 2 hours. To the reaction mixture was added saturated aqueous solution of sodium hydrogen carbonate. The mixture was extracted with chloroform and ethyl acetate. The organic layer was combined and dried over anhydrous sodium sulfate. The solvent was then evaporated under reduced pressure. The obtained residue was purified by amino silica-gel column chromatography (hexane-ethyl acetate) to give Compound 5a (110.0 g, yield 88%).

1H-NMR (CDCl3) δ: 0.98-1.12 (m, 4H), 1.19-1.28 (m, 1H), 1.38-1.44 (m, 11H), 1.75-1.78 (m, 2H), 1.98-2.00 (m, 2H), 2.57-2.61 (m, 2H), 2.70-2.73 (m, 2H), 2.77-2.86 (m, 6H), 3.37 (br, 1H), 4.36 (br, 1H), 4.71 (q, J=8.3 Hz, 2H).

Step 4 Synthesis of Compound 6a

Compound 5a (2.73 g, 5.72 mmol) was dissolved in dichloromethane (27.3 mL). To the solution was added TFA (8.81 mL, 114 mmol). The mixture was stirred at room temperature for 15 minutes. The solvent was evaporated under reduced pressure. To the residue were added chloroform and 2 mol/L aqueous sodium carbonate solution. The mixture was extracted with chloroform. The organic layer was dried over anhydrous sodium sulfate. The solvent was evaporated under reduced pressure. The obtained residue was purified by silica-gel column chromatography (chloroform-methanol) to give Compound 6a (2.08 g, yield 96%).

1H-NMR (CDCl3) δ: 0.94-1.12 (m, 4H), 1.18-1.27 (m, 1H), 1.38-1.44 (m, 2H), 1.74-1.77 (m, 2H), 1.83-1.86 (m, 2H), 2.56-2.62 (m, 3H), 2.71-2.74 (m, 2H), 2.78-2.86 (m, 6H), 4.72 (q, J=8.4 Hz, 2H).

Example 1 Synthesis of Compound I-048

[Chemical Formula 169]

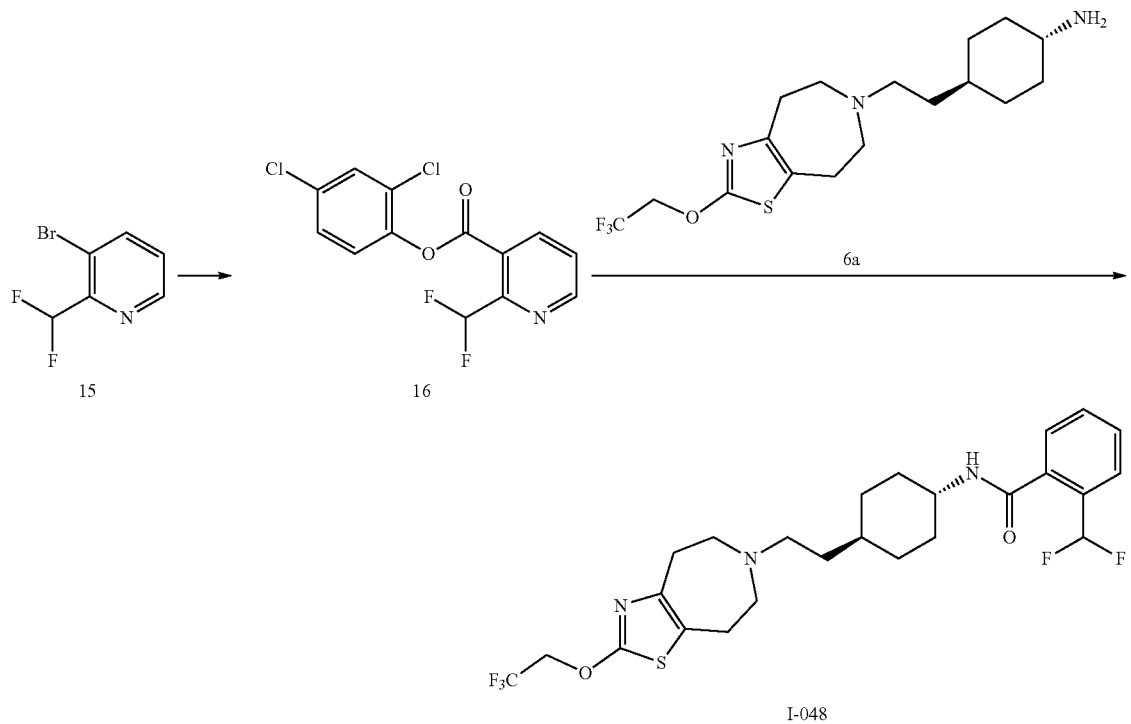

Step 1: Synthesis of Compound 16

Under nitrogen atmosphere, Compound 15 (50 mg, 0.240 mmol), 2,4,6-trichlorophenyl formate (108 mg, 0.481 mmol), palladium acetate (5.4 mg, 0.024 mmol), and xantphos (27.8 mg, 0.048 mmol) were dissolved in toluene (1 mL). To the solution was added triethylamine (50 μL, 0.361 mmol). The tube was sealed and the mixture was stirred at 100° C. for 3 hours. The reaction mixture was filtered and then the solvent was evaporated under reduced pressure. The obtained residue was purified by silica-gel column chromatography (hexane-ethyl acetate) to give Compound 16 (70.6 mg, yield 83%).

$^1$H-NMR (CDCl$_3$) δ: 7.44 (t, J=54.1 Hz, 1H), 7.46 (s, 2H), 7.65 (dd, J=8.0, 4.8 Hz, 1H), 8.64 (d, J=8.0 Hz, 1H), 9.00 (dd, J=4.8, 1.5 Hz, 1H).

Step 2 Synthesis of Compound I-048

Compound 6a (58.9 mg, 0.156 mmol), Compound 16 (50 mg, 0.142 mmol), DMAP (0.87 mg, 7.09 μmol), and triethylamine (22 μL, 0.156 mmol) were dissolved in tetrahydrofuran (1 mL) and the mixture was stirred at 45° C. for 4 hours. To the reaction mixture was added saturated aqueous solution of sodium hydrogen carbonate. The mixture was extracted with ethyl acetate. The organic layer was washed with brine, and then dried over anhydrous sodium sulfate. The solvent was evaporated under reduced pressure. The obtained residue was purified by silica-gel column chromatography (chloroform-methanol) to give Compound I-048 (49.3 mg, yield 65%).

1H-NMR (CDCl3) δ: 1.08-1.34 (m, 5H), 1.43-1.48 (m, 2H), 1.82-1.87 (m, 2H), 2.10-2.14 (m, 2H), 2.60-2.64 (m, 2H), 2.72-2.75 (m, 2H), 2.80-2.87 (m, 6H), 3.89-3.98 (br, 1H), 4.72 (q, J=8.3 Hz, 2H), 5.85 (d, J=7.9 Hz, 1H), 6.91 (t, J=54.7 Hz, 1H), 7.48 (dd, J=7.5, 4.8 Hz, 1H), 7.94 (d, J=7.7 Hz, 1H), 8.72 (d, J=3.9 Hz, 1H).

Reference Example 2 Synthesis of Compound 9a

[Chemical Formula 170]

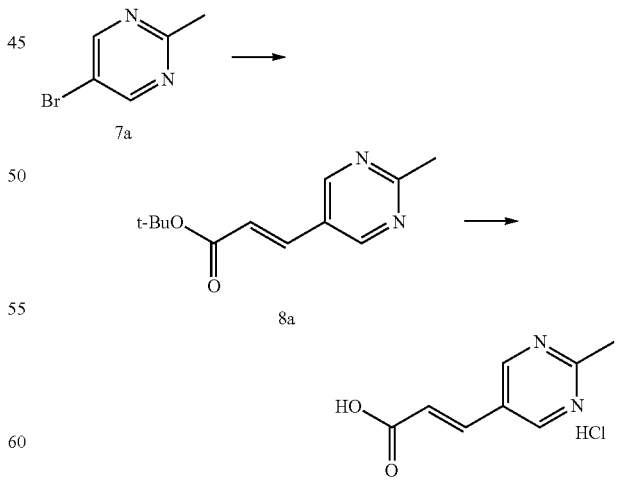

Step 1 Synthesis of Compound 8a

Under nitrogen atmosphere, Compound 7a (100 mg, 0.578 mmol), tert-butyl acrylate (222 mg, 1.734 mmol), palladium acetate (26 mg, 0.116 mmol), tris (4-methylphenyl) phosphine (52.8 mg, 0.173 mmol) and DIEA (404 μL, 2.312 mmol) were dissolved in acetonitrile (1.5 mL). The tube was sealed and the mixture was stirred at 145° C. under microwave irradiation for 25 minutes. The reaction mixture was filtered and then the solvent was evaporated under reduced pressure. The obtained residue was purified by silica-gel column chromatography (hexane-ethyl acetate) to give Compound 8a (87.7 mg, yield 69%).

1H-NMR (CDCl3) δ: 1.54 (s, 9H), 2.77 (s, 3H), 6.47 (d, J=16.2 Hz, 1H), 7.49 (d, J=16.1 Hz, 1H), 8.75 (s, 2H).

Step 2 Synthesis of Compound 9a

Compound 8a (650 mg, 2.95 mmol) was dissolved in 1,4-dioxane (33 mL). To the solution was added 4 mol/L hydrochloric acid (1,4-dioxane solution, 13 mL, 52.0 mmol). The mixture was stirred at 50° C. for 16.5 hours. The solvent was evaporated under reduced pressure, and the obtained residue was washed with ethyl acetate to give Compound 9a (540 mg) as a crude product.

1H-NMR (DMSO-d6) δ: 2.66 (s, 3H), 6.79 (d, J=16.1 Hz, 1H), 7.58 (d, J=16.1 Hz, 1H), 9.06 (s, 2H).

Example 2 Synthesis of Compound I-037

[Chemical Formula 171]

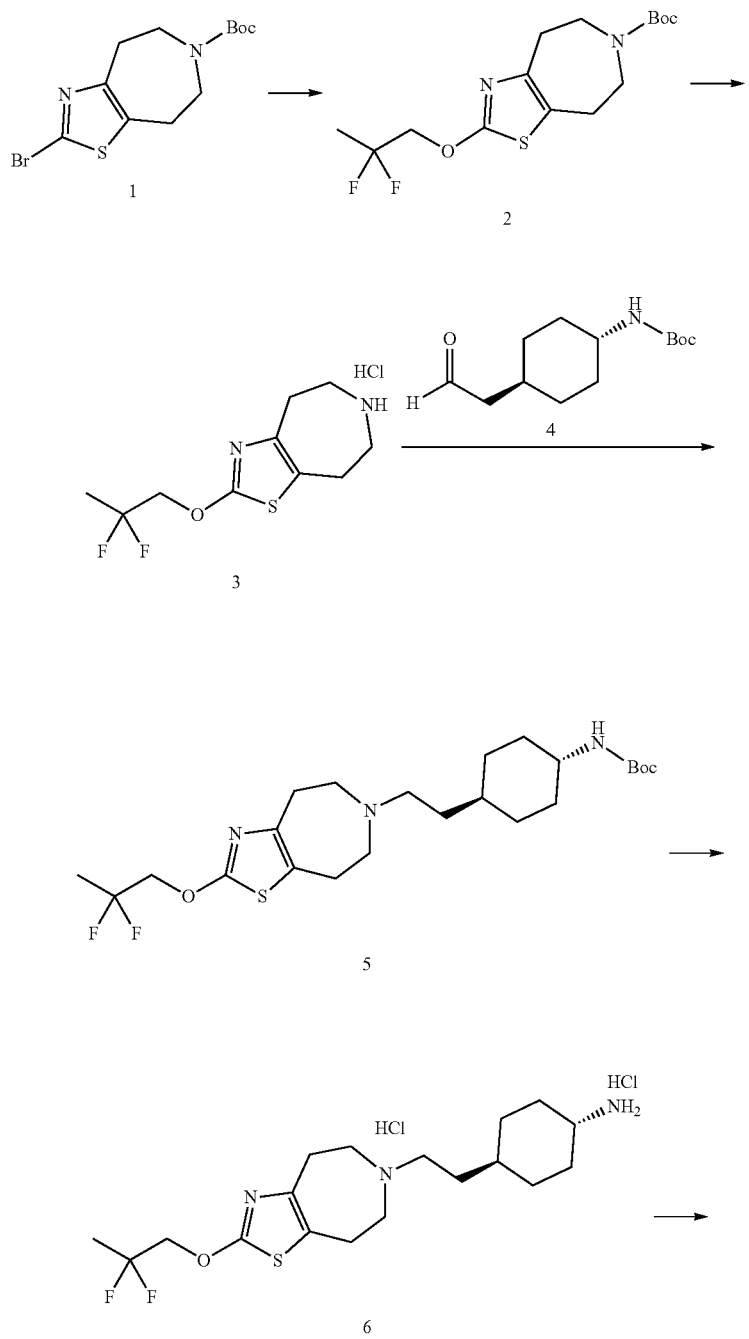

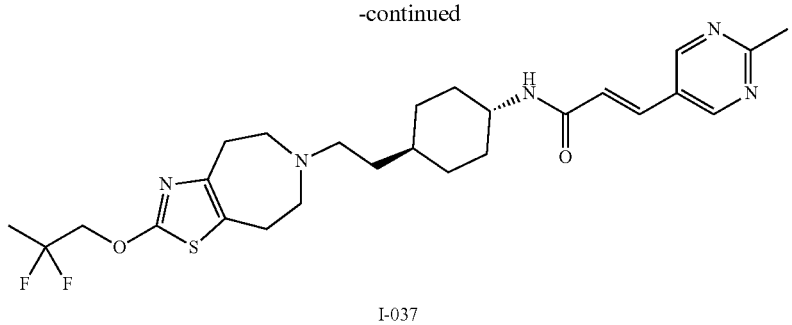

I-037

Step 1 Synthesis of Compound 2

Compound 2 was obtained by using 2,2-difluoropropanol instead of 2,2,2-trifluoroethanol in Step 1 of Reference Example 1.

1H-NMR (CDCl3) δ: 1.48 (s, 9H), 1.72 (t, J=18.7 Hz, 3H), 2.75-2.81 (brm, 2H), 2.86-2.90 (brm, 2H), 3.55-3.63 (brm, 4H), 4.48 (t, J=11.8 Hz, 2H).

Step 2 Synthesis of Compound 3

Compound 2 (471 mg, 1.352 mmol) was dissolved in dichloromethane (2 mL). To the solution was added 4 mol/L hydrochloric acid (1,4-dioxane solution, 5 mL, 20.0 mmol). The mixture was stirred at room temperature for 3 hours. The solvent was evaporated under reduced pressure to give Compound 3 (375 mg, yield 97%) as a crude product.

1H-NMR (DMSO-d6) δ: 1.71 (t, J=19.3 Hz, 3H), 3.03-3.07 (brm, 4H), 3.22-3.28 (brm, 4H), 4.62 (t, J=13.1 Hz, 2H), 9.56 (br, 2H).

Step 3 Synthesis of Compound 5

To Compound 3 (200 mg, 0.702 mmol) were added dichloromethane (4 mL), triethylamine (195 μL, 1.405 mmol) and Compound 4 (178 mg, 0.737 mmol), and the mixture was stirred for 5 minutes. To the mixture, sodium triacetoxyborohydride (298 mg, 1.405 mmol) was added portionwise. The mixture was stirred at room temperature for 1 hour. To the reaction mixture was added saturated aqueous solution of sodium hydrogen carbonate. The mixture was extracted with ethyl acetate. The organic layer was washed with saturated aqueous solution of sodium hydrogen carbonate and brine, and then dried over anhydrous sodium sulfate. The solvent was evaporated under reduced pressure. The obtained residue was purified by amino silica-gel column chromatography (hexane-ethyl acetate) to give Compound 5 (270 mg, yield 81%).

1H-NMR (CDCl3) δ: 0.98-1.12 (m, 4H), 1.19-1.28 (m, 1H), 1.38-1.44 (m, 11H), 1.66-1.78 (m, 5H), 1.98-2.01 (m, 2H), 2.57-2.61 (m, 2H), 2.70-2.72 (m, 2H), 2.80-2.85 (m, 6H), 3.36 (br, 1H), 4.35 (br, 1H), 4.47 (t, J=11.8 Hz, 2H).

Step 4 Synthesis of Compound 6

Compound 5 (270 mg, 0.570 mmol) was dissolved in dichloromethane (4 mL). To the solution was added TFA (1 mL, 12.98 mmol). The mixture was stirred at room temperature for 2 hours. The solvent was evaporated under reduced pressure. To the residue, excess amount of 4 mol/L hydrochloric acid (1,4-dioxane solution) was added, and the mixture was stirred. The solvent was evaporated under reduced pressure to give Compound 6 (272 mg) as a crude product.

1H-NMR (DMSO-d6) δ: 0.96-1.06 (m, 2H), 1.24-1.36 (m, 3H), 1.61-1.80 (m, 7H), 1.93-1.96 (m, 2H), 2.88-2.97 (m, 1H), 3.01-3.31 (m, 8H), 4.63 (t, J=13.2 Hz, 2H), 8.05 (br, 3H), 11.22 (br, 1H).

Step 5 Synthesis of Compound I-037

Compound 6 (25 mg, 0.067 mmol), Compound 9a (12.35 mg, 0.087 mmol), HATU (30.5 mg, 0.080 mmol) and triethylamine (46 μL, 0.335 mmol) were dissolved in DMF (1 mL). The mixture was stirred at room temperature for 2 hours. To the reaction mixture was added water. The mixture was extracted with chloroform. The organic layer was separated and the solvent was evaporated under reduced pressure. The obtained residue was purified by reverse-phase chromatography (acetonitrile-10 mM aqueous ammonium carbonate solution) to give Compound I-037 (24.2 mg, yield 70%).

1H-NMR (CDCl3) δ: 1.07-1.33 (m, 6H), 1.41-1.47 (m, 2H), 1.72 (t, J=18.8 Hz, 3H), 1.80-1.84 (m, 2H), 2.04-2.08 (m, 2H), 2.59-2.63 (m, 2H), 2.71-2.87 (m, 11H), 3.82-3.90 (m, 1H), 4.47 (t, J=11.8 Hz, 2H), 5.46 (d, J=8.0 Hz, 1H), 6.45 (d, J=15.8 Hz, 1H), 7.54 (d, J=15.6 Hz, 1H), 8.75 (s, 2H).

Example 3 Synthesis of I-044

[Chemical Formula 172]

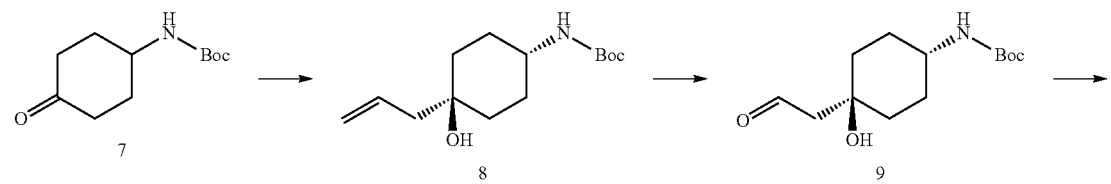

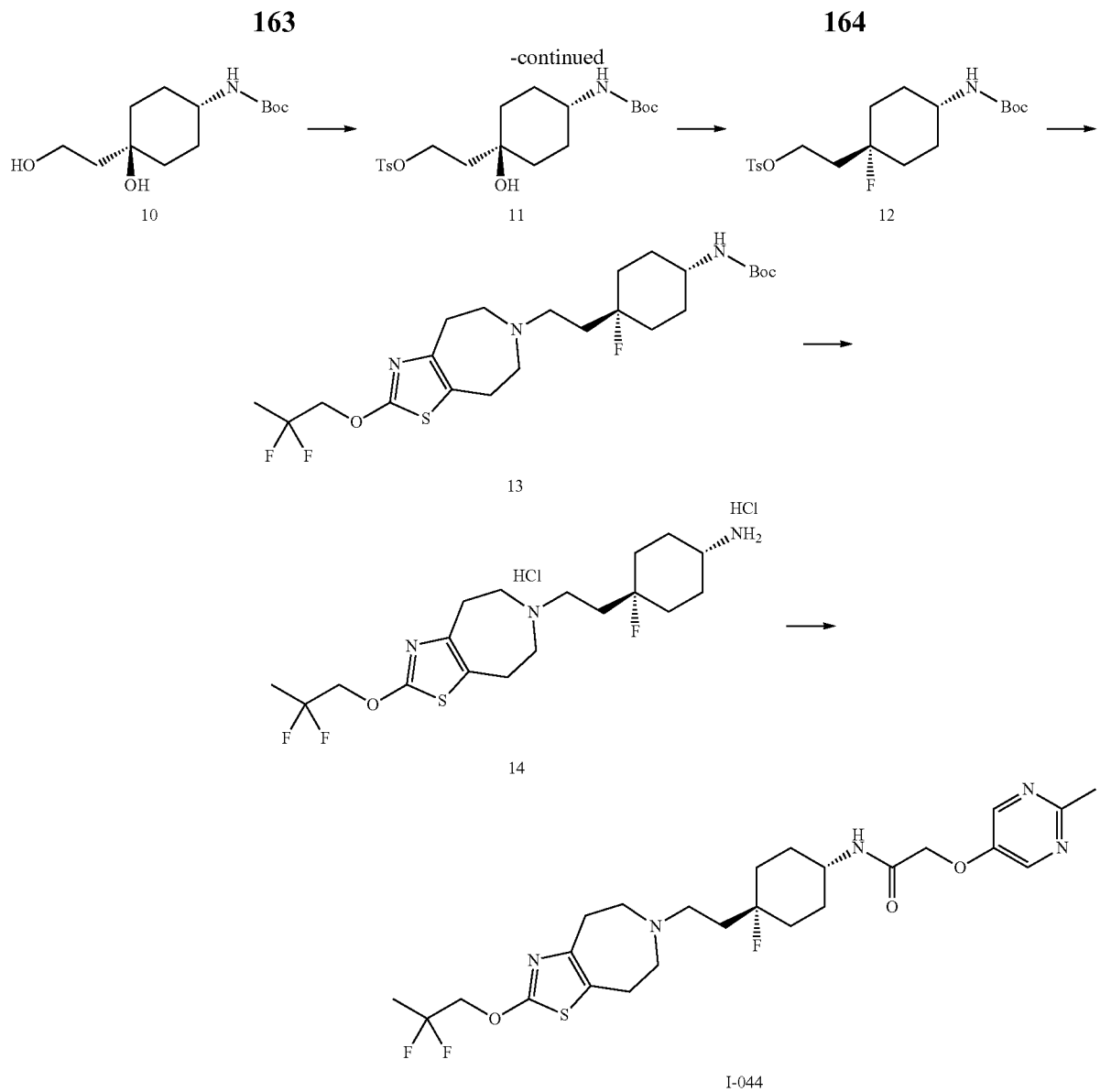

I-044

Step 1 Synthesis of Compound 8

Compound 7 (90.0 g, 422.2 mmol) was dissolved in THF (1000 mL). To the solution was added allylmagnesium bromide (1.0 mol/L diethyl ether solution, 1266 mL, 1266 mmol) at −70° C. The mixture was stirred for 1 hour. To the reaction mixture was added ice water. The mixture was extracted with ethyl acetate. The organic layer was washed with water and brine, and then dried over anhydrous sodium sulfate. The solvent was evaporated under reduced pressure. The obtained residue was purified by silica-gel column chromatography (petroleum ether-ethyl acetate) to give Compound 8 (35.0 g, yield 32%).

1H NMR (CDCl3) δ 1.38-1.53 (m, 15H), 1.62-1.64 (m, 1H), 1.91-1.94 (m, 2H), 2.28 (d, J=7.5 Hz, 2H), 3.61 (brs, 1H), 4.51 (brs, 1H), 5.12-5.20 (m, 2H), 5.85-5.90 (m, 1H).

Step 2 Synthesis of Compound 9

Compound 8 (35.0 g, 137.2 mmol) was dissolved in THF (500 mL) and water (500 mL). To the solution were added potassium osmate (VI) dihydrate (5.05 g, 13.72 mmol) and sodium periodate (117.34 g, 548.63 mmol) at 0° C. The mixture was stirred at room temperature for 8 hours. To the reaction mixture were added water and aqueous solution of sodium thiosulfate. The mixture was extracted with ethyl acetate. The organic layer was washed with water and brine, and then dried over anhydrous sodium sulfate. The solvent was evaporated under reduced pressure to give Compound 9 (35.0 g) as a crude product.

Step 3 Synthesis of Compound 10

Compound 9 (15.0 g, 58.33 mmol) was dissolved in a mixed solvent of THF (150 mL) and methanol (150 mL). To the solution was added sodium borohydride (4.41 g, 116.66 mmol) portionwise at 0° C. The reaction mixture was stirred at 0° C. for 1 hour. To the reaction mixture was added saturated aqueous solution of ammonium chloride. The mixture was extracted with ethyl acetate. The organic layer was washed with brine, and then dried over anhydrous sodium sulfate. The solvent was evaporated under reduced pressure to give Compound 10 (12.0 g) as a crude product.

Step 4 Synthesis of Compound 11

Compound 10 (713 mg, 2.75 mmol) was dissolved in dichloromethane (7.4 mL). To the solution were added 4-dimethylaminopyridine (33.6 mg, 0.275 mmol), triethylamine (0.762 mL, 5.50 mmol) and p-toluenesulfonyl chloride (577 mg, 3.02 mmol) at 0° C. The mixture was stirred at 0° C. for 4 hours. To the reaction mixture was added 0.1 mol/L hydrochloric acid. The mixture was extracted with ethyl acetate. The organic layer was washed with saturated aqueous solution of sodium hydrogen carbonate, water and brine, and then dried over anhydrous sodium sulfate. The solvent was evaporated under reduced pressure. The obtained residue was purified by silica-gel column chromatography (hexane-ethyl acetate) to give Compound 11 (761 mg, yield 67%).

1H-NMR (CDCl3) δ: 1.29-1.38 (m, 3H), 1.43-1.50 (m, 11H), 1.57-1.66 (m, 2H), 1.86-1.93 (m, 4H), 2.46 (s, 3H), 3.57 (brs, 1H), 4.22 (t, J=6.7 Hz, 2H), 4.46 (brs, 1H), 7.36 (d, J=8.0 Hz, 2H), 7.79 (d, J=8.3 Hz, 2H).

Step 5 Synthesis of Compound 12

Compound 11 (759 mg, 1.83 mmol) was dissolved in dichloromethane (30.4 mL). To the solution was added (diethylamino)sulfur trifluoride (1.45 mL, 11.0 mmol) at −78° C. The reaction mixture was stirred at −78° C. for 40 minutes. To the reaction mixture was added water and the mixture was extracted with ethyl acetate. The organic layer was washed with water and brine, and then dried over anhydrous sodium sulfate. The solvent was evaporated under reduced pressure. The obtained residue was purified by silica-gel column chromatography (hexane-ethyl acetate) to give Compound 12 (345 mg, yield 45%).

1H-NMR (CDCl3) δ: 1.36-1.48 (m, 13H), 1.80-1.99 (m, 6H), 2.46 (s, 3H), 3.40 (brs, 1H), 4.17 (t, J=6.7 Hz, 2H), 4.38 (brs, 1H), 7.35 (d, J=8.0 Hz, 2H), 7.79 (d, J=8.3 Hz, 2H).

Step 6 Synthesis of Compound 13

The dehydrochlorinated Compound 3 (1.00 g, 4.03 mmol, prepared by neutralizing Compound 3 with saturated aqueous solution of sodium hydrogen carbonate, then extracting with chloroform) was dissolved in acetonitrile (40 mL). To the solution were added potassium carbonate (1.67 g, 12.09 mmol) and Compound 12 (1.67 g, 4.03 mmol). The mixture was stirred at 80° C. for 58 hours. To the reaction mixture was added water. The mixture was extracted with ethyl acetate. The organic layer was washed with brine, and then dried over anhydrous sodium sulfate. The solvent was evaporated under reduced pressure, and the obtained residue was purified by silica-gel column chromatography (chloroform-methanol) to give Compound 13 (1.45 g, yield 73%).

1H-NMR (CDCl3) δ: 1.38-1.56 (m, 13H), 1.67-1.86 (m, 7H), 1.91-2.01 (m, 2H), 2.71-2.74 (m, 4H), 2.77-2.86 (m, 6H), 3.44 (brs, 1H), 4.41-4.50 (m, 3H).

Step 7 Synthesis of Compound 14

Compound 13 (1.45 g, 2.95 mmol) was dissolved in methanol (30 mL). To the solution was added 4 mol/L hydrochloric acid (1,4-dioxane solution, 30 mL, 120.0 mmol). The mixture was stirred at room temperature for 2 hours. The solvent was evaporated under reduced pressure to give Compound 14 (1.47 g) as a crude product.

Step 8 Synthesis of Compound I-044

Compound I-044 was obtained by using 2-((2-methylpyrimidin-5-yl)oxy) acetic acid instead of Compound 9a and using Compound 14 instead of Compound 6 in Step 5 of Example 2.

1H-NMR (CDCl3) δ: 1.45-1.65 (m, 4H), 1.72 (t, J=18.7 Hz, 3H), 1.78-1.90 (m, 4H), 1.97-2.03 (m, 2H), 2.70-2.86 (m, 13H), 3.86-3.96 (m, 1H), 4.44-4.53 (m, 4H), 6.35 (d, J=8.5 Hz, 1H), 8.37 (s, 2H).

Example 4 Synthesis of Compound I-026

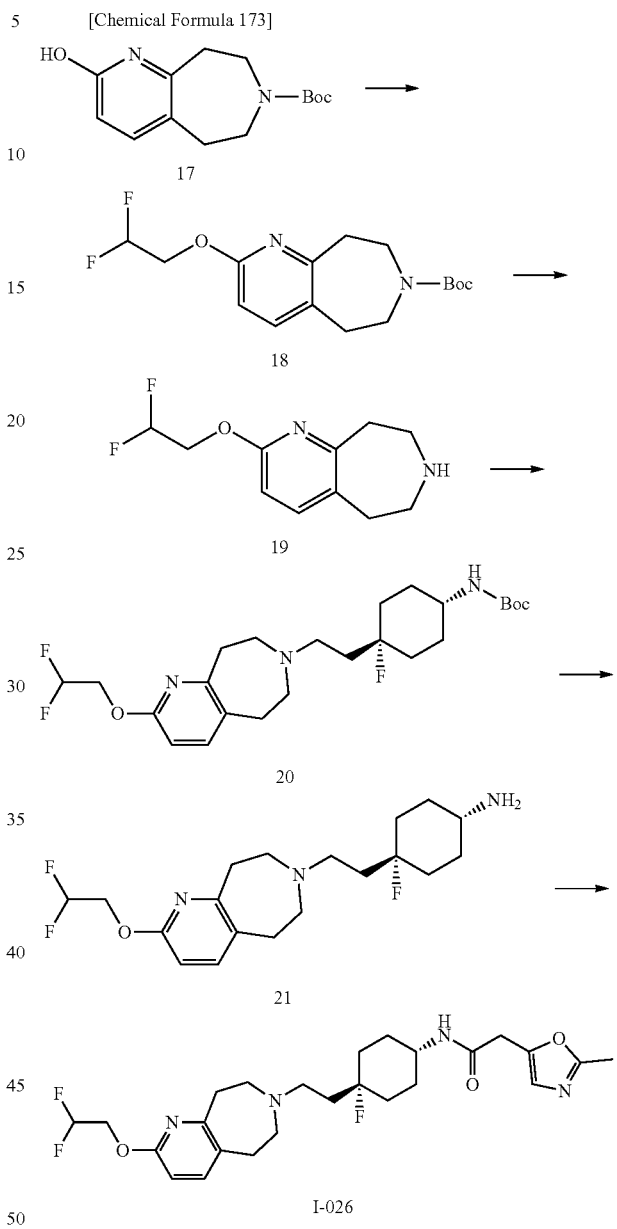

Step 1 Synthesis of Compound 18

Compound 17 (200 mg, 0.76 mmol) was dissolved in DMF (4 mL). To the solution were added 2,2-difluoroethyl trifluoromethanesulfonate (324 mg, 1.51 mmol) and potassium carbonate (282 mg, 2.04 mmol). The mixture was stirred at room temperature overnight. To the reaction mixture was added water. The mixture was extracted with ethyl acetate. The organic layer was washed with brine, and then dried over anhydrous sodium sulfate. The solvent was evaporated under reduced pressure. The obtained residue was purified by silica-gel column chromatography (hexane-ethyl acetate) to give Compound 18 (225 mg, yield 91%).

1H-NMR (CDCl3) δ: 1.49 (s, 9H), 2.81 (m, 2H), 3.02 (m, 2H), 3.56 (m, 4H), 4.51 (td, J=13.6, 4.3 Hz, 2H), 6.12 (tt, J=55.8, 4.3 Hz, 1H), 6.57 (d, J=8.3 Hz, 1H), 7.34 (d, J=8.3 Hz, 1H).

Step 2 Synthesis of Compound 19

Compound 18 (5.31 g, 16.17 mmol) was dissolved in 1,4-dioxane (40 mL), and 4 mol/L hydrochloric acid (1,4-dioxane solution, 80.6 mL, 323 mmol) was added. The mixture was stirred at room temperature for 4.5 hours. The solvent was evaporated under reduced pressure, and then to the mixture was added 10% aqueous potassium carbonate solution. The mixture was extracted with chloroform. The organic layer was washed with brine, and then dried over anhydrous sodium sulfate. The solvent was evaporated under reduced pressure to give Compound 19 (3.87 g) as a crude product.

1H-NMR (CDCl3) δ: 2.80-2.83 (m, 2H), 2.93-2.99 (m, 4H), 3.03-3.05 (m, 2H), 4.51 (td, J=13.6, 4.3 Hz, 2H), 6.13 (tt, J=55.9, 4.3 Hz, 1H), 6.54 (d, J=8.2 Hz, 1H), 7.32 (d, J=8.2 Hz, 1H).

Step 3 Synthesis of Compound 20

To Compound 19 (0.958 g, 3.78 mmol) were added potassium carbonate (2.089 g, 15.11 mmol), acetonitrile (31.4 mL) and Compound 12 (1.57 g, 3.78 mmol). The mixture was stirred at 70° C. for 22.5 hours. To the reaction mixture was added water. The mixture was extracted with ethyl acetate. The organic layer was washed with brine, and then dried over anhydrous magnesium sulfate. The solvent was evaporated under reduced pressure, and the obtained residue was purified by silica-gel column chromatography (chloroform-methanol) to give Compound 20 (1.643 g, yield 92%).

1H-NMR (CDCl3) δ: 1.44-1.97 (m, 19H), 2.60-2.66 (m, 6H), 2.80-2.83 (m, 2H), 3.01-3.04 (m, 2H), 3.43 (br, 1H), 4.42-4.55 (m, 3H), 6.13 (tt, J=55.8, 4.3 Hz, 1H), 6.55 (d, J=8.0 Hz, 1H), 7.31 (d, J=8.2 Hz, 1H).

Step 4 Synthesis of Compound 21

Compound 21 was obtained by using Compound 20 instead of Compound 5a in Step 4 of Reference Example 1.

Step 5 Synthesis of Compound I-026

Compound 21 (25 mg, 0.067 mmol), 2-(2-methyloxazol-5-yl) acetic acid (12.35 mg, 0.087 mmol), HATU (30.7 mg, 0.081 mmol) and triethylamine (47 μL, 0.337 mmol) were dissolved in DMF (1 mL) and the mixture was stirred at room temperature for 2 hours. To the reaction mixture was added water. The mixture was extracted with chloroform. The organic layer was separated and the solvent was evaporated under reduced pressure. The obtained residue was purified by reverse-phase chromatography (acetonitrile-10 mM aqueous ammonium carbonate solution) to give Compound I-026 (23 mg, yield 69%).

1H-NMR (CDCl3) δ: 1.41-1.52 (m, 4H), 1.77-1.85 (m, 4H), 1.93-1.98 (m, 2H), 2.44 (s, 3H), 2.59-2.65 (m, 6H), 2.80-2.82 (m, 2H), 3.01-3.04 (m, 2H), 3.56 (s, 2H), 3.75-3.83 (m, 1H), 4.51 (td, J=13.6, 4.2 Hz, 2H), 5.41 (d, J=8.0 Hz, 1H), 6.12 (tt, J=55.9, 4.3 Hz, 1H), 6.55 (d, J=8.2 Hz, 1H), 6.82 (s, 1H), 7.30 (d, J=8.0 Hz, 1H).

Example 5 Synthesis of Compound I-022

[Chemical Formula 174]

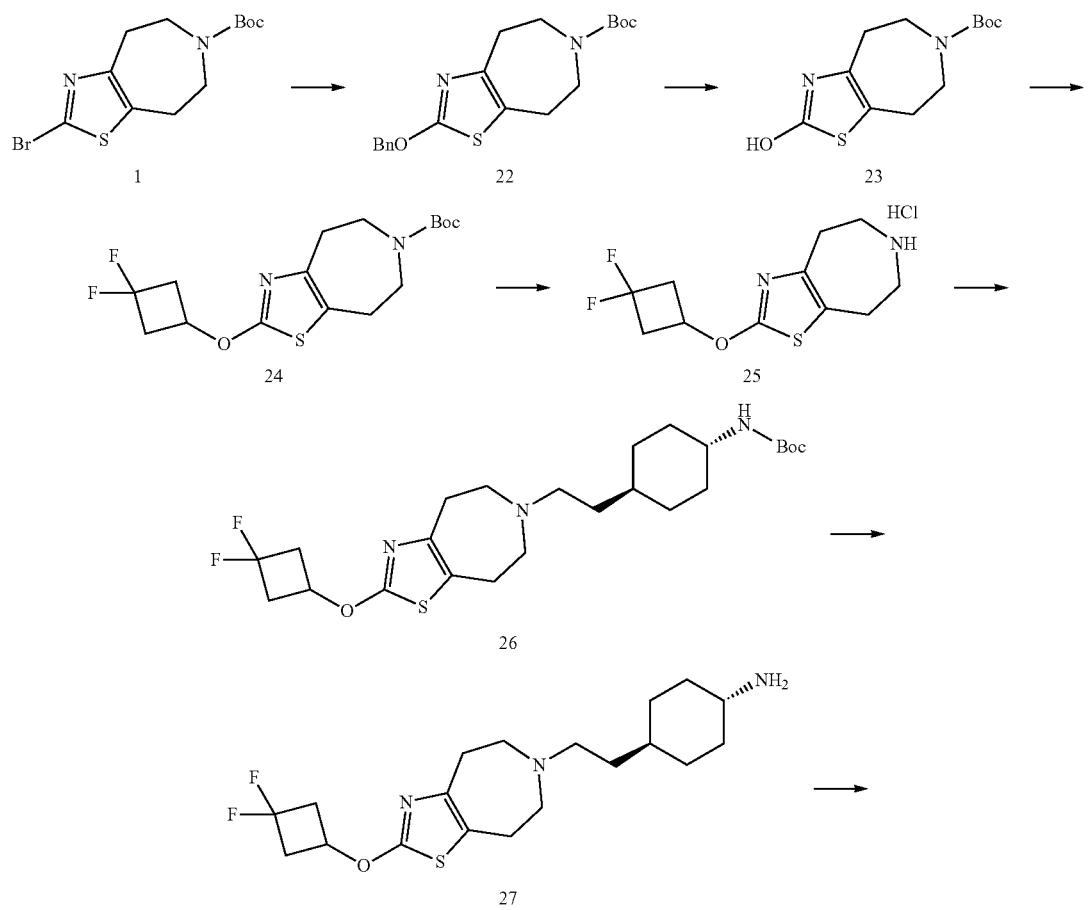

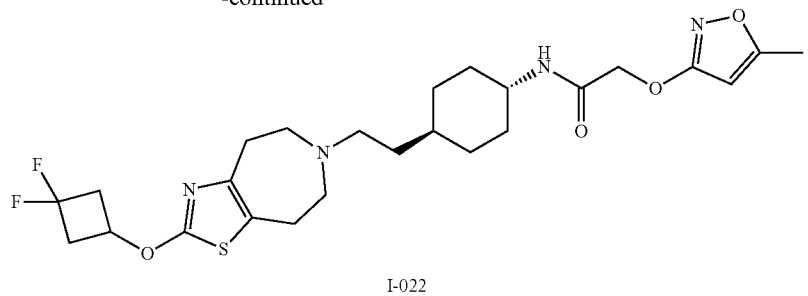

I-022

Step 1 Synthesis of Compound 22

Compound 22 was obtained by using benzyl alcohol instead of 2,2,2-trifluoroethanol in Step 1 of Example 1.

1H-NMR (CDCl3) δ: 1.48 (s, 9H), 2.74-2.80 (brm, 2H), 2.89-2.95 (brm, 2H), 3.55-3.64 (brm, 4H), 5.34 (s, 2H), 7.34-7.44 (m, 5H).

Step 2 Synthesis of Compound 23

Compound 22 (11.06 g, 30.7 mmol) was dissolved in a mixed solvent of ethyl acetate (83 mL) and methanol (83 mL). To the solution was added 10% palladium carbon (4.40 g). The mixture was stirred at room temperature under hydrogen atmosphere overnight. The reaction mixture was filtered to remove palladium carbon, and then the solvent was evaporated under reduced pressure. The obtained residue was recrystallized with ethyl acetate to give Compound 23 (7.05 g, yield 85%).

1H-NMR (CDCl3) δ: 1.47 (s, 9H), 2.57-2.68 (brm, 4H), 3.53-3.62 (brm, 4H), 9.41 (brs, 0.5H), 9.79 (brs, 0.511).

Step 3 Synthesis of Compound 24

Compound 23 (50 mg, 0.185 mmol), 3,3-difluorocyclobutan-1-ol (100 mg, 0.925 mmol) and triphenylphosphine (388.5 mg, 1.481 mmol) were dissolved in tetrahydrofuran (4 mL). To the solution was added DIAD (180 μL, 0.925 mmol). The mixture was stirred at 65° C. The solvent was evaporated under reduced pressure. The obtained residue was purified by silica-gel column chromatography (hexane-ethyl acetate) to give Compound 24 (53 mg, yield 80%).

1H-NMR (CDCl3) δ: 1.48 (s, 9H), 2.71-2.90 (m, 6H), 3.05-3.15 (m, 2H), 3.53-3.64 (m, 4H), 5.02-5.09 (br, 1H).

Step 4 Synthesis of Compound 25

Compound 24 (1.58 g, 4.38 mmol) was dissolved in methanol (22 mL). To the solution was added 4 mol/L hydrochloric acid (1,4-dioxane solution, 21.92 mL, 88 mmol). The mixture was stirred at room temperature for 2 hours. The solvent was evaporated under reduced pressure to give Compound 25 (1.56 g) as a crude product.

Step 5 Synthesis of Compound 26

Compound 26 was obtained by using Compound 25 instead of Compound 3a in Step 3 of Reference Example 1.

Step 6 Synthesis of Compound 27

Compound 27 was obtained by using Compound 26 instead of Compound 5a in Step 4 of Reference Example 1.

Step 7 Synthesis of Compound I-022

Compound I-022 was obtained by using Compound 27 instead of Compound 21 and using 2-((5-methylisoxazol-3-yl)oxy) acetic acid instead of 2-(2-methyloxazol-5-yl) acetic acid in Step 5 of Example 4.

1H-NMR (CDCl3) δ: 1.04-1.31 (m, 5H), 1.40-1.45 (m, 2H), 1.79-1.82 (m, 2H), 1.99-2.02 (m, 2H), 2.36 (s, 3H), 2.58-2.62 (m, 2H), 2.70-2.86 (m, 10H), 3.04-3.14 (m, 2H), 3.76-3.86 (m, 111), 4.66 (s, 2H), 5.02-5.08 (brm, 1H), 5.70 (s, 1H), 6.15 (d, J=8.3 Hz, 1H).

Example 6 Synthesis of Compound I-041

[Chemical Formula 175]

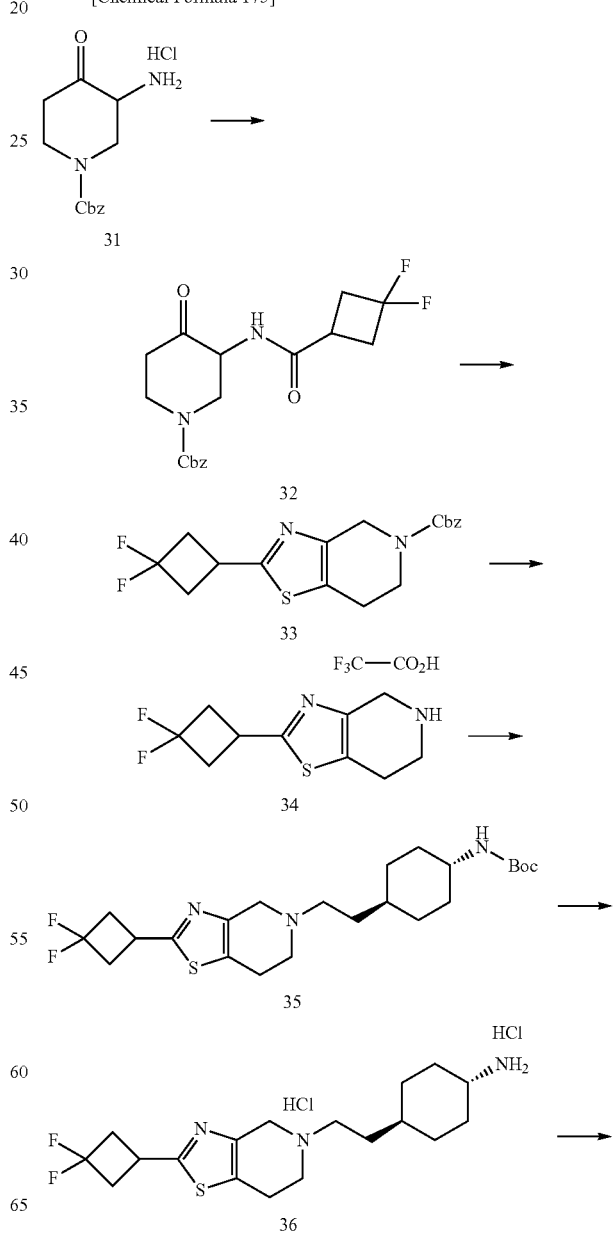

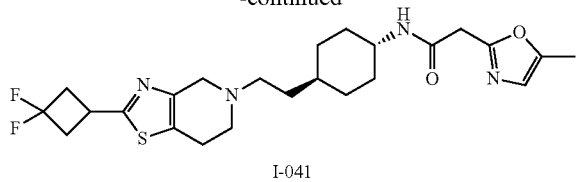

I-041

Step 1 Synthesis of Compound 32

3,3-Difluorocyclobutane-1-carboxylic acid (28.7 mg, 0.211 mmol) was dissolved in dichloromethane (1 mL). To the solution were added the catalyst amount of DMF and oxalyl chloride (23 μL, 0.263 mmol) at 0° C. The reaction mixture was stirred at room temperature for 3 hours to prepare an acid chloride. To Compound 31 (50 mg, 0.176 mmol) was added tetrahydrofuran (1 mL), followed by a solution of the prepared acid chloride at 0° C. A solution of triethylamine (85 μL, 0.615 mmol) in tetrahydrofuran (1 mL) was slowly added dropwise and the mixture was stirred at room temperature overnight. To the reaction mixture was added saturated aqueous solution of sodium hydrogen carbonate. The mixture was extracted with ethyl acetate. The organic layer was washed with water and brine, and then dried over anhydrous magnesium sulfate. The solvent was evaporated under reduced pressure to give Compound 32 (62 mg, yield 96%) as a crude product.

Step 2 Synthesis of Compound 33

The crude product of Compound 32 (62 mg) obtained in step 1 was dissolved in tetrahydrofuran (2 mL). To the solution was added 2,4-bis(4-methoxyphenyl)-1,3,2,4-dithiadiphosphetan-2,4-disulfide (68.4 mg, 0.169 mmol). The mixture was stirred at 60° C. for 3 hours. The solvent was evaporated under reduced pressure. The obtained residue was purified by amino silica-gel column chromatography (hexane-ethyl acetate) to give Compound 33 (20 mg, yield 32%).

1H-NMR (CDCl3) δ: 2.85-3.08 (m, 6H), 3.56-3.65 (m, 1H), 3.81 (br, 2H), 4.67 (s, 2H), 5.18 (s, 2H), 7.31-7.39 (m, 5H).

Step 3 Synthesis of Compound 34

Compound 33 (5.1 g, 14 mmol) was dissolved in TFA (51 mL). The solution was stirred at 80° C. for 4 hours. The solvent was evaporated under reduced pressure to give Compound 34 as a crude product.

Step 4 Synthesis of Compound 35

Compound 35 was obtained by using Compound 34 instead of Compound 3a in Step 3 of Reference Example 1.

Step 5 Synthesis of Compound 36

Compound 35 (6.5 g, 24.37 mmol) was dissolved in 1,4-dioxane (20 mL). To the solution was added 4 mol/L hydrochloric acid (1,4-dioxane solution, 30 mL, 120 mmol). The mixture was stirred at room temperature overnight. The precipitated solid was filtered and washed with 1,4-dioxane and hexane to give Compound 36 (6.68 g) as a crude product.

Step 6 Synthesis of Compound I-041

Compound I-041 was obtained by using Compound 36 instead of Compound 21 and using potassium 2-(5-methyloxazol-2-yl) acetate instead of 2-(2-methyloxazol-5-yl) acetic acid in Step 5 of Example 4.

1H-NMR (CDCl3) δ: 1.03-1.36 (m, 5H), 1.47-1.52 (m, 2H), 1.78-1.82 (m, 2H), 1.95-2.00 (m, 2H), 2.29 (d, J=0.6 Hz, 3H), 2.55-2.59 (m, 2H), 2.77 (t, J=5.4 Hz, 2H), 2.84-3.07 (m, 6H), 3.56-3.79 (m, 6H), 6.66 (d, J=0.9 Hz, 1H), 7.29 (d, J=7.9 Hz, 1H)

Example 7 Synthesis of Compound I-045

[Chemical Formula 176]

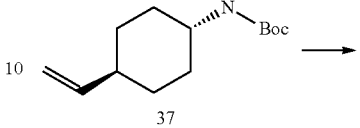

37

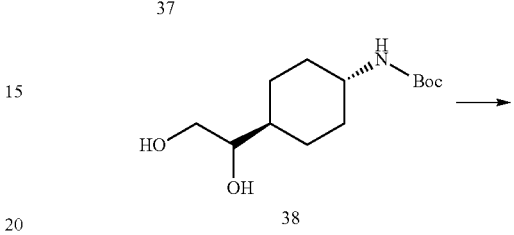

38

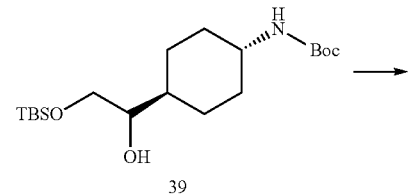

39

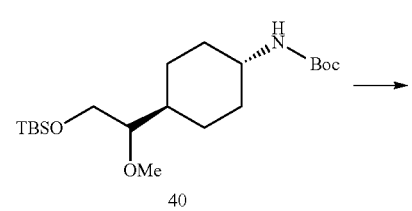

40

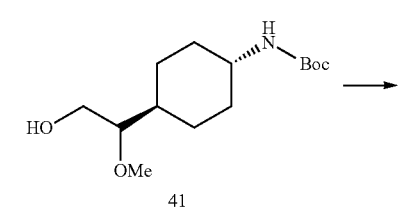

41

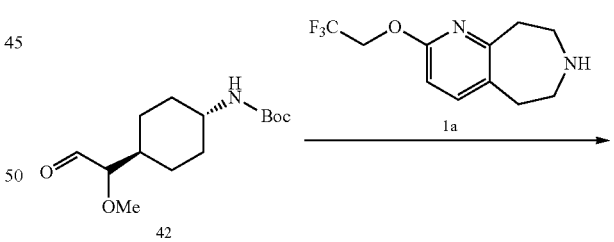

42

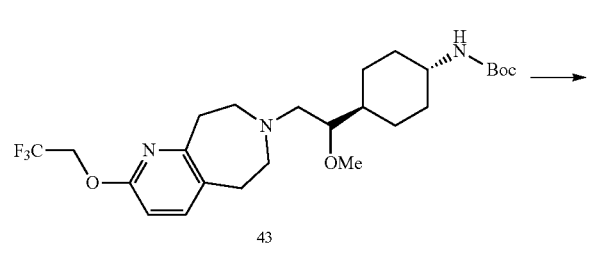

43

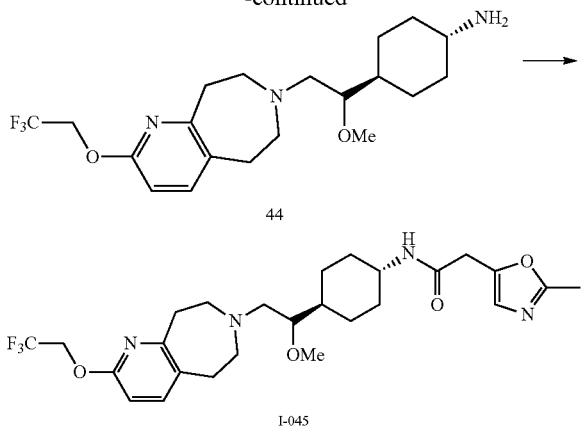

Step 1 Synthesis of Compound 38

Compound 37 (500 mg, 2.22 mmol), N-methylmorpholin-N-oxide (780 mg, 6.66 mmol) and potassium osmate dihydrate (82 mg, 0.222 mmol) were dissolved in a mixed solvent of acetone (5 mL) and water (5 mL) at 0° C., and then the mixture was stirred for 2 hours. The mixture was then stirred at room temperature and left standing overnight at room temperature. Then the reaction mixture was filtered and the obtained filtrate was extracted with chloroform. The organic layer was dried over anhydrous sodium sulfate and then the solvent was evaporated under reduced pressure. The obtained residue was purified by silica-gel column chromatography (chloroform-methanol) to give Compound 38 (472 mg, yield 82%).

Step 2 Synthesis of Compound 39

Compound 38 (150 mg, 0.578 mmol) was dissolved in DMF (3 mL). To the solution were added imidazole (79 mg, 1.157 mmol) and tert-butyldimethylsilyl chloride (122 mg, 0.809 mmol) at 0° C. The mixture was stirred at 0° C. for 6 hours, then at room temperature for 1 hour. To the reaction mixture were added water and saturated aqueous solution of sodium hydrogen carbonate. The mixture was extracted with ethyl acetate. The organic layer was washed with water and brine, and then dried over anhydrous sodium sulfate. The solvent was evaporated under reduced pressure. The obtained residue was purified by silica-gel column chromatography (hexane-ethyl acetate) to give Compound 39 (187 mg, yield 87%).

1H-NMR (CDCl3) δ: 0.07 (s, 6H), 0.90 (s, 9H), 1.01-1.20 (m, 4H), 1.24-1.37 (m, 2H), 1.44 (s, 9H), 1.62-1.68 (m, 1H), 1.98-2.06 (m, 2H), 2.49 (d, J=3.3 Hz, 1H), 3.33-3.38 (m, 2H), 3.46 (t, J=8.8 Hz, 1H), 3.67 (dd, J=9.8, 3.3 Hz, 1H), 4.36 (s, 1H).

Step 3 Synthesis of Compound 40

To 1,8-bis(dimethylamino)naphthalene (6.75 g, 31.5 mmol) and trimethyloxonium tetrafluoroborate (2.33 g, 15.74 mmol) was added dichloromethane (60 mL). The mixture was stirred. A solution of Compound 39 (2.94 g, 7.87 mmol) in dichloromethane (30 mL) was added dropwise over 30 minutes at room temperature, and then the mixture was stirred for 50 minutes. To the reaction mixture was added an aqueous solution of sodium hydrogen carbonate. The mixture was filtered and the resulting filtrate was extracted with dichloromethane. The organic layer was washed with 1 mol/L aqueous citric acid solution and then dried over anhydrous sodium sulfate. The solvent was evaporated under reduced pressure. The obtained residue was purified by silica-gel column chromatography (hexane-ethyl acetate) to give Compound 40 (2.74 g, yield 90%).

1H-NMR (CDCl3) δ: 0.05 (s, 6H), 0.89 (s, 9H), 0.98-1.30 (m, 5H), 1.43 (s, 9H), 1.67-1.72 (m, 1H), 1.84-1.88 (m, 1H), 2.01-2.04 (m, 2H), 2.91-2.95 (m, 1H), 3.37 (br, 1H), 3.41 (s, 3H), 3.58-3.68 (m, 2H), 4.34 (s, 1H).

Step 4 Synthesis of Compound 41

Compound 40 (145 mg, 0.374 mmol) was dissolved in tetrahydrofuran (3 mL). To the solution was added TBAF (374 µL, 1 mol/L tetrahydrofuran solution). The mixture was stirred at room temperature for 4 hours. To the reaction mixture was added saturated aqueous solution of ammonium chloride. The mixture was extracted with ethyl acetate. The organic layer was washed with brine, and then dried over anhydrous sodium sulfate. The solvent was evaporated under reduced pressure. The obtained residue was purified by silica-gel column chromatography (hexane-ethyl acetate) to give Compound 41 (82 mg, yield 81%).

Step 5 Synthesis of Compound 42

Compound 41 (80 mg, 0.293 mmol) was dissolved in dichloromethane (2 mL). To the solution were added sodium hydrogen carbonate (73.8 mg, 0.878 mmol) and Dess-Martin periodinane (186 mg, 0.439 mmol) at 0° C. The mixture was stirred at 0° C. for 3.5 hours. To the reaction mixture was added aqueous solution of sodium hydrogen carbonate. The mixture was filtered and the resulting filtrate was extracted with ethyl acetate. The organic layer was washed with brine, and then dried over anhydrous sodium sulfate. The solvent was evaporated under reduced pressure. The obtained residue was purified by silica-gel column chromatography (hexane-ethyl acetate) to give Compound 42 (61.7 mg, yield 78%).

Step 6 Synthesis of Compound 43

Compound 43 was obtained by using Compound 42 instead of Compound 4 and using Compound 1a (synthesized by the similar method as Compound 19 in Example 4) instead of Compound 3a in Step 3 of Reference Example 1.

Step 7 Synthesis of Compound 44

Compound 44 was obtained by using Compound 43 instead of Compound 5a in Step 4 of Reference Example 1.

Step 8 Synthesis of Compound I-045

To Compound 44 (32.1 mg, 0.08 mmol) were added DMF (2 mL), 2-(2-methyloxazol-5-yl) acetic acid (12.42 mg, 0.088 mmol), EDC hydrochloride (16.87 mg, 0.088 mmol), HOBt (11.89 mg, 0.088 mmol) and triethylamine (33 µL, 0.240 mmol). The mixture was stirred at room temperature overnight. To the reaction mixture was added aqueous solution of sodium hydrogen carbonate. The mixture was extracted with ethyl acetate. The organic layer was washed with brine, and then dried over anhydrous sodium sulfate. The solvent was evaporated under reduced pressure. The obtained residue was purified by silica-gel column chromatography (hexane-ethyl acetate) and then subjected to SFC chiral preparative separation to give Compound I-045 (10.8 mg) as an optically active compound.

1H-NMR (CDCl3) δ: 1.01-1.14 (m, 2H), 1.16-1.34 (m, 3H), 1.70-1.85 (m, 2H), 1.97-2.06 (m, 2H), 2.44 (s, 311), 2.54 (d, J=5.3 Hz, 2H), 2.59-2.75 (m, 4H), 2.80 (t, J=4.8 Hz, 2H), 3.01 (t, J=4.9 Hz, 2H), 3.06-3.13 (m, 1H), 3.41 (s, 3H), 3.55 (s, 2H), 3.68-3.76 (m, 1H), 4.74 (q, J=8.7 Hz, 2H), 5.35 (d, J=7.8 Hz, 1H), 6.59 (d, J=8.0 Hz, 1H), 6.82 (s, 1H), 7.32 (d, J=8.0 Hz, 1H).

SFC Preparative Condition
Preparative column (IF—IF, Daicel)
Flow rate: 30 mL/min
Mobile phase: methanol+0.1% diethylamine 30%
Sample: 17.5 mg/mL (methanol/chloroform=1/1)

Loading amount: 35 mg
Detection wavelength: 220 nm, Back pressure: 8 MPa

Reference Example 3 Synthesis of Compound 12a

[Chemical Formula 177]

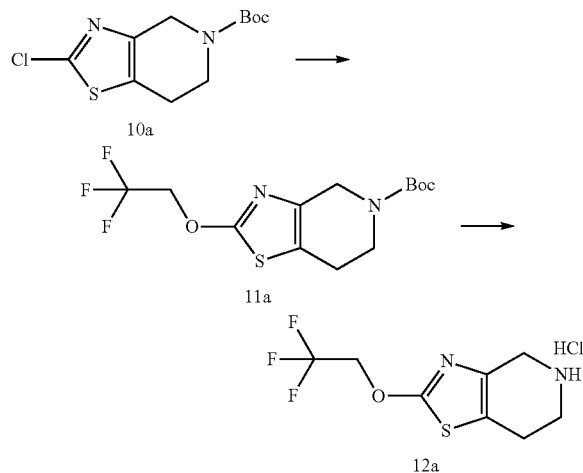

Step 1 Synthesis of Compound 11a

Compound 11a was obtained by using Compound 10a instead of Compound 1 in Step 1 of Reference Example 1.

1H-NMR (CDCl$_3$) δ: 1.49 (s, 9H), 2.70 (br, 2H), 3.72 (br, 2H), 4.39 (s, 2H), 4.76 (q, J=8.2 Hz, 2H).

Step 2 Synthesis of Compound 12a

Compound 12a was obtained by using Compound 11a instead of Compound 2 in Step 2 of Example 2.

1H-NMR (DMSO-d$_6$) δ: 2.93-2.96 (m, 2H), 3.40-3.42 (m, 2H), 4.10 (s, 2H), 5.13 (q, J=8.8 Hz, 2H), 9.58 (br, 2H).

Example 8 Synthesis of Compound I-134

[Chemical Formula 178]

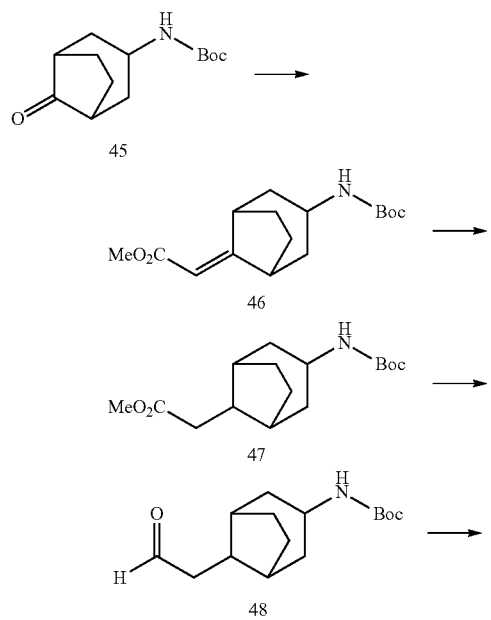

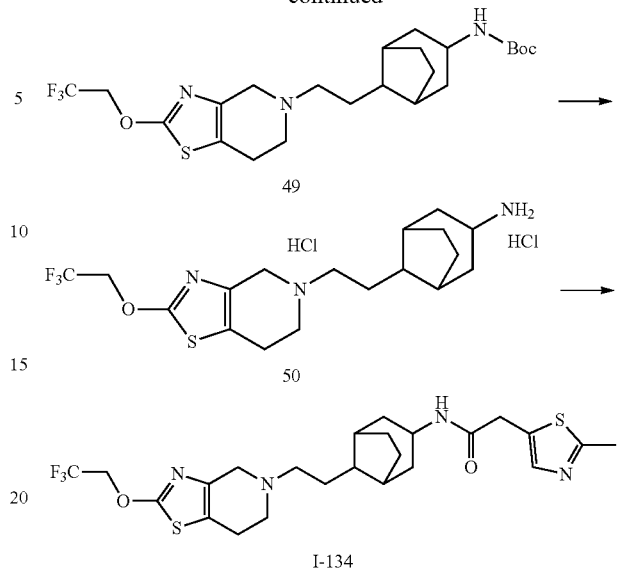

Step 1 Synthesis of Compound 46

Sodium hydride (54.3 mg, 1.358 mmol, 60 wt %) was suspended in tetrahydrofuran (4 mL), and trimethyl phosphonoacetate (228 mg, 1.254 mmol) was added at 0° C. The mixture was stirred for 30 minutes. A solution of Compound 45 (endo-exo mixture, 250 mg, 1.045 mmol) in tetrahydrofuran (4 mL) was added, and the mixture was stirred at room temperature for 3 hours. To the reaction mixture were added saturated aqueous solution of ammonium chloride and water. The mixture was extracted with ethyl acetate. The organic layer was washed with water and brine, and then dried over anhydrous magnesium sulfate. The solvent was evaporated under reduced pressure to give Compound 46 (261 mg) as a mixture of diastereomers.

Step 2 Synthesis of Compound 47

Compound 46 (258 mg, 0.873 mmol), a mixture of stereoisomers, was dissolved in a mixture of methanol (3 mL) and tetrahydrofuran (3 mL). To the solution was added 10% palladium carbon (186 mg). The mixture was then stirred under a hydrogen atmosphere at room temperature for 5 hours. The reaction mixture was filtered through Celite, and then the solvent was evaporated under reduced pressure. The obtained residue was purified by silica-gel column chromatography (hexane-ethyl acetate) to give Compound 47 (148 mg).

Step 3 Synthesis of Compound 48

Under nitrogen atmosphere, Compound 47 (144 mg, 0.484 mmol) was dissolved in dichloromethane (3 mL), and DIBAL (1 mol/L hexane solution, 1452 μL, 1.452 mmol) was added at −78° C. The mixture was stirred for 2 hours. To the reaction mixture was added 10% aqueous potassium sodium tartrate solution. The mixture was stirred at room temperature for 1 hour. To the reaction mixture was added water, and the mixture was extracted with ethyl acetate. The organic layer was washed with water and brine, and then dried over anhydrous magnesium sulfate. The solvent was evaporated under reduced pressure. The obtained residue was purified by silica-gel column chromatography (hexane-ethyl acetate) to give Compound 48 (61 mg) as a mixture of diastereomers.

Step 4 Synthesis of Compound 49

Compound 49 was obtained by using Compound 12a instead of Compound 3 and using Compound 48 instead of Compound 4 in Step 3 of Example 2.

Step 5 Synthesis of Compound 50

Compound 49 (57 mg, 0.116 mmol) was dissolved in 1,4-dioxane (1 mL). To the solution was added 4 mol/L hydrochloric acid (1,4-dioxane solution, 582 μL, 2.33 mmol). The mixture was stirred at room temperature overnight. The solvent was evaporated under reduced pressure to give Compound 50 (55 mg) as a crude product.

Step 6 Synthesis of Compound I-134

To Compound 50 (54 mg, 0.117 mmol) were added DMF (1 mL), 2-(2-methylthiazol-5-yl) acetic acid (22.03 mg, 0.140 mmol), EDC hydrochloride (26.9 mg, 0.140 mmol), HOBt (18.94 mg, 0.140 mmol) and triethylamine (81 μL, 0.584 mmol). The mixture was stirred at room temperature overnight. To the reaction mixture was added saturated aqueous solution of sodium hydrogen carbonate. The mixture was extracted with ethyl acetate. The organic layer was washed with water and brine, and then dried over anhydrous magnesium sulfate. The solvent was evaporated under reduced pressure. The obtained residue was purified by silica-gel column chromatography (ethyl acetate-methanol) and then subjected to SFC chiral preparative separation to give Compound I-134 as an optically active compound.

1H-NMR (CDCl3) δ: 1.10-1.16 (m, 2H), 1.35-1.41 (m, 2H), 1.46-1.49 (m, 1H), 1.52-1.57 (m, 2H), 1.74-1.77 (m, 2H), 1.87-1.92 (m, 2H), 2.03 (br, 2H), 2.50-2.54 (m, 2H), 2.68 (s, 3H), 2.70-2.78 (m, 4H), 3.45 (s, 2H), 3.65 (s, 2H), 4.06-4.14 (m, 1H), 4.73 (q, J=8.2 Hz, 2H), 5.24 (d, J=8.4 Hz, 1H), 7.39 (s, 1H).

SFC Preparative Condition

Preparative column (IC-IC, Daicel)
Flow rate: 30 mL/min
Mobile phase: methanol+0.1% diethylamine 35%
Sample: 20 mg/mL (methanol/chloroform=1/1)
Loading amount: 14 mg
Detection wavelength: 220 nm, Back pressure: 8 MPa Example 9 Synthesis of I-028

[Chemical Formula 179]

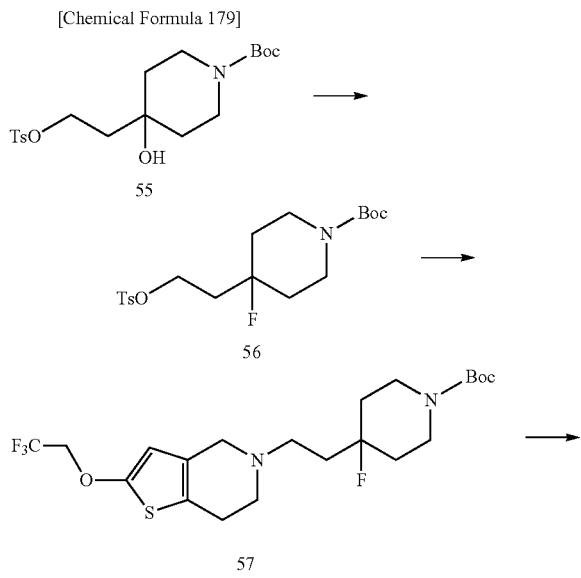

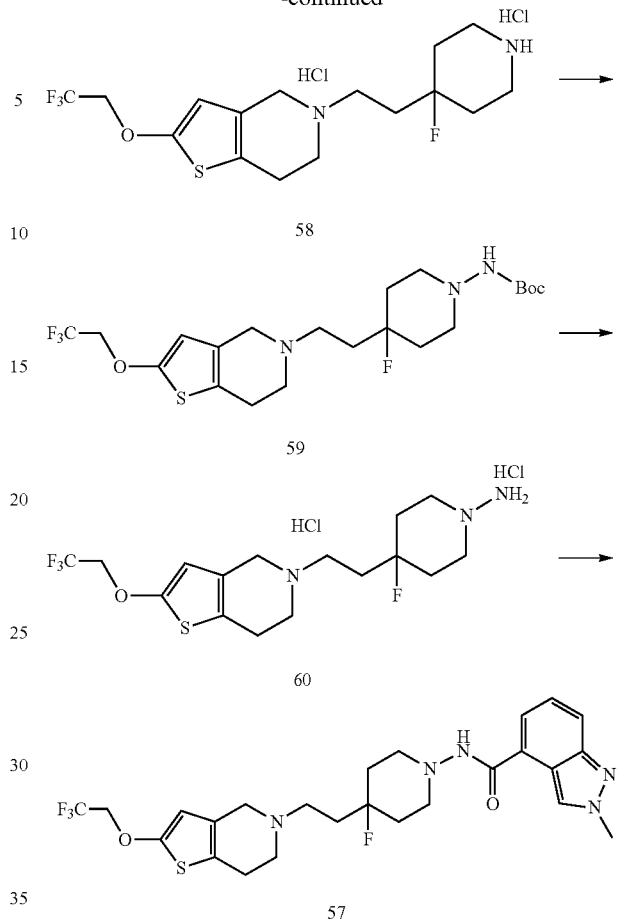

Step 1 Synthesis of Compound 56

Compound 55, which can be synthesized by the method described in WO 2006001752, (273 mg, 0.683 mmol) was dissolved in dichloromethane (3 mL). To the solution was added (diethylamino) sulfur trifluoride (542 μL, 4.10 mmol) at −78° C. The mixture was stirred for 2 hours. To the reaction mixture was added saturated aqueous solution of sodium hydrogen carbonate. The mixture was extracted with chloroform. The obtained organic layer was purified by silica-gel column chromatography (hexane-ethyl acetate). The obtained residue was dissolved in dichloromethane (2 mL). To the solution were added sodium hydrogen carbonate (80 mg, 0.956 mmol) and m-chloroperbenzoic acid (236 mg). The mixture was stirred at 0° C. for 2 hours, and left standing overnight. To the reaction mixture was added saturated aqueous solution of sodium thiosulfate. The mixture was extracted with ethyl acetate. The organic layer was washed with 5% aqueous potassium carbonate solution and water, and then dried over anhydrous sodium sulfate. The solvent was evaporated under reduced pressure. The obtained residue was purified by silica-gel column chromatography (hexane-ethyl acetate) to give Compound 56 (37.1 mg).

1H-NMR (CDCl3) δ: 1.45 (s, 9H), 1.49-1.63 (m, 2H), 1.72-1.79 (m, 2H), 1.99 (dt, J=20.6, 6.5 Hz, 2H), 2.46 (s, 3H), 3.02 (brs, 2H), 3.89 (brs, 2H), 4.19 (t, J=6.4 Hz, 2H), 7.36 (d, J=8.0 Hz, 2H), 7.79 (d, J=8.3 Hz, 2H).

Step 2 Synthesis of Compound 57

Compound 56 (37.1 mg, 0.092 mmol) and Compound 12a (25.4 mg, 0.092 mmol) were dissolved in acetonitrile (4 mL). To the solution was added potassium carbonate (38.3 mg, 0.277 mmol). The mixture was stirred at 70° C. for 29 hours. To the reaction mixture was added water. The mixture was extracted with chloroform. The organic layer was separated and the solvent was evaporated under reduced pressure. The obtained residue was purified by silica-gel column chromatography (hexane-ethyl acetate) to give Compound 57 (25 mg, yield 58%).

1H-NMR (CDCl3) δ: 1.46 (s, 9H), 1.49-1.68 (m, 2H), 1.81-1.94 (m, 4H), 2.68-2.81 (m, 6H), 3.05-3.11 (m, 2H), 3.47 (brs, 2H), 3.92 (brs, 2H), 4.74 (q, J=8.3 Hz, 2H).

Step 3 Synthesis of Compound 58

Compound 57 (25 mg, 0.053 mmol) was dissolved in methanol (1 mL). To the solution was added 4 mol/L hydrochloric acid (1,4-dioxane solution, 1 mL, 4.00 mmol). The mixture was stirred at room temperature for 1 hour. The solvent was evaporated under reduced pressure to give Compound 58 as a crude product.

Step 4 Synthesis of Compound 59

To the crude product of Compound 58 obtained in step 3 were added dichloromethane (2 mL), DIEA (22 μL, 0.127 mmol) and N-Boc-3(4-cyanophenyl)oxaziridine (15.66 mg, 0.063 mmol) at 0° C. The mixture was stirred for 2 hours. The solvent was evaporated under reduced pressure. The obtained residue was purified by amino silica-gel column chromatography (hexane-ethyl acetate) to give Compound 59 (15 mg, yield 59%).

1H-NMR (CDCl3) δ: 1.46 (s, 9H), 1.83-2.00 (m, 6H), 2.61-2.80 (m, 8H), 2.98-3.02 (m, 2H), 3.46 (s, 2H), 4.74 (q, J=8.3 Hz, 2H), 5.42 (s, 1H).

Step 5 Synthesis of Compound 60

Compound 60 was obtained as a crude product by using Compound 59 instead of Compound 57 in Step 3 of Example 9.

Step 6 Synthesis of I-028

To the crude product of Compound 60 (14.12 mg) obtained in step 5 were added DMF (1 mL), 2-methyl-2H-indazole-4-carboxylic acid (6.01 mg, 0.034 mmol), EDC hydrochloride (6.54 mg, 0.034 mmol), HOBt (4.61 mg, 0.034 mmol) and triethylamine (26 μL, 0.186 mmol). The mixture was stirred at room temperature for 3 hours. To the reaction mixture was added saturated aqueous solution of sodium hydrogen carbonate. The mixture was extracted with chloroform. The organic layer was separated and the solvent was evaporated under reduced pressure. The obtained residue was purified by silica-gel column chromatography (chloroform-methanol) and reverse phase chromatography (acetonitrile-10 mM aqueous ammonium carbonate solution) to give I-028 (3.8 mg, yield 23%).

1H-NMR (CDCl3) δ: 1.88-2.14 (m, 6H), 2.69-2.86 (m, 8H), 3.17-3.19 (m, 2H), 3.48 (s, 2H), 4.25 (s, 3H), 4.75 (q, J=8.3 Hz, 2H), 6.93 (brs, 1H), 7.26-7.30 (m, 1H), 7.35 (d, J=6.5 Hz, 1H), 7.85 (d, J=8.5 Hz, 1H), 8.43 (s, 1H).

Example 10 Synthesis of I-047

[Chemical Formula 180]

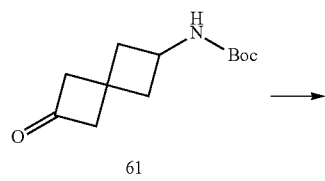

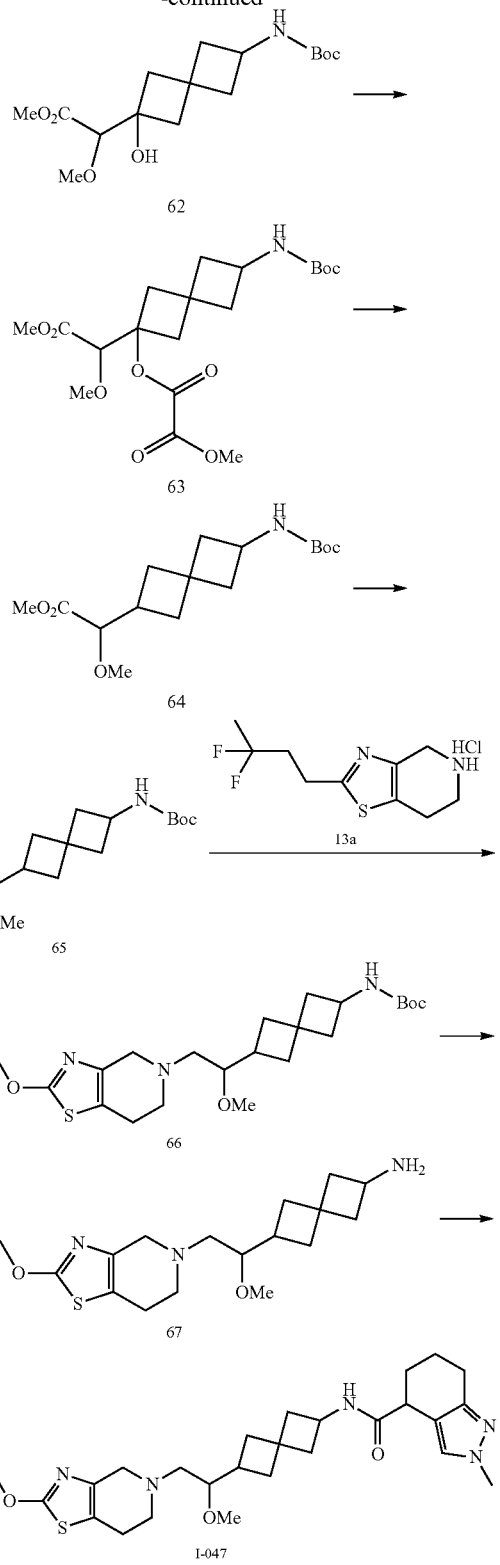

Step 1 Synthesis of Compound 62

Under nitrogen atmosphere, to a solution of 1 mol/L of LHMDS in tetrahydrofuran (38.9 mL) was added dropwise a solution of methyl methoxyacetate (4.05 g, 38.9 mmol) in tetrahydrofuran (40 mL) at −68° C. After the mixture was stirred for 30 minutes, a solution of Compound 61 (4.176 g, 18.54 mmol) in tetrahydrofuran (40 mL) was added dropwise over 1 hour. The mixture was stirred at −68° C. for 30 minutes. To the reaction mixture was added saturated aqueous solution of ammonium chloride. The mixture was extracted with ethyl acetate. The organic layer was washed with brine, and then dried over anhydrous magnesium sulfate. The solvent was evaporated under reduced pressure. The obtained residue was purified by silica-gel column chromatography (hexane-ethyl acetate) to give Compound 62 (6.20 g, yield 100%) as a mixture of diastereomers.

$^1$H-NMR (CDCl$_3$) δ: 1.43 (9H, s), 1.78-1.95 (2H, m), 2.01-2.17 (2H, m), 2.26-2.52 (4H, m), 2.74 (1H, d, J=11.0 Hz), 3.44 (1.5H, s), 3.45 (1.5H, s), 3.66 (1H, s), 3.78 (1.5H, s), 3.79 (1.5H, s), 3.94-4.07 (1H, m), 4.53-4.66 (1H, m).

Step 2 Synthesis of Compound 63

Compound 62 (6.11 g, 18.54 mmol), triethylamine (3.21 mL, 23.18 mmol) and N,N-dimethyl-4-aminopyridine (0.227 g, 1.854 mmol) were dissolved in tetrahydrofuran (60 mL). To the solution, methyl chloroglyoxylate (2.131 mL, 23.18 mmol) was added at 0° C. under nitrogen atmosphere and the mixture was stirred for 20 minutes. To the reaction mixture was added water at 0° C. The solution was made basic with saturated aqueous solution of sodium hydrogen carbonate, and then the mixture was extracted with ethyl acetate. The organic layer was washed with brine, and then dried over anhydrous magnesium sulfate. The solvent was evaporated under reduced pressure. The obtained residue was purified by silica-gel column chromatography (hexane-ethyl acetate) to give Compound 63 (5.68 g, yield 74%) as a mixture of diastereomers.

$^1$H-NMR (CDCl$_3$) δ: 1.42 (9H, s), 1.80-1.94 (2H, m), 2.27-2.55 (4H, m), 2.66-2.74 (1H, m), 2.78-2.86 (1H, m), 3.41 (1.5H, s), 3.42 (1.5H, s), 3.73 (1.5H, s), 3.74 (1.5H, s), 3.88 (3H, s), 3.92-4.05 (1H, m), 4.16 (1H, d, J=10.5 Hz), 4.53-4.64 (1H, m).

Step 3 Synthesis of Compound 64

Compound 63 (5.67 g, 13.65 mmol) was dissolved in toluene (280 mL). To the solution were added 1 mol/L tributyltin hydride (27.3 mL, 27.3 mmol, cyclohexane solution) and azobis(isobutyronitrile) (0.493 g, 3 mmol). The mixture was stirred at 115° C. under nitrogen atmosphere for 4 hours. The solvent was evaporated under reduced pressure. The obtained residue was purified by silica-gel column chromatography (hexane-ethyl acetate), and then amino silica-gel column chromatography (ethyl acetate) to give Compound 64 (3.66 g, yield 86%) as a mixture of diastereomers.

$^1$H-NMR (CDCl$_3$) δ: 1.42 (9H, s), 1.70-1.84 (2H, m), 1.84-2.16 (4H, m), 2.23-2.34 (1H, m), 2.38-2.58 (2H, m), 3.37 (3H, s), 3.60-3.64 (1H, m), 3.73 (3H, s), 3.90-4.07 (1H, m), 4.50-4.66 (1H, m).

Step 4 Synthesis of Compound 65

Under nitrogen atmosphere, Compound 64 (842 mg, 2.69 mmol) was dissolved in dichloromethane (25 mL). To the solution was added DIBAL (1.02 mol/L hexane solution, 6.58 mL, 6.72 mol) at −78° C. The mixture was stirred for 2 hours and 20 minutes. To the reaction mixture was added methanol, followed by ethyl acetate and 1 mol/L hydrochloric acid. The mixture was extracted with ethyl acetate. The organic layer was washed with dilute hydrochloric acid, saturated aqueous sodium hydrogen carbonate solution and brine, and then dried over anhydrous magnesium sulfate. The solvent was evaporated under reduced pressure to give Compound 65 (763 mg) as a mixture of diastereomers.

Step 5 Synthesis of Compound 66

Compound 66 was obtained by using Compound 13a (synthesized by the similar method as in Reference Example 3) instead of Compound 3 and using Compound 65 instead of Compound 4 in Step 3 of Example 2. [M+H]502.30, method 3, retention time 1.50 min Step 6 Synthesis of Compound 67

Compound 67 was obtained by using Compound 66 instead of Compound 5a in Step 4 of Reference Example 1. [M+H]402, method 1, retention time 1.66 min Step 7 Synthesis of I-047

To Compound 67 (173 mg, 0.432 mmol) were added DMF (2 mL), 2-methyl-2H-indazole-4-carboxylic acid (107 mg, 0.605 mmol), EDC hydrochloride (124 mg, 0.648 mmol) and triethylamine (120 μL, 0.864 mmol). The mixture was stirred at room temperature overnight. To the reaction mixture was added saturated aqueous solution of sodium hydrogen carbonate. The mixture was extracted with ethyl acetate. The organic layer was washed with water and brine, and then dried over anhydrous magnesium sulfate. The solvent was evaporated under reduced pressure. The obtained residue was purified by silica-gel column chromatography (ethyl acetate-methanol), and then amino silica-gel chromatography (hexane-ethyl acetate) and then subjected to SFC chiral preparative separation to give Compound I-047 (9.5 mg, yield 4%) as an optically active compound.

1H-NMR. (CDCl3) δ: 1.72 (t, J=18.7 Hz, 3H), 1.90-2.07 (m, 5H), 2.12-2.17 (m, 1H), 2.38-2.47 (m, 3H), 2.54-2.73 (m, 4H), 2.81-2.84 (m, 2H), 3.26-3.31 (m, 1H), 3.43-3.57 (m, 5H), 4.24 (s, 3H), 4.47-4.53 (m, 3H), 6.27 (d, J=7.5 Hz, 1H), 7.28-7.33 (m, 2H), 7.84 (d, J=8.3 Hz, 1H), 8.46 (s, 1H).

SFC Preparative Condition
Preparative column (ID-ID, Daicel)
Flow rate: 30 mL/min
Mobile phase: 2-propanol+0.1% diethylamine 40%
Sample: 16 mg/mL (methanol/chloroform=1/1)
Loading amount: 3.5 mg
Detection wavelength: 220 nm, Back pressure: 8 MPa Reference Example 4 Synthesis of Compounds 18a, 19a

[Chemical Formula 181]

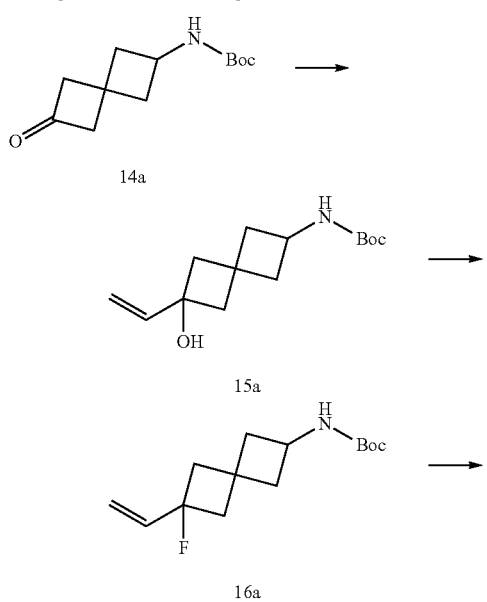

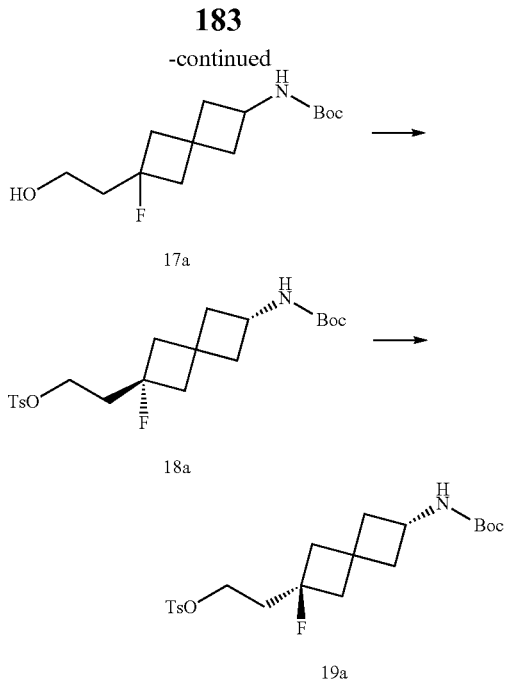

17a

18a

19a

Step 1 Synthesis of Compound 15a

Compound 14a (3.0 g, 13.32 mmol) was dissolved in tetrahydrofuran (30 mL). To the solution was added dropwise vinyl magnesium bromide (1 mol/L tetrahydrofuran solution, 39.9 mL, 39.9 mmol) at −78° C., and then the mixture was stirred. To the mixture was added water, and the mixture was extracted with ethyl acetate. The solvent was evaporated under reduced pressure. The obtained residue was purified by silica-gel column chromatography (hexane-ethyl acetate) to give Compound 15a (1.49 g, yield 44%).

1H-NMR (CDCl3) δ: 1.43 (s, 9H), 1.77 (s, 1H), 1.82 (t, J=9.9 Hz, 1H), 1.91 (t, J=10.2 Hz, 1H), 2.15-2.26 (m, 3H), 2.36-2.47 (m, 3H), 4.01 (br, 1H), 4.61 (br, 1H), 5.05 (dd, J=10.7, 0.9 Hz, 1H), 5.21 (dd, J=17.2, 0.9 Hz, 1H), 6.04 (dd, J=17.2, 10.7 Hz, 1H).

Step 2 Synthesis of Compound 16a

Compound 15a (1.5 g, 5.92 mmol) was dissolved in dichloromethane (5.3 mL). To the solution was added dropwise (diethylamino)sulfur trifluoride (4.66 mL, 35.5 mmol) at −78° C., and then the mixture was stirred for 30 minutes. To the reaction mixture was added water, and the mixture was extracted with dichloromethane. The solvent was evaporated under reduced pressure. The obtained residue was purified by silica-gel column chromatography (hexane-ethyl acetate) to give Compound 16a (600 mg, yield 40%).

1H-NMR (CDCl3) δ: 1.43 (s, 9H), 1.84 (dd, J=10.9, 8.9 Hz, 1H), 1.95 (dd, J=11.2, 8.9 Hz, 1H), 2.27 (td, J=12.5, 4.1 Hz, 1H), 2.37-2.51 (m, 5H), 4.02 (br, 1H), 4.61 (br, 1H), 5.14 (dd, J-11.0, 1.0 Hz, 1H), 5.28 (dd, J=17.2, 1.4 Hz, 1H), 5.98 (td, J=16.9, 10.8 Hz, 1H).

Step 3 Synthesis of Compound 17a

To a borane-tetrahydrofuran complex (1 mol/L tetrahydrofuran solution, 9.79 mL, 9.79 mmol) was added cyclohexene (1.98 mL, 19.58 mmol) at 0° C. The mixture was stirred for 1 hour to prepare dicyclohexylborane. Compound 16a (500 mg, 1.958 mmol) was dissolved in tetrahydrofuran (5 mL). To the solution was added dropwise the prepared dicyclohexylborane at 0° C., and the mixture was stirred. To the reaction mixture were added 2 mol/L sodium hydroxide (19.58 mL, 39.2 mmol) and hydrogen peroxide solution (20%, 1.67 g, 9.79 mmol). The mixture was stirred for 30 minutes. The reaction mixture was extracted with ethyl acetate, and the organic layer was dried over anhydrous sodium sulfate. The solvent was evaporated under reduced pressure. The obtained residue was purified by silica-gel column chromatography (hexane-ethyl acetate) to give Compound 17a (500 mg, yield 93%).

1H-NMR (CDCl3) δ: 1.43 (s, 9H), 1.82-1.99 (m, 4H), 2.18 (td, J=12.5, 4.2 Hz, 1H), 2.28-2.47 (m, 511), 3.79 (q, J=5.8 Hz, 2H), 4.02 (s, 1H), 4.62 (s, 1H).

Step 4 Synthesis of Compounds 18a, 19a

Compound 17a (500 mg, 1.83 mmol) was dissolved in dichloromethane (4 mL). To the solution were added N,N-dimethyl-4-aminopyridine (22.4 mg, 0.183 mmol), triethylamine (514 µL, 3.66 mmol) and p-toluenesulfonyl chloride (366 mg, 1.92 mmol) at 0° C. The mixture was stirred at 0° C. for 4 hours. To the reaction mixture was added saturated aqueous ammonium chloride solution. The mixture was extracted with chloroform. The organic layer was separated and then the solvent was evaporated under reduced pressure. The obtained residue was purified by silica-gel column chromatography (hexane-ethyl acetate) and then subjected to SFC chiral preparative separation to give Compound 18a (260 mg, yield 33%) and Compound 19a (260 mg, yield 33%), respectively, as optically active compounds.

1H-NMR (CDCl3) δ: 1.43 (s, 9H), 1.83 (dd, J=10.9, 8.7 Hz, 111), 1.91 (dd, J=11.3, 8.8 Hz, 111), 1.99-2.08 (m, 2H), 2.14 (td, J=12.9, 4.0 Hz, 111), 2.21-2.44 (m, 5H), 2.46 (s, 311), 3.99 (br, 1H), 4.11-4.15 (m, 2H), 4.61 (br, 1H), 7.36 (d, J=8.0 Hz, 2H), 7.78 (d, J=8.3 Hz, 2H).

SFC Preparative Condition
Preparative column (IA-IA-IA, Daicel)
Flow rate: 30 mL/min
Mobile phase: methanol 10%
Sample: 63 mg/mL (methanol/chloroform=1/1)
Loading amount: 21 mg
Detection wavelength: 220 nm, Back pressure: 10 MPa Reference Example 5 Synthesis of Compound 23a

[Chemical Formula 182]

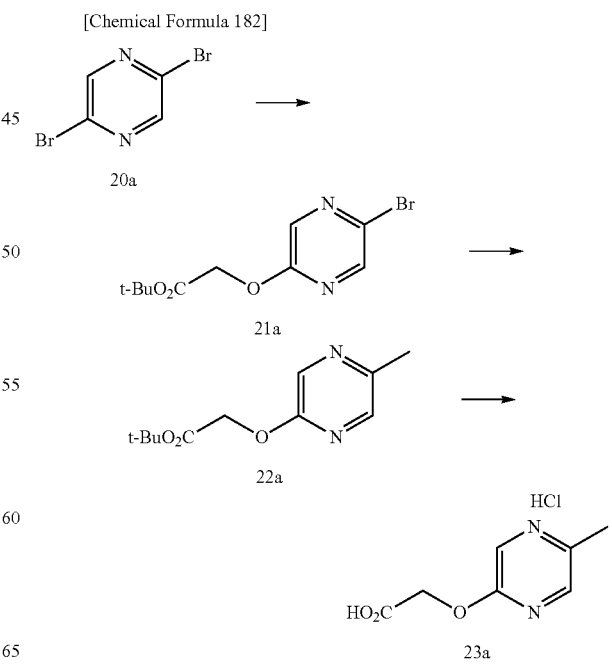

20a

21a

22a

23a

Step 1 Synthesis of Compound 21a

Tert-butyl 2-hydroxyacetate (278 mg, 2.10 mmol) was dissolved in DMF (3 mL). To the solution was added sodium hydride (60 wt %, 101 mg, 2.52 mmol). The mixture was stirred at 0° C. for 30 minutes. To the reaction mixture was added a solution of Compound 20a (500 mg, 2.10 mmol) in DMF (2 mL). The mixture was stirred at room temperature for 4 hours. To the reaction mixture was added water, and the mixture was extracted with ethyl acetate. The organic layer was washed with water and dried over anhydrous sodium sulfate. The solvent was evaporated under reduced pressure. The obtained residue was purified by silica-gel column chromatography (hexane-ethyl acetate) to give Compound 21a (396 mg, yield 65%).

1H-NMR (CDCl3) δ: 1.47 (s, 9H), 4.78 (s, 2H), 8.13 (d, J=1.4 Hz, 1H), 8.15 (d, J=1.3 Hz, 1H).

Step 2 Synthesis of Compound 22a

Compound 21a (314 mg, 1.086 mmol), dimethyl zinc (1 mol/L heptane solution, 3.26 mL, 3.26 mmol), and [1,1'-bis(di-tert-butylphosphino)ferrocene] palladium(II) dichloride (70.8 mg, 0.109 mmol) were dissolved in tetrahydrofuran (3 mL). The mixture was stirred at 60° C. for 1 hour. To the reaction mixture was added saturated aqueous solution of ammonium chloride. The mixture was extracted with ethyl acetate. The organic layer was washed with water and brine, and then dried over anhydrous sodium sulfate. The solvent was evaporated under reduced pressure. The obtained residue was purified by silica-gel chromatography (hexane-ethyl acetate) to give Compound 22a (196 mg, yield 81%).

1H-NMR (CDCl3) δ: 1.46 (s, 9H), 2.47 (s, 3H), 4.77 (s, 2H), 7.89 (s, 1H), 8.25 (s, 1H).

Step 3 Synthesis of Compound 23a

Compound 22a (196 mg, 0.874 mmol) was dissolved in dichloromethane (2 mL). To the solution was added TFA (674 μL, 8.74 mmol). The mixture was stirred at room temperature for 8 hours. The solvent was evaporated under reduced pressure. To the obtained residue were added ethyl acetate and 4 mol/L hydrochloric acid (ethyl acetate solution). The obtained solid was taken by filtration to give Compound 23a (173 mg).

1H-NMR (DMSO-d6) δ: 2.40 (s, 3H), 4.84 (s, 2H), 8.05 (s, 1H), 8.27 (d, J=1.4 Hz, 1H).

Example 10 I'-37 and I'-38 were Synthesized in Similar Manners as Described Above.

[Chemical Formula 183]

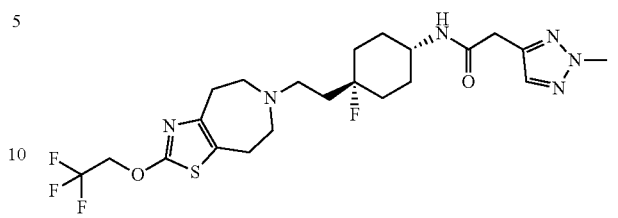

I'-37

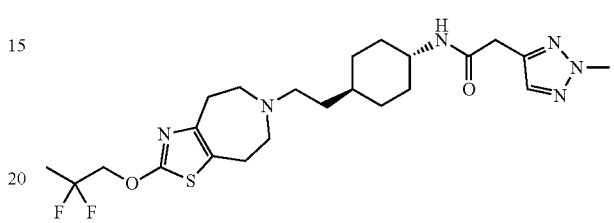

I'-38

Compound I'-37

$^1$H-NMR (CDCl$_3$) δ: 1.41-1.52 (m, 4H), 1.76-1.84 (m, 4H), 1.92-1.98 (m, 2H), 2.70-2.73 (m, 4H), 2.77-2.85 (m, 6H), 3.61 (s, 2H), 3.74-3.82 (m, 1H), 4.18 (s, 3H), 4.71 (q, J=8.3 Hz, 2H), 5.91 (d, J=7.9 Hz, 1H), 7.48 (s, 1H).

Compound I'-38

$^1$H-NMR (CDCl$_3$) δ: 1.01-1.13 (m, 4H), 1.21-1.28 (br m, 1H), 1.38-1.44 (m, 2H), 1.67-1.78 (m, 5H), 1.93-1.98 (br m, 2H), 2.56-2.60 (m, 2H), 2.70-2.72 (m, 2H), 2.77-2.85 (m, 6H), 3.59 (s, 2H), 3.66-3.75 (br m, 1H), 4.17 (s, 3H), 4.47 (t, J=11.7 Hz, 2H), 5.77 (d, J=7.8 Hz, 1H), 7.49 (s, 1H).

The following compounds were synthesized in similar manners as described above. In the tables, RT represents LC/MS retention time (min). In the following tables, regarding stereo-information, the stereostructures of the compounds were determined as described in the structural formulas. If there are no specific descriptions of stereo-information, it indicates the compounds are racemates.

I-045, I-049, I-112, I-119, I-123, and I-124 are respectively either R enantiomer or S enantiomer, though the stereo-information is unknown.

I-047 and I-134 are respectively a single optically active compound, though the stereo-information is unknown.

TABLE 1

| Compound No. | Structure | LC/MS method | RT (min) | MS (m/z) |
|---|---|---|---|---|
| I-001 | 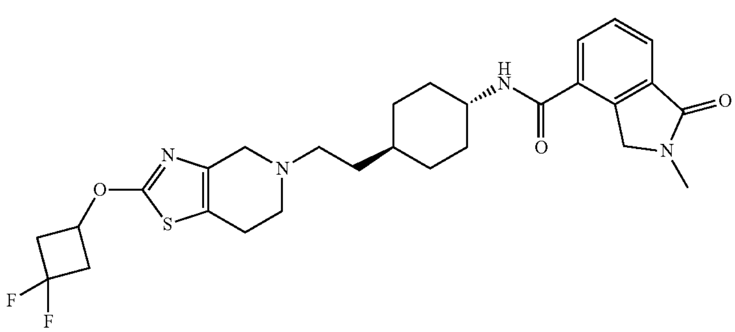 [SMILES: CN1Cc2c(C(=O)N[C@H]3CC[C@H](CCN4CCc5sc(OC6CC(F)(F)C6)nc5C4)CC3)cccc2C1=O] | 2 | 1.40 | 545 |

TABLE 1-continued
| Compound No. | Structure | LC/MS method | RT (min) | MS (m/z) |
|---|---|---|---|---|
| I-002 | 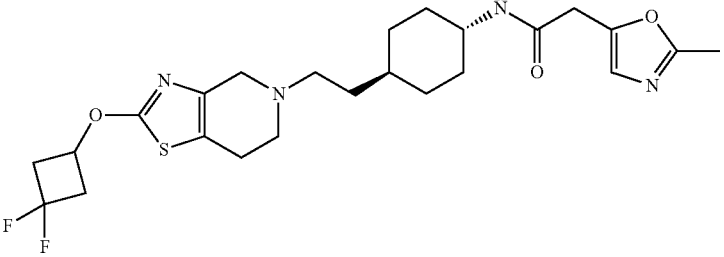 | 2 | 1.32 | 495 |
| I-003 | 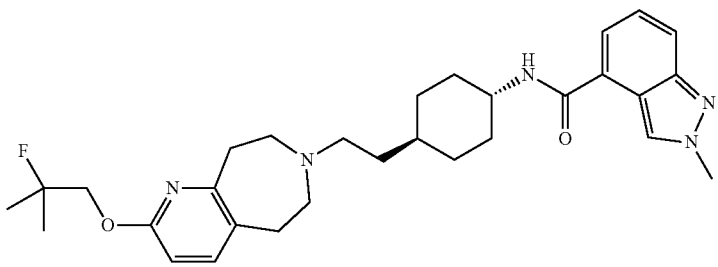 [SMILES: Cn1cc2c(C(=O)N[C@H]3CC[C@H](CCN4CCc5ccc(OCC(C)(C)F)nc5CC4)CC3)cccc2n1] | 2 | 1.49 | 261.7 |
| I-004 | 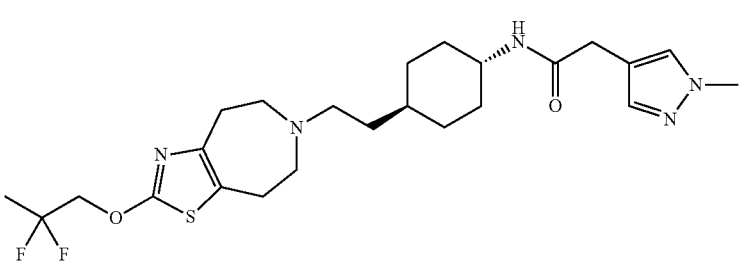 [SMILES: Cn1cc(CC(=O)N[C@H]2CC[C@H](CCN3CCc4nc(OCC(C)(F)F)sc4CC3)CC2)cn1] | 2 | 1.34 | 496 |
| I-005 | 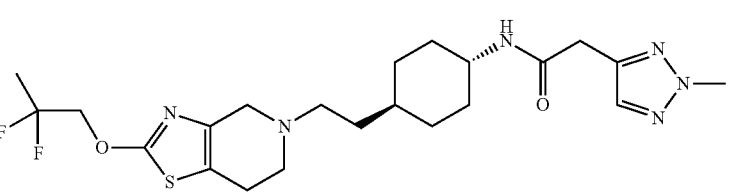 [SMILES: Cn1ncc(CC(=O)N[C@H]2CC[C@H](CCN3CCc4sc(OCC(C)(F)F)nc4C3)CC2)n1] | 2 | 1.28 | 483.4 |
| I-006 | 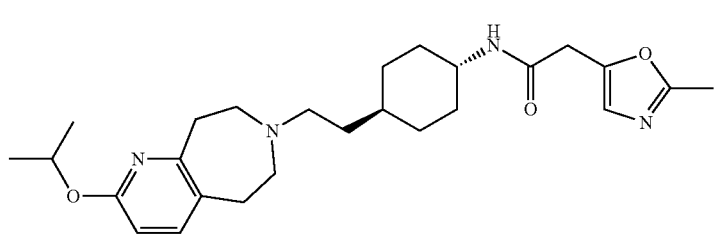 [SMILES: Cc1ncc(CC(=O)N[C@H]2CC[C@H](CCN3CCc4ccc(OC(C)C)nc4CC3)CC2)o1] | 1 | 2.04 | 455 |
| I-007 | 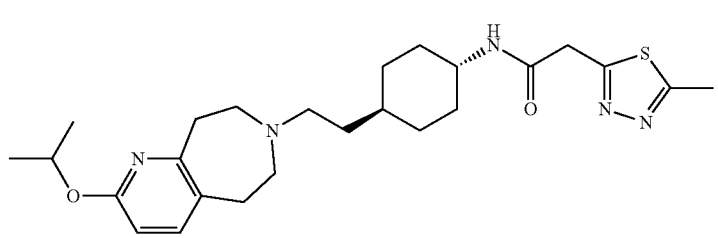 [SMILES: Cc1nnc(CC(=O)N[C@H]2CC[C@H](CCN3CCc4ccc(OC(C)C)nc4CC3)CC2)s1] | 1 | 2.05 | 472 |

TABLE 2

| | | | | |
|---|---|---|---|---|
| I-008 | | 2 | 1.29 | 500.15 |
| I-009 | | 2 | 1.40 | 534.2 |
| I-010 | | 2 | 1.38 | 515.15 |
| I-011 | | 2 | 1.21 | 480.1 |
| I-012 | | 2 | 1.37 | 529.2 |
| I-013 | | 2 | 1.36 | 516.15 |

TABLE 2-continued
| | | | | |
|---|---|---|---|---|
| I-014 | 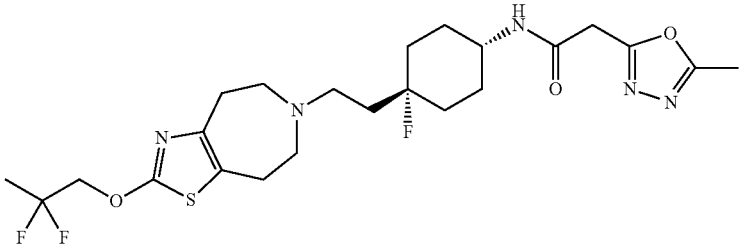 [SMILES: Cc1nnc(CC(=O)N[C@H]2CC[C@](F)(CCN3CCc4nc(OCC(C)(F)F)sc4CC3)CC2)o1] | 2 | 1.30 | 516.2 |
TABLE 3
| | | | | |
|---|---|---|---|---|
| I-015 | 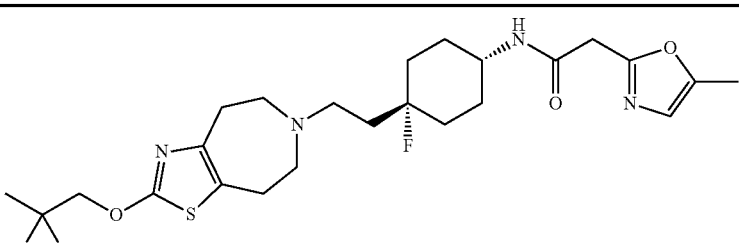 | 2 | 1.42 | 515.2 |
| I-016 | 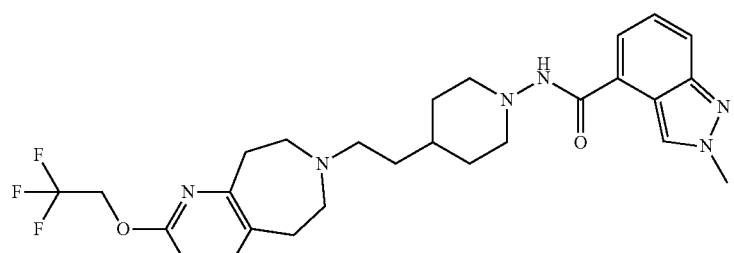 | 2 | 1.44 | 531 |
| I-017 | 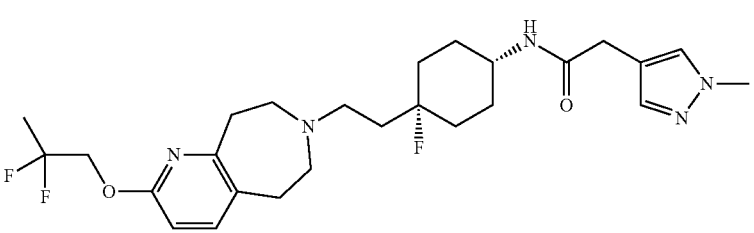 [SMILES: Cn1cc(CC(=O)N[C@H]2CC[C@](F)(CCN3CCc4ccc(OCC(C)(F)F)nc4CC3)CC2)cn1] | 2 | 1.39 | 508.3 |
| I-018 | 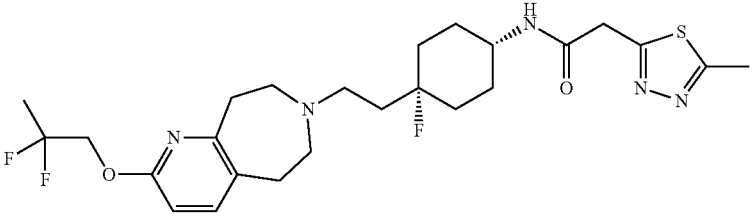 [SMILES: Cc1nnc(CC(=O)N[C@H]2CC[C@](F)(CCN3CCc4ccc(OCC(C)(F)F)nc4CC3)CC2)s1] | 2 | 1.40 | 526.2 |
| I-019 | 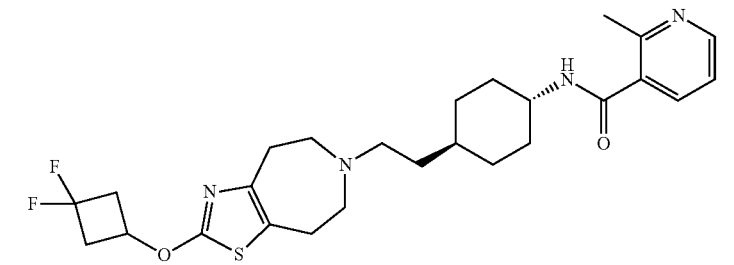 [SMILES: Cc1ncccc1C(=O)N[C@H]1CC[C@H](CCN2CCc3nc(OC4CC(F)(F)C4)sc3CC2)CC1] | 2 | 1.16 | 505.2 |

TABLE 3-continued
| | | | | |
|---|---|---|---|---|
| I-020 | 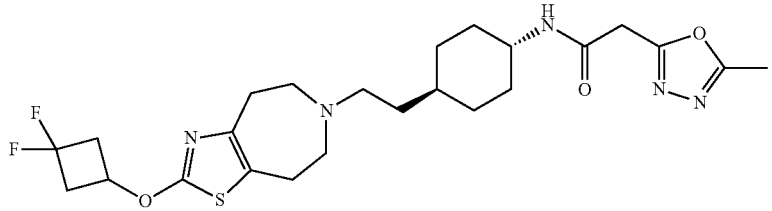 [SMILES: Cc1nnc(CC(=O)N[C@H]2CC[C@H](CCN3CCc4nc(OC5CC(F)(F)C5)sc4CC3)CC2)o1] | 2 | 1.33 | 510.2 |
| I-021 | 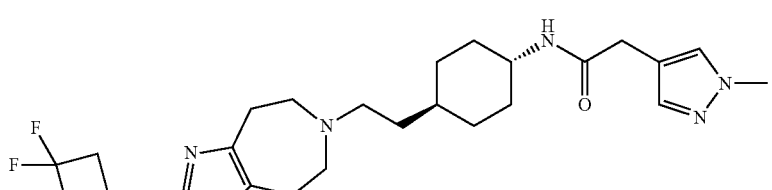 | 2 | 1.34 | 508.3 |
TABLE 4
| | | | | |
|---|---|---|---|---|
| I-022 | 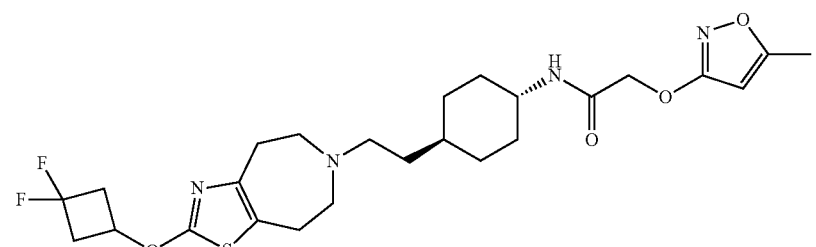 | 2 | 1.51 | 525.2 |
| I-023 | 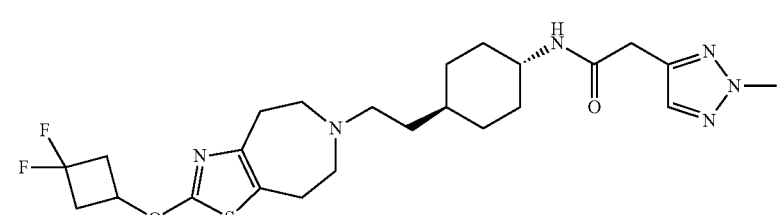 | 2 | 1.37 | 509.2 |
| I-024 | 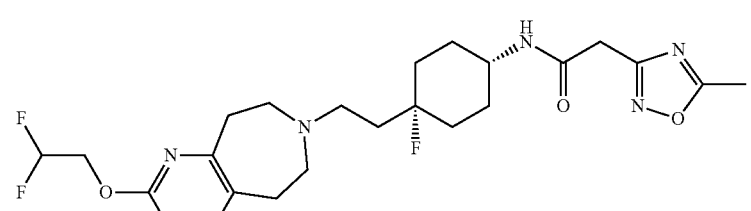 | 2 | 1.33 | 496.2 |
| I-025 | 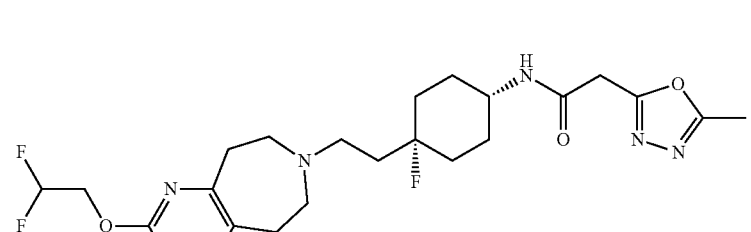 | 2 | 1.26 | 496.2 |

TABLE 4-continued
| I-026 | 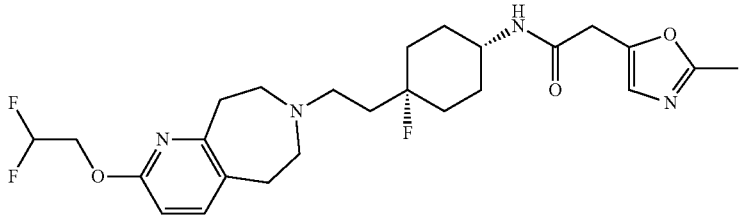 [SMILES: Cc1ncc(CC(=O)N[C@H]2CC[C@](F)(CCN3CCc4ccc(OCC(F)F)nc4CC3)CC2)o1] | 2 | 1.31 | 495.2 |
| I-027 | 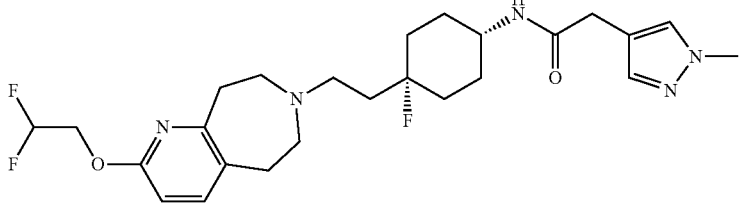 | 2 | 1.29 | 494.2 |
| I-028 | 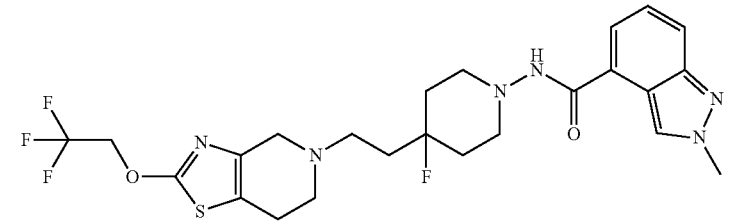 [SMILES: Cn1cc2c(C(=O)NN3CCC(F)(CCN4CCc5sc(OCC(F)(F)F)nc5C4)CC3)cccc2n1] | 2 | 1.37 | 541.15 |
TABLE 5
| I-029 | 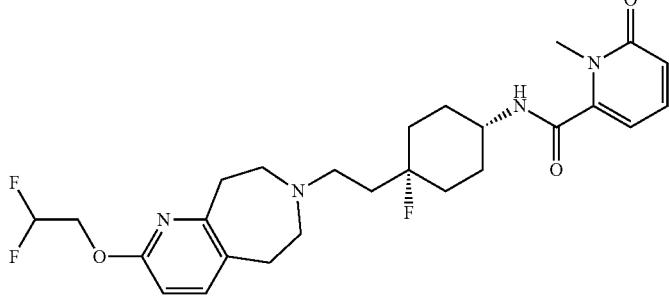 | 2 | 1.28 | 507.2 |
| I-030 | 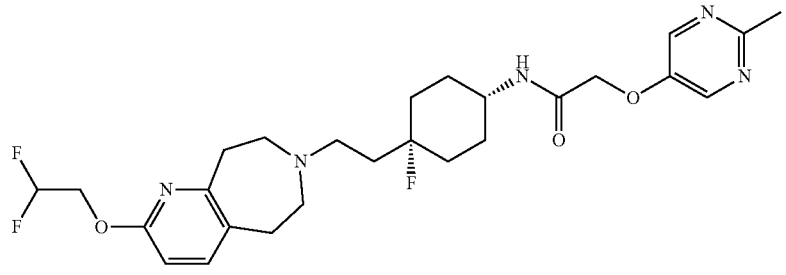 [SMILES: Cc1ncc(OCC(=O)N[C@H]2CC[C@](F)(CCN3CCc4ccc(OCC(F)F)nc4CC3)CC2)cn1] | 2 | 1.32 | 522.3 |
| I-031 | 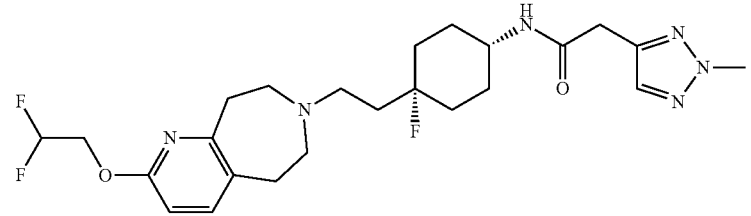 [SMILES: Cn1ncc(CC(=O)N[C@H]2CC[C@](F)(CCN3CCc4ccc(OCC(F)F)nc4CC3)CC2)n1] | 2 | 1.32 | 495.3 |

TABLE 5-continued
| I-032 | 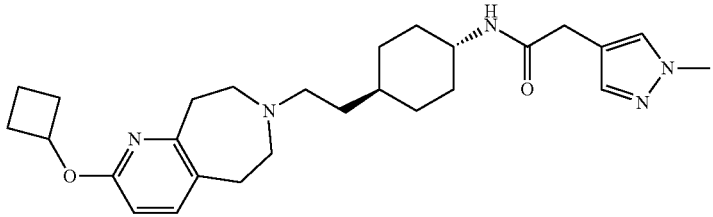 [SMILES: Cn1cc(CC(=O)N[C@H]2CC[C@H](CCN3CCc4ccc(OC5CCC5)nc4CC3)CC2)cn1] | 2 | 1.35 | 466.3 |
| I-033 | 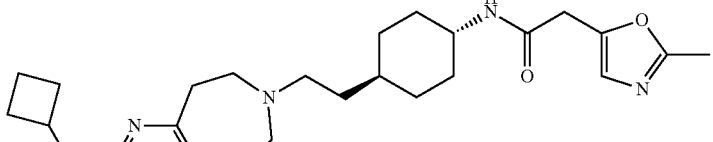 | 2 | 1.38 | 467 |
TABLE 6
| I-034 | 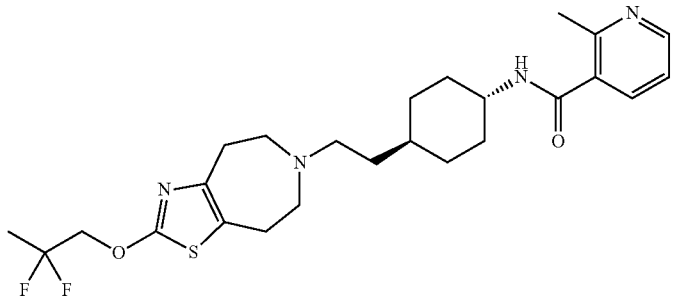 [SMILES: Cc1ncccc1C(=O)N[C@H]1CC[C@H](CCN2CCc3nc(OCC(C)(F)F)sc3CC2)CC1] | 2 | 1.13 | 493 |
| I-035 | 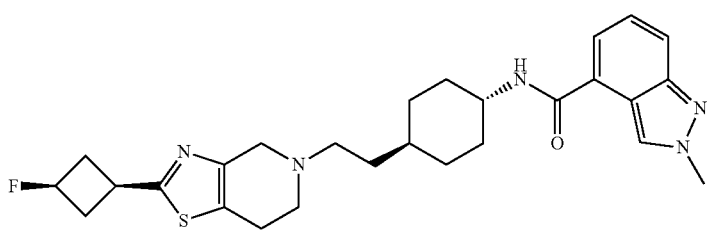 [SMILES: Cn1cc2c(C(=O)N[C@H]3CC[C@H](CCN4CCc5sc([C@H]6C[C@@H](F)C6)nc5C4)CC3)cccc2n1] | 2 | 1.29 | 496 |
| I-036 | 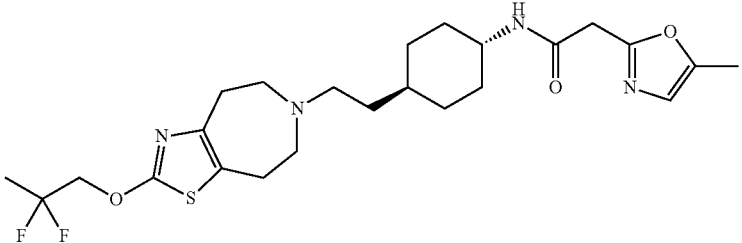 [SMILES: Cc1cnc(CC(=O)N[C@H]2CC[C@H](CCN3CCc4nc(OCC(C)(F)F)sc4CC3)CC2)o1] | 2 | 1.44 | 497 |

TABLE 6-continued
| | | | | |
|---|---|---|---|---|
| I-037 | 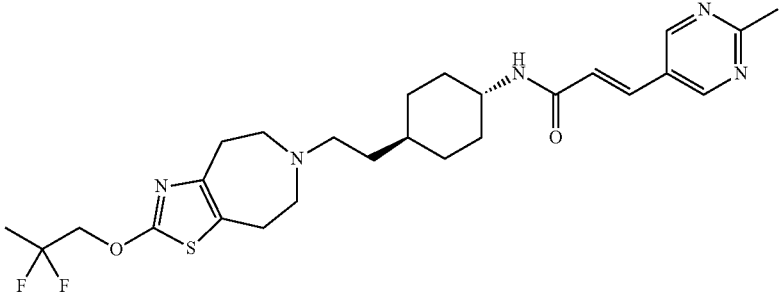 [SMILES: Cc1ncc(/C=C/C(=O)N[C@H]2CC[C@H](CCN3CCc4nc(OCC(C)(F)F)sc4CC3)CC2)cn1] | 2 | 1.39 | 520 |
| I-038 | 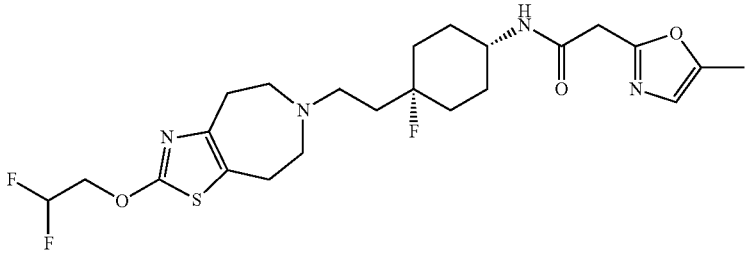 [SMILES: Cc1cnc(CC(=O)N[C@H]2CC[C@](F)(CCN3CCc4nc(OCC(F)F)sc4CC3)CC2)o1] | 2 | 1.35 | 501.2 |
| I-039 | 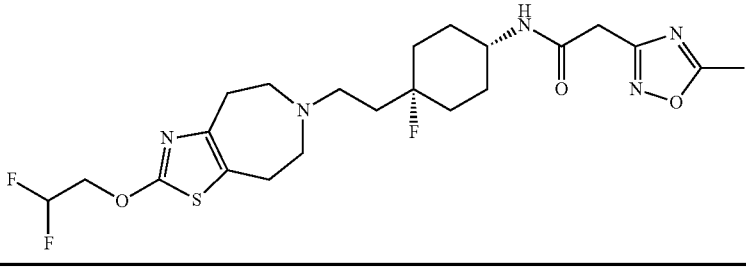 | 2 | 1.29 | 502.2 |
TABLE 7
| | | | | |
|---|---|---|---|---|
| I-040 | 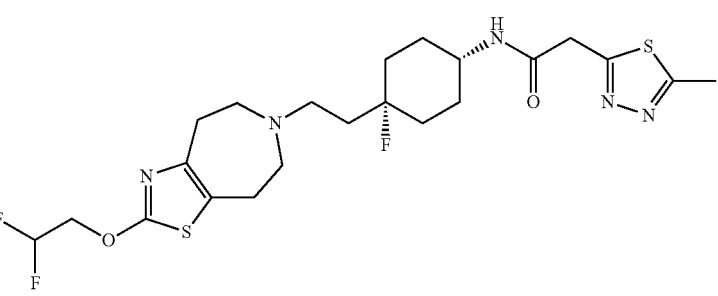 | 2 | 1.27 | 518.2 |
| I-041 | 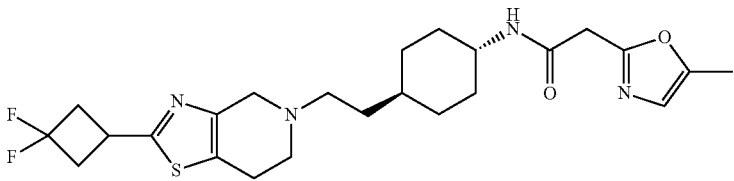 [SMILES: Cc1cnc(CC(=O)N[C@H]2CC[C@H](CCN3CCc4sc(C5CC(F)(F)C5)nc4C3)CC2)o1] | 2 | 1.34 | 479.1 |

TABLE 7-continued
I-042 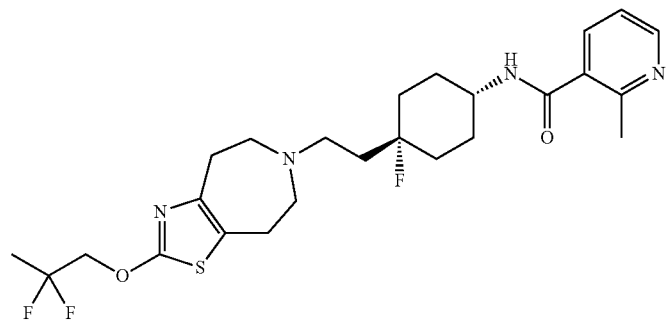 [SMILES: Cc1ncccc1C(=O)N[C@H]1CC[C@](F)(CCN2CCc3nc(OCC(C)(F)F)sc3CC2)CC1] 2 1.14 511.2
I-043 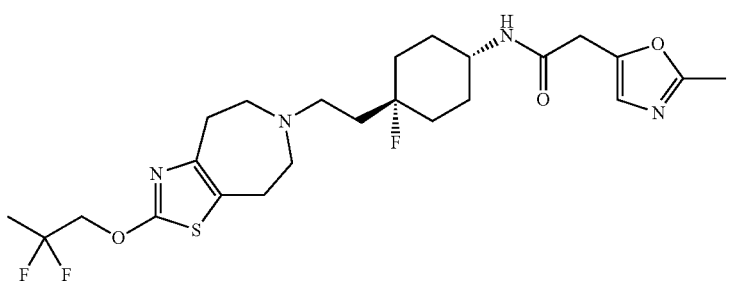 [SMILES: Cc1ncc(CC(=O)N[C@H]2CC[C@](F)(CCN3CCc4nc(OCC(C)(F)F)sc4CC3)CC2)o1] 2 1.36 515.2
I-044 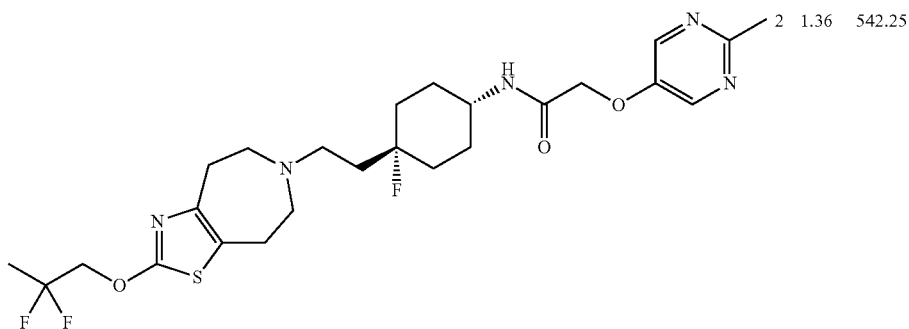 2 1.36 542.25
TABLE 8
I-045 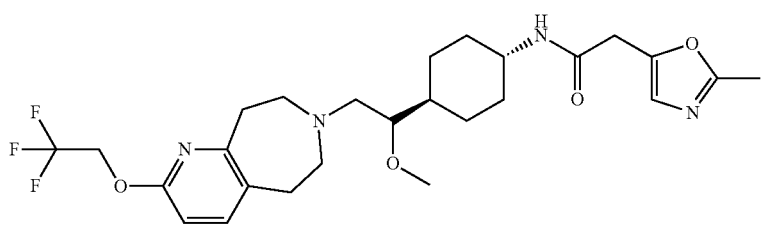 [SMILES: COC(CN1CCc2ccc(OCC(F)(F)F)nc2CC1)[C@H]1CC[C@H](NC(=O)Cc2cnc(C)o2)CC1] 2 1.4 525
I-046 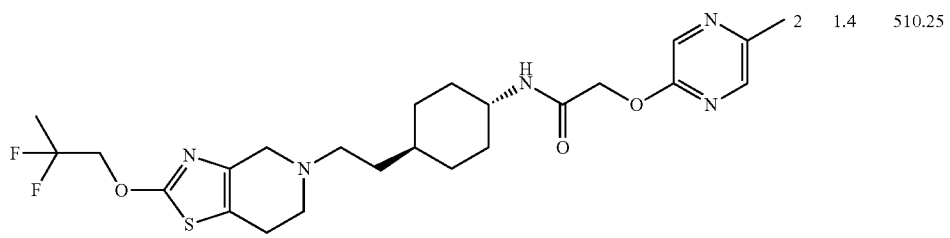 2 1.4 510.25

TABLE 8-continued
| I-047 | 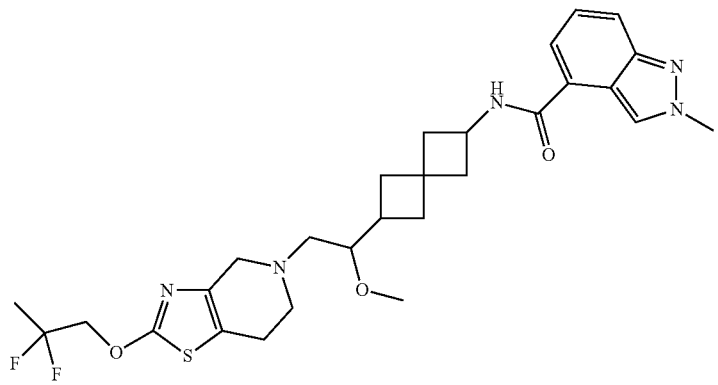 [SMILES: COC(CN1CCc2sc(OCC(C)(F)F)nc2C1)C1CC2(CC(NC(=O)c3cccc4nn(C)cc34)C2)C1] | 3 | 1.33 | 560.3 |
| I-048 | 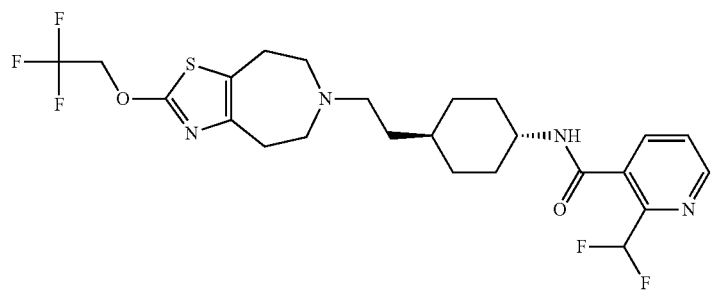 [SMILES: O=C(N[C@H]1CC[C@H](CCN2CCc3nc(OCC(F)(F)F)sc3CC2)CC1)c1cccnc1C(F)F] | 3 | 1.28 | 533 |
| I-049 | 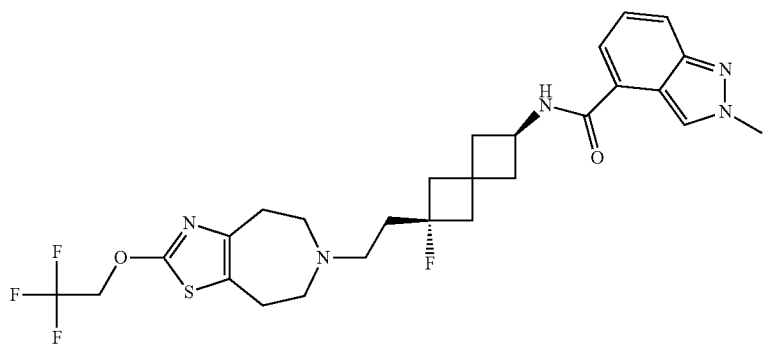 [SMILES: Cn1cc2c(C(=O)N[C@H]3CC4(C3)C[C@@](F)(CCN3CCc5nc(OCC(F)(F)F)sc5CC3)C4)cccc2n1] | 2 | 1.66 | 566 |
TABLE 9
| I-050 | 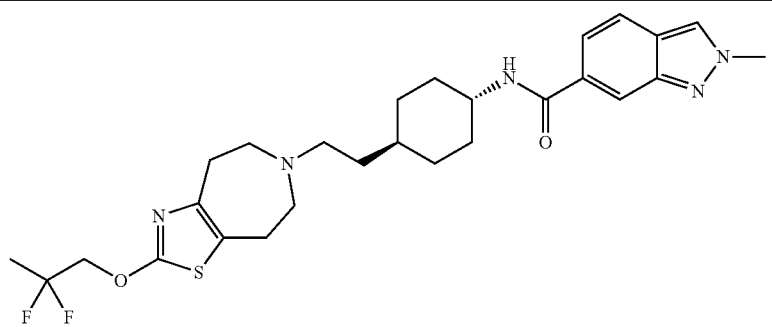 | 2 | 1.49 | 532 |

TABLE 9-continued
| I-051 | 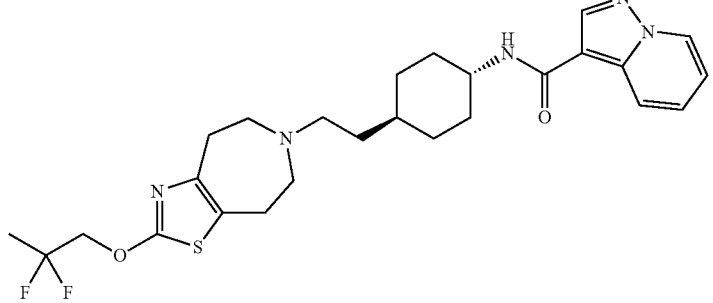 | 2 | 1.51 | 518 |
| I-052 | 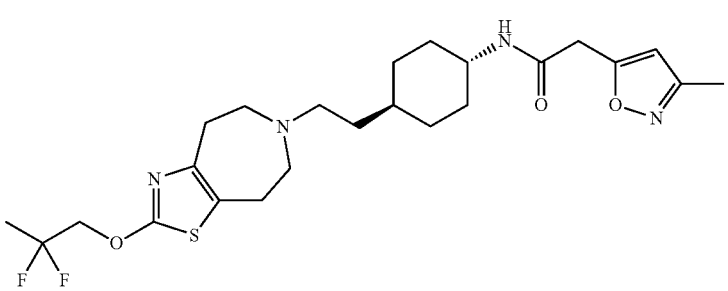 [SMILES: Cc1cc(CC(=O)N[C@H]2CC[C@H](CCN3CCc4nc(OCC(C)(F)F)sc4CC3)CC2)on1] | 2 | 1.43 | 497 |
| I-053 | 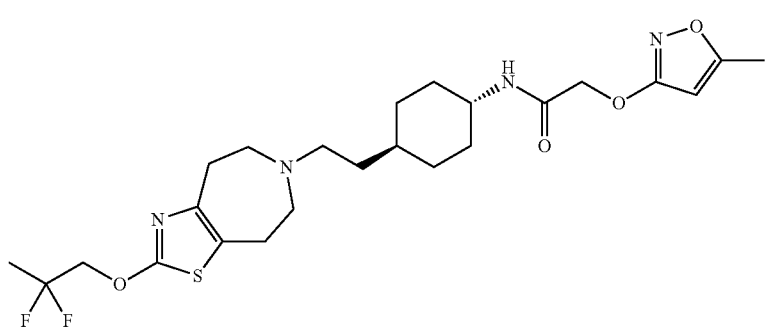 [SMILES: Cc1cc(OCC(=O)N[C@H]2CC[C@H](CCN3CCc4nc(OCC(C)(F)F)sc4CC3)CC2)no1] | 2 | 1.52 | 513 |
| I-054 | 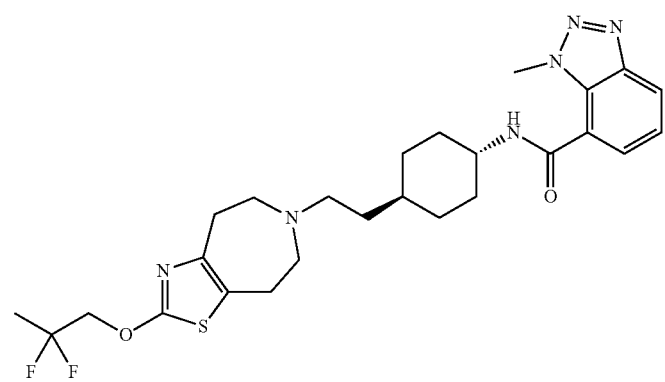 [SMILES: Cn1nnc2cccc(C(=O)N[C@H]3CC[C@H](CCN4CCc5nc(OCC(C)(F)F)sc5CC4)CC3)c21] | 2 | 1.47 | 533 |
| I-055 | 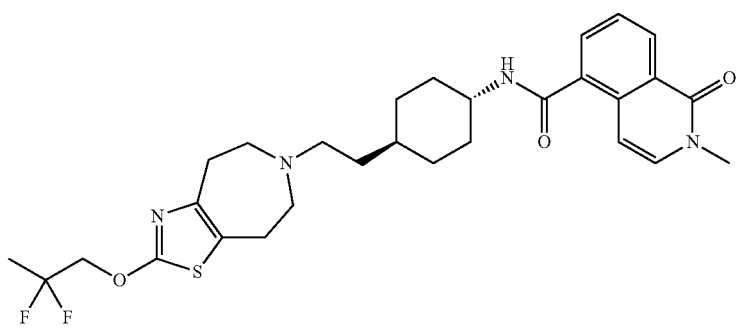 [SMILES: Cn1ccc2c(C(=O)N[C@H]3CC[C@H](CCN4CCc5nc(OCC(C)(F)F)sc5CC4)CC3)cccc2c1=O] | 2 | 1.45 | 559 |

TABLE 10
I-056 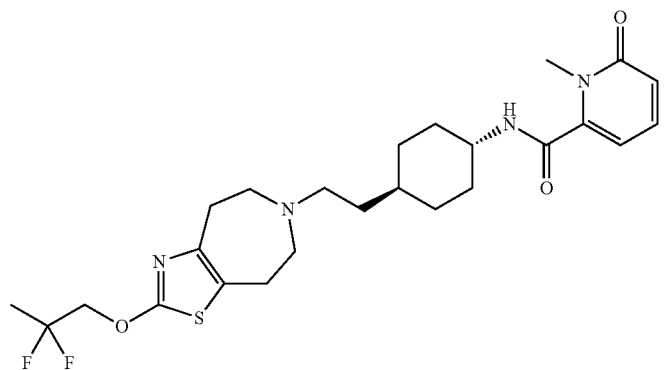 [SMILES: Cn1c(C(=O)N[C@H]2CC[C@H](CCN3CCc4nc(OCC(C)(F)F)sc4CC3)CC2)cccc1=O] 2 1.34 509
I-057 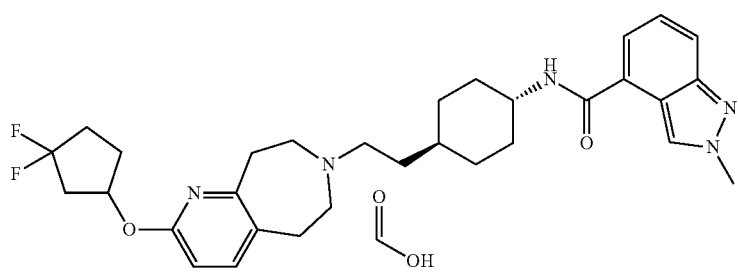 2 1.63 552
I-058 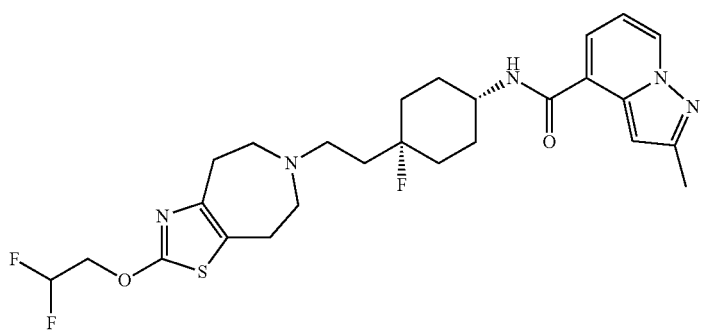 [SMILES: Cc1cc2c(C(=O)N[C@H]3CC[C@](F)(CCN4CCc5nc(OCC(F)F)sc5CC4)CC3)cccn2n1] 2 1.43 536.2
I-059 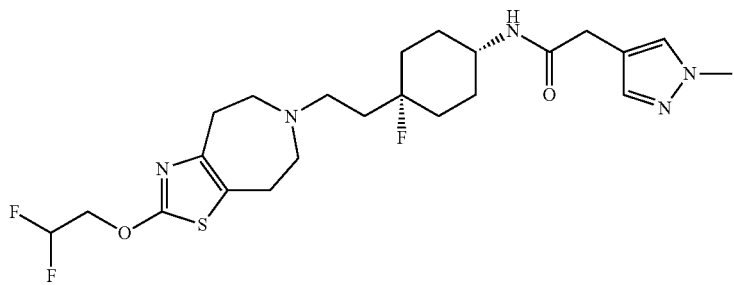 [SMILES: Cn1cc(CC(=O)N[C@H]2CC[C@](F)(CCN3CCc4nc(OCC(F)F)sc4CC3)CC2)cn1] 2 1.26 500.2
I-060 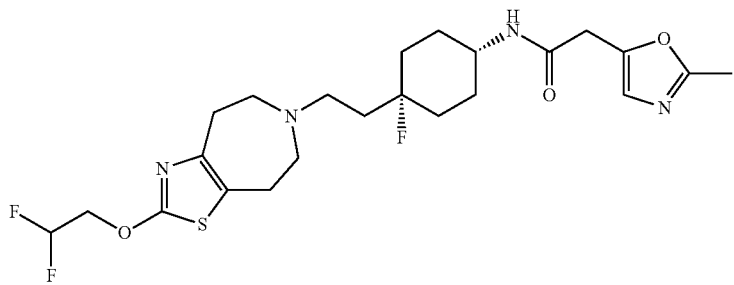 [SMILES: Cc1ncc(CC(=O)N[C@H]2CC[C@](F)(CCN3CCc4nc(OCC(F)F)sc4CC3)CC2)o1] 2 1.29 501.2

TABLE 10-continued
| I-061 | 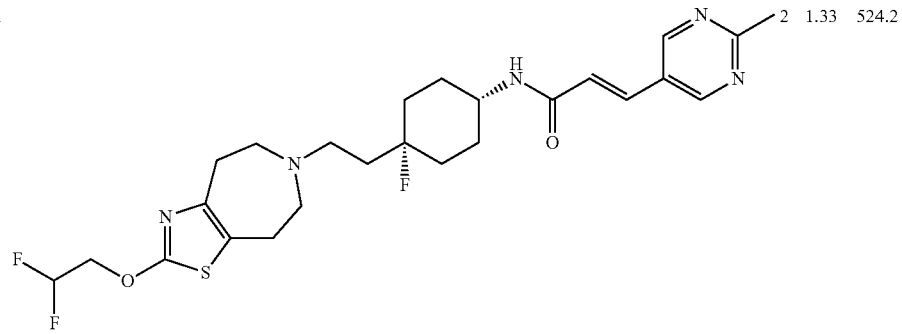 | 2 | 1.33 | 524.2 |
TABLE 11
| I-062 | 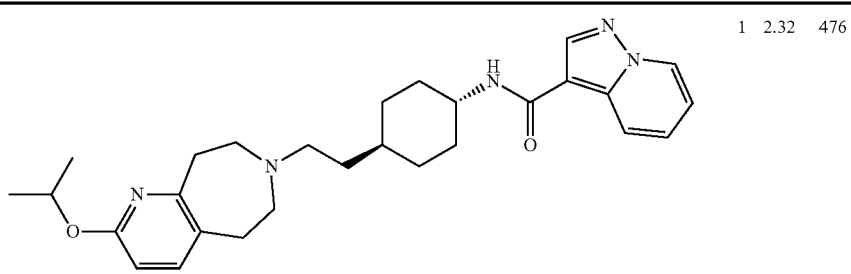 | 1 | 2.32 | 476 |
| I-063 | 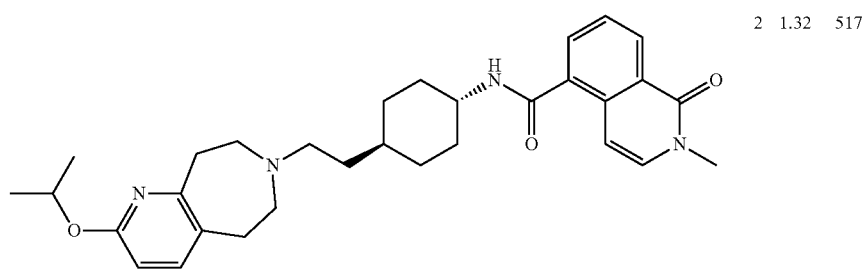 | 2 | 1.32 | 517 |
| I-064 | 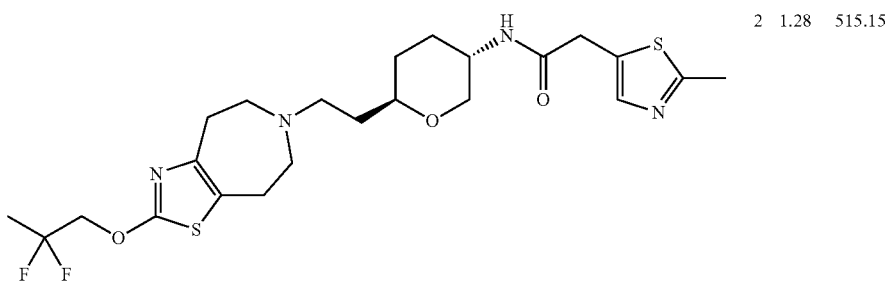 | 2 | 1.28 | 515.15 |
| I-065 | 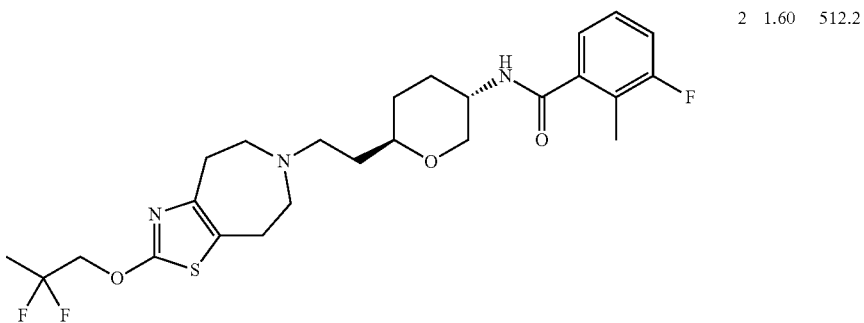 | 2 | 1.60 | 512.2 |

TABLE 11-continued
| I-066 | 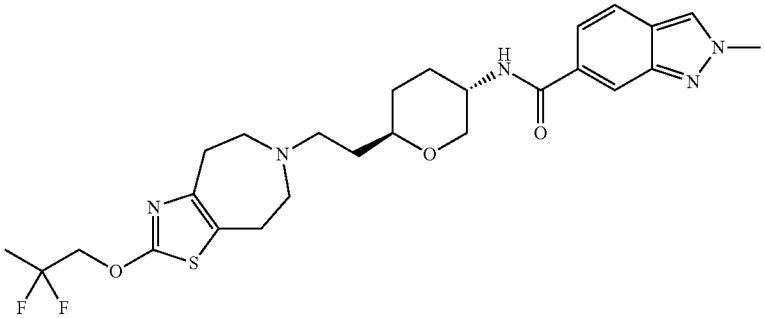 | 2 | 1.41 | 534.2 |
| I-067 | 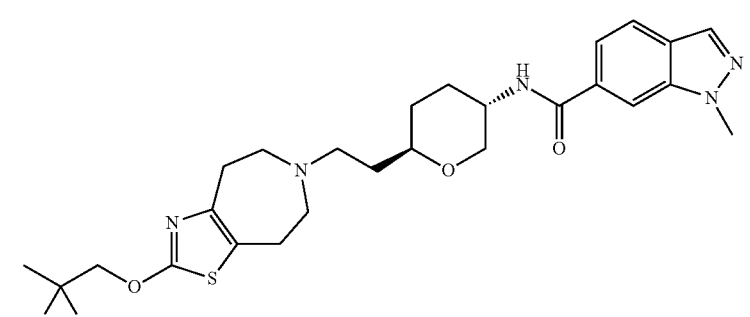 | 2 | 1.47 | 534.2 |
TABLE 12
| I-068 | 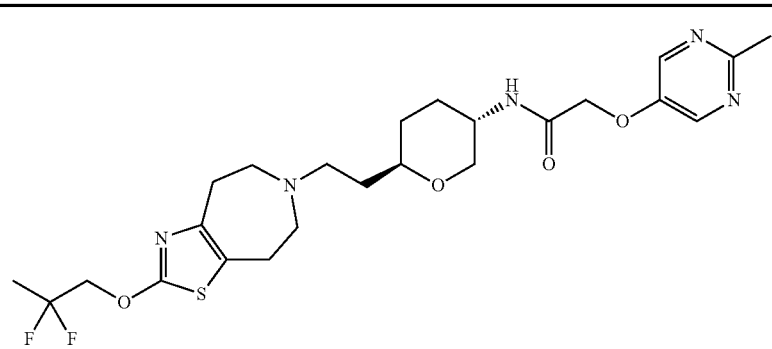 | 2 | 1.28 | 526.2 |
| I-069 | 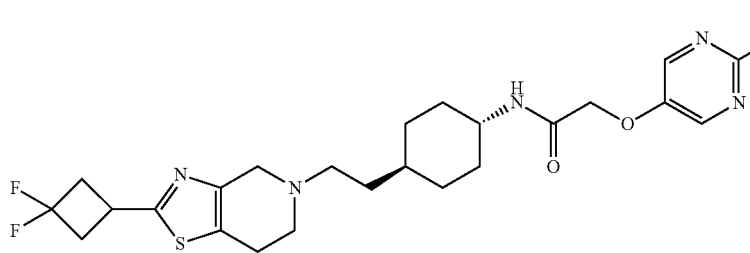 | 2 | 1.28 | 506.2 |
| I-070 | 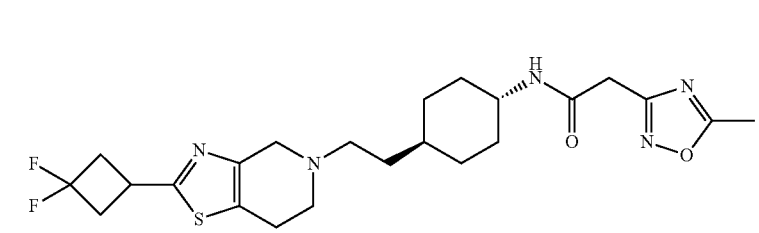 [SMILES: Cc1nc(CC(=O)N[C@H]2CC[C@H](CCN3CCc4sc(C5CC(F)(F)C5)nc4C3)CC2)no1] | 2 | 1.28 | 480.2 |

TABLE 12-continued

| ID | Structure | a | b | c |
|---|---|---|---|---|
| I-071 | 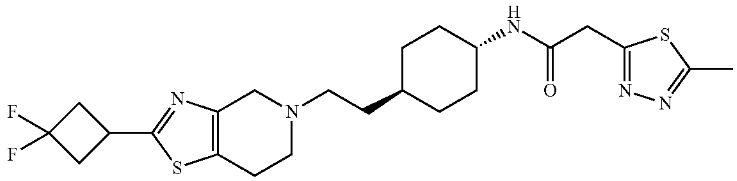 | 2 | 1.28 | 496.1 |
| I-072 | 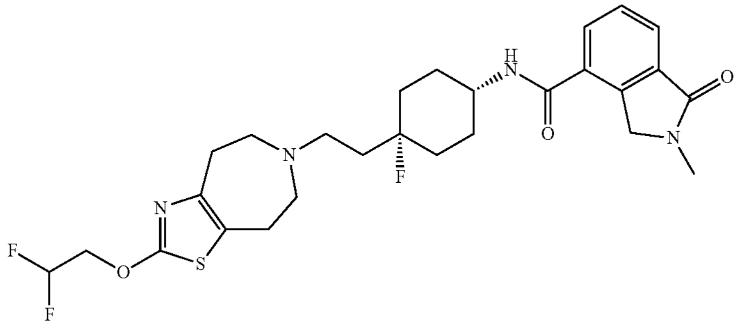 [SMILES: CN1Cc2c(C(=O)N[C@H]3CC[C@](F)(CCN4CCc5nc(OCC(F)F)sc5CC4)CC3)cccc2C1=O] | 2 | 1.30 | 551.15 |
| I-073 | 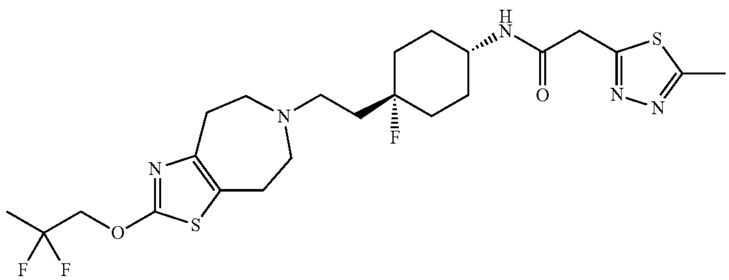 [SMILES: Cc1nnc(CC(=O)N[C@H]2CC[C@](F)(CCN3CCc4nc(OCC(C)(F)F)sc4CC3)CC2)s1] | 2 | 1.34 | 532.15 |
| I-074 | 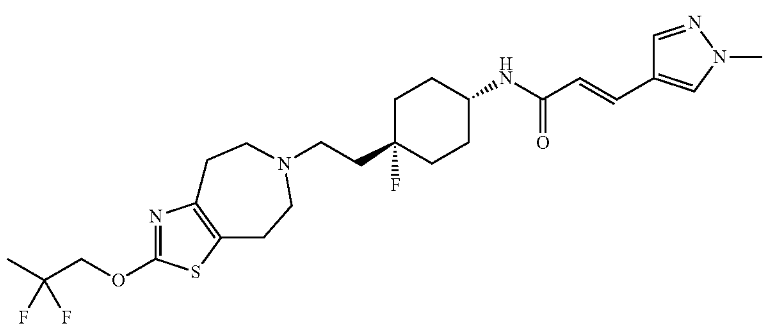 [SMILES: Cn1cc(/C=C/C(=O)N[C@H]2CC[C@](F)(CCN3CCc4nc(OCC(C)(F)F)sc4CC3)CC2)cn1] | 2 | 1.41 | 526.2 |

TABLE 13

| ID | Structure | a | b | c |
|---|---|---|---|---|
| I-075 | 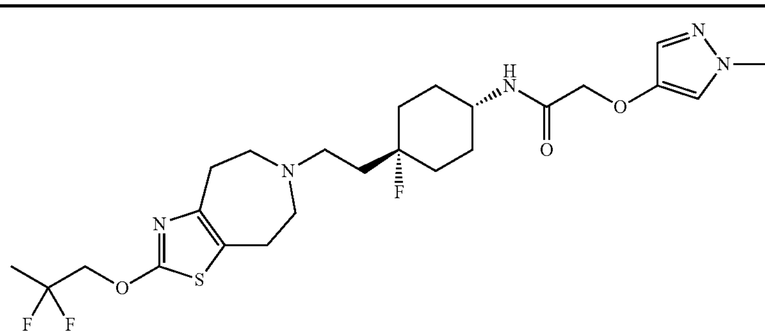 | 2 | 1.38 | 530.2 |

TABLE 13-continued
I-076 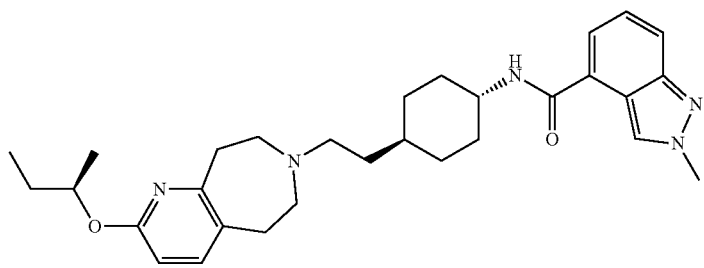 [SMILES: CC[C@@H](C)Oc1ccc2c(n1)CCN(CC[C@H]1CC[C@H](NC(=O)c3cccc4nn(C)cc34)CC1)CC2] 2 1.54 504
I-077 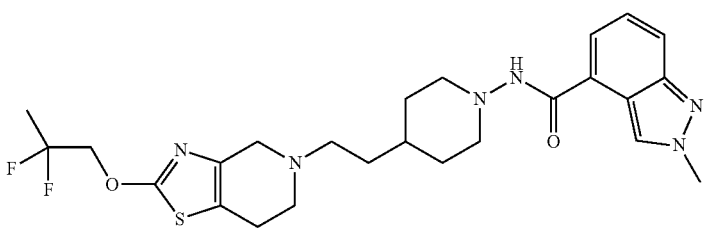 [SMILES: Cn1cc2c(C(=O)NN3CCC(CCN4CCc5sc(OCC(C)(F)F)nc5C4)CC3)cccc2n1] 2 1.30 519
I-078 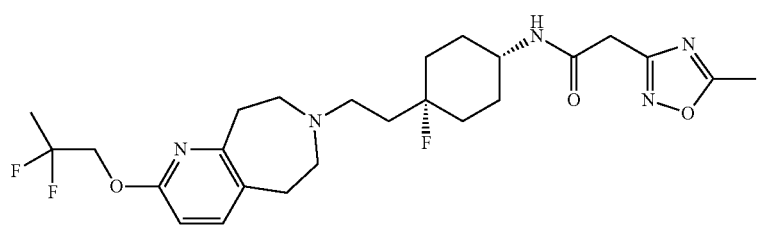 [SMILES: Cc1nc(CC(=O)N[C@H]2CC[C@](F)(CCN3CCc4ccc(OCC(C)(F)F)nc4CC3)CC2)no1] 2 1.43 510.3
I-079 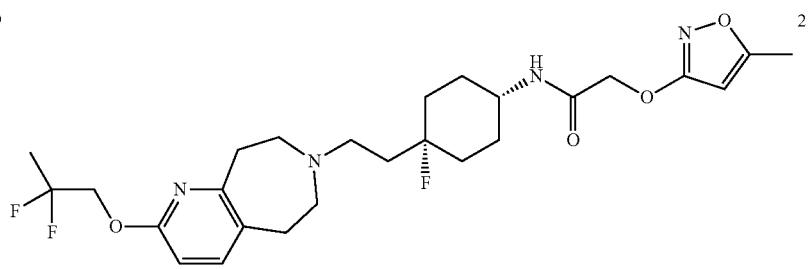 2 1.57 525.3
I-080 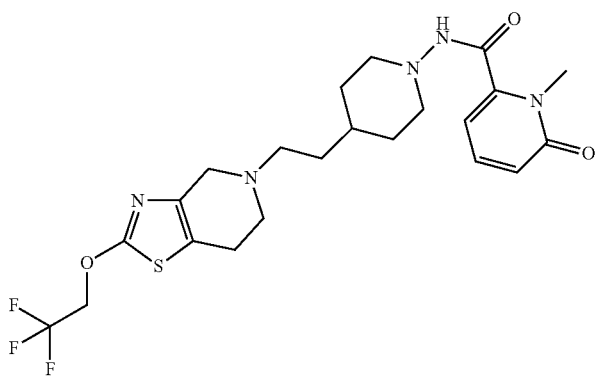 [SMILES: Cn1c(C(=O)NN2CCC(CCN3CCc4sc(OCC(F)(F)F)nc4C3)CC2)cccc1=O] 2 1.15 500.1

TABLE 14
| | | | | |
|---|---|---|---|---|
| I-081 | 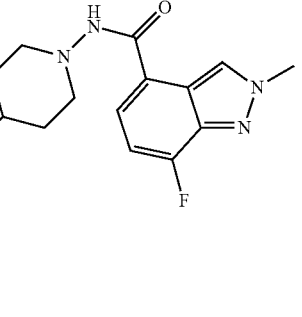 | 2 | 1.37 | 541.1 |
| I-082 | 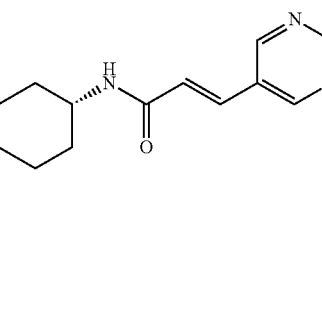 | 2 | 1.40 | 532.2 |
| I-083 | 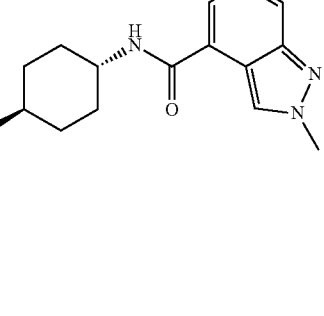 | 2 | 1.59 | 550.2 |
| I-084 | 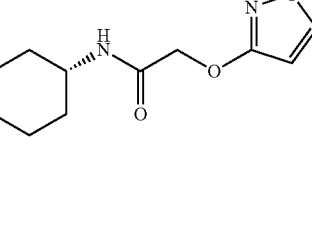 | 2 | 1.48 | 511.2 |
| I-085 | 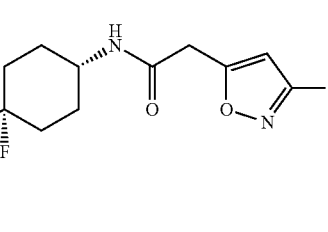 | 2 | 1.42 | 511.3 |

TABLE 14-continued

| | | | | |
|---|---|---|---|---|
| I-086 | | 2 | 1.39 | 495.3 |
| I-087 | | 2 | 1.47 | 467.3 |

TABLE 15

| | | | | |
|---|---|---|---|---|
| I-088 | | 2 | 1.23 | 477.3 |
| I-089 | | 2 | 1.50 | 502.3 |
| I-090 | | 2 | 1.44 | 467 |
| I-091 | | 2 | 1.11 | 473 |

TABLE 15-continued
I-092 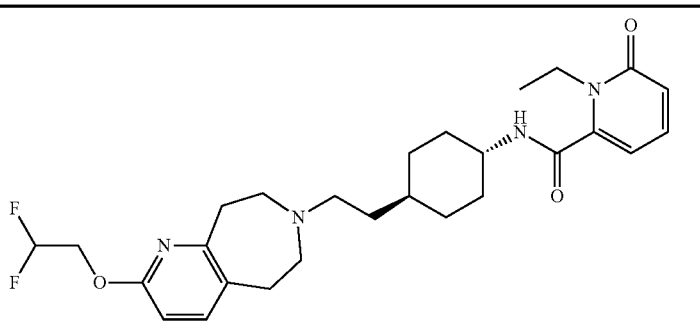 2  1.35  503
I-093 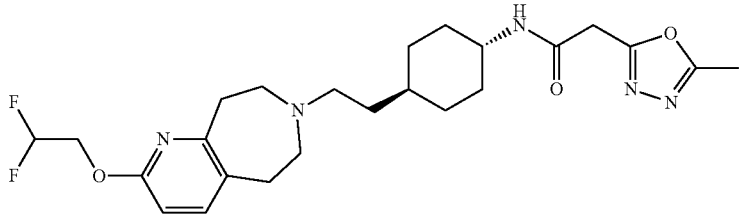 [SMILES: Cc1nnc(CC(=O)N[C@H]2CC[C@H](CCN3CCc4ccc(OCC(F)F)nc4CC3)CC2)o1] 2  1.28  478
I-094 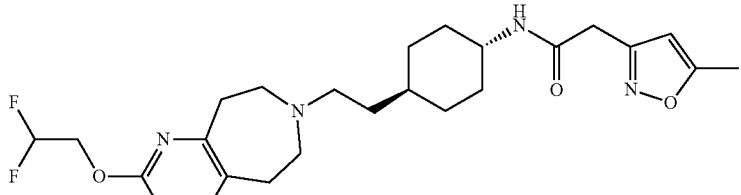 2  1.42  477
TABLE 16
I-095 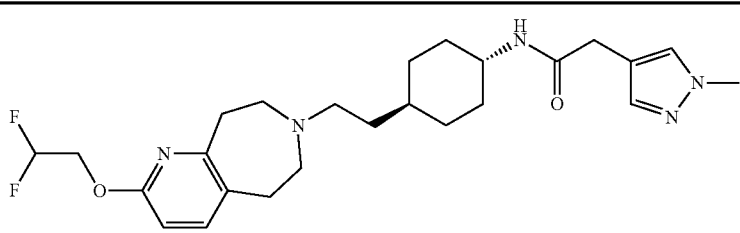 2  1.30  476
I-096 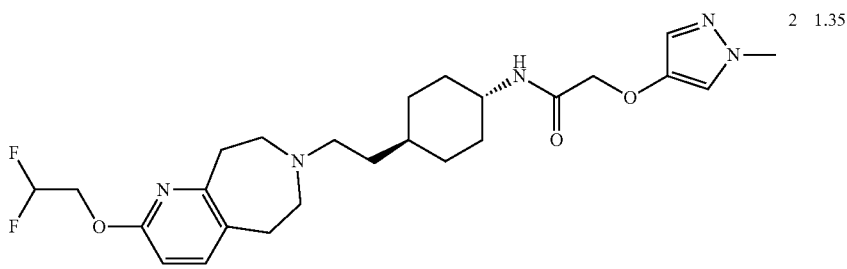 2  1.35  492

TABLE 16-continued
I-097 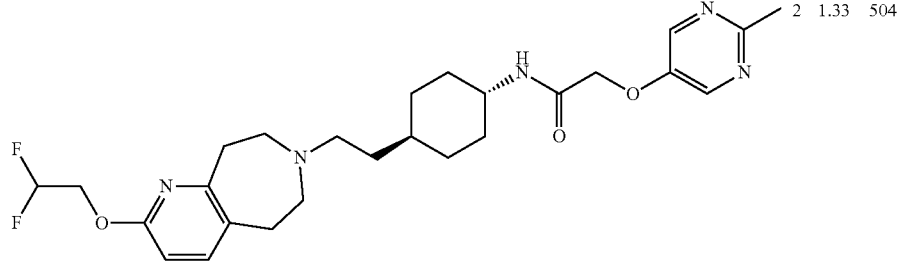 2 1.33 504
I-098 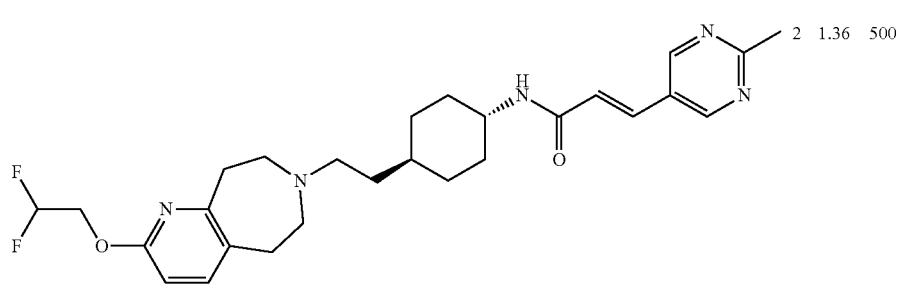 2 1.36 500
I-099 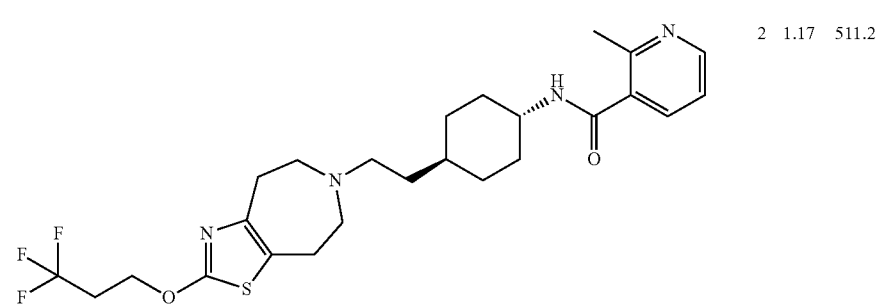 2 1.17 511.2
I-100 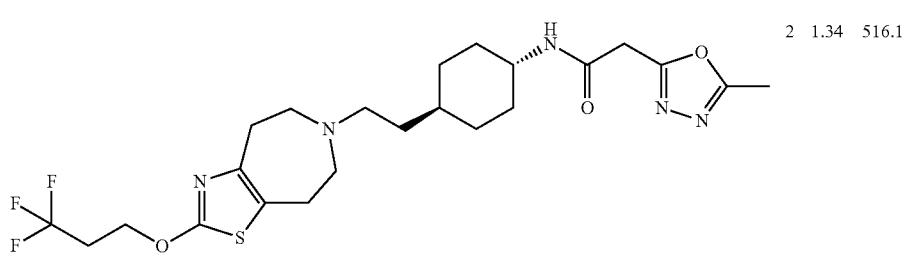 2 1.34 516.1
I-101 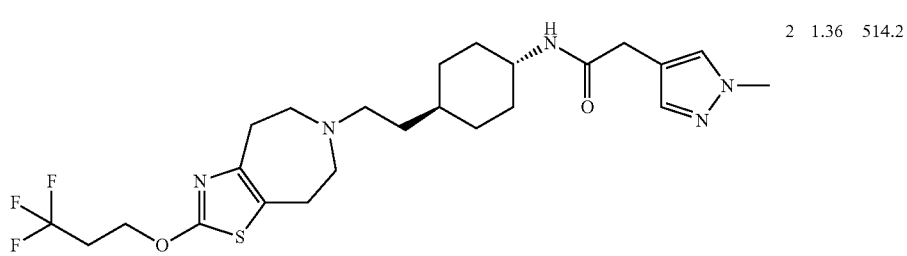 2 1.36 514.2

TABLE 17
I-102 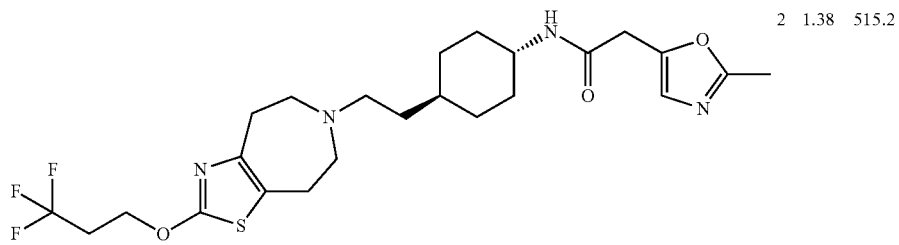 2 1.38 515.2
I-103 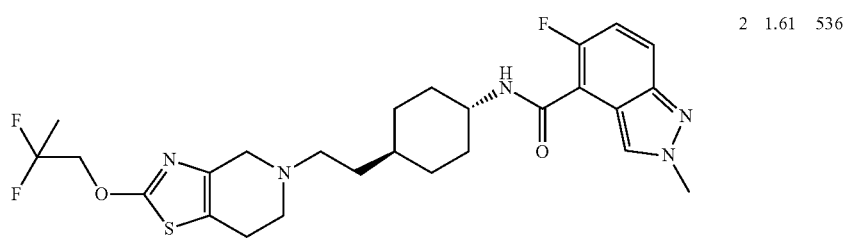 2 1.61 536
I-104 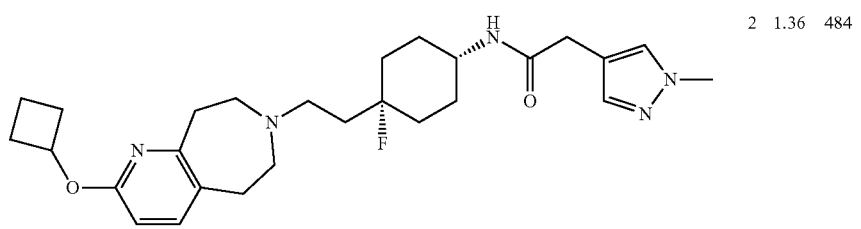 2 1.36 484
I-105 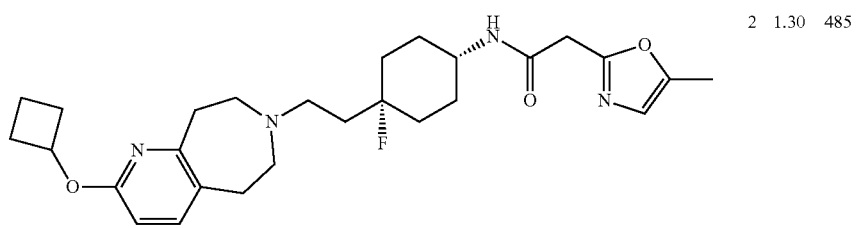 2 1.30 485
I-106 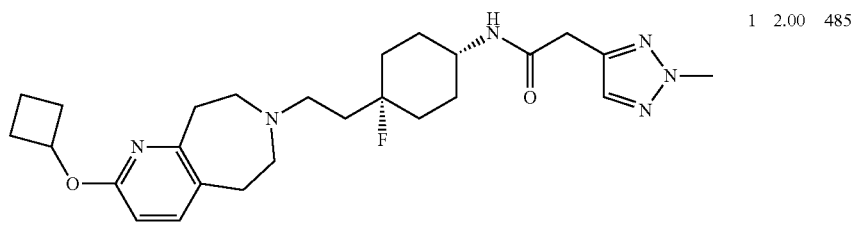 1 2.00 485
I-107 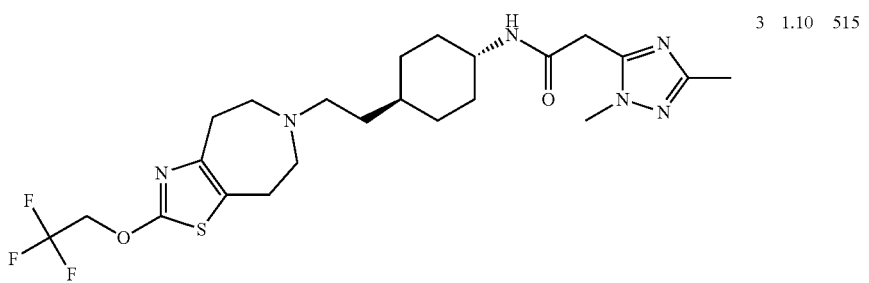 3 1.10 515

TABLE 17-continued
| ID | Structure | a | b | c |
|---|---|---|---|---|
| I-108 | 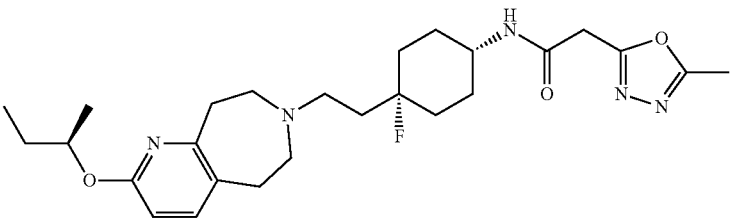 [SMILES: CC[C@@H](C)Oc1ccc2c(n1)CCN(CC[C@]1(F)CC[C@@H](NC(=O)Cc3nnc(C)s3)CC1)CC2] | 2 | 1.41 | 488.3 |
| I-109 | 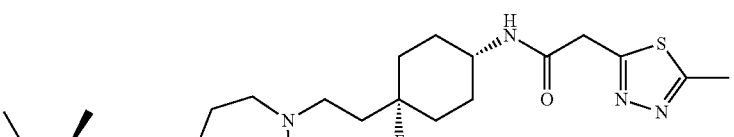 | 2 | 1.44 | 504.2 |
TABLE 18
| ID | Structure | a | b | c |
|---|---|---|---|---|
| I-110 | 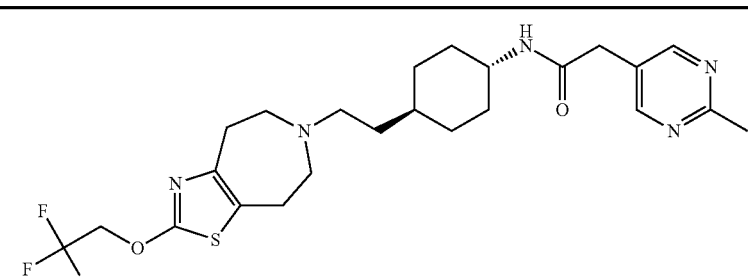 | 3 | 1.11 | 512 |
| I-111 | 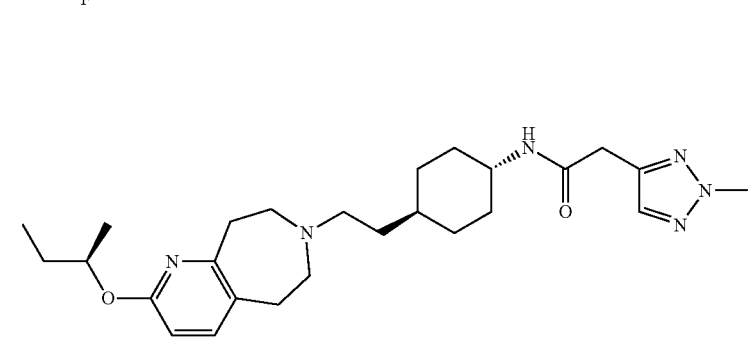 | 2 | 1.44 | 469.3 |
| I-112 | 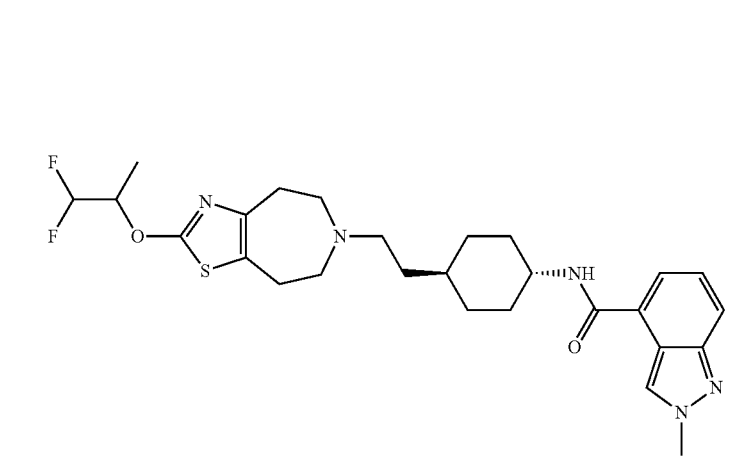 [SMILES: CC(Oc1nc2c(s1)CCN(CC[C@H]1CC[C@H](NC(=O)c3cccc4nn(C)cc34)CC1)CC2)C(F)F] | 3 | 1.29 | 532 |

TABLE 18-continued
| I-113 | 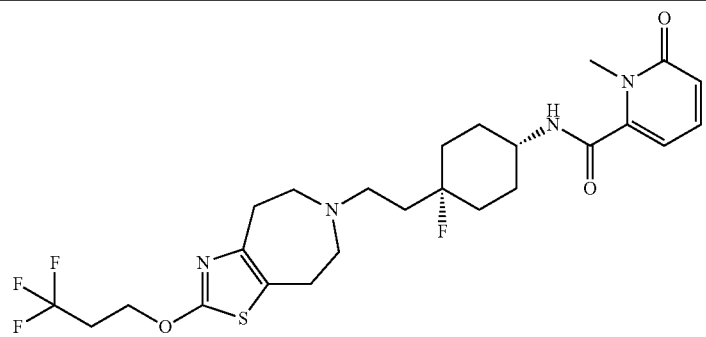 | 2 | 1.38 | 545.2 |
| I-114 | 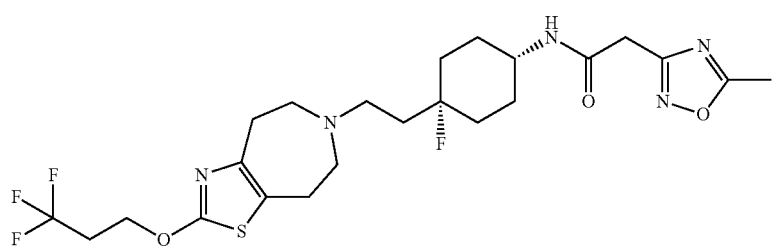 [SMILES: Cc1nc(CC(=O)N[C@H]2CC[C@](F)(CCN3CCc4nc(OCCC(F)(F)F)sc4CC3)CC2)no1] | 2 | 1.42 | 534.1 |
| I-115 | 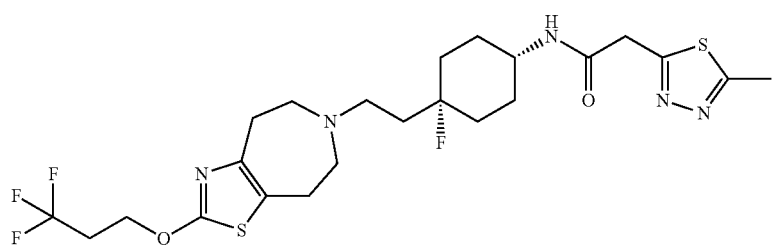 | 2 | 1.41 | 550.1 |
| I-116 | 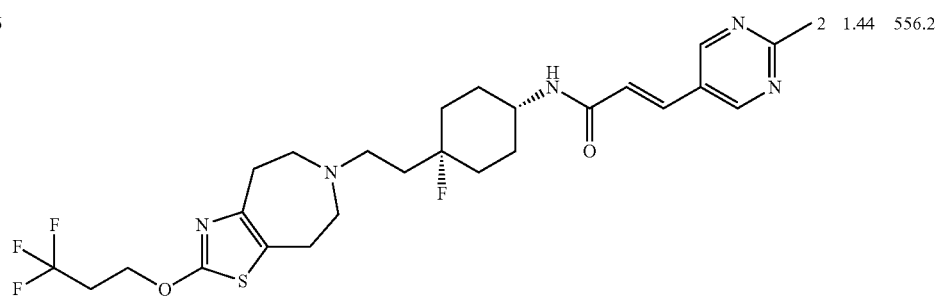 | 2 | 1.44 | 556.2 |
TABLE 19
| I-117 | 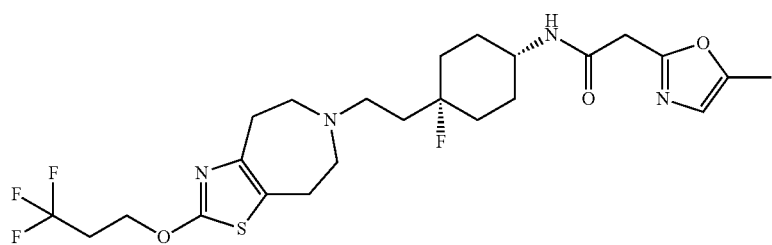 [SMILES: Cc1nnc(CC(=O)N[C@H]2CC[C@](F)(CCN3CCc4nc(OCCC(F)(F)F)sc4CC3)CC2)s1] | 2 | 1.46 | 533.2 |

TABLE 19-continued
| I-118 | 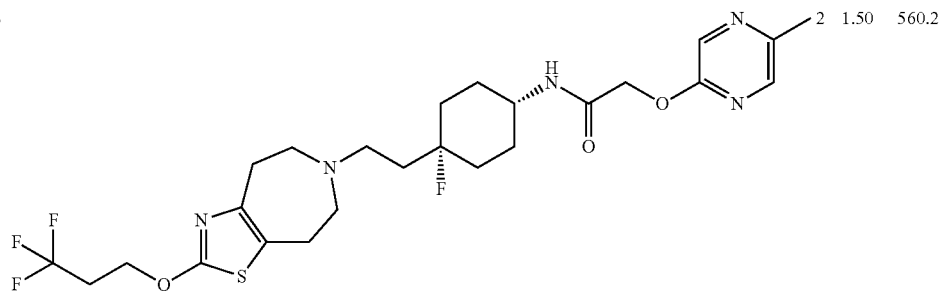 | 2 | 1.50 | 560.2 |
| I-119 | 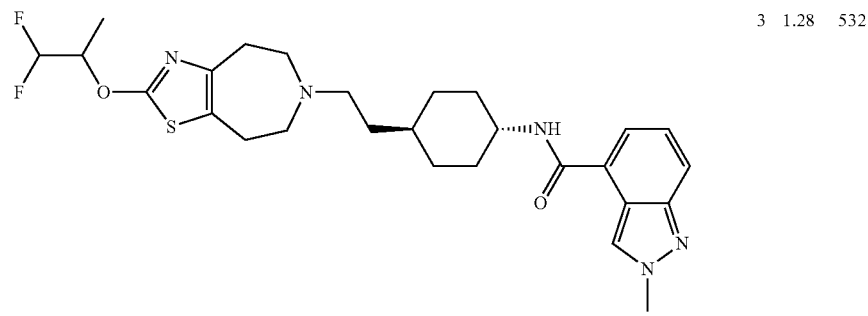 | 3 | 1.28 | 532 |
| I-120 | 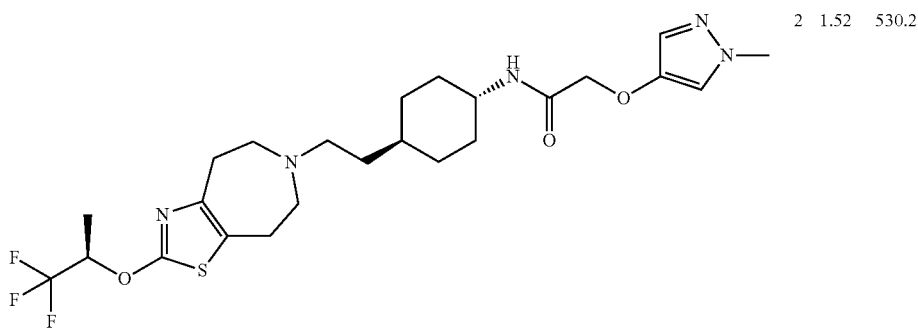 | 2 | 1.52 | 530.2 |
| I-121 | 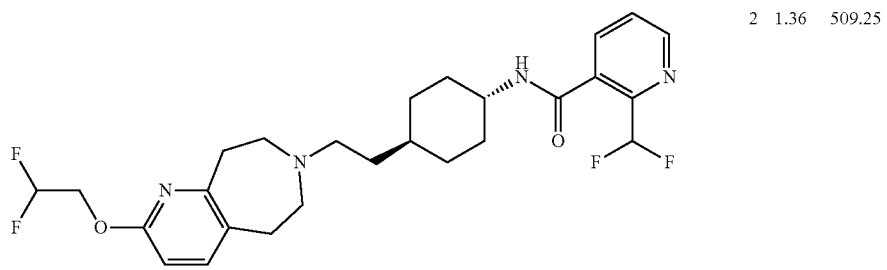 | 2 | 1.36 | 509.25 |
| I-122 | 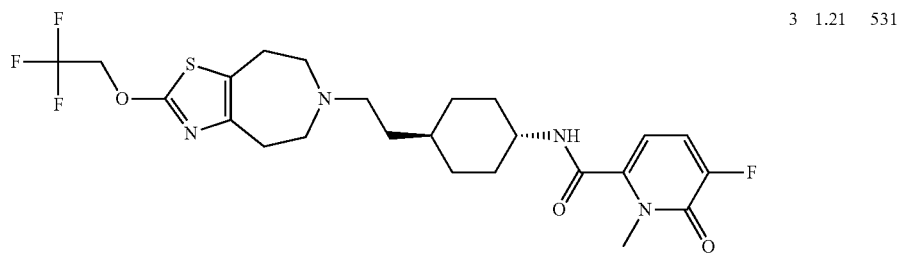 | 3 | 1.21 | 531 |

TABLE 20
I-123 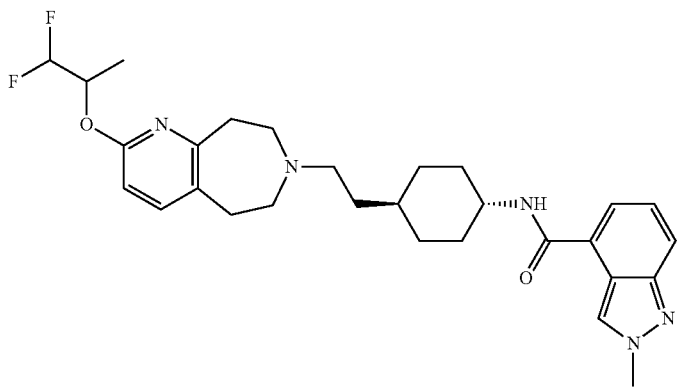 [SMILES: CC(Oc1ccc2c(n1)CCN(CC[C@H]1CC[C@H](NC(=O)c3cccc4nn(C)cc34)CC1)CC2)C(F)F] 3 1.38 526
I-124 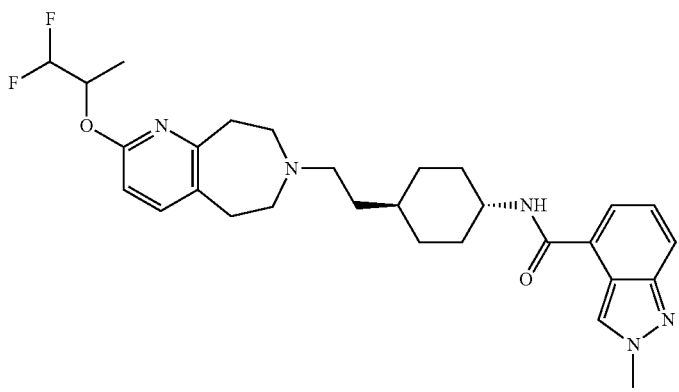 [SMILES: CC(Oc1ccc2c(n1)CCN(CC[C@H]1CC[C@H](NC(=O)c3cccc4nn(C)cc34)CC1)CC2)C(F)F] 3 1.38 526
I-125 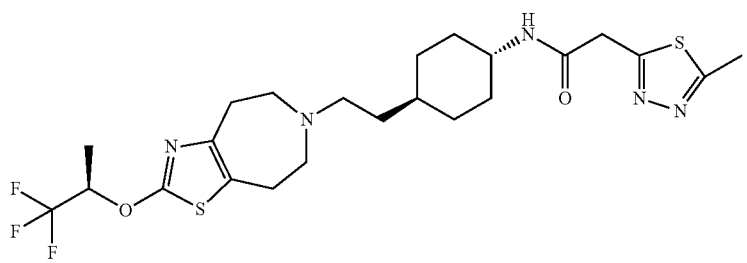 [SMILES: Cc1nnc(CC(=O)N[C@H]2CC[C@H](CCN3CCc4nc(O[C@H](C)C(F)(F)F)sc4CC3)CC2)s1] 2 1.51 532.1
I-126 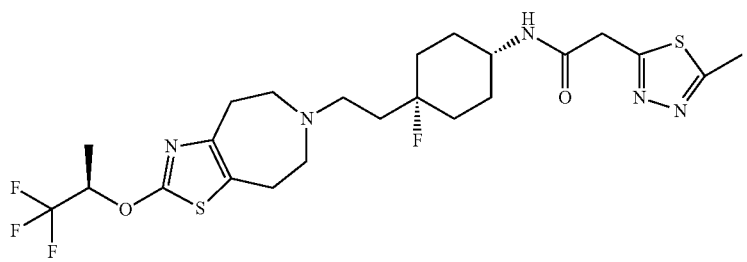 [SMILES: Cc1nnc(CC(=O)N[C@H]2CC[C@](F)(CCN3CCc4nc(O[C@H](C)C(F)(F)F)sc4CC3)CC2)s1] 2 1.43 550
I-127 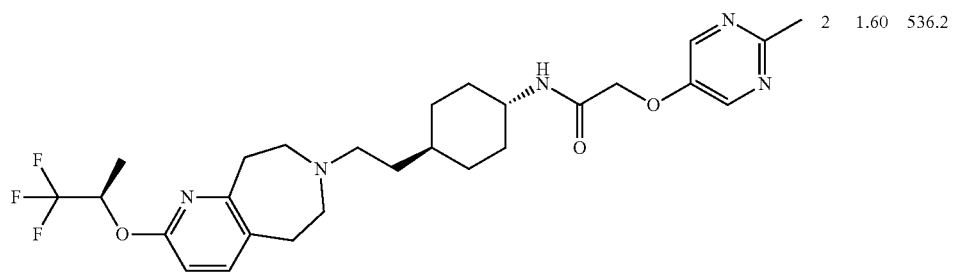 2 1.60 536.2

TABLE 20-continued

| I-128 | [structure] | 2 | 1.61 | 509.3 |

TABLE 21

| I-129 | [structure] | 2 | 1.61 | 526.1 |
| I-130 | [structure] | 2 | 1.52 | 523.2 |
| I-131 | [structure] | 2 | 1.57 | 520.2 |
| I-132 | [structure] | 2 | 1.58 | 521.3 |
| I-133 | [structure] | 2 | 1.63 | 524.2 |

TABLE 21-continued

| I-134 | [structure] | 2 | 1.54 | 529.3 |

TABLE 22

| I-135 | [structure] | 2 | 1.37 | 508 |
| I-136 | [structure] | 2 | 1.38 | 537.25 |
| I-137 | [structure] | 2 | 0.94 | 507.3 |
| I-138 | [structure] | 2 | 1.16 | 537.3 |

TABLE 22-continued
| I-139 | 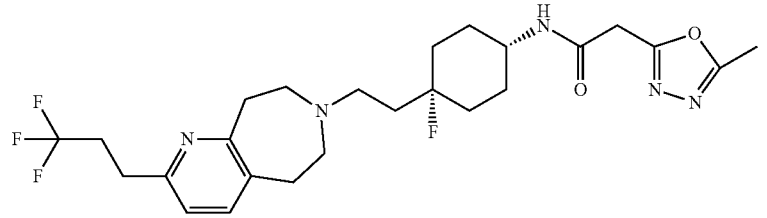 | 2 | 1.09 | 512.3 |
| I-140 | 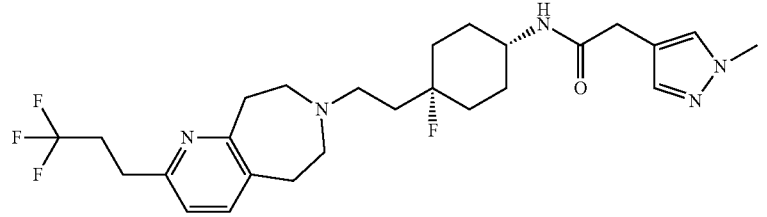 [SMILES: Cn1cc(CC(=O)N[C@H]2CC[C@](F)(CCN3CCc4ccc(CCC(F)(F)F)nc4CC3)CC2)cn1] | 2 | 1.13 | 510.3 |
| I-141 | 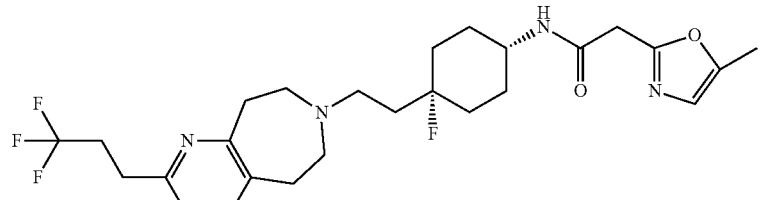 | 2 | 1.23 | 511.3 |
TABLE 23
| I-142 | 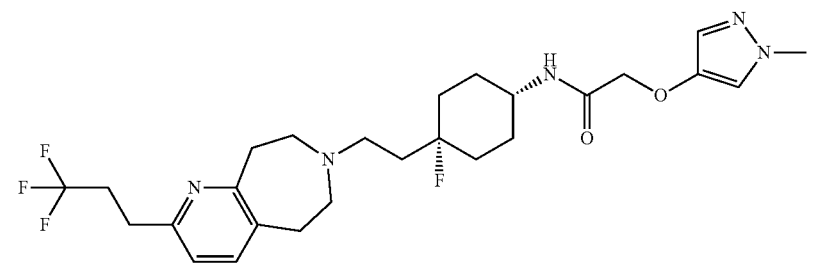 [SMILES: Cn1cc(OCC(=O)N[C@H]2CC[C@](F)(CCN3CCc4ccc(CCC(F)(F)F)nc4CC3)CC2)cn1] | 2 | 1.19 | 526.2 |
| I-143 | 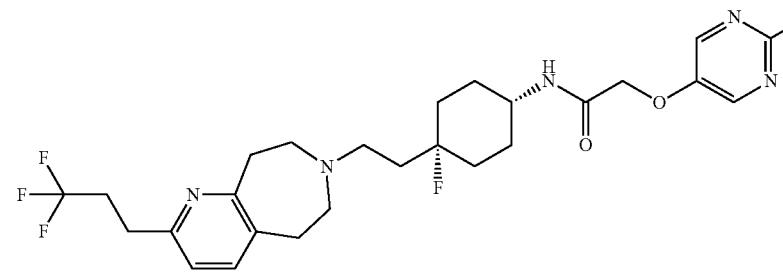 | 2 | 1.17 | 538.3 |
| I-144 | 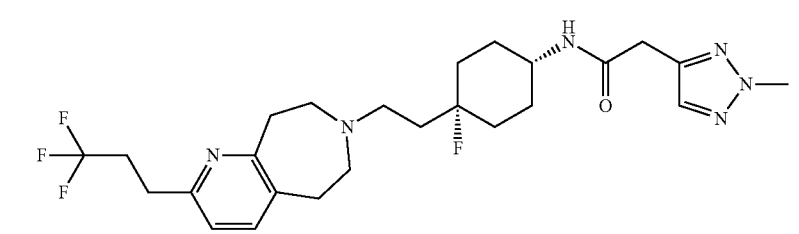 [SMILES: Cn1ncc(CC(=O)N[C@H]2CC[C@](F)(CCN3CCc4ccc(CCC(F)(F)F)nc4CC3)CC2)n1] | 2 | 1.15 | 511.3 |

TABLE 23-continued
| | | | | | |
|---|---|---|---|---|---|
| I-145 | 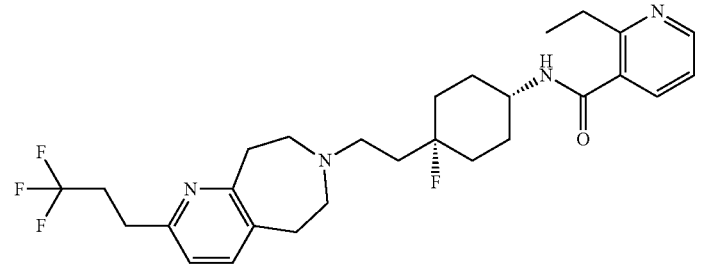 [SMILES: CCc1ncccc1C(=O)N[C@H]1CC[C@](F)(CCN2CCc3ccc(CCC(F)(F)F)nc3CC2)CC1] | | 2 | 1.01 | 521.3 |
| I-146 | 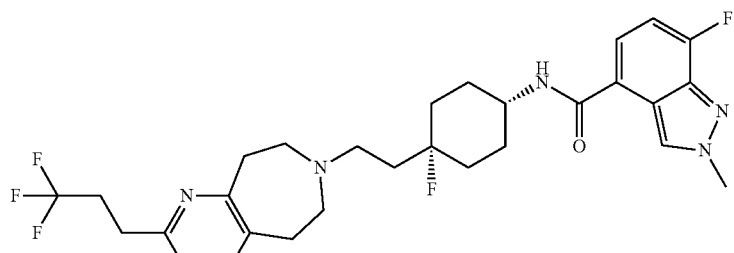 | | 2 | 1.38 | 564.3 |
| I-147 | 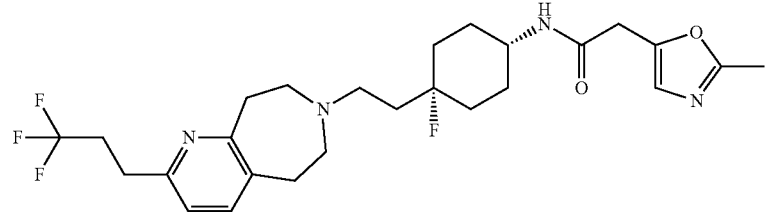 [SMILES: Cc1ncc(CC(=O)N[C@H]2CC[C@](F)(CCN3CCc4ccc(CCC(F)(F)F)nc4CC3)CC2)o1] | | 2 | 1.15 | 511.3 |
| I-148 | 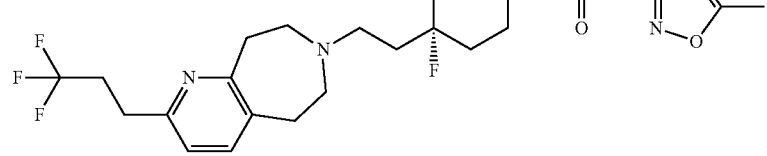 | | 2 | 1.16 | 512.3 |
| I-149 | 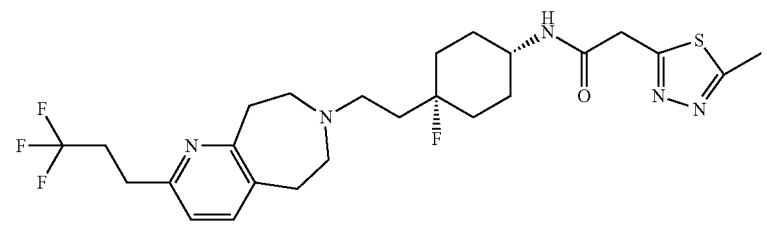 [SMILES: Cc1nnc(CC(=O)N[C@H]2CC[C@](F)(CCN3CCc4ccc(CCC(F)(F)F)nc4CC3)CC2)s1] | | 2 | 1.15 | 528.2 |
TABLE 24
| | | | | | |
|---|---|---|---|---|---|
| I-150 | 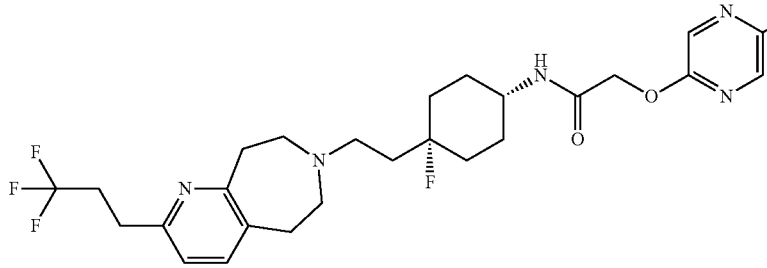 | | 2 | 1.28 | 538.3 |

TABLE 24-continued
| | | | | |
|---|---|---|---|---|
| I-151 | 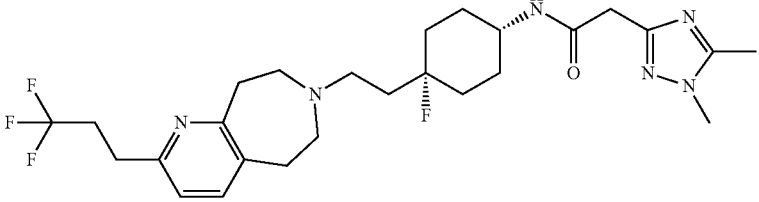 | 2 | 1.05 | 525.3 |
| I-152 | 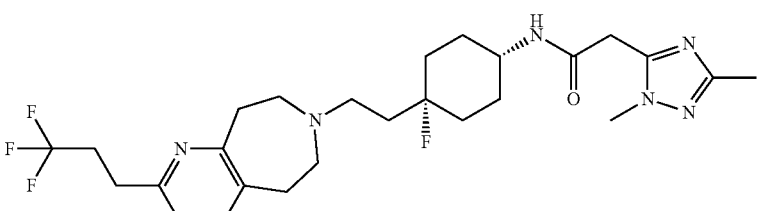 | 2 | 1.06 | 525.3 |
| I-153 | 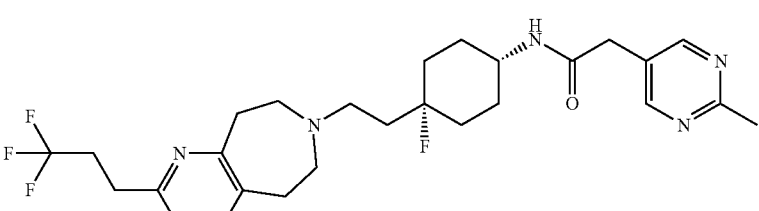 | 2 | 1.1 | 522.3 |
| I-154 | 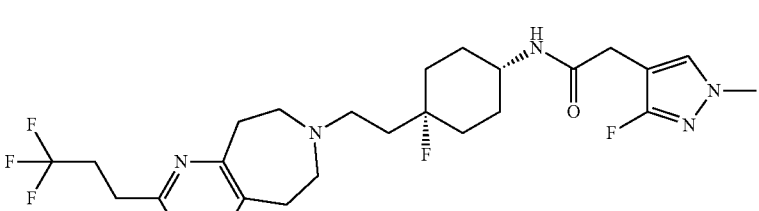 | 2 | 1.22 | 528.2 |
| I-155 | 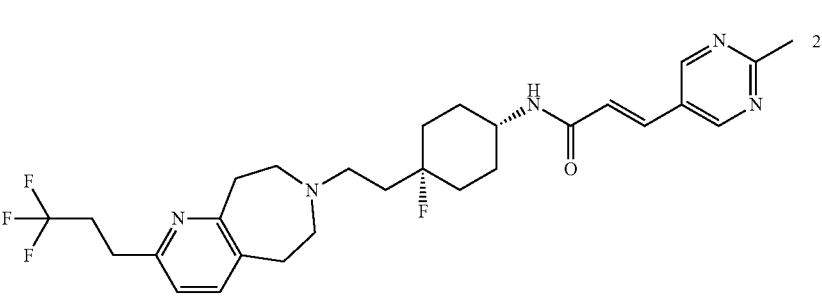 | 2 | 1.21 | 534.3 |
| I-156 | 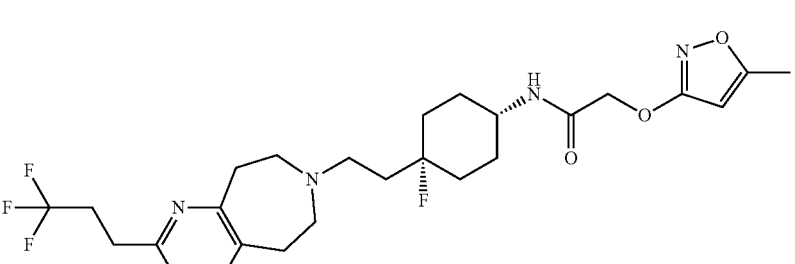 | 2 | 1.33 | 527.2 |

TABLE 24-continued

| ID | Structure | | | |
|---|---|---|---|---|
| I-157 | (structure) | 2 | 1.23 | 511.3 |

TABLE 25

| ID | Structure | | | |
|---|---|---|---|---|
| I-158 | (structure) | 2 | 1.4 | 527.2 |
| I-159 | (structure) | 2 | 1.47 | 551.1 |
| I-160 | (structure) | 2 | 1.33 | 533.1 |
| I-161 | (structure) | 2 | 1.34 | 515.1 |
| I-162 | (structure) | 2 | 1.42 | 547.2 |

TABLE 25-continued

| I-163 | | 2 | 1.43 | 529.2 |
|---|---|---|---|---|
| I-164 | | 2 | 1.49 | 541.3 |
| I-165 | | 2 | 1.25 | 525.3 |

TABLE 26

| I-166 | | 2 | 1.24 | 543.3 |
|---|---|---|---|---|
| I-167 | | 2 | 1.48 | 529.2 |

TABLE 26-continued

| ID | Structure | | | |
|---|---|---|---|---|
| I-168 | (3,3-difluorocyclobutoxy-thiazolo-fused azepine)-CH₂CH₂-(cyclohexyl)-NHC(O)-(2-(difluoromethyl)pyridin-3-yl) | 2 | 1.47 | 541.3 |
| I-169 | ((S)-1,1,1-trifluoropropan-2-yloxy-naphthyridine-fused azepine)-CH₂CH₂-(4-fluorocyclohexyl)-NHC(O)-(2-methylpyridin-3-yl) | 2 | 1.33 | 523.2 |
| I-170 | ((S)-1,1,1-trifluoropropan-2-yloxy-naphthyridine-fused azepine)-CH₂CH₂-(4-fluorocyclohexyl)-NHC(O)CH₂-(5-methyl-1,3,4-oxadiazol-2-yl) | 2 | 1.51 | 528.2 |
| I-171 | ((S)-1,1,1-trifluoropropan-2-yloxy-naphthyridine-fused azepine)-CH₂CH₂-(4-fluorocyclohexyl)-NHC(O)CH₂-(1-methyl-1H-pyrazol-4-yl) | 2 | 1.53 | 526.3 |
| I-172 | ((S)-1,1,1-trifluoropropan-2-yloxy-naphthyridine-fused azepine)-CH₂CH₂-(4-fluorocyclohexyl)-NHC(O)CH₂-(5-methyloxazol-2-yl) | 2 | 1.61 | 527.3 |
| I-173 | ((S)-1,1,1-trifluoropropan-2-yloxy-naphthyridine-fused azepine)-CH₂CH₂-(4-fluorocyclohexyl)-NHC(O)CH₂O-(1-methyl-1H-pyrazol-4-yl) | 2 | 1.58 | 542.3 |

TABLE 27
| | | | | |
|---|---|---|---|---|
| I-174 | 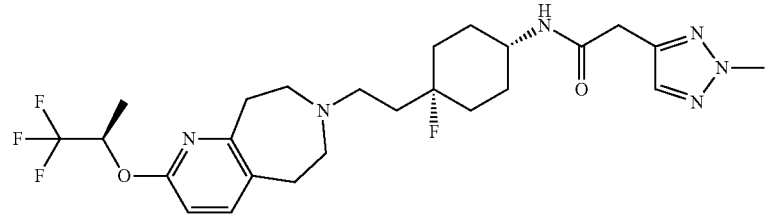 [SMILES: C[C@@H](Oc1ccc2c(n1)CCN(CC[C@]1(F)CC[C@@H](NC(=O)Cc3cnn(C)n3)CC1)CC2)C(F)(F)F] | 2 | 1.56 | 527.3 |
| I-175 | 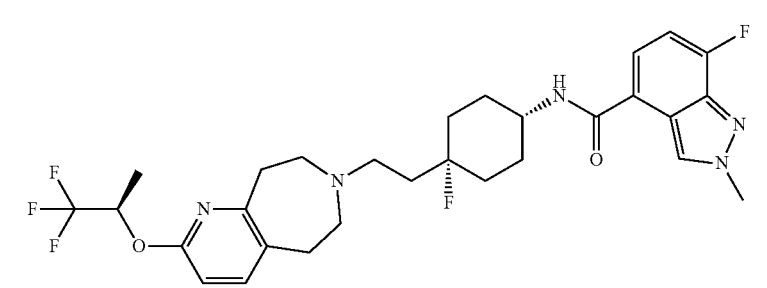 [SMILES: C[C@@H](Oc1ccc2c(n1)CCN(CC[C@]1(F)CC[C@@H](NC(=O)c3ccc(F)c4nn(C)cc34)CC1)CC2)C(F)(F)F] | 2 | 1.71 | 580.3 |
| I-176 | 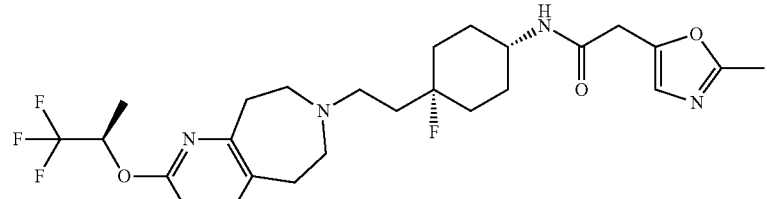 | 2 | 1.55 | 527.3 |
| I-177 | 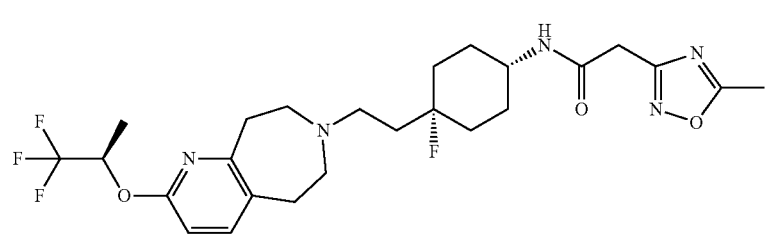 [SMILES: Cc1nc(CC(=O)N[C@H]2CC[C@](F)(CCN3CCc4ccc(O[C@H](C)C(F)(F)F)nc4CC3)CC2)no1] | 2 | 1.57 | 528.2 |
| I-178 | 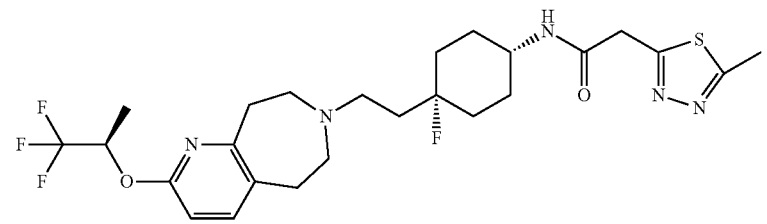 [SMILES: Cc1nnc(CC(=O)N[C@H]2CC[C@](F)(CCN3CCc4ccc(O[C@H](C)C(F)(F)F)nc4CC3)CC2)s1] | 2 | 1.55 | 544.2 |
| I-179 | 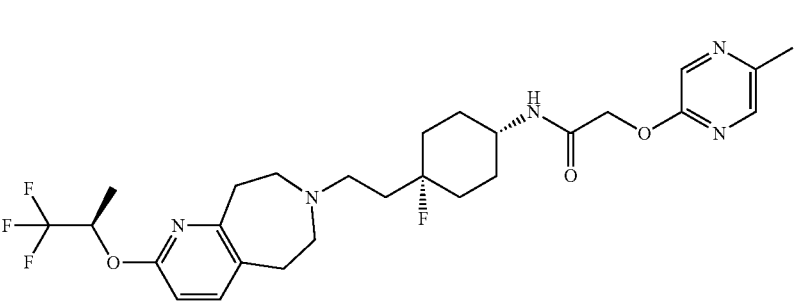 [SMILES: Cc1cnc(OCC(=O)N[C@H]2CC[C@](F)(CCN3CCc4ccc(O[C@H](C)C(F)(F)F)nc4CC3)CC2)cn1] | 2 | 1.64 | 554.2 |

TABLE 27-continued

| | | | | |
|---|---|---|---|---|
| I-180 | | 2 | 1.46 | 541.3 |
| I-181 | | 2 | 1.48 | 541.3 |

TABLE 28

| | | | | |
|---|---|---|---|---|
| I-182 | | 2 | 1.5 | 538.3 |
| I-183 | | 2 | 1.61 | 544.3 |
| I-184 | | 2 | 1.57 | 550.2 |
| I-185 | | 2 | 1.53 | 539.3 |

TABLE 28-continued

| | | LC-MS method | RT (min) | MS (m/z) |
|---|---|---|---|---|
| I-186 | (structure) | 2 | 1.42 | 552 |

TABLE 29

| Compound No. | Structure | LC-MS method | RT (min) | MS (m/z) |
|---|---|---|---|---|
| I'-1 | (structure) | 2 | 0.88 | 489.2 |
| I'-2 | (structure) | 2 | 1.27 | 509.2 |
| I'-3 | (structure) | 2 | 1.05 | 494.2 |
| I'-4 | (structure) | 2 | 1.09 | 492.2 |

TABLE 29-continued

| Compound No. | Structure | LC-MS method | RT (min) | MS (m/z) |
|---|---|---|---|---|
| I'-5 | 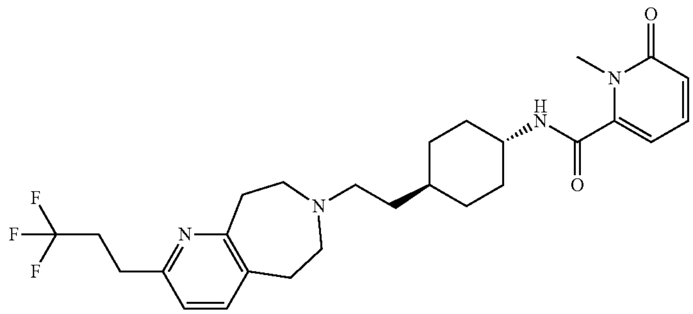 [SMILES: Cn1c(C(=O)N[C@H]2CC[C@H](CCN3CCc4ccc(CCC(F)(F)F)nc4CC3)CC2)cccc1=O] | 2 | 1.1 | 505.3 |
| I'-6 | 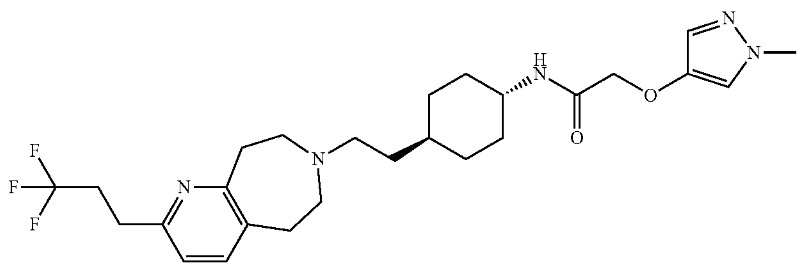 [SMILES: Cn1cc(OCC(=O)N[C@H]2CC[C@H](CCN3CCc4ccc(CCC(F)(F)F)nc4CC3)CC2)cn1] | 2 | 1.18 | 508.2 |
| I'-7 | 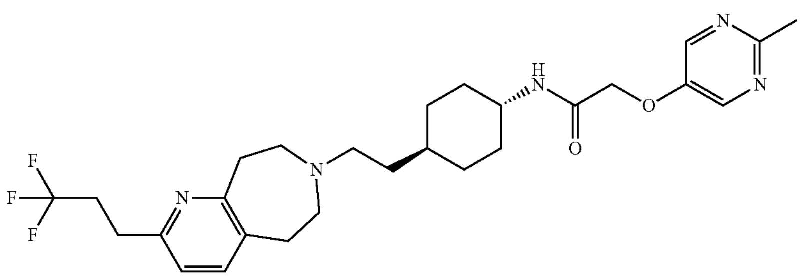 [SMILES: Cc1ncc(OCC(=O)N[C@H]2CC[C@H](CCN3CCc4ccc(CCC(F)(F)F)nc4CC3)CC2)cn1] | 2 | 1.16 | 520.3 |

TABLE 30

| I'-8 | | 2 | 1.33 | 509.2 |
|---|---|---|---|---|
| I'-9 | | 2 | 1.38 | 546.2 |

TABLE 30-continued

| | | | | |
|---|---|---|---|---|
| I'-10 | | 2 | 1.12 | 493.2 |
| I'-11 | | 2 | 1.13 | 494.2 |
| I'-12 | | 2 | 1.15 | 510.2 |
| I'-13 | | 2 | 1.28 | 520.3 |
| I'-14 | | 2 | 0.98 | 507.3 |

TABLE 31

| | | | | |
|---|---|---|---|---|
| I'-15 | | 2 | 1.01 | 507.3 |

TABLE 31-continued

| ID | Structure | n | RT | MS |
|---|---|---|---|---|
| I'-16 | 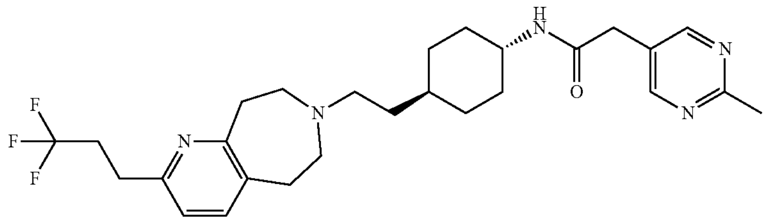 [SMILES: Cc1ncc(CC(=O)N[C@H]2CC[C@H](CCN3CCc4ccc(CCC(F)(F)F)nc4CC3)CC2)cn1] | 2 | 1.06 | 504.2 |
| I'-17 | 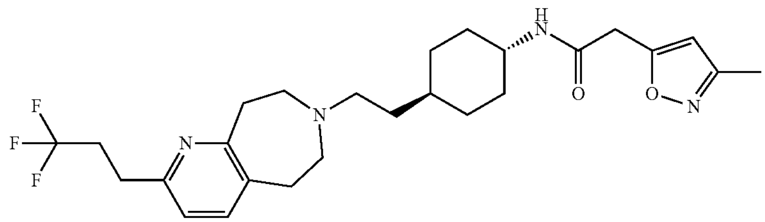 [SMILES: Cc1cc(CC(=O)N[C@H]2CC[C@H](CCN3CCc4ccc(CCC(F)(F)F)nc4CC3)CC2)on1] | 2 | 1.23 | 493.2 |
| I'-18 | 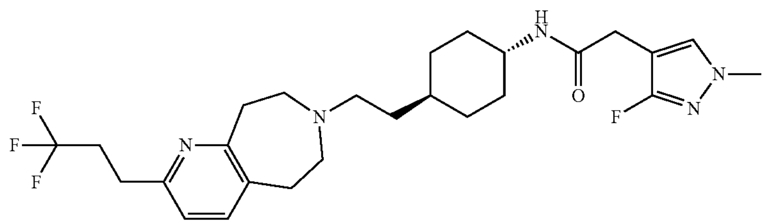 [SMILES: Cn1cc(CC(=O)N[C@H]2CC[C@H](CCN3CCc4ccc(CCC(F)(F)F)nc4CC3)CC2)c(F)n1] | 2 | 1.22 | 510.3 |
| I'-19 | 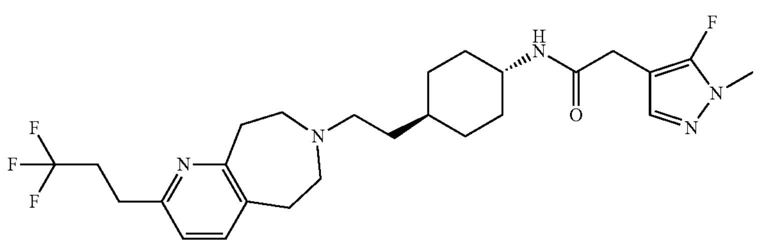 [SMILES: Cn1ncc(CC(=O)N[C@H]2CC[C@H](CCN3CCc4ccc(CCC(F)(F)F)nc4CC3)CC2)c1F] | 2 | 1.18 | 510.3 |
| I'-20 | 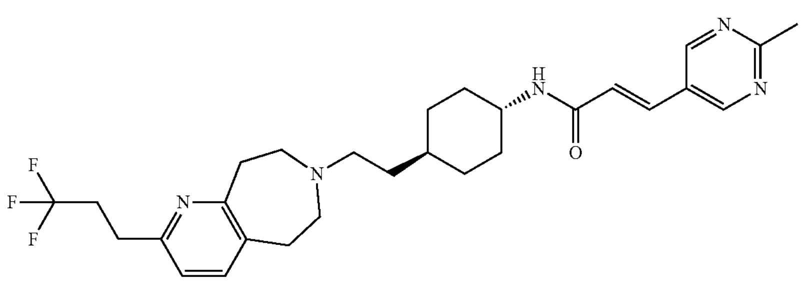 [SMILES: Cc1ncc(/C=C/C(=O)N[C@H]2CC[C@H](CCN3CCc4ccc(CCC(F)(F)F)nc4CC3)CC2)cn1] | 2 | 1.21 | 516.2 |
| I'-21 | 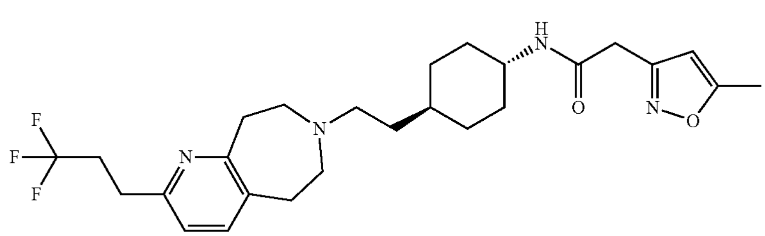 [SMILES: Cc1cc(CC(=O)N[C@H]2CC[C@H](CCN3CCc4ccc(CCC(F)(F)F)nc4CC3)CC2)no1] | 2 | 1.26 | 493.2 |

TABLE 31-continued
| I'-22 | 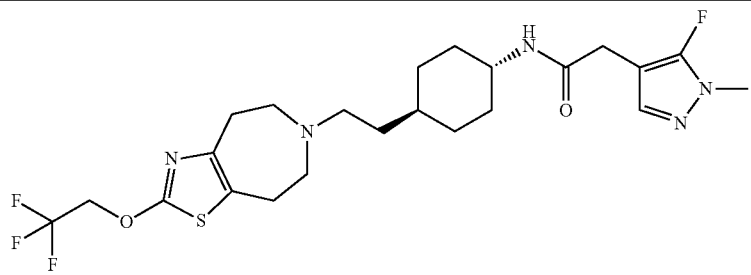 | 2 | 1.41 | 518.2 |
TABLE 32
| I'-23 | 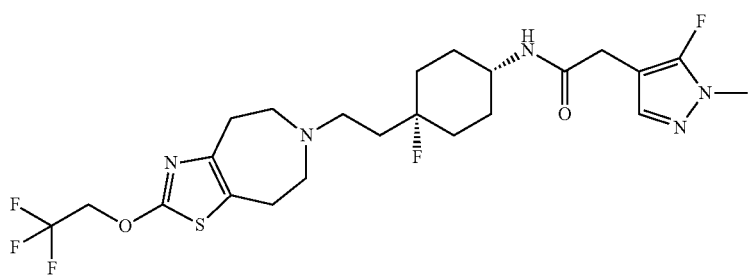 | 2 | 1.4 | 536.1 |
| I'-24 | 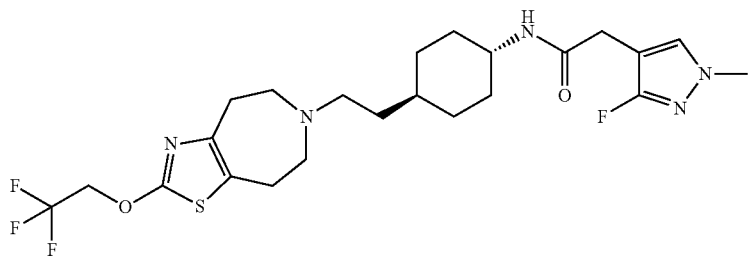 [SMILES: Cn1cc(CC(=O)N[C@H]2CC[C@H](CCN3CCc4nc(OCC(F)(F)F)sc4CC3)CC2)c(F)n1] | 2 | 1.42 | 518.2 |
| I'-25 | 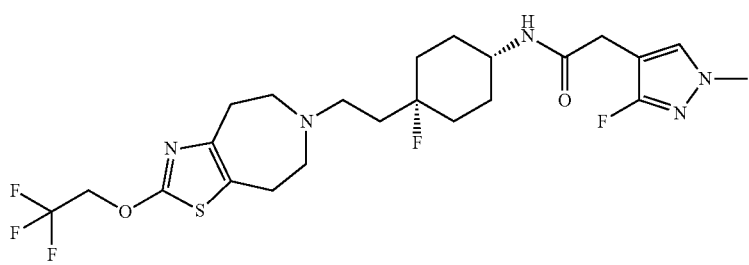 [SMILES: Cn1cc(CC(=O)N[C@H]2CC[C@](F)(CCN3CCc4nc(OCC(F)(F)F)sc4CC3)CC2)c(F)n1] | 2 | 1.43 | 536.3 |
| I'-26 | 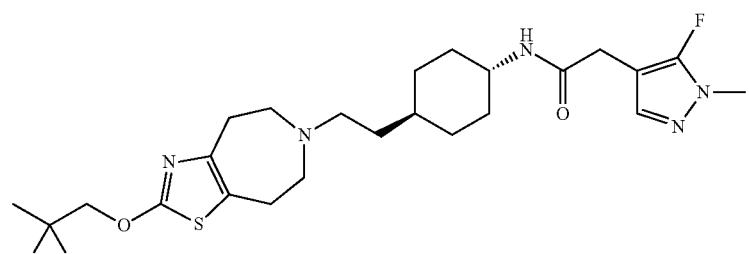 | 2 | 1.38 | 514.2 |

TABLE 32-continued
| | | | | |
|---|---|---|---|---|
| I'-27 | 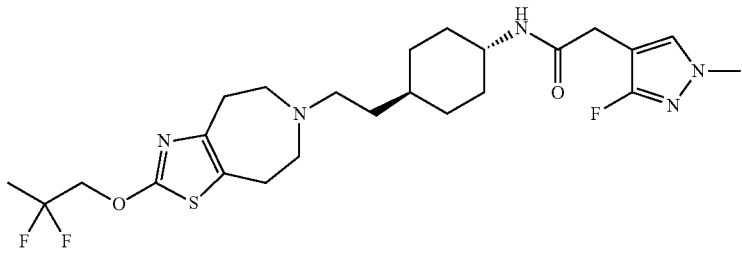 [SMILES: Cn1cc(CC(=O)N[C@H]2CC[C@H](CCN3CCc4nc(OCC(C)(F)F)sc4CC3)CC2)c(F)n1] | 2 | 1.4 | 514.2 |
| I'-28 | 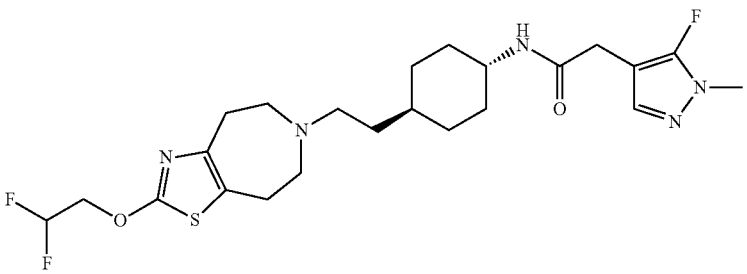 [SMILES: Cn1ncc(CC(=O)N[C@H]2CC[C@H](CCN3CCc4nc(OCC(F)F)sc4CC3)CC2)c1F] | 2 | 1.28 | 500.2 |
| I'-29 | 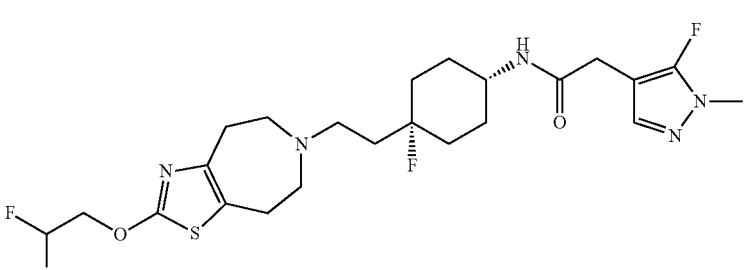 | 2 | 1.28 | 518.1 |
TABLE 33
| | | | | |
|---|---|---|---|---|
| I'-30 | 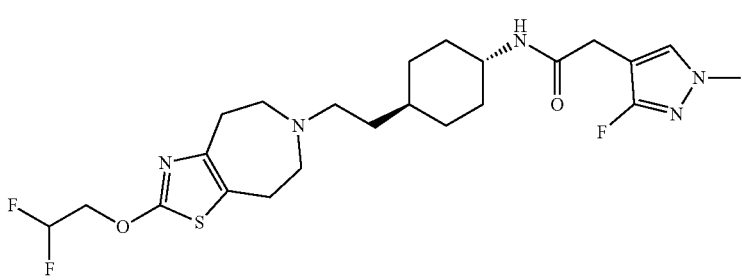 [SMILES: Cn1cc(CC(=O)N[C@H]2CC[C@H](CCN3CCc4nc(OCC(F)F)sc4CC3)CC2)c(F)n1] | 2 | 1.3 | 500.2 |
| I'-31 | 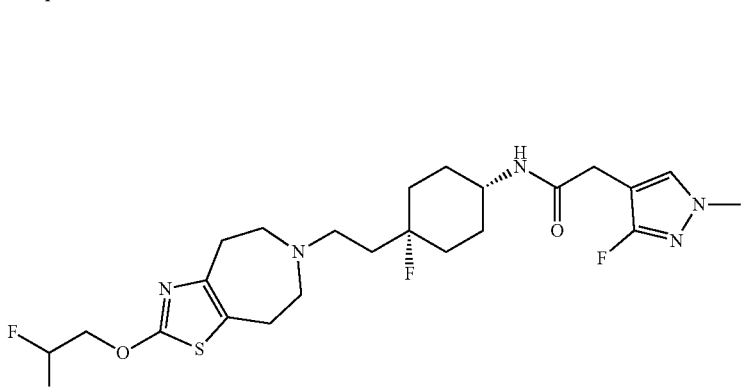 | 2 | 1.3 | 518.1 |

TABLE 33-continued

| ID | Structure | | | |
|---|---|---|---|---|
| I'-32 | (structure) | 2 | 1.36 | 494.2 |
| I'-33 | (structure) | 2 | 1.33 | 494.2 |
| I'-34 | (structure) | 2 | 1.38 | 512.3 |
| I'-35 | (structure) | 2 | 1.36 | 512.3 |
| I'-36 | (structure) | 2 | 1.38 | 501.1 |

TABLE 34

| ID | Structure | | | |
|---|---|---|---|---|
| I'-37 | (structure) | 2 | 1.36 | 519.1 |

TABLE 34-continued

| ID | Structure | n | RT | MS |
|---|---|---|---|---|
| I'-38 | 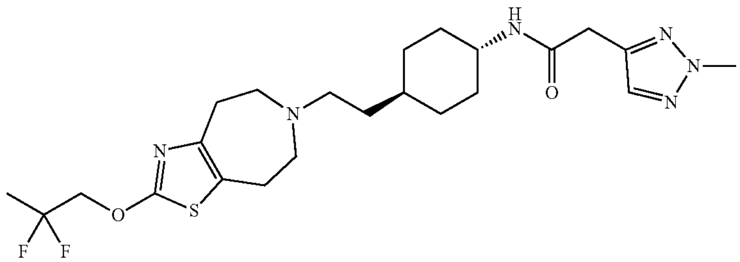 [SMILES: Cn1ncc(CC(=O)N[C@H]2CC[C@H](CCN3CCc4nc(OCC(C)(F)F)sc4CC3)CC2)n1] | 2 | 1.34 | 497.2 |
| I'-39 | 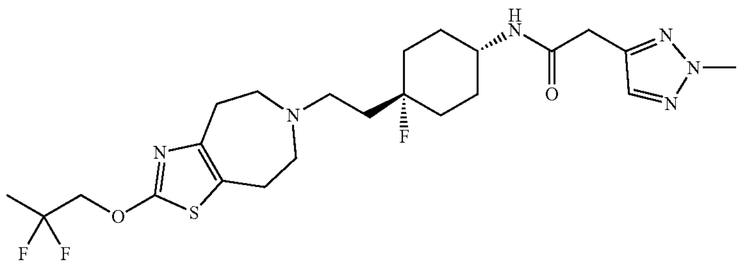 [SMILES: Cn1ncc(CC(=O)N[C@H]2CC[C@](F)(CCN3CCc4nc(OCC(C)(F)F)sc4CC3)CC2)n1] | 2 | 1.33 | 515.2 |
| I'-40 | 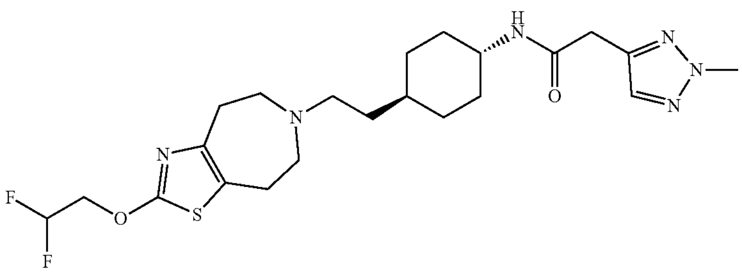 [SMILES: Cn1ncc(CC(=O)N[C@H]2CC[C@H](CCN3CCc4nc(OCC(F)F)sc4CC3)CC2)n1] | 2 | 1.23 | 483.1 |
| I'-41 | 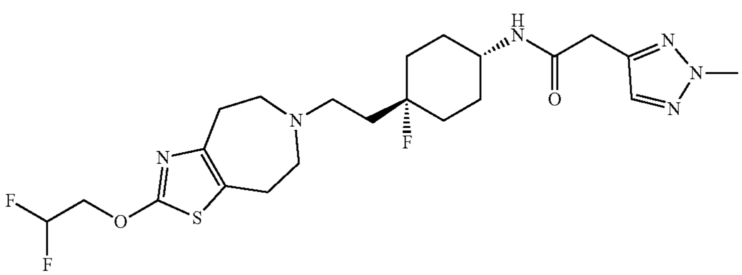 [SMILES: Cn1ncc(CC(=O)N[C@H]2CC[C@](F)(CCN3CCc4nc(OCC(F)F)sc4CC3)CC2)n1] | 2 | 1.24 | 501.2 |
| I'-42 | 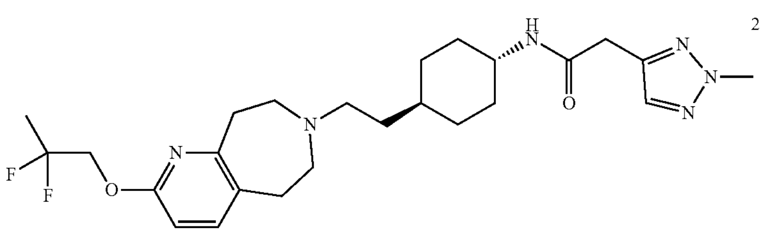 [SMILES: Cn1ncc(CC(=O)N[C@H]2CC[C@](F)(CCN3CCc4ccc(OCC(F)(F)F)nc4CC3)CC2)n1] | 2 | 1.4 | 491.3 |
| I'-43 | 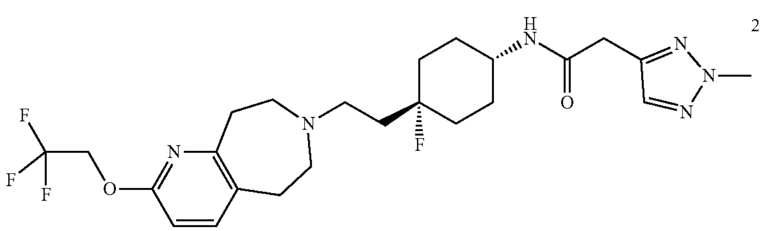 | 2 | 1.38 | 509.3 |

TABLE 34-continued
| | | | | |
|---|---|---|---|---|
| I'-44 | 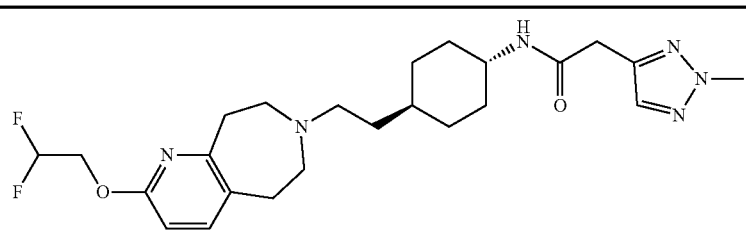 | 2 | 1.27 | 477.25 |
TABLE 35
| | | | | |
|---|---|---|---|---|
| I'-45 | 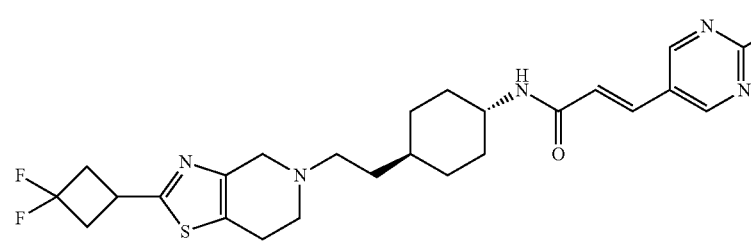 | 2 | 1.32 | 502.2 |
| I'-46 | 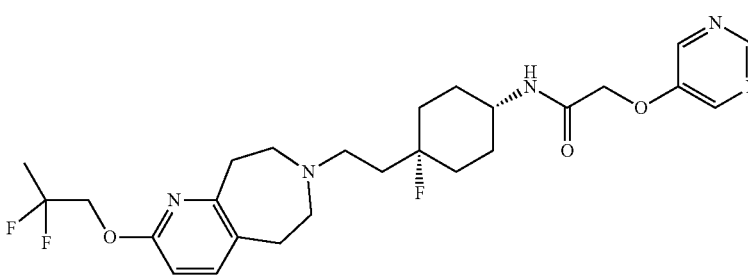 | 2 | 1.35 | 536.25 |
| I'-47 | 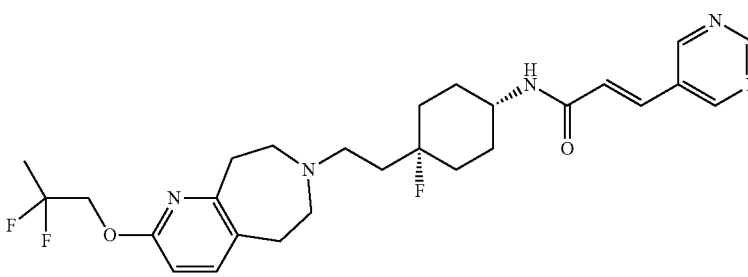 | 2 | 1.38 | 532.2 |
| I'-48 | 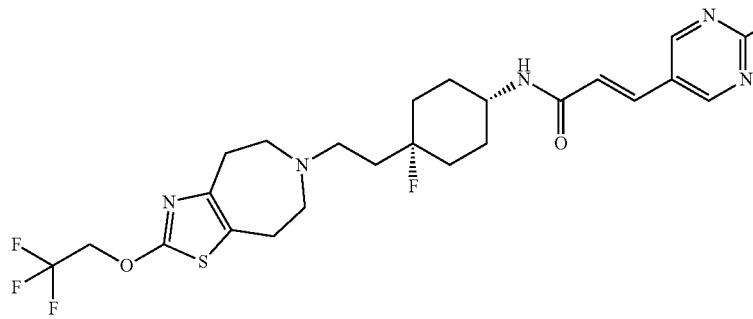 | 2 | 1.4 | 542.2 |

TABLE 35-continued
I'-49 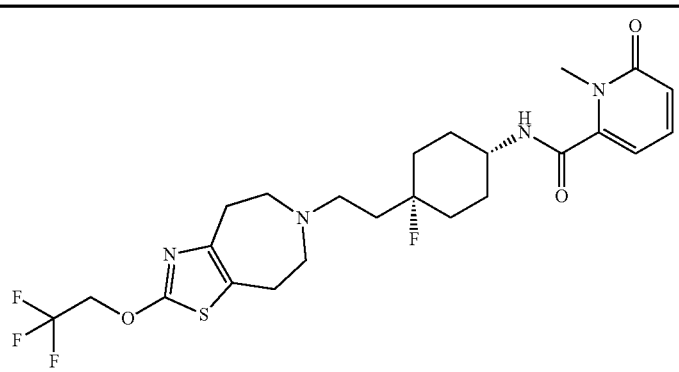 2 1.32 531.2
I'-50 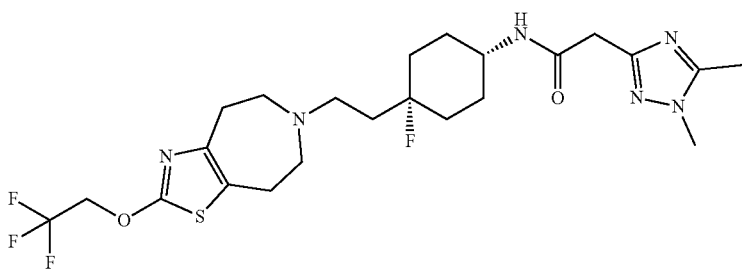 [SMILES: Cc1nc(CC(=O)N[C@H]2CC[C@](F)(CCN3CCc4nc(OCC(F)(F)F)sc4CC3)CC2)nn1C] 2 1.26 533.2
I'-51 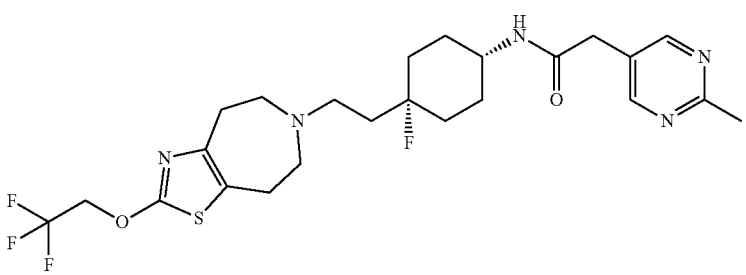 [SMILES: Cc1ncc(CC(=O)N[C@H]2CC[C@](F)(CCN3CCc4nc(OCC(F)(F)F)sc4CC3)CC2)cn1] 2 1.32 530.2
TABLE 36
I'-52 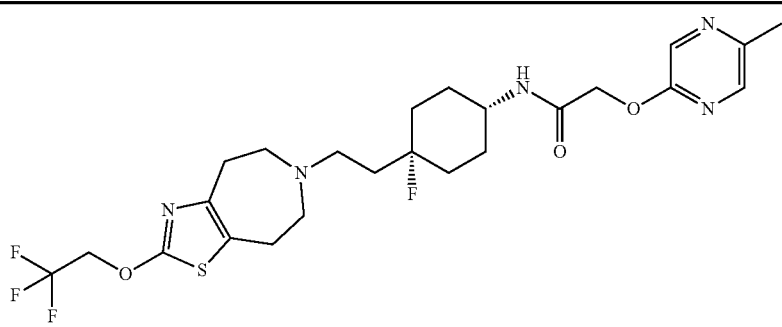 2 1.47 546.2
I'-53 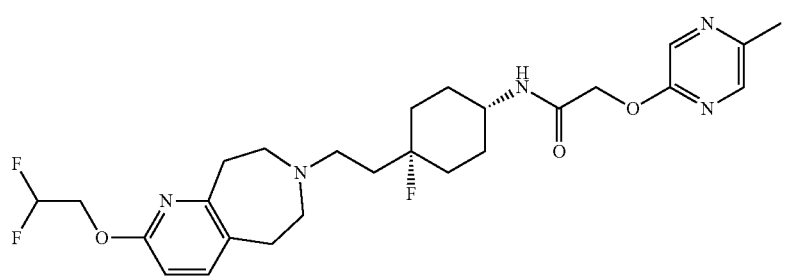 [SMILES: Cc1cnc(OCC(=O)N[C@H]2CC[C@](F)(CCN3CCc4ccc(OCC(F)F)nc4CC3)CC2)cn1] 2 1.43 522.2

TABLE 36-continued
I'-54 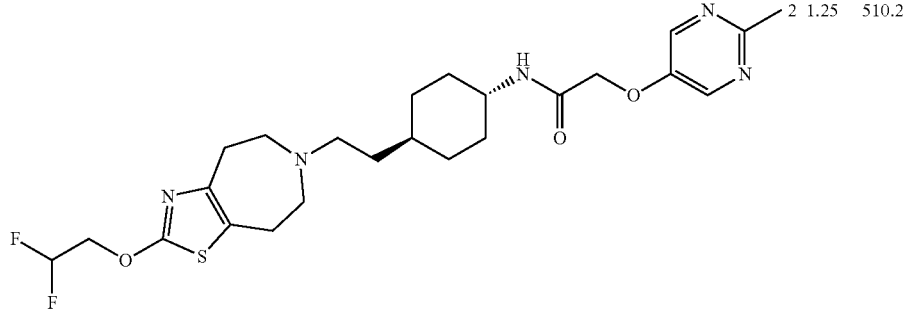 2 1.25 510.2
I'-55 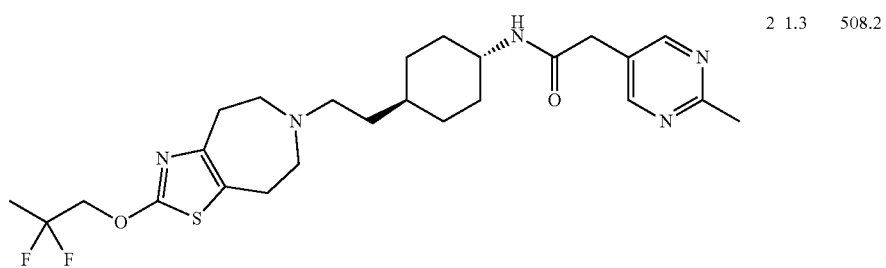 2 1.3 508.2
I'-56 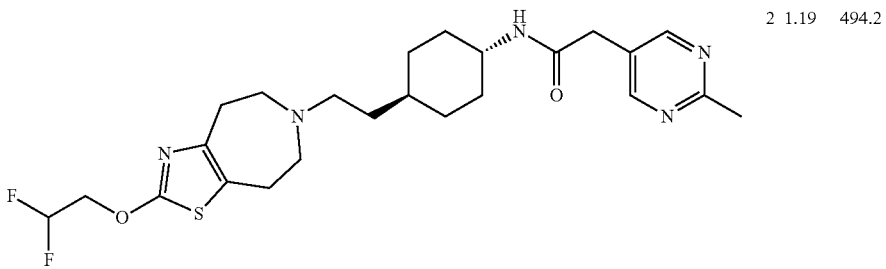 2 1.19 494.2
I'-57 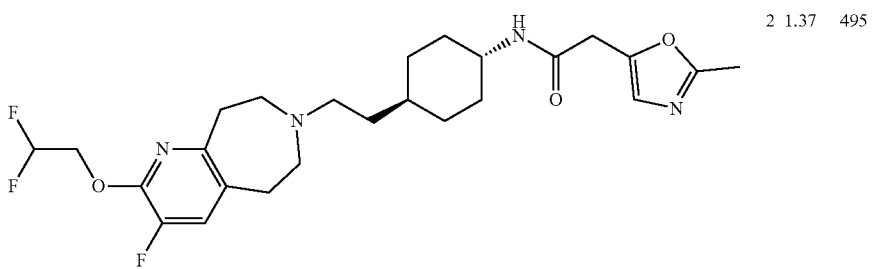 2 1.37 495

TABLE 37

| Compound No. | Structure | LC-MS method | RT (min) | MS (m/z) |
|---|---|---|---|---|
| II-1 | 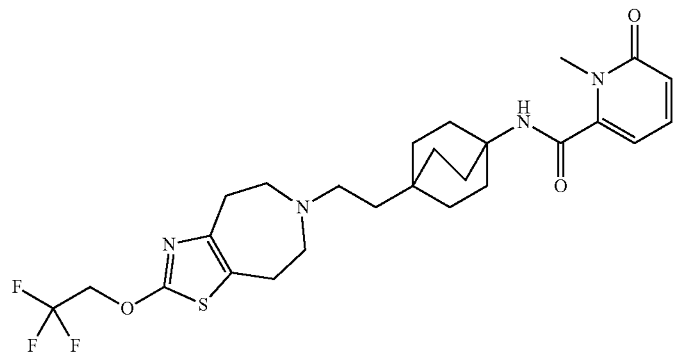 [SMILES: Cn1c(C(=O)NC23CCC(CCN4CCc5nc(OCC(F)(F)F)sc5CC4)(CC2)CC3)cccc1=O] | 2 | 1.40 | 539.2 |
| II-2 | 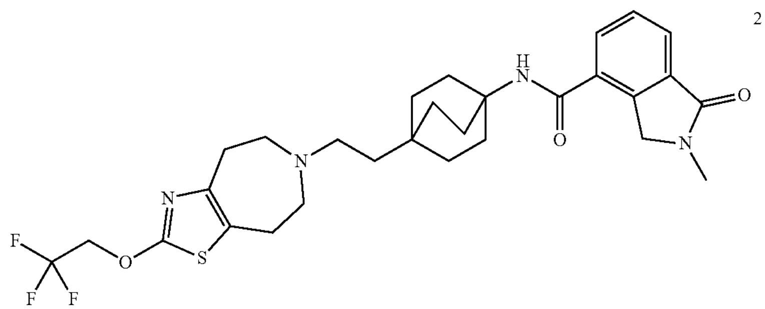 | 2 | 1.51 | 577.2 |
| II-3 | 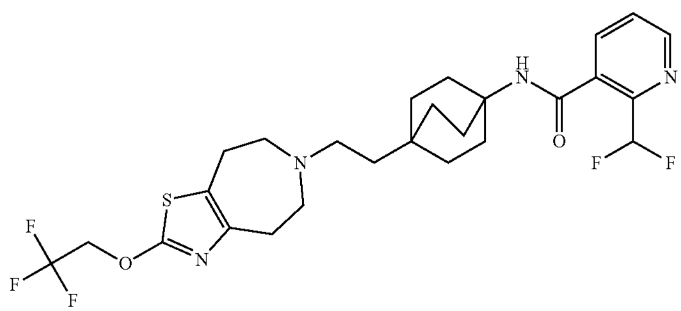 [SMILES: O=C(NC12CCC(CCN3CCc4nc(OCC(F)(F)F)sc4CC3)(CC1)CC2)c1cccnc1C(F)F] | 3 | 1.27 | 559.15 |
| II-4 | 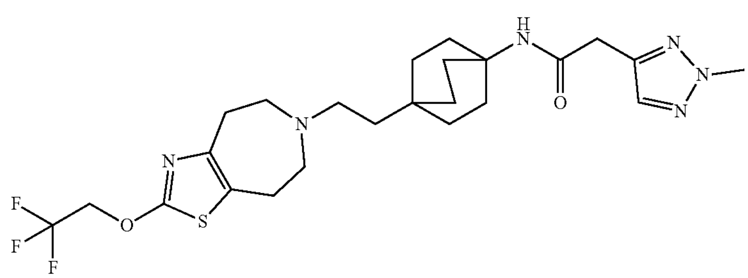 [SMILES: Cn1ncc(CC(=O)NC23CCC(CCN4CCc5nc(OCC(F)(F)F)sc5CC4)(CC2)CC3)n1] | 2 | 1.45 | 527.2 |
| II-5 | 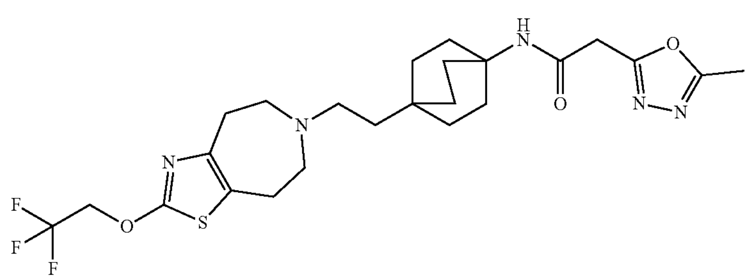 [SMILES: Cc1nnc(CC(=O)NC23CCC(CCN4CCc5nc(OCC(F)(F)F)sc5CC4)(CC2)CC3)o1] | 2 | 1.41 | 528.2 |

TABLE 38
| II-6 | 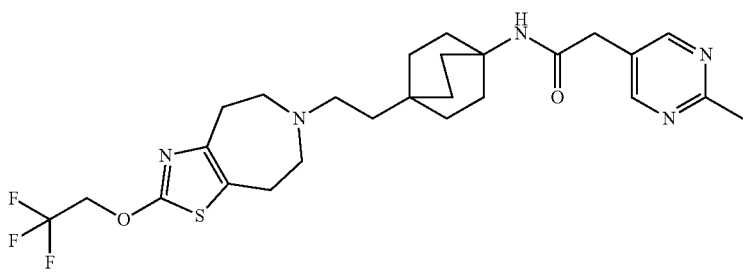 [SMILES: Cc1ncc(CC(=O)NC23CCC(CCN4CCc5nc(OCC(F)(F)F)sc5CC4)(CC2)CC3)cn1] | 2 | 1.39 | 538.2 |
| II-7 | 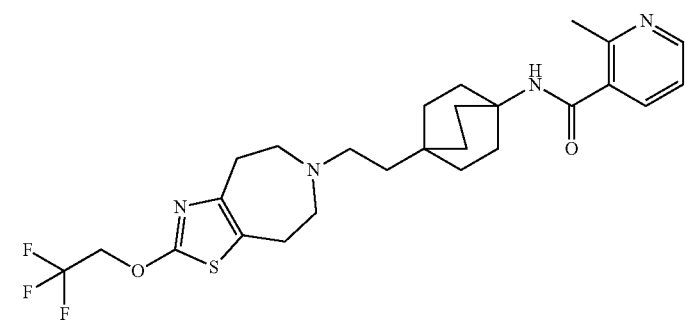 [SMILES: Cc1ncccc1C(=O)NC12CCC(CCN3CCc4nc(OCC(F)(F)F)sc4CC3)(CC1)CC2] | 2 | 1.22 | 523.3 |
| II-8 | 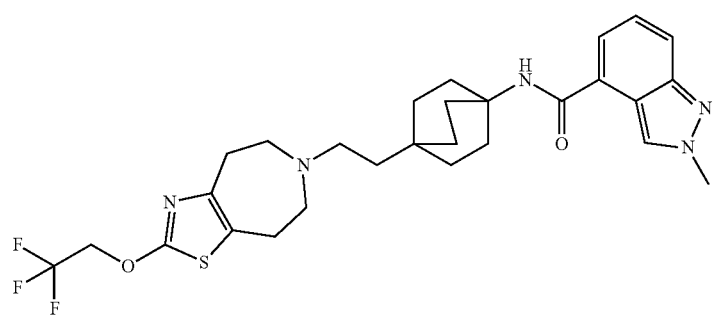 [SMILES: Cn1cc2c(C(=O)NC34CCC(CCN5CCc6nc(OCC(F)(F)F)sc6CC5)(CC3)CC4)cccc2n1] | 2 | 1.59 | 562.2 |
| II-9 | 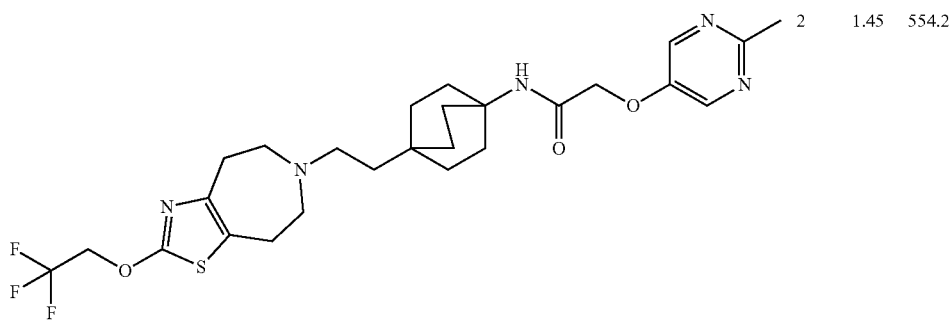 | 2 | 1.45 | 554.2 |
| II-10 | 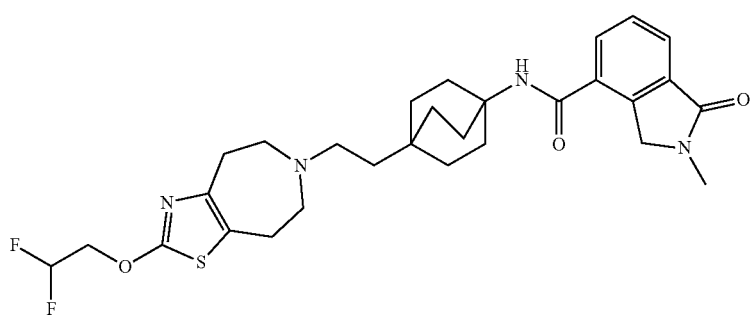 [SMILES: CN1Cc2c(C(=O)NC34CCC(CCN5CCc6nc(OCC(F)F)sc6CC5)(CC3)CC4)cccc2C1=O] | 2 | 1.40 | 559.3 |

TABLE 39
| | | | | |
|---|---|---|---|---|
| II-11 | 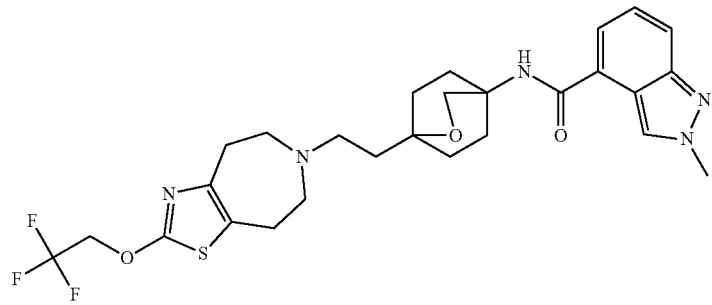 [SMILES: Cn1cc2c(C(=O)NC34CCC(CCN5CCc6nc(OCC(F)(F)F)sc6CC5)(CC3)OC4)cccc2n1] | 3 | 1.23 | 564.15 |
| II-12 | 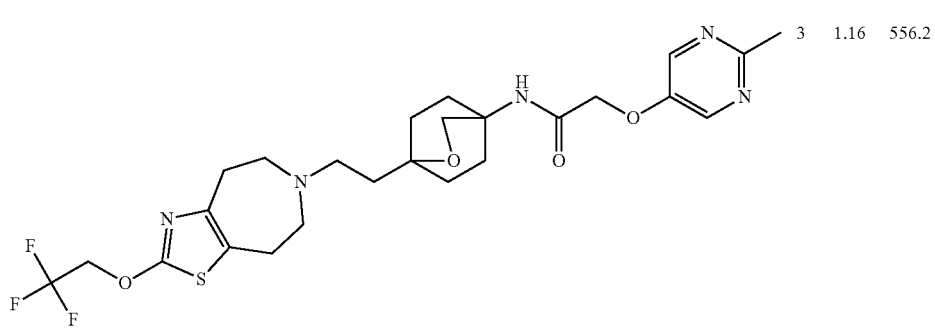 | 3 | 1.16 | 556.2 |
| II-13 | 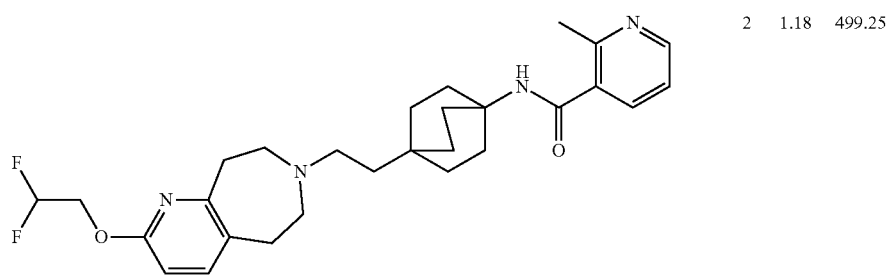 | 2 | 1.18 | 499.25 |
| II-14 | 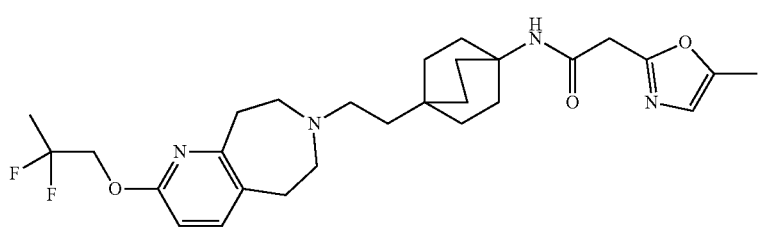 [SMILES: Cc1cnc(CC(=O)NC23CCC(CCN4CCc5ccc(OCC(C)(F)F)nc5CC4)(CC2)CC3)o1] | 2 | 1.50 | 517.30 |
| II-15 | 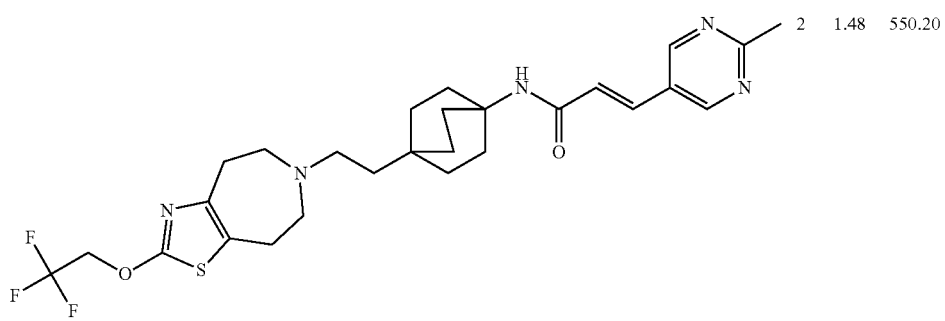 | 2 | 1.48 | 550.20 |

TABLE 40
| Compound No. | Structure | LC-MS method | RT (min) | MS (m/z) |
|---|---|---|---|---|
| III-1 | 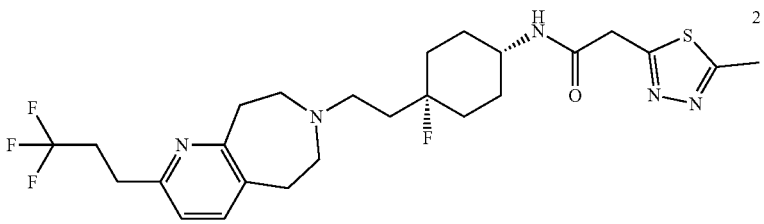 [SMILES: Cc1nnc(CC(=O)N[C@H]2CC[C@](F)(CCN3CCc4ccc(CCC(F)(F)F)nc4CC3)CC2)s1] | 2 | 1.15 | 528.2 |
| III-2 | 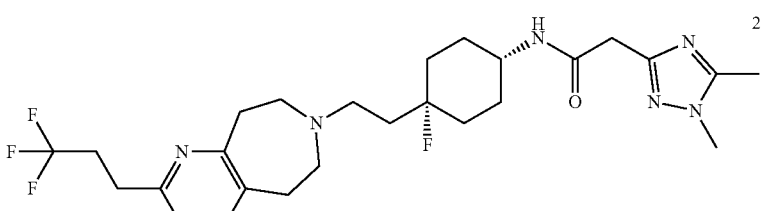 | 2 | 1.05 | 525.3 |
| III-3 | 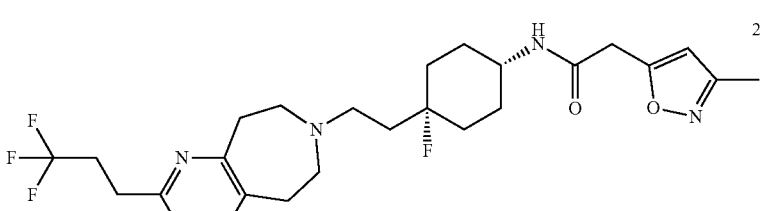 | 2 | 1.23 | 511.3 |
| III-4 | 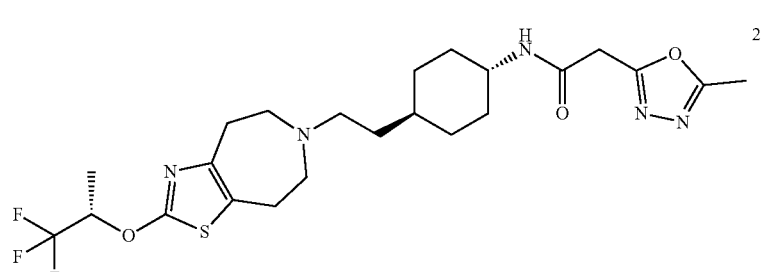 | 2 | 1.46 | 516.1 |
| III-5 | 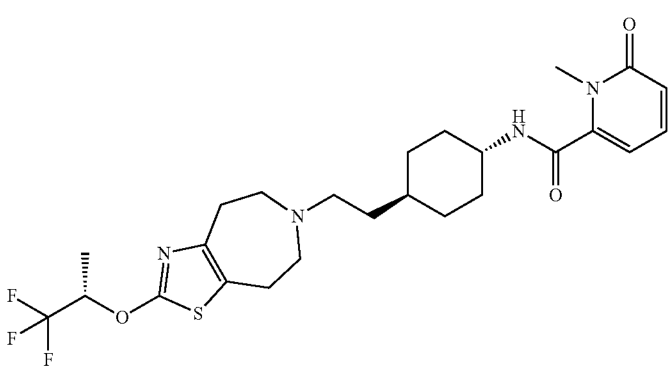 [SMILES: C[C@H](Oc1nc2c(s1)CCN(CC[C@H]1CC[C@H](NC(=O)c3cccc(=O)n3C)CC1)CC2)C(F)(F)F] | 2 | 1.47 | 527.1 |

TABLE 41
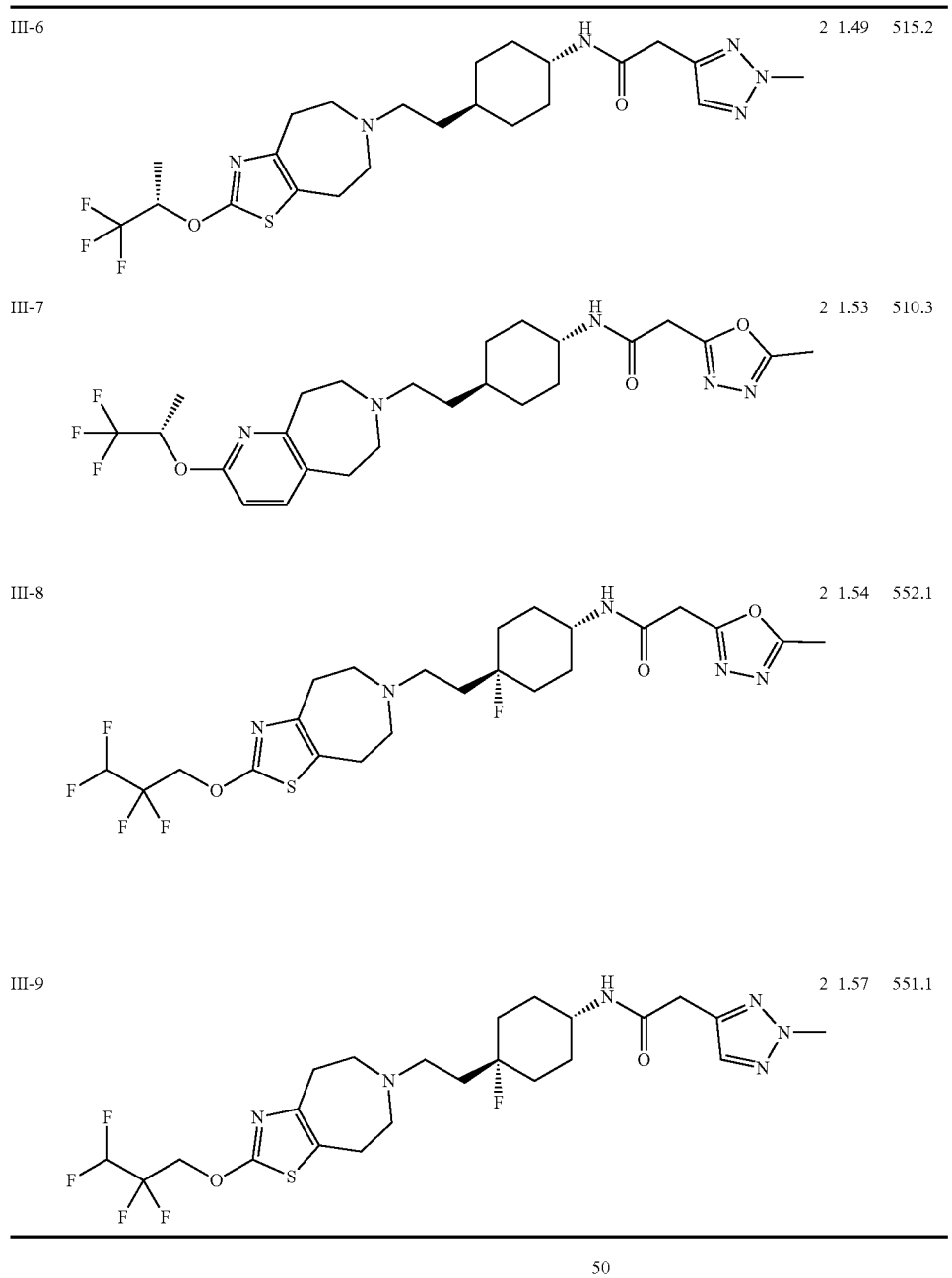
TABLE 42
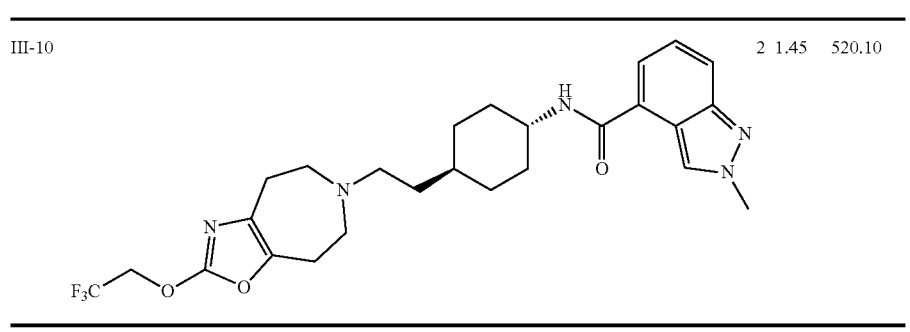

The following compounds can be synthesized in similar manners as described above.
TABLE 43
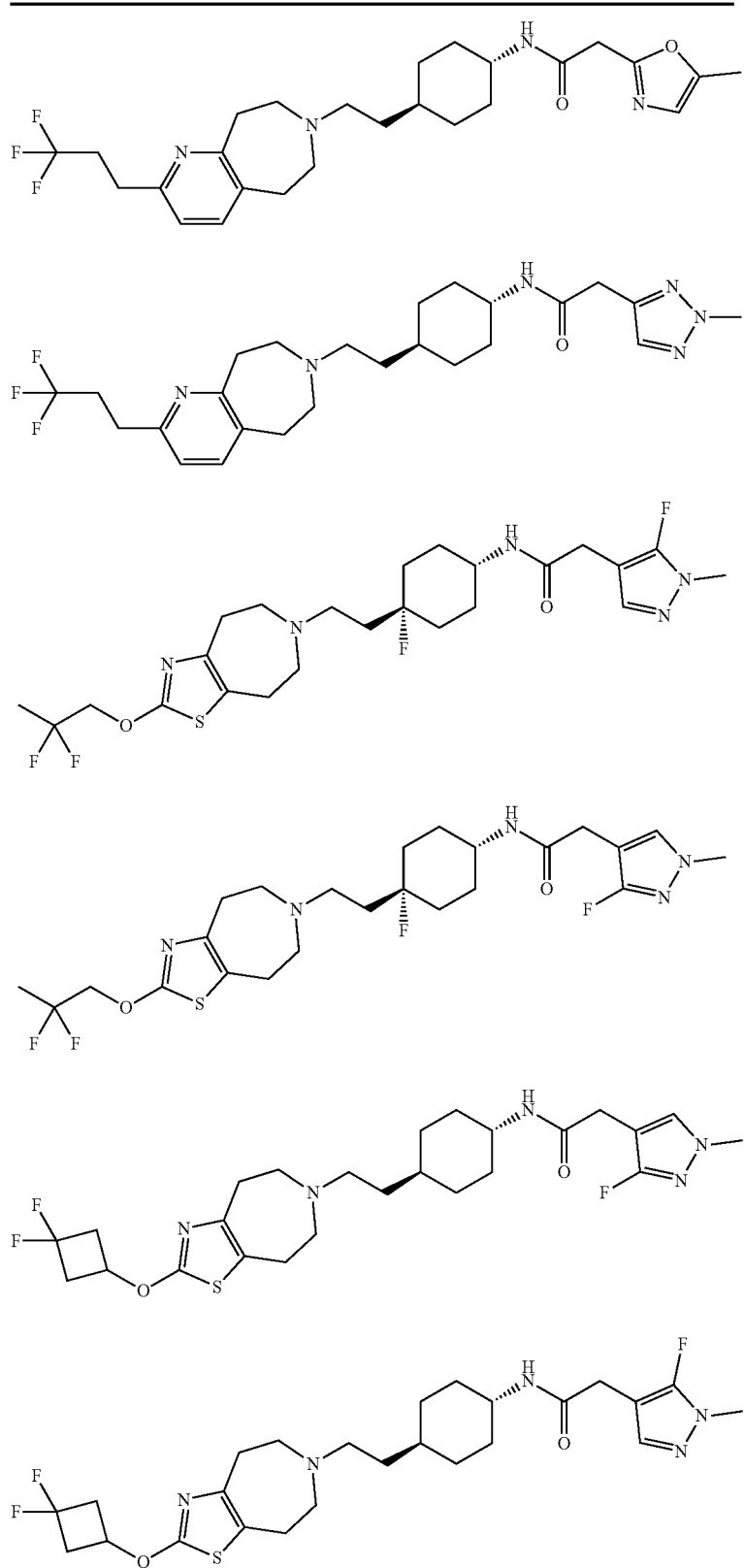

TABLE 43-continued
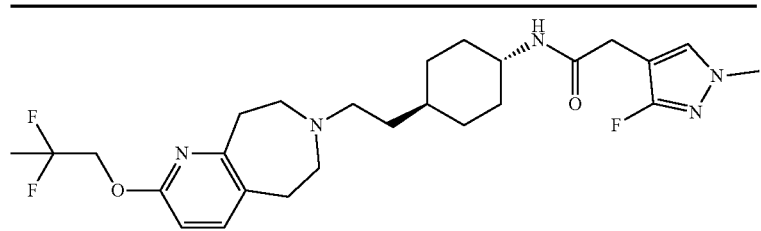
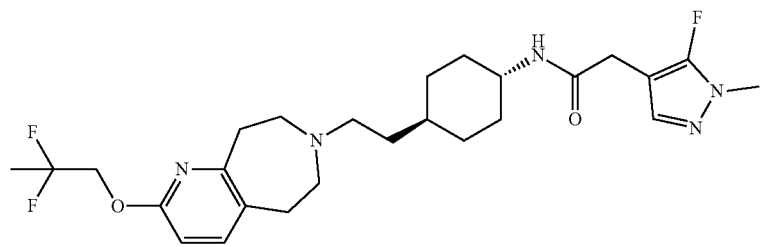 [SMILES: Cn1ncc(CC(=O)N[C@H]2CC[C@H](CCN3CCc4ccc(OCC(C)(F)F)nc4CC3)CC2)c1F]
TABLE 44
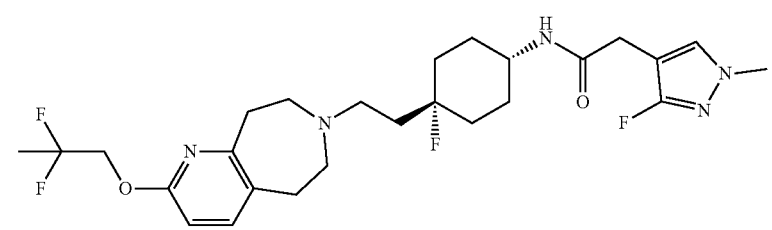 [SMILES: Cn1cc(CC(=O)N[C@H]2CC[C@](F)(CCN3CCc4ccc(OCC(C)(F)F)nc4CC3)CC2)c(F)n1]
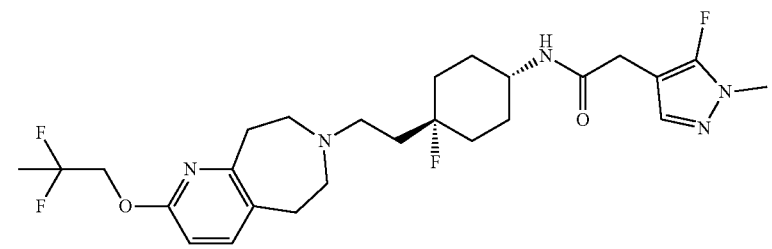
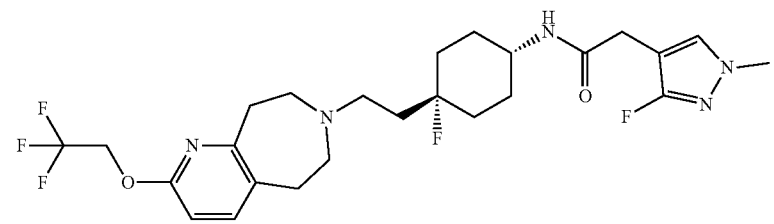 [SMILES: Cn1cc(CC(=O)N[C@H]2CC[C@](F)(CCN3CCc4ccc(OCC(F)(F)F)nc4CC3)CC2)c(F)n1]
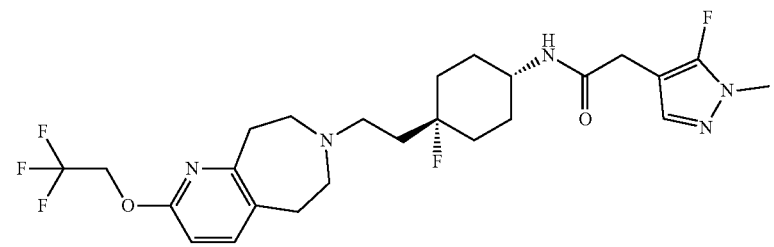 [SMILES: Cn1ncc(CC(=O)N[C@H]2CC[C@](F)(CCN3CCc4ccc(OCC(F)(F)F)nc4CC3)CC2)c1F]

TABLE 44-continued
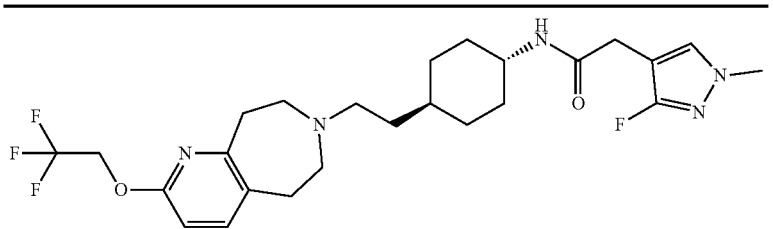
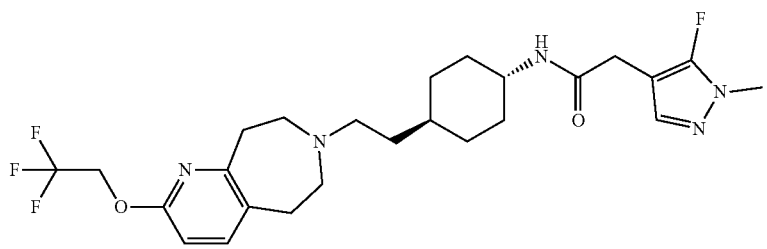
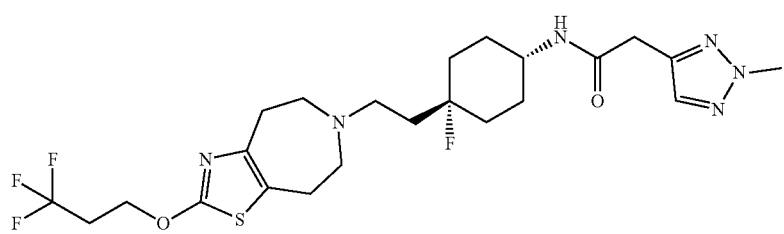 [SMILES: Cn1ncc(CC(=O)N[C@H]2CC[C@](F)(CCN3CCc4nc(OCCC(F)(F)F)sc4CC3)CC2)n1]
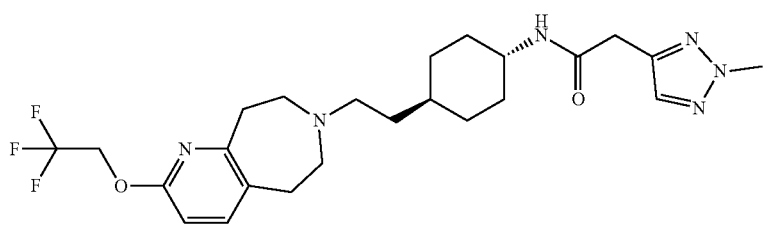 [SMILES: Cn1ncc(CC(=O)N[C@H]2CC[C@H](CCN3CCc4ccc(OCC(F)(F)F)nc4CC3)CC2)n1]
40
TABLE 45
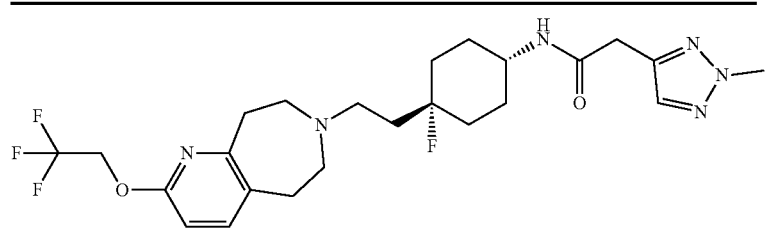
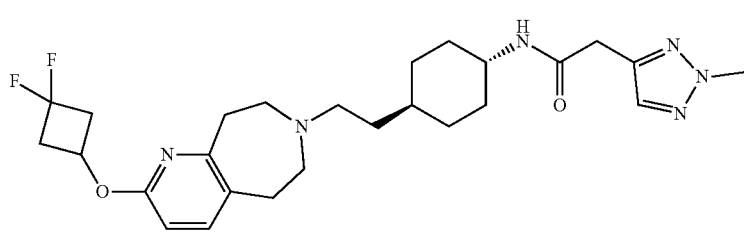 [SMILES: Cn1ncc(CC(=O)N[C@H]2CC[C@H](CCN3CCc4ccc(OC5CC(F)(F)C5)nc4CC3)CC2)n1]

TABLE 45-continued
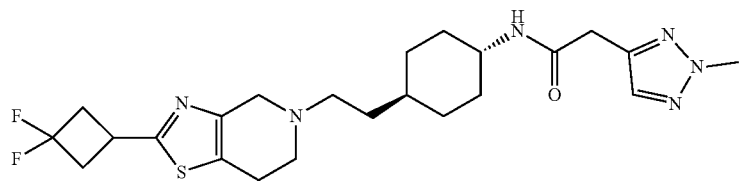 [SMILES: Cn1ncc(CC(=O)N[C@H]2CC[C@H](CCN3CCc4sc(C5CC(F)(F)C5)nc4C3)CC2)n1]
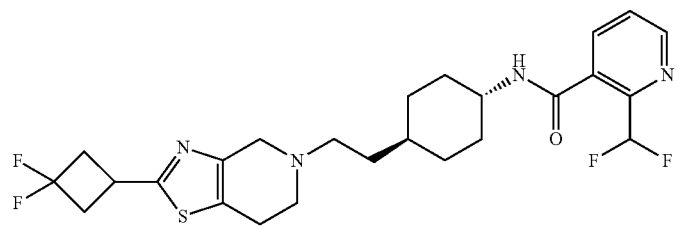 [SMILES: O=C(N[C@H]1CC[C@H](CCN2CCc3sc(C4CC(F)(F)C4)nc3C2)CC1)c1cccnc1C(F)F]
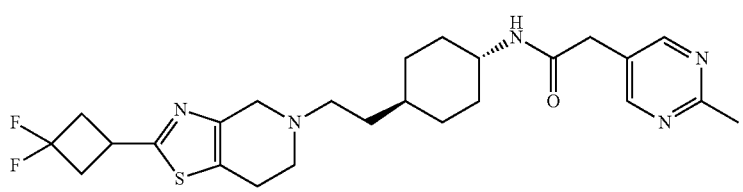 [SMILES: Cc1ncc(CC(=O)N[C@H]2CC[C@H](CCN3CCc4sc(C5CC(F)(F)C5)nc4C3)CC2)cn1]
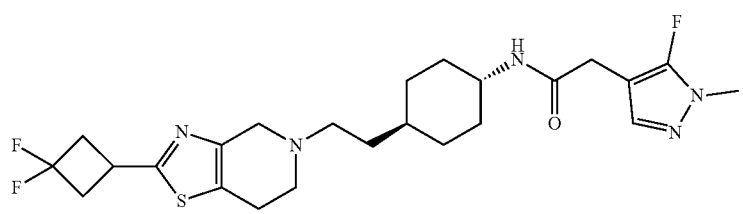 [SMILES: Cn1ncc(CC(=O)N[C@H]2CC[C@H](CCN3CCc4sc(C5CC(F)(F)C5)nc4C3)CC2)c1F]
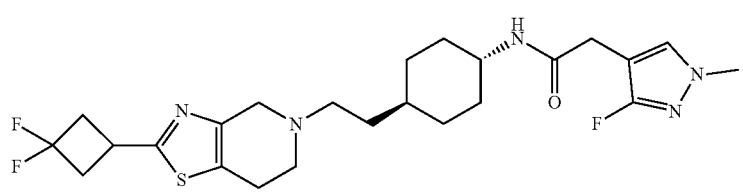 [SMILES: Cn1cc(CC(=O)N[C@H]2CC[C@H](CCN3CCc4sc(C5CC(F)(F)C5)nc4C3)CC2)c(F)n1]
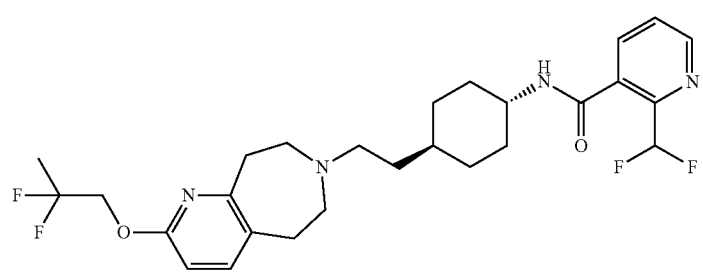 [SMILES: CC(F)(F)COc1ccc2c(n1)CCN(CC[C@H]1CC[C@H](NC(=O)c3cccnc3C(F)F)CC1)CC2]

TABLE 46
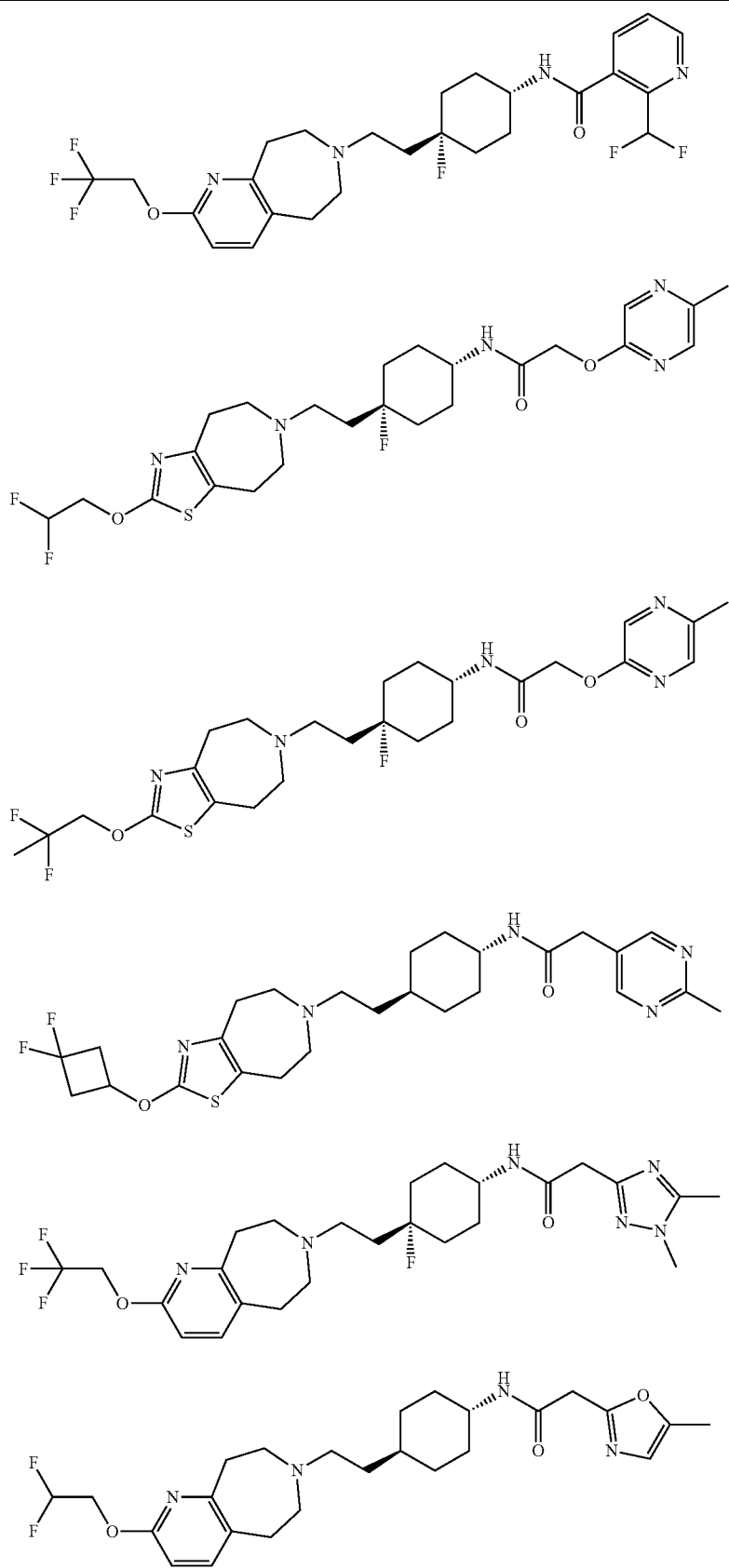

TABLE 46-continued

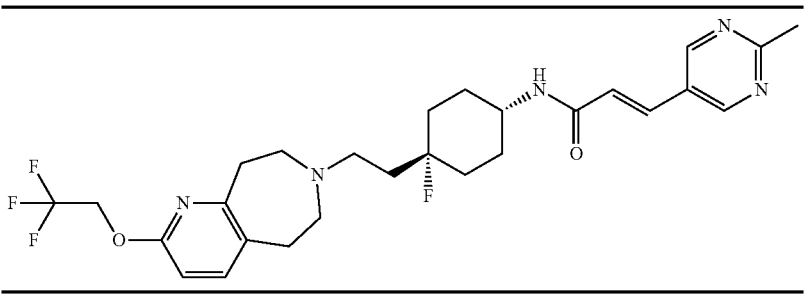

Test examples for the compounds of the present invention are described below.

Test Example 1: Test of Binding Inhibition for Dopamine D3 Receptor (Experimental Conditions)
Cell membranes: Jump-In HEK cell membranes expressing human recombinant dopamine D3 receptor (4 μg/well)
Buffer solution: 50 mM Tris-HCl (35409-45, Nacalai Tesque) (pH 7.4) containing 120 mM NaCl (31320-05, Nacalai Tesque), 1 mM $MgCl_2.6H_2O$ (20909-55, Nacalai Tesque), 5 mM KCl (28514-75, Nacalai Tesque) and 2 mM $CaCl_2$) (067-31, NAKARAI CHEMICALS, LTD.)
Radioligand: (final concentration) 2 nM [$^3$H]-Methylspiperone ([$^3$H—N-methyl-]-Methylspiperone, NET-856, 83.8 Ci/mmol, PerkinElmer)
Non-specific ligand: (final concentration) 10 μM Butaclamol [(+)-Butaclamol Hydrochloride, D033, Sigma]
SPA beads solution: SPA beads [WGA PVT SPA Scintillation Beads, RPNQ0001 (500 mg), RPNQ0060 (2 g), PerkinElmer] (0.2 mg/well)
Incubation time and temperature: 120 min at 25° C.
Kd: 0.321 nM
(Preparation of Solutions of Non-Specific Ligand or the Compounds of the Present Invention)
Butaclamol or the compounds of the present invention were weighed and DMSO was added to make a 10 mM solution. This solution was diluted to each concentration.
(Preparation of Radioligand Solution)
[$^3$H]-Methylspiperone was weighed and the buffer solution was added to make a 6 nM solution.
(Preparation of SPA Beads Solution)
SPA beads were weighed and stirred in water to make a 50 mg/mL solution. Using this solution, a mixture with the cell membranes was prepared.
(Binding Assay of the Compounds of the Present Invention)
225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 4 μg protein/well), the SPA beads solution (final reaction amount: 0.2 mg/well) and the buffer solution were mixed and the mixed solution was left still for 1 hour or more at 4° C. Then, 50 μL of the mixture was added to each well of the plate. In addition, 25 μL of 6 nM [$^3$H]-Methylspiperone (final concentration: 2 nM) was added to each well. The plate was sealed by putting TopSeal-A 96/384 well (6050185, PerkinElmer) on the top of the plate, mixed using stirring deaerator (Well Tornado, FK-62, Sakaki-elc.) and incubated for 120 min at 25° C. After incubation, the radioactivity of [H]-Methylspiperone which was bounded to D3 receptor was determined by liquid scintillation counter (1450 Microbeta, PerkinElmer) in each well. Non-specific binding was calculated based on the radioactivity of [$^3$H]-Methylspiperone in the presence of 10 μM non-labeled Butaclamol. The total binding was calculated using the radioactivity of [H]-Methylspiperone in the absence of the compounds of the present invention (vehicle). The Ki values were calculated from dose-response curves.

Binding activities of the compounds of the present invention were calculated from the following Binding Inhibition Rate (%):

Inhibition Rate (%)=[1−(c−a)/(b−a)]×100 a: Average cpm of non-specific binding
b: Average cpm of total binding
c: Cpm in the presence of each test compound The test results of the compounds of the present invention are shown in the following table.

TABLE 47

| Compound No. | hD3_Ki (nM) |
| --- | --- |
| I-001 | 0.2 |
| I-002 | 0.47 |
| I-003 | 0.15 |
| I-004 | 0.15 |
| I-005 | 0.63 |
| I-006 | 0.59 |
| I-007 | 0.68 |
| I-008 | 0.96 |
| I-009 | 0.12 |
| I-010 | 0.13 |
| I-011 | 0.32 |
| I-012 | 0.15 |
| I-013 | 0.53 |
| I-014 | 0.48 |
| I-015 | 0.26 |
| I-016 | 0.039 |
| I-017 | 0.063 |
| I-018 | 0.035 |
| I-019 | 0.37 |
| I-020 | 0.27 |
| I-021 | 0.15 |
| I-022 | 0.1 |
| I-023 | 0.11 |
| I-024 | 0.2 |
| I-025 | 0.46 |
| I-026 | 0.095 |
| I-027 | 0.23 |
| I-028 | 0.41 |
| I-029 | 0.36 |
| I-030 | 0.3 |
| I-031 | 0.19 |
| I-032 | 0.48 |
| I-033 | 0.78 |
| I-034 | 0.36 |
| I-035 | 0.18 |
| I-036 | 0.54 |

TABLE 47-continued

| Compound No. | hD3_Ki (nM) |
| --- | --- |
| I-037 | 0.097 |
| I-038 | 0.81 |
| I-039 | 1 |
| I-040 | 0.46 |
| I-041 | 0.17 |
| I-042 | 0.57 |
| I-043 | 0.12 |
| I-044 | 0.14 |
| I-045 | 0.81 |
| I-046 | 0.34 |
| I-047 | 0.058 |
| I-048 | 0.048 |
| I-049 | 0.33 |
| I-050 | 0.16 |
| I-051 | 0.43 |
| I-052 | 0.083 |
| I-053 | 0.2 |
| I-054 | 0.13 |
| I-055 | 0.19 |
| I-056 | 0.24 |
| I-057 | 0.18 |
| I-058 | 0.47 |
| I-059 | 0.69 |
| I-060 | 0.59 |
| I-061 | 0.65 |
| I-062 | 1 |
| I-063 | 0.62 |
| I-064 | 0.3 |
| I-065 | 0.26 |
| I-066 | 0.37 |
| I-067 | 0.16 |
| I-068 | 0.47 |
| I-069 | 0.49 |
| I-070 | 0.17 |
| I-071 | 0.16 |
| I-072 | 0.13 |
| I-073 | 0.29 |
| I-074 | 0.025 |
| I-075 | 0.22 |
| I-076 | 0.1 |
| I-077 | 0.38 |
| I-078 | 0.13 |
| I-079 | 0.07 |
| I-080 | 0.81 |
| I-081 | 0.2 |
| I-082 | 0.086 |
| I-083 | 0.16 |
| I-084 | 0.25 |
| I-085 | 0.044 |
| I-086 | 0.52 |
| I-087 | 0.89 |
| I-088 | 0.8 |
| I-089 | 0.22 |
| I-090 | 0.65 |
| I-091 | 0.28 |
| I-092 | 0.16 |
| I-093 | 0.17 |
| I-094 | 0.3 |
| I-095 | 0.18 |
| I-096 | 0.18 |
| I-097 | 0.11 |
| I-098 | 0.17 |
| I-099 | 0.97 |
| I-100 | 0.72 |
| I-101 | 0.3 |
| I-102 | 0.13 |
| I-103 | 0.17 |
| I-104 | 0.68 |
| I-105 | 0.96 |
| I-106 | 0.54 |
| I-107 | 0.54 |
| I-108 | 0.89 |
| I-109 | 0.26 |
| I-110 | 0.17 |
| I-111 | 0.17 |
| I-112 | 0.12 |
| I-113 | 0.87 |
| I-114 | 0.59 |

TABLE 47-continued

| Compound No. | hD3_Ki (nM) |
| --- | --- |
| I-115 | 0.63 |
| I-116 | 1 |
| I-117 | 0.55 |
| I-118 | 0.74 |
| I-119 | 0.11 |
| I-120 | 0.84 |
| I-121 | 0.26 |
| I-122 | 0.24 |
| I-123 | 0.034 |
| I-124 | 0.072 |
| I-125 | 0.61 |
| I-126 | 0.92 |
| I-127 | 0.12 |
| I-128 | 0.073 |
| I-129 | 0.085 |
| I-130 | 0.49 |
| I-131 | 0.35 |
| I-132 | 0.12 |
| I-133 | 0.15 |
| I-134 | 0.17 |
| I-186 | 0.22 |

TABLE 48

| Compound No. | hD3_Ki (nM) |
| --- | --- |
| I'-1 | 0.43 |
| I'-2 | 0.21 |
| I'-3 | 0.18 |
| I'-4 | 0.22 |
| I'-5 | 0.22 |
| I'-6 | 0.33 |
| I'-7 | 0.12 |
| I'-8 | 0.071 |
| I'-9 | 0.11 |
| I'-10 | 0.23 |
| I'-11 | 0.18 |
| I'-12 | 0.29 |
| I'-13 | 0.43 |
| I'-14 | 0.21 |
| I'-15 | 1.4 |
| I'-16 | 0.36 |
| I'-17 | 0.15 |
| I'-18 | 0.38 |
| I'-19 | 0.36 |
| I'-20 | 0.38 |
| I'-21 | 1 |
| I'-22 | 0.1 |
| I'-23 | 0.28 |
| I'-24 | 0.17 |
| I'-25 | 0.29 |
| I'-26 | 0.17 |
| I'-27 | 0.09 |
| I'-28 | 0.21 |
| I'-29 | 3.1 |
| I'-30 | 0.19 |
| I'-31 | 0.57 |
| I'-32 | 0.16 |
| I'-33 | 0.85 |
| I'-34 | 0.15 |
| I'-35 | 0.41 |
| I'-36 | 0.071 |
| I'-37 | 0.18 |
| I'-38 | 0.043 |
| I'-39 | 0.49 |
| I'-40 | 0.19 |
| I'-41 | 0.49 |
| I'-42 | 0.016 |
| I'-43 | 0.078 |
| I'-44 | 0.11 |
| I'-45 | 0.11 |
| I'-46 | 0.33 |
| I'-47 | 0.081 |
| I'-48 | 0.27 |
| I'-49 | 0.59 |

TABLE 48-continued

| Compound No. | hD3_Ki (nM) |
|---|---|
| I'-50 | 0.23 |
| I'-51 | 0.48 |
| I'-52 | 0.17 |
| I'-53 | 0.32 |
| I'-54 | 0.32 |
| I'-55 | 0.16 |
| I'-56 | 0.3 |
| I'-57 | 0.52 |
| II-1 | 0.17 |
| II-2 | 0.079 |
| II-3 | 0.29 |
| II-4 | 0.16 |
| II-5 | 0.2 |
| II-6 | 0.35 |
| II-7 | 0.39 |
| II-8 | 0.084 |
| II-9 | 0.12 |
| II-10 | 0.5 |
| II-11 | 0.23 |
| II-12 | 0.49 |
| II-13 | 0.56 |
| II-14 | 0.23 |
| II-15 | 0.16 |

TABLE 49

| Compound No. | hD3_Ki (nM) |
|---|---|
| I-141 | 0.41 |
| I-144 | 0.32 |
| I-149 | 0.14 |
| I-151 | 0.16 |
| I-157 | 0.029 |
| I-159 | 0.36 |
| I-160 | 0.83 |
| I-161 | 0.32 |
| I-162 | 0.56 |
| I-163 | 0.31 |
| I-168 | 0.31 |
| I-174 | 0.33 |
| I-180 | 0.85 |
| III-1 | 0.14 |
| III-2 | 0.16 |
| III-3 | 0.029 |
| III-4 | 0.16 |
| III-5 | 0.23 |
| III-6 | 0.15 |
| III-7 | 0.09 |
| III-8 | 0.16 |
| III-9 | 0.081 |

Test Example 2: Test of Binding Inhibition for Dopamine D2 Receptor (Experimental Conditions)
Cell membranes: Jump-In HEK cell membranes expressing human recombinant dopamine D2 receptor (2 μg/well)
Buffer solution: 50 mM Tris-HCl (35409-45, Nacalai Tesque) (pH 7.4) containing 120 mM NaCl (31320-05, Nacalai Tesque), 1 mM $MgCl_2.6H_2O$ (20909-55, Nacalai Tesque), 5 mM KCl (28514-75, Nacalai Tesque) and 2 mM $CaCl_2$) (067-31, NAKARAI CHEMICALS, LTD.)
Radioligand: (final concentration) 1.2 nM [$^3$H]-Methylspiperone ([$^3$H—N-methyl-]-Methylspiperone, NET-856, 83.8 Ci/mmol, PerkinElmer)
Non-specific ligand: (final concentration) 10 μM Butaclamol [(+)-Butaclamol Hydrochloride, D033, Sigma]
SPA beads solution: SPA beads [WGA PVT SPA Scintillation Beads, RPNQ0001 (500 mg), RPNQ0060 (2 g), PerkinElmer] (0.2 mg/well)
Incubation time and temperature: 120 min at 25° C.
Kd: 0.272 nM
(Preparation of Solutions of Non-Specific Ligand or the Compounds of the Present Invention)
Butaclamol or the compounds of the present invention were weighed and DMSO was added to make a 10 mM solution. This solution was diluted to each concentration.
(Preparation of Radioligand Solution)
[$^3$H]-Methylspiperone was weighed and the buffer solution was added to make a 3.6 nM solution.
(Preparation of SPA Beads Solution)
SPA beads were weighed and stirred in water to make a 50 mg/mL solution. Using this solution, a mixture with the cell membranes was prepared.
(Binding Assay of the Compounds of the Present Invention)
225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 2 μg protein/well), the SPA beads solution (final reaction amount: 0.2 mg/well) and the buffer solution were mixed, and the mixed solution was left still for 1 hour or more at 4° C. Then, 50 μL of the mixture was added to each well of the plate. In addition, 25 μL of 3.6 nM [3H]-Methylspiperone (final concentration: 1.2 nM) was added to each well. The plate was sealed by putting TopSeal-A 96/384 well (6050185, PerkinElmer) on the top of the plate, mixed using stirring deaerator (Well Tornado, FK-62, Sakaki-elc.) and incubated for 120 min at 25° C. After incubation, the radioactivity of [$^3$H]-Methylspiperone which was bounded to D2 receptor was determined by liquid scintillation counter (1450 Microbeta, PerkinElmer) in each well. Non-specific binding was calculated based on the radioactivity of [$^3$H]-Methylspiperone in the presence of 10 μM non-labeled Butaclamol. The total binding was calculated using the radioactivity of [$^3$H]-Methylspiperone in the absence of the compounds of the present invention (Vehicle). The Ki values were calculated from dose-response curves.
Binding activities of the compounds of the present invention were calculated from the following Binding Inhibition Rate (%):

Inhibition Rate (%)=[1−(c−a)/(b−a)]×100 a: Average cpm of non-specific binding
b: Average cpm of total binding
c: Cpm in the presence of each test compound
The test results of the compounds of the present invention are shown in the following table.

TABLE 50

| Compound No. | hD2_Ki (nM) |
|---|---|
| I-001 | 290 |
| I-002 | 550 |
| I-003 | 780 |
| I-004 | 700 |
| I-005 | 720 |
| I-006 | >1900 |
| I-007 | 1500 |
| I-008 | >1900 |
| I-009 | 690 |
| I-010 | 930 |
| I-011 | 950 |
| I-012 | 260 |
| I-013 | 920 |

TABLE 50-continued

| Compound No. | hD2_Ki (nM) |
|---|---|
| I-014 | 980 |
| I-015 | 1000 |
| I-016 | 850 |
| I-017 | 240 |
| I-018 | 190 |
| I-019 | >1800 |
| I-020 | >1800 |
| I-021 | 1900 |
| I-022 | >2300 |
| I-023 | >2200 |
| I-024 | >2200 |
| I-025 | 820 |
| I-026 | 1100 |
| I-027 | 1000 |
| I-028 | 640 |
| I-029 | 610 |
| I-030 | 610 |
| I-031 | 800 |
| I-032 | >2200 |
| I-033 | >2200 |
| I-034 | 560 |
| I-035 | 210 |
| I-036 | 910 |
| I-037 | 240 |
| I-038 | >1700 |
| I-039 | 1200 |
| I-040 | 890 |
| I-041 | 620 |
| I-042 | 1000 |
| I-043 | 970 |
| I-044 | 610 |
| I-045 | 1700 |
| I-046 | 500 |
| I-047 | 110 |
| I-048 | 390 |
| I-049 | 310 |
| I-050 | >1800 |
| I-051 | 1100 |
| I-052 | 1700 |
| I-053 | 630 |
| I-054 | 270 |
| I-055 | >1800 |
| I-056 | 490 |
| I-057 | 770 |
| I-058 | >1700 |
| I-059 | >1700 |
| I-060 | 1400 |
| I-061 | >1800 |
| I-062 | 1100 |
| I-063 | 1700 |
| I-064 | 950 |
| I-065 | 340 |
| I-066 | 770 |
| I-067 | 370 |
| I-068 | 870 |
| I-069 | 670 |
| I-070 | 780 |
| I-071 | 450 |
| I-072 | >1700 |
| I-073 | 450 |
| I-074 | 63 |
| I-075 | 240 |
| I-076 | >1900 |
| I-077 | >1800 |
| I-078 | >1800 |
| I-079 | >1800 |
| I-080 | 2100 |
| I-081 | 640 |
| I-082 | 670 |
| I-083 | >2200 |
| I-084 | >2200 |
| I-085 | >2200 |
| I-086 | >2200 |
| I-087 | >2200 |
| I-088 | 1300 |
| I-089 | >2200 |
| I-090 | >2400 |
| I-091 | 940 |
| I-092 | 310 |
| I-093 | 1200 |
| I-094 | 910 |
| I-095 | 1400 |
| I-096 | 570 |
| I-097 | 900 |
| I-098 | 350 |
| I-099 | 1600 |
| I-100 | 1500 |
| I-101 | 2200 |
| I-102 | 670 |
| I-103 | 340 |
| I-104 | >2300 |
| I-105 | >2300 |
| I-106 | >2300 |
| I-107 | 1000 |
| I-108 | 1200 |
| I-109 | 610 |
| I-110 | 460 |
| I-111 | 1600 |
| I-112 | >2200 |
| I-113 | >2200 |
| I-114 | >2200 |
| I-115 | >2200 |
| I-116 | >2200 |
| I-117 | >2200 |
| I-118 | >2200 |
| I-119 | 1200 |
| I-120 | 840 |
| I-121 | 650 |
| I-122 | 360 |
| I-123 | 200 |
| I-124 | 180 |
| I-125 | 1100 |
| I-126 | >2300 |
| I-127 | 410 |
| I-128 | 510 |
| I-129 | 290 |
| I-130 | 1200 |
| I-131 | 410 |
| I-132 | 300 |
| I-133 | 190 |
| I-134 | 300 |
| I-186 | 270 |

TABLE 51

| Compound No. | hD2_Ki (nM) |
|---|---|
| I'-1 | 920 |
| I'-2 | >2300 |
| I'-3 | 1100 |
| I'-4 | 1200 |
| I'-5 | 610 |
| I'-6 | 540 |
| I'-7 | 1100 |
| I'-8 | >2300 |
| I'-9 | 530 |
| I'-10 | 1100 |
| I'-11 | 1200 |
| I'-12 | 820 |
| I'-13 | 910 |
| I'-14 | >2300 |
| I'-15 | 1700 |
| I'-16 | 1800 |
| I'-17 | >2300 |
| I'-18 | 1000 |
| I'-19 | 1100 |
| I'-20 | 260 |
| I'-21 | >2300 |
| I'-22 | 2000 |
| I'-23 | >2200 |
| I'-24 | 630 |
| I'-25 | 730 |
| I'-26 | 870 |

TABLE 51-continued

| Compound No. | hD2_Ki (nM) |
|---|---|
| I'-27 | >2200 |
| I'-28 | 1500 |
| I'-29 | >2200 |
| I'-30 | 1600 |
| I'-31 | 1300 |
| I'-32 | 1200 |
| I'-33 | 1600 |
| I'-34 | 1600 |
| I'-35 | 1800 |
| I'-36 | 740 |
| I'-37 | 1600 |
| I'-38 | 1000 |
| I'-39 | 960 |
| I'-40 | 1900 |
| I'-41 | 1900 |
| I'-42 | 500 |
| I'-43 | 350 |
| I'-44 | 2000 |
| I'-45 | 210 |
| I'-46 | 260 |
| I'-47 | 41 |
| I'-48 | >2200 |
| I'-49 | 290 |
| I'-50 | 1600 |
| I'-51 | 890 |
| I'-52 | >2200 |
| I'-53 | >2200 |
| I'-54 | 1600 |
| I'-55 | 950 |
| I'-56 | 1400 |
| I'-57 | >2200 |
| II-1 | 830 |
| II-2 | >2200 |
| II-3 | 1400 |
| II-4 | 1400 |
| II-5 | 1300 |
| II-6 | 1200 |
| II-7 | 1700 |
| II-8 | 1600 |
| II-9 | 960 |
| II-10 | >2300 |
| II-11 | >2300 |
| II-12 | 1500 |
| II-13 | 2100 |
| II-14 | 760 |
| II-15 | 240 |

TABLE 52

| Compound No. | hD2_Ki (nM) |
|---|---|
| I-141 | >2300 |
| I-144 | 1500 |
| I-149 | >2300 |
| I-151 | 1200 |
| I-157 | >2300 |
| I-159 | 580 |
| I-160 | 1100 |
| I-161 | 940 |
| I-162 | 740 |
| I-163 | 430 |
| I-168 | 1000 |
| I-174 | 370 |
| I-180 | 850 |
| III-1 | >2300 |
| III-2 | 1200 |
| III-3 | >2300 |
| III-4 | 780 |
| III-5 | 1000 |
| III-6 | 1600 |
| III-7 | 290 |
| III-8 | 480 |
| III-9 | 770 |

Test Example 3: Effect of Suppressing Impulsivity in Rat

Male Crl: WI rats are obtained at post-natal day 14 and weaning is occurred at post-natal day 21. Starting from then, the rats are housed 2-3 per cage and food-restricted (Day 1). The feeding amount is 5 g/day at post-natal day 21-28 (Day 1-8), 8.5 g/day at post-natal day 29-32 (Day 9-12), and 10 g/day at post-natal day 33-36 (Day 13-16), preventing their body weight from being 60% or less of the weight of the free feeding rats.

Four days after the beginning of the food restriction (Day 5), pellets are put on goal boxes located in the left-side and the right-side of T-maze. Then, the rats are allowed to freely explore the T-maze box for 5 min to get habituated to the T-maze box and learn that the pellets are put on the goal boxes located in the left-side and the right-side. For 4 consecutive days from the next day (Day 6-9), one pellet (20 mg×1) is put in one side of the goal box as a small reward, and 5 pellets (20 mg×5) are put in the other side of the goal box as a large reward, and the rats are trained to learn their positions. Each rat undergoes 10-trial per day trainings. The rats that did not select the large reward more than or equal to 9 times of the 10 trials in the 4 days trainings are given additional training until they select the large reward more than or equal to 9 times of the 10 trials. The evaluations of the drug efficacy are started on Day 12. The compounds of the present invention are dissolved in 0.5% methylcellulose (WAKO) and administered p.o. to the trained rats to attain the dose of 1, 3 or 10 mg/kg. Vehicle control group is administered 0.5% methylcellulose. The administering tests are conducted with 6-8 rats in each group. The administrations are conducted daily over 5 days from Day 12-16. After 60 min from the administration, it is tested whether which of large reward and small reward is selected. When the rat selects the arm leading to the large reward, the rat is shut for 15 seconds in the arm to introduce delay before the rat is allowed to access to the reward. In the arm leading to the small reward, the door is opened immediately and no delay is introduced. These tests are conducted over 5 days from Day 12-16, 10 trials per day. The numbers of choices of the large reward during total 50 trials of 5 days are compared between the vehicle control group and the group which is treated with the compounds of the present invention.

Test Example 4: Rat Dopamine D3/D2 Receptor Occupancy

Five-week-old male Crl WI rats were housed in groups of 4-5 rats after arrival and allowed free access to food and water.

Occupancy was measured by autoradiography with [$^3$H]-(+)-4-propyl-9-hydroxynaphthoxazine ([$^3$H]—(+)—PHNO), a selective radiolabeled ligand for dopamine D3/D2 receptors, at 6 weeks of age (the week following arrival). The compound of the present invention was dissolved in 0.5% methylcellulose. The mixture was orally administered to rats at the dose of 0.3, 1, or 3 mg/kg (the dosage varied for each compound). 0.5% methylcellulose was administered to the vehicle control group. The occupancy tests were conducted with 3-4 rats in each group. After a certain time from the oral administration of the compound of the present invention, [$^3$H]—PHNO was administered intravenously. At 30 minutes after the intravenous administration of [$^3$H]-(+)—PHNO, blood collection was performed from the abdominal postcaval vein under isoflurane anesthesia using a syringe treated with heparin. The collected blood was centrifuged to obtain plasma. The rat was sacrificed by decapitation immediately after blood collection, and whole brain was removed, then immediately frozen on dry ice. Frozen brain sections (20 μm each in thickness) were prepared by cryostat. The frozen brain sections were dried thoroughly and exposed to imaging plate for $^3$H-labeled compound for approximately two weeks. After the exposure, autoradiograms were obtained by scanning the imaging plates with an image analyzer. The regions of interest were set on the striatum, cerebellum, and cerebellar lobes 9 & 10 on each autoradiogram with image analysis software to analyze radioactivity concentrations in each region.

D3 receptor occupancy was calculated as follows, with cerebellar lobes 9 & 10 as the target region.

Receptor occupancy (%)=[(a−b)/a]×100 a; specific binding ratio of the vehicle control group (mean value)
b; specific binding ratio of the administration group of the compound of the present invention Each specific binding ratio was calculated as follows.

Specific binding ratio=(c−d)/d c; radioactivity concentrations in Cerebellar lobes 9 & 10
d; radioactivity concentration in cerebellum, a non-specific binding region FIG. 1 shows the measurement results of D3 receptor occupancy of Compound I-015.

The D2 receptor occupancy can be calculated in similar manners as described above, using striatum as the target region. Plasma can also be used in the measurement of drug concentrations in plasma at LC/MS/MS.

Test Example 5: CYP Inhibition Test

Using commercially available pooled human liver microsomes, an inhibitory degree of each metabolite production amount by the compound of the present invention is assessed as marker reactions of human main five CYP isoforms (CYPA2, 2C9, 2C19, 2D6, and 3A4), 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4).

The reaction conditions are as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenadine (CYP3A4); reaction time, 15 minutes; reaction temperature, 37° C.; enzyme, pooled human liver microsome 0.2 mg protein/mL; concentration of the compound of the present invention, 1, 5, 10, 20 μmol/L (four points).

Each five kinds of substrates, human liver microsomes, and the compound of the present invention in 50 mmol/L Hepes buffer are added as reaction solutions to a 96-well plate at the composition as described above, and NADPH, as a cofactor, is added to initiate the marker metabolism reactions. After the incubation at 37° C. for 15 minutes, a methanol/acetonitrile=1/1 (VV) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite), 4'hydroxymephenytoin (CYP2C19 metabolite), dextrorphan (CYP2D6 metabolite), and terfenadine alcohol metabolite (CYP3A4 metabolite) are quantified by LC/MS/MS.

The sample obtained by adding only DMSO which is a solvent of the compound of the present invention to a reaction system is adopted as a control (100%). Remaining activity (%) is calculated at each concentration of the compound of the present invention compared to the control, and $IC_{50}$ is calculated by reverse presumption by a logistic model using a concentration and an inhibition rate.

Test Example 6: BA Test

Materials and Methods for experiments to evaluate oral absorption
(1) Animals: SD rats are used.
(2) Breeding conditions: The SD rats are allowed to freely take solid food and sterilized tap water.
(3) Dose and grouping: orally or intravenously administered at a predetermined dose. Grouping is set as follows. (Dose can be changed depends on the compound)
  Oral administration: 1 mg/kg or 2 μmol/kg (n=2)
  Intravenous administration: 0.5 mg/kg or 1 μmol/kg (n=2)
(4) Preparation of dosing solution: for oral administration, in a solution or a suspension state using 0.5% methylcellulose solution or dimethyl sulfoxide/0.5% methylcellulose solution=1/4 solution; for intravenous administration, in a solubilized state using dimethylacetamide/propylene glycol=1/1 or dimethyl sulfoxide/propylene glycol=1/1 solvent.
(5) Administration method: in oral administration, forcedly administer into ventriculus with oral probe; in intravenous administration, administer from caudal vein with a needle-equipped syringe.
(6) Evaluation item: blood is collected over time, and the concentration of the compound of the present invention in plasma is measured by LC/MS/MS.
(7) Statistical analysis: regarding the transition of the plasma concentration of the compound of the present invention, the area under the plasma concentration-time curve (AUC) is calculated by non-linear least squares program WinNonlin (registered trademark), and the bioavailability (BA) of the compound of the present invention is calculated from the AUCs of the oral administration group and the intravenous administration group.

Test Example 7: Metabolism Stability Test

Using commercially available pooled human liver microsomes, the compound of the present invention is reacted for a constant time, a remaining rate is calculated by comparing a reacted sample and an unreacted sample, thereby, a degree of metabolism in liver is assessed.

A reaction is performed (oxidative reaction) at 37C for 0 minutes or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a methanol/acetonitrile=1/1 (v/v) solution, mixed and centrifuged at 3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 8: CYP3A4 (MDZ) MBI Test

CYP3A4 (MDZ) MBI test is a test of investigating Mechanism based inhibition (MBI) potential on CYP3A4 by the enhancement of inhibitory degree of a metabolic reaction caused by the compound of the present invention. CYP3A4 inhibition is evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention at pre-reaction time, 1, 5, 10, 20 μmol/L (four points).

Pooled human liver microsomes and a solution of the compound of the present invention in 100 mmol/L K-Pi buffer (pH 7.4) as a pre-reaction solution are added to a 96-well plate at the composition of the pre-reaction. A part of pre-reaction solution is transferred to another 96-well plate, and 1/10 diluted by 100 mmol/L K-Pi buffer containing a substrate. NADPH as a co-factor is added to initiate a reaction as a marker reaction (without preincubation). After a predetermined time of the reaction, methanol/acetonitrile=l/1 (V/V) solution is added to stop the reaction. In addition, NADPH is added to a remaining pre-reaction solution to initiate a pre-reaction (with preincubation). After a predetermined time of the pre-reaction, a part is transferred to another plate, and 1/10 diluted by K-Pi buffer containing a substrate to initiate a reaction as a marker reaction. After a predetermined time of the reaction, methanol/acetonitrile=1/1 (V/V) solution is added to stop the reaction. After centrifuging at 3000 rpm for 15 minutes the plates having been subjected to a marker reaction, 1-hydroxymidazolam in the supernatant is quantified by LC/MS/MS.

The sample obtained by adding only DMSO which is a solvent of the compound of the present invention to a reaction system is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 9: Fluctuation Ames Test

Mutagenicity of the compound of the present invention is evaluated.

A 20 μL of freezing-stored *Salmonella typhimurium* (TA98 strain, TA100 strain) was inoculated on 10 mL of a liquid nutrient medium (2.5% Oxoid nutrient broth No. 2), and this was incubated at 37° C. for 10 hours under shaking. The 7.70 to 8.00 mL of TA98 culture medium is centrifuged (2000×g, 10 minutes) to remove the culture solution. Bacteria are suspended in a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4 \cdot 7H_2O$: 0.1 g/L) with the same volume as that of the culture medium used for centrifugation. The suspension is added to 120 mL of Exposure medium (Micro F buffer containing biotin: 8 μg/mL, histidine: 0.2 μg/mL, and glucose: 8 mg/mL). The 3.10 to 3.42 mL of TA100 culture medium strain is mixed with 120 to 130 mL Exposure medium to prepare a test bacterial suspension. Each 12 μL of DMSO solution of the compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain and 0.25 μg/mL of 2-(2-furyl)-3-(5-nitro-2-furyl)acrylamide DMSO solution for the TA100 strain in the assay without metabolic activation, 40 μg/mL of 2-aminoanthracene DMSO solution for the TA98 strain and 20 μg/mL of 2-aminoanthracene DMSO solution for the TA100 strain in the assay with metabolic activation as a positive control, and 588 μL of the test bacterial suspension (498 μL of the test bacterial suspension and 90 μL of 89 mixture in the case of metabolic activation assay) are mixed, and this is incubated at 37° C. for 90 minutes under shaking. A 460 μL of the mixture is mixed with 2300 μL of Indicator medium (Micro F buffer containing 8 μg/mL biotin, 0.2 μg/mL histidine, 8 mg/mL glucose, 37.5 μg/mL bromocresol purple), each 50 μL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 10: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration in the extracellular solution, was applied to the cell at room temperature for 7 minutes or more. From the recording $I_{Kr}$, an absolute value of the tail peak current was measured based on the current value at the resting membrane potential using analysis software (QPatch Assay software; Sophion Bioscience A/S). Further, the % inhibition of tail peak current for the compound of the present invention relative to the tail peak current after application of the solution (0.1% dimethyl sulfoxide solution) was calculated to assess influence of the compound of the present invention on $I_{Kr}$.

The hERG inhibition rate (%) at 3 μM of the compounds of the present invention is shown below.

TABLE 53

| Compound No. | hERG inhibition(%) at 3 μM |
| --- | --- |
| I-001 | 21.3 |
| I-002 | 30.3 |
| I-003 | 31 |
| I-004 | 21.6 |
| I-005 | 15.3 |
| I-006 | 23 |
| I-007 | 33.7 |
| I-008 | 20.8 |
| I-009 | 33.8 |

TABLE 53-continued

| Compound No. | hERG inhibition(%) at 3 μM |
| --- | --- |
| I-010 | 32 |
| I-011 | 10.6 |
| I-012 | 19 |
| I-013 | 21.4 |
| I-014 | 3.83 |
| I-015 | 24.3 |
| I-016 | 19.1 |
| I-017 | 21.6 |
| I-018 | 33.8 |
| I-019 | 8.86 |
| I-020 | 23.1 |
| I-021 | 24.3 |
| I-022 | 32.6 |
| I-023 | 16.5 |
| I-024 | 18.7 |
| I-025 | 14.9 |
| I-026 | 20.1 |
| I-027 | 14.3 |
| I-028 | 9.09 |
| I-029 | 8.37 |
| I-030 | 26.1 |
| I-031 | 23.8 |
| I-032 | 31.9 |
| I-033 | 12.2 |
| I-034 | 34.3 |
| I-035 | 16 |
| I-036 | 29.8 |
| I-037 | 28 |
| I-038 | 21.4 |
| I-039 | 22.3 |
| I-040 | 23.2 |
| I-041 | 18.1 |
| I-042 | 10.8 |
| I-043 | 20.7 |
| I-044 | 23.7 |
| I-045 | 18.3 |
| I-046 | 14.3 |
| I-047 | 13.6 |
| I-048 | 3.52 |
| I-049 | 36.8 |

TABLE 54

| Compound No. | hERG inhibition(%) at 3 μM |
| --- | --- |
| I-056 | 10.7 |
| I-059 | 6.72 |
| I-060 | 17.7 |
| I-066 | 14.3 |
| I-069 | 34.2 |
| I-071 | 16.6 |
| I-073 | 25.9 |
| I-074 | 31 |
| I-075 | 33.8 |
| I-076 | 13.4 |
| I-077 | 4.33 |
| I-080 | 5.68 |
| I-081 | 5.59 |
| I-082 | 11.1 |
| I-083 | 25.1 |
| I-088 | 32 |
| I-099 | 29.4 |
| I-100 | 33.9 |
| I-101 | 34.9 |
| I-102 | 32.2 |
| I-103 | 26 |
| I-104 | 16.3 |
| I-105 | 30.1 |
| I-107 | 3.75 |
| I-108 | 1.06 |
| I-109 | 27 |
| I-111 | 14.6 |
| I-112 | 23.5 |
| I-113 | 6.89 |
| I-114 | 29 |

TABLE 54-continued

| Compound No. | hERG inhibition(%) at 3 μM |
| --- | --- |
| I-119 | 23.1 |
| I-186 | 16.8 |

TABLE 55

| Compound No. | hERG inhibition(%) at 3 μM |
| --- | --- |
| I'-37 | 19.6 |
| I'-38 | 20.6 |
| I'-39 | 17.3 |
| I'-41 | 24 |

Test Example 11: Solubility Test

The solubility of the compound of the present invention was determined under 1% DMSO addition conditions. A 10 mmol/L solution of the compound was prepared with DMSO. 2 μL of the solution of the compound of the present invention was respectively added to 198 μL of JP-1 fluid or JP-2 fluid, or 6 μL of the solution of the compound of the present invention was respectively added to 594 μL of JP-1 fluid or JP-2 fluid. The mixture was left standing for 16 hours at 25° C. (condition 1) or shaking at room temperature for 3 hours (condition 2), and the mixture was vacuum-filtered. The filtrates were diluted 10- or 100-fold with methanol/water=1/1 (V/V) or acetonitrile/methanol/water=1/1/2 (V/V/V), and concentrations in the filtrates were measured by the absolute calibration curve method using LC/MS or solid-phase extraction (SPE)/MS. The dilution rate or dilution solvent was changed as necessary.

The composition of the JP-1 fluid was as below.
Water was added to 2.0 g of sodium chloride and 7.0 mL of hydrochloric acid to reach 1000 mL.

The composition of the JP-2 fluid was as below.
Composition 1. 3.40 g of potassium dihydrogen phosphate and 3.55 g of anhydrous disodium hydrogen phosphate were dissolved in water to reach 1000 mL.
Composition 2. 1 volume of water was added to 1 volume of the solution in which 3.40 g of potassium dihydrogen phosphate and 3.55 g of anhydrous disodium hydrogen phosphate were dissolved in water to reach 1000 mL.

TABLE 56

| Compound No. | JP-1 (μM) | JP-2 (μM) |
| --- | --- | --- |
| II-8 | >50 | >50 |
| II-9 | >50 | >50 |
| II-11 | >50 | >50 |
| II-12 | >50 | >50 |

Test Example 12: Powder Solubility Test

Appropriate quantity of the compound of the present invention is put in suitable containers. 200 μL of JP-1 fluid (water is added to 2.0 g of sodium chloride and 7.0 mL of hydrochloric acid to reach 1000 mL), 200 μL of JP-2 fluid (500 mL of water is added to 500 mL of pH 6.8 phosphate buffer solution)) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate or dilution solvent is changed as necessary. After checking that there is no bubble and precipitate, the container is sealed and shaken. The compound of the present invention is measured using HPLC by absolute calibration curve method.

Test Example 13: Brain Distribution Test

The compound of the present invention is intravenous administered at a dose of 1 µmol/mL/kg or 0.5 mg/mL/kg to rats. After 30 minutes, the rats are killed by exsanguination through whole blood collection from the abdominal aorta under isoflurane anesthesia.

Then, the brain is excised, and 20 to 25% homogenate is prepared with distilled water.

The obtained blood is centrifuged, and plasma is then obtained. Then, control plasma and control brain are added to the brain sample and the plasma sample, respectively, at 1:1, and each sample is assayed using LC/MS/MS. The measured area ratio (blain/plasma) obtained is used as a brain Kp value.

Test Example 14: P-Gp Substrate Test

The compound of the present invention was added to one side of Transwell (registered trademark, CORNING) where human MDR1-expressing cells or parent cells have been monolayer-cultured. The cells were reacted for a constant time. The membrane permeability coefficients from the apical side toward the basolateral side (A→B) and from the basolateral side toward the apical side (B→A) were calculated for the MDR1-expressing cells or the parent cells, and the efflux ratio (ER; ratio of the membrane permeability coefficients of B→A and A→B) values of the MDR1-expressing cells and the parent cells were calculated. The efflux ratio (ER values) of the MDR1-expressing cells and the parent cells were compared to confirm whether or not the compound of the present invention would be a P-gp substrate.

The measurement results of the compounds of the present invention are shown in the following table.

TABLE 57

| Compound No. | P-gp ER ratio |
| --- | --- |
| I-005 | 1.5 |
| I-031 | 1.5 |
| I'-39 | 1.9 |

Test Example 15: Mdr1a (−/−) B6 Mouse P-Gp Substrate Test

Animal Used
mdr1a (−/−) B6 mice (knockout mice) or C57BL16J mice (wild mice)
Method
1. The mice are allowed to freely take solid food and sterilized tap water.
2. The compound of the present invention is administered to 3 animals at each point in time. Blood and brain samples are collected at a predetermined point in time (e.g., 15 minutes, 30 minutes, 1 hour, 2 hours, 4 hours, 6 hours, 8 hours or 24 hours) after administration. The blood (0.3-0.7 mL) is collected with a syringe containing anticoagulants (EDTA and heparin). The blood and brain samples are immediately cooled in ice.
3. The blood sample is centrifugated (1780×g, 10 minutes) for removal of cells to obtain plasma. Then, the plasma sample is transferred to a tube, and stored at −70° C.
4. The brain sample is homogenized at a tissue weight: distilled water weight ratio=1:3, transferred to a tube, and stored at −70° C.
5. The plasma and brain samples are deproteinized, and analyzed by LC/MS/MS. A calibration curve prepared from blank plasma or blank brain is used in measurement. A sample for quality control is used to confirm measurement trueness and accuracy.
6. Concentrations (ng/mL and ng/g) in the plasma and the brain are analyzed by an appropriate method for determining pharmacokinetic parameters, for example, WinNonlin (registered trademark) pharmacokinetic analysis software program.
Analysis
Kp; brain/plasma concentration ratio $$Kp \text{ ratio}=\text{knockout mouse(KO)}Kp \text{ value/wild mouse (Wild)}Kp \text{ value}$$

$$KO/\text{Wild ratio of brain AUC/plasma AUC}=\{\text{brain AUC/plasma AUC(KO)}\}/\{\text{brain AUC/plasma AUC(Wild)}\}$$

Formulation Example

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to give powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds of the present invention and microcrystalline cellulose are mixed, granulated and compressed into tablets to give orally disintegrated tablets.

Formulation Example 5: Dry Syrups

The compounds of the present invention and lactose are mixed, crushed, granulated and sieved to give suitable sizes of dry syrups.

315

Formulation Example 6: Injections

The compounds of the present invention and phosphate buffer are mixed to give injections.

Formulation Example 7: Infusions

The compounds of the present invention and phosphate buffer are mixed to give infusions.

Formulation Example 8: Inhalations

The compounds of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compound of the present invention can be a medicament useful as an agent for treating and/or preventing diseases associated with D3 receptor.

The invention claimed is:
1. A compound selected from the group consisting of:

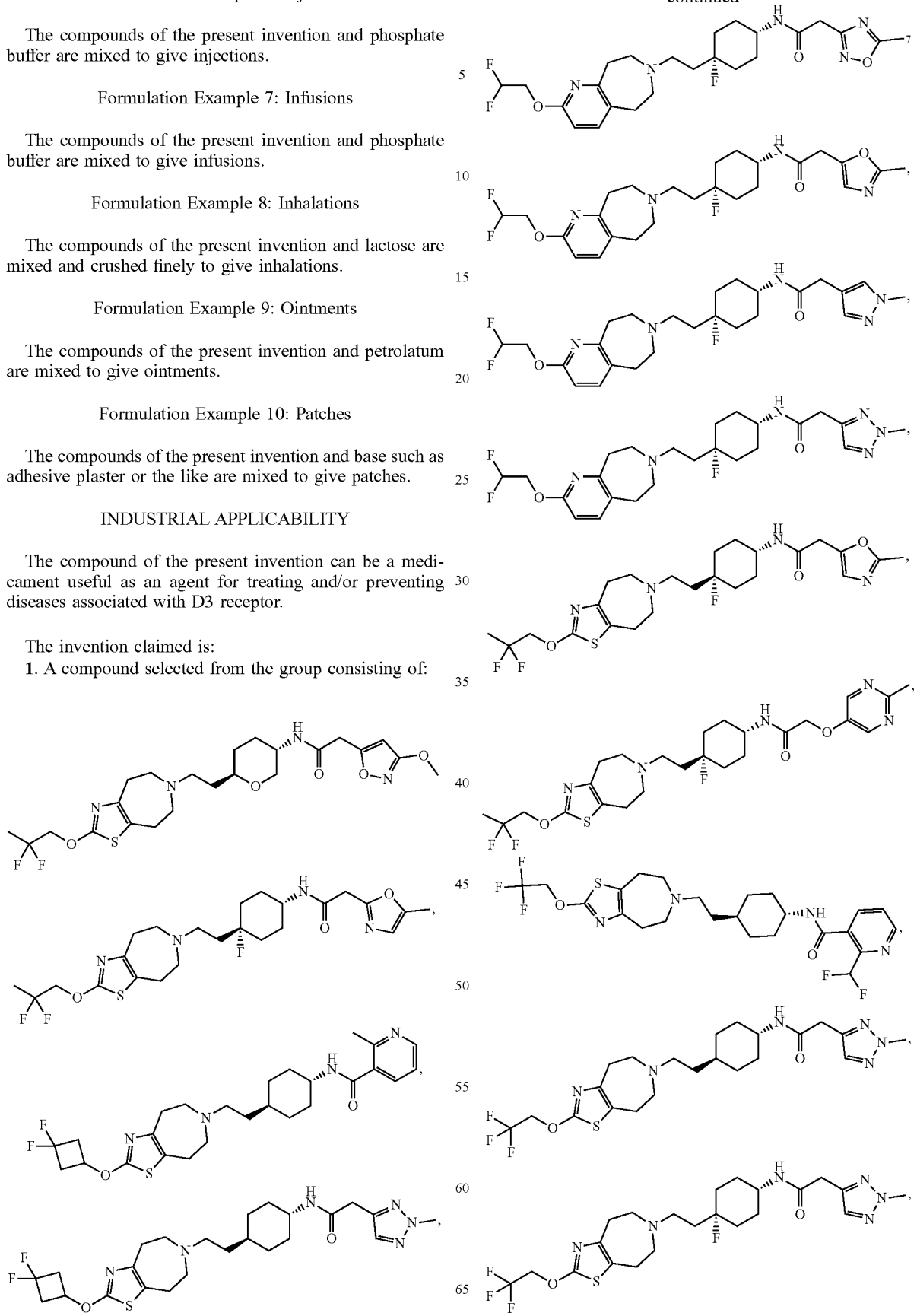

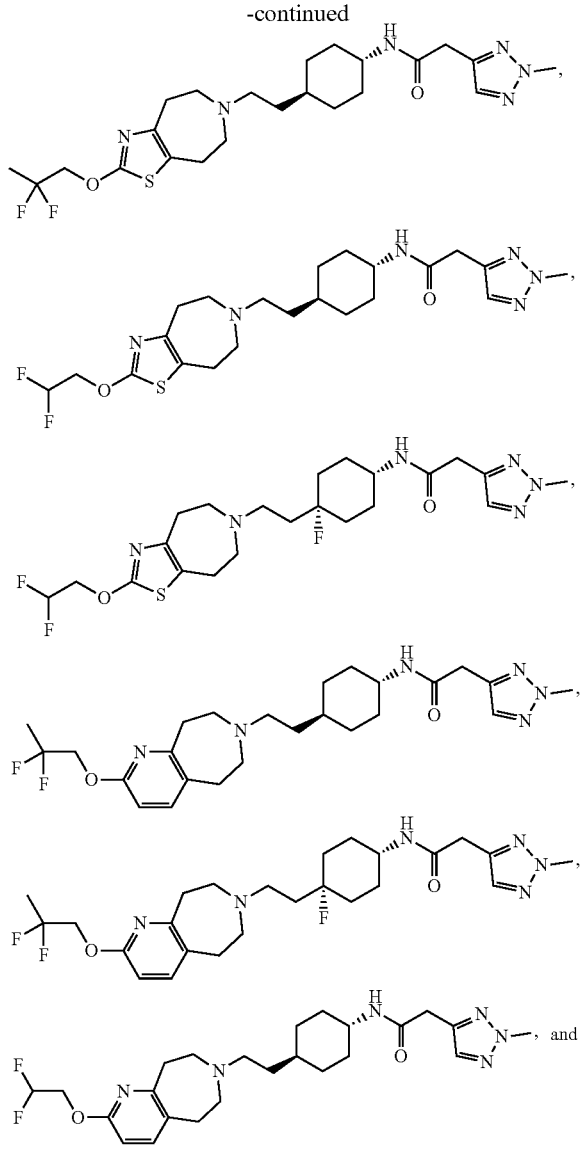

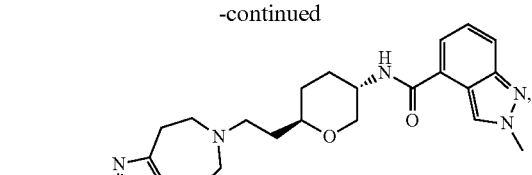

or a pharmaceutically acceptable salt thereof.

2. A pharmaceutical composition comprising the compound according to claim 1, or a pharmaceutically acceptable salt thereof, and a pharmaceutical additive.

3. A compound selected from the group consisting of:

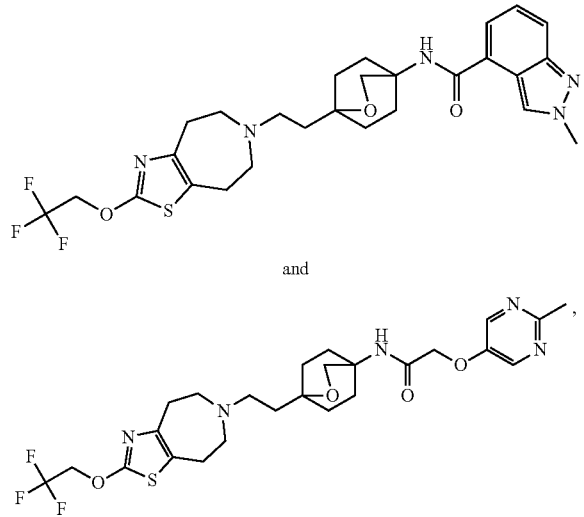

or a pharmaceutically acceptable salt thereof.

4. A pharmaceutical composition comprising the compound according to claim 3, or a pharmaceutically acceptable salt thereof, and a pharmaceutical additive.

* * * * *